US012569166B2

(12) United States Patent
Rao et al.

(10) Patent No.: US 12,569,166 B2
(45) Date of Patent: Mar. 10, 2026

(54) SYSTEMS, DEVICES AND METHODS FOR ANALYTE SENSOR INSERTION

(71) Applicant: ABBOTT DIABETES CARE INC., Alameda, CA (US)

(72) Inventors: Vivek S. Rao, Alameda, CA (US); Louis G. Pace, San Carlos, CA (US); Hyun Cho, Berkeley, CA (US); Benjamin Jay Feldman, Berkeley, CA (US); Yi Wang, San Ramon, CA (US); Tuan Nguyen, San Jose, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 17/667,220

(22) Filed: Feb. 8, 2022

(65) Prior Publication Data

US 2022/0151517 A1      May 19, 2022

Related U.S. Application Data

(63) Continuation of application No. 17/357,090, filed on Jun. 24, 2021, which is a continuation of application
(Continued)

(51) Int. Cl.
| | |
|---|---|
| *A61B 5/145* | (2006.01) |
| *A61B 5/00* | (2006.01) |
| *A61B 17/34* | (2006.01) |

(52) U.S. Cl.
CPC ............ *A61B 5/14503* (2013.01); *A61B 5/00* (2013.01); *A61B 5/6849* (2013.01);
(Continued)

(58) Field of Classification Search
None
See application file for complete search history.

(56) References Cited

U.S. PATENT DOCUMENTS

| | | |
|---|---|---|
| 2,402,306 A | 6/1946 | Turkel |
| 2,752,918 A | 7/1956 | Uytenbogaart |
| | (Continued) | |

FOREIGN PATENT DOCUMENTS

| | | |
|---|---|---|
| AU | 2003259741 | 2/2004 |
| CA | 2291105 | 12/1998 |
| | (Continued) | |

OTHER PUBLICATIONS

AU, 2007309066 Examiner's Report, dated Jul. 12, 2012.
(Continued)

*Primary Examiner* — Michael R Bloch
(74) *Attorney, Agent, or Firm* — ONE LLP

(57) ABSTRACT

Systems, devices and methods are provided for inserting at least a portion of an in vivo analyte sensor, such as a dermal sensor, for sensing an analyte level in a bodily fluid of a subject. An applicator is positioned against a skin surface and a force is applied to the applicator causing at least a portion of a sharp and an in vivo analyte sensor to be positioned in the body of the subject. In particular, disclosed herein are embodiments of applicators designed to prevent premature sharp withdrawal and/or reduce the likelihood of improper sensor insertion. Also disclosed are embodiments of applicators including sharp modules having an angled sharp which can be configured to create an insertion path for a sensor.

19 Claims, 42 Drawing Sheets

Related U.S. Application Data

No. 15/877,331, filed on Jan. 22, 2018, now Pat. No. 11,071,478.

(60) Provisional application No. 62/449,570, filed on Jan. 23, 2017.

(52) U.S. Cl.
CPC ........ *A61B 17/3468* (2013.01); *A61B 5/0004* (2013.01); *A61B 5/14532* (2013.01); *A61B 2017/347* (2013.01); *A61B 2560/0443* (2013.01); *A61B 2560/063* (2013.01)

(56) References Cited

U.S. PATENT DOCUMENTS

| | | |
|---|---|---|
| 3,123,790 A | 3/1964 | Tyler |
| 3,132,123 A | 5/1964 | Harris, Jr. et al. |
| 3,173,200 A | 3/1965 | Dunmire et al. |
| 3,211,001 A | 10/1965 | Petit |
| 3,260,656 A | 7/1966 | Ross, Jr. |
| 3,517,670 A | 6/1970 | Speelman |
| 3,522,807 A | 8/1970 | Millenbach |
| 3,581,062 A | 5/1971 | Aston |
| 3,653,841 A | 4/1972 | Klein |
| 3,670,727 A | 6/1972 | Reiterman |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,960,497 A | 6/1976 | Acord et al. |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,033,330 A | 7/1977 | Willis et al. |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danniger et al. |
| 4,172,770 A | 10/1979 | Semersky et al. |
| 4,178,916 A | 12/1979 | McNamara |
| 4,203,446 A | 5/1980 | Hofert et al. |
| 4,206,755 A | 6/1980 | Klein |
| 4,224,125 A | 9/1980 | Nakamura et al. |
| 4,240,438 A | 12/1980 | Updike et al. |
| 4,240,889 A | 12/1980 | Yoda et al. |
| 4,245,634 A | 1/1981 | Albisser et al. |
| 4,247,297 A | 1/1981 | Berti et al. |
| 4,294,258 A | 10/1981 | Bernard |
| 4,305,401 A | 12/1981 | Reissmueller et al. |
| 4,308,981 A | 1/1982 | Miura |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,353,888 A | 10/1982 | Sefton |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,392,849 A | 7/1983 | Petre et al. |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,004 A | 1/1984 | Miller et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,441,968 A | 4/1984 | Emmer et al. |
| 4,450,842 A | 5/1984 | Zick et al. |
| 4,458,686 A | 7/1984 | Clark, Jr. |
| 4,461,691 A | 7/1984 | Frank |
| 4,464,170 A | 8/1984 | Clemens et al. |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,553,541 A | 11/1985 | Burns |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,592,745 A | 6/1986 | Rex et al. |
| 4,595,011 A | 6/1986 | Phillips |
| 4,619,754 A | 10/1986 | Niki et al. |
| 4,619,793 A | 10/1986 | Lee |
| 4,622,966 A | 11/1986 | Beard |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardien |
| 4,637,403 A | 1/1987 | Garcia et al. |
| 4,639,062 A | 1/1987 | Taniguchi et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,663,824 A | 5/1987 | Kenmochi |
| 4,665,906 A | 5/1987 | Jervis |
| 4,671,288 A | 6/1987 | Gough |
| 4,675,346 A | 6/1987 | Lin et al. |
| 4,679,562 A | 7/1987 | Luksha |
| 4,680,268 A | 7/1987 | Clark, Jr. |
| 4,682,602 A | 7/1987 | Prohaska |
| 4,684,245 A | 8/1987 | Goldring |
| 4,684,537 A | 8/1987 | Graetzel et al. |
| 4,685,463 A | 8/1987 | Williams |
| 4,685,466 A | 8/1987 | Rau |
| 4,690,675 A | 9/1987 | Katz |
| 4,698,057 A | 10/1987 | Joishy |
| 4,703,324 A | 10/1987 | White |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |

(56)                References Cited

U.S. PATENT DOCUMENTS

| | | |
|---|---|---|
| 4,777,953 A | 10/1988 | Ash et al. |
| 4,779,618 A | 10/1988 | Gough |
| 4,781,683 A | 11/1988 | Wozniak et al. |
| 4,781,798 A | 11/1988 | Gough |
| 4,784,736 A | 11/1988 | Lonsdale et al. |
| 4,785,868 A | 11/1988 | Koenig, Jr. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,817,603 A | 4/1989 | Turner et al. |
| 4,818,994 A | 4/1989 | Orth et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,847,785 A | 7/1989 | Stephens |
| 4,848,351 A | 7/1989 | Finch |
| 4,852,025 A | 7/1989 | Herpichböhm |
| 4,854,322 A | 8/1989 | Ash et al. |
| 4,856,648 A | 8/1989 | Krueger |
| 4,865,038 A | 9/1989 | Rich et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,890,622 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villavecs |
| 4,923,586 A | 5/1990 | Katayama et al. |
| 4,924,879 A | 5/1990 | O'Brien |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagara |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,985,142 A | 1/1991 | Laycock et al. |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,002,054 A | 3/1991 | Ash et al. |
| 5,006,110 A | 4/1991 | Garrison et al. |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,051,688 A | 9/1991 | Murase et al. |
| 5,055,171 A | 10/1991 | Peck |
| 5,058,592 A | 10/1991 | Whisler |
| 5,067,957 A | 11/1991 | Jervis |
| 5,068,536 A | 11/1991 | Rosenthal |
| 5,070,535 A | 12/1991 | Hochmair et al. |
| 5,082,550 A | 1/1992 | Rishpon et al. |
| 5,082,786 A | 1/1992 | Nakamoto |
| 5,086,246 A | 2/1992 | Dymond et al. |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,124,661 A | 6/1992 | Zellin et al. |
| 5,126,034 A | 6/1992 | Carter et al. |
| 5,133,856 A | 7/1992 | Yamaguchi et al. |
| 5,135,003 A | 8/1992 | Souma |
| 5,135,004 A | 8/1992 | Adams et al. |
| 5,140,985 A | 8/1992 | Schroeder et al. |
| 5,141,868 A | 8/1992 | Shanks et al. |
| 5,161,532 A | 11/1992 | Joseph |
| 5,162,407 A | 11/1992 | Turner |
| 5,165,407 A | 11/1992 | Wilson et al. |
| 5,173,165 A | 12/1992 | Schmid et al. |
| 5,174,291 A | 12/1992 | Schoonen et al. |
| 5,190,041 A | 3/1993 | Palti |
| 5,190,546 A | 3/1993 | Jervis |
| 5,192,416 A | 3/1993 | Wang et al. |
| 5,193,545 A | 3/1993 | Marsoner et al. |
| 5,198,367 A | 3/1993 | Aizawa et al. |
| 5,202,261 A | 4/1993 | Musho et al. |
| 5,204,264 A | 4/1993 | Kaminer et al. |
| 5,205,297 A | 4/1993 | Montecalvo et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,228,449 A | 7/1993 | Christ et al. |
| 5,229,282 A | 7/1993 | Yoshioka et al. |
| 5,231,988 A | 8/1993 | Wernicke et al. |
| 5,234,835 A | 8/1993 | Nestor et al. |
| 5,238,729 A | 8/1993 | Debe |
| 5,243,696 A | 9/1993 | Carr et al. |
| 5,245,314 A | 9/1993 | Kah et al. |
| 5,246,867 A | 9/1993 | Lakowicz et al. |
| 5,250,439 A | 10/1993 | Musho et al. |
| 5,251,126 A | 10/1993 | Kahn et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,267,963 A | 12/1993 | Bachynsky |
| 5,271,815 A | 12/1993 | Wong |
| 5,279,294 A | 1/1994 | Anderson |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,289,497 A | 2/1994 | Jackobson et al. |
| 5,293,546 A | 3/1994 | Tadros et al. |
| 5,293,877 A | 3/1994 | O'Hara et al. |
| 5,299,571 A | 4/1994 | Mastrototaro |
| 5,305,008 A | 4/1994 | Turner et al. |
| 5,318,583 A | 6/1994 | Rabenau et al. |
| 5,320,098 A | 6/1994 | Davidson |
| 5,320,715 A | 6/1994 | Berg |
| 5,320,725 A | 6/1994 | Gregg et al. |
| 5,322,063 A | 6/1994 | Allen et al. |
| 5,333,615 A | 8/1994 | Craelius et al. |
| 5,337,747 A | 8/1994 | Neftei |
| 5,340,722 A | 8/1994 | Wolfbeis et al. |
| 5,342,789 A | 8/1994 | Chick et al. |
| 5,352,348 A | 10/1994 | Young et al. |
| 5,356,420 A | 10/1994 | Czernecki et al. |
| 5,356,786 A | 10/1994 | Heller et al. |
| 5,360,404 A | 11/1994 | Novacek et al. |

(56)　　　　　References Cited

U.S. PATENT DOCUMENTS

| | | |
|---|---|---|
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,384,547 A | 1/1995 | Lynk et al. |
| 5,387,327 A | 2/1995 | Khan |
| 5,390,670 A | 2/1995 | Centa et al. |
| 5,390,671 A | 2/1995 | Lord et al. |
| 5,391,250 A | 2/1995 | Cheney, II et al. |
| 5,394,877 A | 3/1995 | Orr et al. |
| 5,395,504 A | 3/1995 | Saurer et al. |
| 5,400,782 A | 3/1995 | Beaubiah |
| 5,400,794 A | 3/1995 | Gorman |
| 5,402,780 A | 4/1995 | Faasse, Jr. |
| 5,407,431 A | 4/1995 | Botich et al. |
| 5,408,999 A | 4/1995 | Singh et al. |
| 5,410,326 A | 4/1995 | Goldstein |
| 5,411,647 A | 5/1995 | Johnson et al. |
| 5,425,361 A | 6/1995 | Fenzlein et al. |
| 5,425,868 A | 6/1995 | Pedersen |
| 5,431,160 A | 7/1995 | Wilkins |
| 5,431,921 A | 7/1995 | Thombre |
| 5,437,999 A | 8/1995 | Dieboid et al. |
| 5,438,983 A | 8/1995 | Falcone |
| 5,462,051 A | 10/1995 | Oka et al. |
| 5,462,645 A | 10/1995 | Albery et al. |
| 5,469,846 A | 11/1995 | Khan |
| 5,472,317 A | 12/1995 | Field et al. |
| 5,482,473 A | 1/1996 | Lord et al. |
| 5,484,403 A | 1/1996 | Yoakum et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,499,243 A | 3/1996 | Hall |
| 5,507,288 A | 4/1996 | Bocker et al. |
| 5,509,410 A | 4/1996 | Hill et al. |
| 5,514,718 A | 5/1996 | Lewis et al. |
| 5,516,832 A | 5/1996 | Kennan et al. |
| 5,527,288 A | 6/1996 | Gross et al. |
| 5,531,878 A | 7/1996 | Vadgama et al. |
| 5,532,686 A | 7/1996 | Urbas et al. |
| 5,533,977 A | 7/1996 | Metcalf et al. |
| 5,536,259 A | 7/1996 | Utterberg |
| 5,543,326 A | 8/1996 | Heller et al. |
| 5,544,196 A | 8/1996 | Tiedmann, Jr. et al. |
| 5,545,191 A | 8/1996 | Mann et al. |
| 5,549,368 A | 8/1996 | Shields |
| 5,549,568 A | 8/1996 | Sheilds |
| 5,551,427 A | 9/1996 | Altman |
| 5,555,190 A | 9/1996 | Derby et al. |
| 5,558,638 A | 9/1996 | Evers et al. |
| 5,560,357 A | 10/1996 | Faupei et al. |
| 5,562,713 A | 10/1996 | Silvian |
| 5,564,434 A | 10/1996 | Halperin et al. |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,571,022 A | 11/1996 | Schaarschmidt |
| 5,575,563 A | 11/1996 | Chiu et al. |
| 5,581,206 A | 12/1996 | Chevallier et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halli et al. |
| 5,589,326 A | 12/1996 | Deng et al. |
| 5,593,852 A | 1/1997 | Heller et al. |
| 5,596,150 A | 1/1997 | Arndt et al. |
| 5,597,378 A | 1/1997 | Jervis |
| 5,600,301 A | 2/1997 | Robinson, III |
| 5,601,435 A | 2/1997 | Quy |
| 5,609,575 A | 3/1997 | Larson et al. |
| 5,613,978 A | 3/1997 | Harding |
| 5,617,851 A | 4/1997 | Lipkovker |
| 5,623,933 A | 4/1997 | Amano et al. |
| 5,626,566 A | 5/1997 | Petersen et al. |
| 5,628,310 A | 5/1997 | Rao et al. |
| 5,628,324 A | 5/1997 | Sarbach |
| 5,628,890 A | 5/1997 | Carter et al. |
| 5,632,557 A | 5/1997 | Simons |
| 5,634,468 A | 6/1997 | Platt et al. |
| 5,636,640 A | 6/1997 | Staehlin |
| 5,638,832 A | 6/1997 | Singer et al. |
| 5,640,954 A | 6/1997 | Pfeiffer et al. |
| 5,651,869 A | 7/1997 | Yoshioka et al. |
| 5,653,239 A | 8/1997 | Pompei et al. |
| 5,659,454 A | 8/1997 | Vermesse |
| 5,660,163 A | 8/1997 | Schulman et al. |
| 5,665,071 A | 9/1997 | Wyrick |
| 5,665,222 A | 9/1997 | Heller et al. |
| 5,669,543 A | 9/1997 | Ueno |
| 5,669,890 A | 9/1997 | Grimm |
| 5,670,031 A | 9/1997 | Hintsche et al. |
| 5,673,322 A | 9/1997 | Pepe et al. |
| 5,680,858 A | 10/1997 | Hansen et al. |
| 5,682,233 A | 10/1997 | Brinda |
| 5,695,623 A | 12/1997 | Michel et al. |
| 5,707,502 A | 1/1998 | McCaffrey et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,724,030 A | 3/1998 | Urbas et al. |
| 5,726,646 A | 3/1998 | Bane et al. |
| 5,733,044 A | 3/1998 | Rose et al. |
| 5,733,259 A | 3/1998 | Valcke et al. |
| 5,733,262 A | 3/1998 | Paul |
| 5,733,313 A | 3/1998 | Barreras, Sr. et al. |
| 5,735,285 A | 4/1998 | Albert et al. |
| 5,738,220 A | 4/1998 | Geszler |
| 5,741,211 A | 4/1998 | Renirie et al. |
| 5,743,262 A | 4/1998 | Lepper, Jr. et al. |
| 5,746,217 A | 5/1998 | Erickson et al. |
| 5,746,697 A | 5/1998 | Swedlow et al. |
| 5,748,103 A | 5/1998 | Flach et al. |
| 5,749,656 A | 5/1998 | Boehm et al. |
| 5,749,907 A | 5/1998 | Mann |
| 5,758,290 A | 5/1998 | Nealon et al. |
| 5,766,131 A | 6/1998 | Kondo et al. |
| 5,770,028 A | 6/1998 | Maley et al. |
| 5,771,001 A | 6/1998 | Cobb |
| 5,771,891 A | 6/1998 | Gozani |
| 5,772,586 A | 6/1998 | Heinonen et al. |
| 5,778,879 A | 7/1998 | Ota et al. |
| 5,779,665 A | 7/1998 | Mastrototaro et al. |
| 5,786,439 A | 7/1998 | Van Antwerp et al. |
| 5,791,344 A | 8/1998 | Schulman et al. |
| 5,798,961 A | 8/1998 | Heyden et al. |
| 5,800,420 A | 9/1998 | Gross et al. |
| 5,804,047 A | 9/1998 | Karube et al. |
| 5,807,375 A | 9/1998 | Gross et al. |
| 5,814,020 A | 9/1998 | Gross |
| 5,820,551 A | 10/1998 | Hill et al. |
| 5,820,570 A | 10/1998 | Erickson et al. |
| 5,820,622 A | 10/1998 | Gross et al. |
| 5,822,715 A | 10/1998 | Worthington et al. |
| 5,823,802 A | 10/1998 | Bartley |
| 5,827,184 A | 10/1998 | Netherly et al. |
| 5,830,064 A | 11/1998 | Bradish et al. |
| 5,833,603 A | 11/1998 | Kovacs et al. |
| 5,840,020 A | 11/1998 | Heinonen et al. |
| 5,842,983 A | 12/1998 | Abel et al. |
| 5,851,197 A | 12/1998 | Marano et al. |
| 5,856,758 A | 1/1999 | Joffe et al. |
| 5,858,001 A | 1/1999 | Tsals et al. |
| 5,865,804 A | 2/1999 | Bachynsky |
| 5,871,494 A | 2/1999 | Simons et al. |
| 5,875,186 A | 2/1999 | Belanger et al. |

(56) References Cited

U.S. PATENT DOCUMENTS

| | | | |
|---|---|---|---|
| 5,879,311 A | 3/1999 | Duchon et al. |
| 5,885,211 A | 3/1999 | Eppstein et al. |
| 5,891,049 A | 4/1999 | Cyrus et al. |
| 5,899,855 A | 5/1999 | Brown |
| 5,899,856 A | 5/1999 | Schoendorfer et al. |
| 5,914,026 A | 6/1999 | Blubaugh, Jr. et al. |
| 5,918,603 A | 7/1999 | Brown |
| 5,919,141 A | 7/1999 | Money et al. |
| 5,921,963 A | 7/1999 | Erez et al. |
| 5,924,979 A | 7/1999 | Sedlow et al. |
| 5,925,021 A | 7/1999 | Castellano et al. |
| 5,931,814 A | 8/1999 | Alex et al. |
| 5,935,224 A | 8/1999 | Svancarek et al. |
| 5,938,679 A | 8/1999 | Freeman et al. |
| 5,942,979 A | 8/1999 | Luppino |
| 5,948,006 A | 9/1999 | Mann |
| 5,951,485 A | 9/1999 | Cyrus et al. |
| 5,951,492 A | 9/1999 | Douglas et al. |
| 5,951,521 A | 9/1999 | Mastrototaro et al. |
| 5,951,582 A | 9/1999 | Thorne et al. |
| 5,954,643 A | 9/1999 | Van Antwerp et al. |
| 5,954,685 A | 9/1999 | Tierny |
| 5,957,854 A | 9/1999 | Besson et al. |
| 5,961,451 A | 10/1999 | Reber et al. |
| 5,964,718 A | 10/1999 | Duchon et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,971,941 A | 10/1999 | Simons et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,017,335 A | 1/2000 | Burnham |
| 6,022,315 A | 2/2000 | Iliff |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,028,413 A | 2/2000 | Brockmann |
| 6,032,064 A | 2/2000 | Devlin et al. |
| 6,036,924 A | 3/2000 | Simons et al. |
| 6,048,352 A | 4/2000 | Douglas et al. |
| 6,049,727 A | 4/2000 | Crothall |
| 6,052,565 A | 4/2000 | Ishikura et al. |
| 6,054,194 A | 4/2000 | Kane |
| 6,056,718 A | 5/2000 | Funderburk et al. |
| 6,059,946 A | 5/2000 | Yukawa et al. |
| 6,066,243 A | 5/2000 | Anderson et al. |
| 6,068,399 A | 5/2000 | Tseng |
| 6,071,294 A | 6/2000 | Simons et al. |
| 6,071,391 A | 6/2000 | Gotoh et al. |
| 6,083,710 A | 7/2000 | Heller et al. |
| 6,085,342 A | 7/2000 | Marholev et al. |
| 6,088,605 A | 7/2000 | Griffith et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,097,480 A | 8/2000 | Kaplan |
| 6,099,484 A | 8/2000 | Douglas et al. |
| 6,102,896 A | 8/2000 | Roser |
| 6,103,033 A | 8/2000 | Say et al. |
| 6,106,484 A | 8/2000 | Terwilliger |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,129,666 A | 10/2000 | DeLuca et al. |
| 6,130,623 A | 10/2000 | MacLellan et al. |
| 6,132,449 A | 10/2000 | Lum et al. |
| 6,134,461 A | 10/2000 | Say et al. |
| 6,141,573 A | 10/2000 | Kurnik et al. |
| 6,143,164 A | 11/2000 | Heller et al. |
| 6,144,837 A | 11/2000 | Quy |
| 6,144,871 A | 11/2000 | Saito et al. |
| 6,144,922 A | 11/2000 | Douglas et al. |
| 6,149,626 A | 11/2000 | Bachynsky et al. |
| 6,157,850 A | 12/2000 | Diab et al. |
| 6,159,147 A | 12/2000 | Lichter et al. |
| 6,159,181 A | 12/2000 | Crossman et al. |
| 6,161,095 A | 12/2000 | Brown |
| 6,162,611 A | 12/2000 | Heller et al. |
| 6,168,606 B1 | 1/2001 | Levin et al. |
| 6,175,752 B1 | 1/2001 | Say et al. |
| 6,186,982 B1 | 2/2001 | Gross et al. |
| 6,192,891 B1 | 2/2001 | Gravel et al. |
| 6,197,040 B1 | 3/2001 | LeVaughn et al. |
| 6,198,946 B1 | 3/2001 | Shin et al. |
| 6,200,265 B1 | 3/2001 | Walsh et al. |
| 6,203,495 B1 | 3/2001 | Bardy et al. |
| 6,212,416 B1 | 4/2001 | Ward et al. |
| 6,213,972 B1 | 4/2001 | Butterfield et al. |
| 6,219,574 B1 | 4/2001 | Cormier et al. |
| 6,223,283 B1 | 4/2001 | Chaiken et al. |
| 6,231,531 B1 | 5/2001 | Lum et al. |
| 6,233,471 B1 | 5/2001 | Berner et al. |
| 6,237,394 B1 | 5/2001 | Harris et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,264,810 B1 | 7/2001 | Stol et al. |
| 6,270,455 B1 | 8/2001 | Brown |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,298,255 B1 | 10/2001 | Cordero et al. |
| 6,299,347 B1 | 10/2001 | Pompei |
| 6,299,757 B1 | 10/2001 | Feldman et al. |
| 6,302,866 B1 | 10/2001 | Marggi |
| 6,304,766 B1 | 10/2001 | Colvin, Jr. |
| 6,306,104 B1 | 10/2001 | Cunningham et al. |
| 6,306,141 B1 | 10/2001 | Jervis |
| 6,309,884 B1 | 10/2001 | Cooper et al. |
| 6,314,317 B1 | 11/2001 | Willis |
| 6,329,161 B1 | 12/2001 | Heller et al. |
| 6,331,244 B1 | 12/2001 | Lewis et al. |
| 6,336,269 B1 | 1/2002 | Eldridge et al. |
| 6,338,790 B1 | 1/2002 | Feldman et al. |
| 6,341,232 B1 | 1/2002 | Conn et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,364,890 B1 | 4/2002 | Lum et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,368,339 B1 | 4/2002 | Amplatz |
| 6,377,828 B1 | 4/2002 | Chaiken et al. |
| 6,377,829 B1 | 4/2002 | Al-Ali |
| 6,377,894 B1 | 4/2002 | Deweese et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,409,740 B1 | 6/2002 | Kuhr et al. |
| 6,413,393 B1 | 7/2002 | Van Antwerp et al. |
| 6,416,471 B1 | 7/2002 | Kumar et al. |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |

(56) References Cited

U.S. PATENT DOCUMENTS

| | | |
|---|---|---|
| 6,427,088 B1 | 7/2002 | Bowman, IV et al. |
| 6,433,743 B1 | 8/2002 | Massy et al. |
| 6,435,017 B1 | 8/2002 | Nowicki, Jr. et al. |
| 6,437,679 B1 | 8/2002 | Roques |
| 6,438,414 B1 | 8/2002 | Conn et al. |
| 6,440,068 B1 | 8/2002 | Brown et al. |
| 6,442,413 B1 | 8/2002 | Silver |
| 6,445,374 B2 | 9/2002 | Albert et al. |
| 6,451,025 B1 | 9/2002 | Jervis |
| 6,458,109 B1 | 10/2002 | Henley et al. |
| 6,461,496 B1 | 10/2002 | Feldman et al. |
| 6,471,689 B1 | 10/2002 | Joseph et al. |
| 6,472,220 B1 | 10/2002 | Simons et al. |
| 6,478,736 B1 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,493,069 B1 | 12/2002 | Nagashimada et al. |
| 6,494,830 B1 | 12/2002 | Wessel |
| 6,496,729 B2 | 12/2002 | Thompson |
| 6,497,655 B1 | 12/2002 | Linberg et al. |
| 6,503,381 B1 | 1/2003 | Gotoh et al. |
| 6,510,344 B1 | 1/2003 | Halpern |
| 6,514,460 B1 | 2/2003 | Fendrock |
| 6,514,689 B2 | 2/2003 | Han et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,533,805 B1 | 3/2003 | Jervis |
| 6,537,242 B1 | 3/2003 | Palmer |
| 6,540,891 B1 | 4/2003 | Stewart et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,551,496 B1 | 4/2003 | Moles et al. |
| 6,554,795 B2 | 4/2003 | Bagaoisan et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,572,566 B2 | 6/2003 | Effenhauser |
| 6,574,490 B2 | 6/2003 | Abbink et al. |
| 6,574,510 B2 | 6/2003 | Von Arx et al. |
| 6,575,895 B1 | 6/2003 | Blair |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,584,335 B1 | 6/2003 | Haar et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,602,268 B2 | 8/2003 | Kuhr et al. |
| 6,603,995 B1 | 8/2003 | Carter |
| 6,604,050 B2 | 8/2003 | Trippel et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,607,543 B2 | 8/2003 | Purcell et al. |
| 6,608,562 B1 | 8/2003 | Kimura et al. |
| 6,610,012 B2 | 8/2003 | Mault |
| 6,611,206 B2 | 8/2003 | Eshelman et al. |
| 6,613,015 B2 | 9/2003 | Sandstrom et al. |
| 6,616,819 B1 | 9/2003 | Liamos et al. |
| 6,618,934 B1 | 9/2003 | Feldman et al. |
| 6,627,154 B1 | 9/2003 | Goodman et al. |
| 6,631,281 B1 | 10/2003 | Kastle |
| 6,633,772 B2 | 10/2003 | Ford et al. |
| 6,635,014 B2 | 10/2003 | Starkweather et al. |
| 6,635,167 B1 | 10/2003 | Batman et al. |
| 6,637,611 B2 | 10/2003 | Luch |
| 6,641,533 B2 | 11/2003 | Causey, III et al. |
| 6,645,359 B1 | 11/2003 | Bhullar et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,662,439 B1 | 12/2003 | Bhullar |
| 6,666,849 B1 | 12/2003 | Marshall et al. |
| 6,668,196 B1 | 12/2003 | Villegas et al. |
| 6,671,534 B2 | 12/2003 | Putz |
| 6,675,030 B2 | 1/2004 | Ciurczak et al. |
| 6,676,290 B1 | 1/2004 | Lu |
| 6,676,816 B2 | 1/2004 | Mao et al. |
| 6,682,546 B2 | 1/2004 | Amplatz |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,699,188 B2 | 3/2004 | Wessel |
| 6,702,857 B2 | 3/2004 | Brauker et al. |
| 6,706,159 B2 | 3/2004 | Moerman et al. |
| 6,721,582 B2 | 4/2004 | Trepagnier et al. |
| 6,730,025 B1 | 5/2004 | Platt |
| 6,730,072 B2 | 5/2004 | Shawgo et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,735,479 B2 | 5/2004 | Fabian et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,743,635 B2 | 6/2004 | Neel et al. |
| 6,746,582 B2 | 6/2004 | Heller et al. |
| 6,748,445 B1 | 6/2004 | Darcey et al. |
| 6,749,740 B2 | 6/2004 | Liamos et al. |
| 6,758,810 B2 | 7/2004 | Lebel et al. |
| 6,758,835 B2 | 7/2004 | Close et al. |
| 6,764,581 B1 | 7/2004 | Forrow et al. |
| 6,767,440 B1 | 7/2004 | Bhullar et al. |
| 6,770,030 B1 | 8/2004 | Schaupp et al. |
| 6,773,671 B1 | 8/2004 | Lewis et al. |
| 6,781,522 B2 | 8/2004 | Sleva et al. |
| 6,790,178 B1 | 9/2004 | Mault et al. |
| 6,804,558 B2 | 10/2004 | Haller et al. |
| 6,804,561 B2 | 10/2004 | Stover |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,814,844 B2 | 11/2004 | Bhullar et al. |
| 6,830,551 B1 | 12/2004 | Uchigaki et al. |
| 6,837,858 B2 | 1/2005 | Cunningham et al. |
| 6,837,885 B2 | 1/2005 | Koblish et al. |
| 6,837,988 B2 | 1/2005 | Leong et al. |
| 6,849,052 B2 | 2/2005 | Uchigaki et al. |
| 6,850,790 B2 | 2/2005 | Berner et al. |
| 6,850,859 B1 | 2/2005 | Schuh |
| 6,854,882 B2 | 2/2005 | Chen |
| 6,862,465 B2 | 3/2005 | Shults et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |

(56) References Cited

U.S. PATENT DOCUMENTS

| | | | |
|---|---|---|---|
| 6,923,763 | B1 | 8/2005 | Kovatchev et al. |
| 6,923,764 | B2 | 8/2005 | Aceti et al. |
| 6,925,393 | B1 | 8/2005 | Kalatz et al. |
| 6,931,327 | B2 | 8/2005 | Goode, Jr. et al. |
| 6,932,892 | B2 | 8/2005 | Chen |
| 6,932,894 | B2 | 8/2005 | Mao et al. |
| 6,936,006 | B2 | 8/2005 | Sabra |
| 6,937,222 | B2 | 8/2005 | Numao |
| 6,940,403 | B2 | 9/2005 | Kail, IV |
| 6,941,163 | B2 | 9/2005 | Ford et al. |
| 6,942,518 | B2 | 9/2005 | Liamos et al. |
| 6,950,708 | B2 | 9/2005 | Bowman IV et al. |
| 6,954,662 | B2 | 10/2005 | Freger et al. |
| 6,958,705 | B2 | 10/2005 | Lebel et al. |
| 6,959,211 | B2 | 10/2005 | Rule et al. |
| 6,960,192 | B1 | 11/2005 | Flaherty et al. |
| 6,968,294 | B2 | 11/2005 | Gutta et al. |
| 6,971,274 | B2 | 12/2005 | Olin |
| 6,971,999 | B2 | 12/2005 | Py et al. |
| 6,973,706 | B2 | 12/2005 | Say et al. |
| 6,974,437 | B2 | 12/2005 | Lebel et al. |
| 6,975,893 | B2 | 12/2005 | Say et al. |
| 6,983,867 | B1 | 1/2006 | Fugere |
| 6,990,366 | B2 | 1/2006 | Say et al. |
| 6,997,907 | B2 | 2/2006 | Safabash et al. |
| 6,998,247 | B2 | 2/2006 | Monfre et al. |
| 6,999,854 | B2 | 2/2006 | Roth |
| 7,003,336 | B2 | 2/2006 | Holker et al. |
| 7,003,340 | B2 | 2/2006 | Say et al. |
| 7,003,341 | B2 | 2/2006 | Say et al. |
| 7,005,857 | B2 | 2/2006 | Stiene et al. |
| 7,009,511 | B2 | 3/2006 | Mazar et al. |
| 7,010,356 | B2 | 3/2006 | Jog et al. |
| 7,015,817 | B2 | 3/2006 | Copley et al. |
| 7,016,713 | B2 | 3/2006 | Gardner et al. |
| 7,020,508 | B2 | 3/2006 | Stivoric et al. |
| 7,022,072 | B2 | 4/2006 | Fox et al. |
| 7,022,219 | B2 | 4/2006 | Mansouri et al. |
| 7,024,236 | B2 | 4/2006 | Ford et al. |
| 7,024,245 | B2 | 4/2006 | Lebel et al. |
| 7,025,743 | B2 | 4/2006 | Mann et al. |
| 7,025,774 | B2 | 4/2006 | Freeman et al. |
| 7,027,848 | B2 | 4/2006 | Robinson et al. |
| 7,027,859 | B1 | 4/2006 | McNichols et al. |
| 7,027,931 | B1 | 4/2006 | Jones et al. |
| 7,029,444 | B2 | 4/2006 | Shin et al. |
| 7,041,057 | B1 | 5/2006 | Faupel et al. |
| 7,041,068 | B2 | 5/2006 | Freeman et al. |
| 7,041,468 | B2 | 5/2006 | Drucker et al. |
| 7,043,305 | B2 | 5/2006 | KenKnight et al. |
| 7,046,153 | B2 | 5/2006 | Oja et al. |
| 7,052,483 | B2 | 5/2006 | Wojcik |
| 7,056,302 | B2 | 6/2006 | Douglas |
| 7,058,453 | B2 | 6/2006 | Nelson et al. |
| 7,060,031 | B2 | 6/2006 | Webb et al. |
| 7,073,246 | B2 | 7/2006 | Bhullar et al. |
| 7,074,307 | B2 | 7/2006 | Simpson et al. |
| 7,081,195 | B2 | 7/2006 | Simpson et al. |
| 7,082,334 | B2 | 7/2006 | Boute et al. |
| 7,097,637 | B2 | 8/2006 | Triplett et al. |
| 7,098,803 | B2 | 8/2006 | Mann et al. |
| 7,108,778 | B2 | 9/2006 | Simpson et al. |
| 7,110,803 | B2 | 9/2006 | Shults et al. |
| 7,113,821 | B1 | 9/2006 | Sun et al. |
| 7,118,667 | B2 | 10/2006 | Lee |
| 7,120,483 | B2 | 10/2006 | Russel et al. |
| 7,123,950 | B2 | 10/2006 | Mannheimer |
| 7,124,027 | B1 | 10/2006 | Ernst et al. |
| 7,125,382 | B2 | 10/2006 | Zhou et al. |
| 7,131,984 | B2 | 11/2006 | Sato et al. |
| 7,134,999 | B2 | 11/2006 | Brauker et al. |
| 7,136,689 | B2 | 11/2006 | Shults et al. |
| 7,144,384 | B2 | 12/2006 | Gorman et al. |
| 7,146,202 | B2 | 12/2006 | Ward et al. |
| 7,154,398 | B2 | 12/2006 | Chen et al. |
| 7,155,290 | B2 | 12/2006 | Von Arx et al. |
| 7,167,818 | B2 | 1/2007 | Brown |
| 7,169,600 | B2 | 1/2007 | Hoss et al. |
| 7,171,274 | B2 | 1/2007 | Starkweather et al. |
| 7,174,199 | B2 | 2/2007 | Berner et al. |
| 7,179,226 | B2 | 2/2007 | Crothall et al. |
| 7,183,102 | B2 | 2/2007 | Monfre et al. |
| 7,190,988 | B2 | 3/2007 | Say et al. |
| 7,192,450 | B2 | 3/2007 | Brauker et al. |
| 7,198,606 | B2 | 4/2007 | Boecker et al. |
| 7,203,549 | B2 | 4/2007 | Schommer et al. |
| 7,207,974 | B2 | 4/2007 | Safabash et al. |
| 7,220,387 | B2 | 5/2007 | Flaherty et al. |
| 7,223,276 | B2 | 5/2007 | List et al. |
| 7,225,535 | B2 | 6/2007 | Feldman et al. |
| 7,226,442 | B2 | 6/2007 | Sheppard et al. |
| 7,226,978 | B2 | 6/2007 | Tapsak et al. |
| 7,228,162 | B2 | 6/2007 | Ward et al. |
| 7,228,182 | B2 | 6/2007 | Healy et al. |
| 7,237,712 | B2 | 7/2007 | DeRocco et al. |
| 7,267,665 | B2 | 9/2007 | Steil et al. |
| 7,276,029 | B2 | 10/2007 | Goode, Jr. et al. |
| 7,276,146 | B2 | 10/2007 | Wilsey |
| 7,276,147 | B2 | 10/2007 | Wilsey |
| 7,278,983 | B2 | 10/2007 | Ireland et al. |
| 7,286,894 | B1 | 10/2007 | Grant et al. |
| 7,287,318 | B2 | 10/2007 | Bhullar et al. |
| 7,291,497 | B2 | 11/2007 | Holmes et al. |
| 7,295,867 | B2 | 11/2007 | Berner et al. |
| 7,297,151 | B2 | 11/2007 | Boecker et al. |
| 7,299,082 | B2 | 11/2007 | Feldman et al. |
| 7,310,544 | B2 | 12/2007 | Brister et al. |
| 7,318,816 | B2 | 1/2008 | Bobroff et al. |
| 7,324,012 | B2 | 1/2008 | Mann et al. |
| 7,324,850 | B2 | 1/2008 | Persen et al. |
| 7,329,239 | B2 | 2/2008 | Safabash et al. |
| 7,335,294 | B2 | 2/2008 | Heller et al. |
| 7,340,287 | B2 | 3/2008 | Mason et al. |
| 7,340,309 | B2 | 3/2008 | Miazga et al. |
| 7,344,500 | B2 | 3/2008 | Talbot et al. |
| 7,347,819 | B2 | 3/2008 | Lebel et al. |
| 7,354,420 | B2 | 4/2008 | Steil et al. |
| 7,364,592 | B2 | 4/2008 | Carr-Brendel et al. |
| 7,366,556 | B2 | 4/2008 | Brister et al. |
| 7,379,765 | B2 | 5/2008 | Petisce et al. |
| 7,381,184 | B2 | 6/2008 | Funderburk et al. |
| 7,384,397 | B2 | 6/2008 | Zhang et al. |
| 7,386,937 | B2 | 6/2008 | Bhullar et al. |
| 7,387,010 | B2 | 6/2008 | Sunshine et al. |
| 7,399,277 | B2 | 7/2008 | Saidara et al. |
| 7,400,111 | B2 | 7/2008 | Batman et al. |
| 7,401,111 | B1 | 7/2008 | Batman et al. |
| 7,402,153 | B2 | 7/2008 | Steil et al. |
| 7,404,796 | B2 | 7/2008 | Ginsberg |
| 7,407,493 | B2 | 8/2008 | Cane |
| 7,408,132 | B2 | 8/2008 | Wambsganss et al. |
| 7,416,541 | B2 | 8/2008 | Yuzhakov et al. |
| 7,419,573 | B2 | 9/2008 | Gundel |
| 7,424,318 | B2 | 9/2008 | Brister et al. |
| 7,429,255 | B2 | 9/2008 | Thompson |
| 7,433,727 | B2 | 10/2008 | Ward |
| 7,448,996 | B2 | 11/2008 | Khanuja et al. |
| 7,455,663 | B2 | 11/2008 | Bikovsky |
| 7,460,898 | B2 | 12/2008 | Brister et al. |
| 7,462,264 | B2 | 12/2008 | Heller et al. |
| 7,467,003 | B2 | 12/2008 | Brister et al. |
| 7,468,125 | B2 | 12/2008 | Kraft et al. |
| 7,471,972 | B2 | 12/2008 | Rhodes et al. |
| 7,476,827 | B1 | 1/2009 | Bhullar et al. |
| 7,481,819 | B2 | 1/2009 | Koeppel et al. |
| 7,492,254 | B2 | 2/2009 | Bandy et al. |
| 7,494,465 | B2 | 2/2009 | Brister et al. |
| 7,497,827 | B2 | 3/2009 | Brister et al. |
| 7,499,002 | B2 | 3/2009 | Blasko et al. |
| 7,519,408 | B2 | 4/2009 | Rasdal et al. |
| 7,545,272 | B2 | 6/2009 | Goodnow et al. |
| 7,547,281 | B2 | 6/2009 | Hayes et al. |
| 7,565,197 | B2 | 7/2009 | Haubrich et al. |
| 7,568,619 | B2 | 8/2009 | Todd et al. |

(56) References Cited

U.S. PATENT DOCUMENTS

| | | | |
|---|---|---|---|
| 7,569,030 B2 | 8/2009 | Lebel et al. |
| 7,574,266 B2 | 8/2009 | Dudding et al. |
| 7,582,059 B2 | 9/2009 | Funderburk et al. |
| 7,583,990 B2 | 9/2009 | Goode, Jr. et al. |
| 7,585,287 B2 | 9/2009 | Bresina et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,604,592 B2 | 10/2009 | Freeman et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,643,798 B2 | 1/2010 | Ljung |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,660,615 B2 | 2/2010 | VanAntwerp et al. |
| 7,666,149 B2 | 2/2010 | Simons et al. |
| 7,668,596 B2 | 2/2010 | Von Arx et al. |
| 7,682,338 B2 | 3/2010 | Griffin |
| 7,697,967 B2 | 4/2010 | Stafford |
| 7,699,775 B2 | 4/2010 | Desai et al. |
| 7,699,807 B2 | 4/2010 | Faust et al. |
| 7,701,052 B2 | 4/2010 | Borland et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,729,737 B2 | 6/2010 | Ward |
| 7,731,657 B2 | 6/2010 | Stafford |
| 7,731,691 B2 | 6/2010 | Cote et al. |
| 7,736,310 B2 | 6/2010 | Taub et al. |
| 7,736,344 B2 | 6/2010 | Moberg et al. |
| 7,741,734 B2 | 6/2010 | Joannopoulos et al. |
| 7,757,022 B2 | 7/2010 | Kato et al. |
| 7,763,042 B2 | 7/2010 | Iio et al. |
| 7,766,829 B2 | 8/2010 | Sloan et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,775,444 B2 | 8/2010 | DeRocco et al. |
| 7,778,680 B2 | 8/2010 | Goode, Jr. et al. |
| 7,779,332 B2 | 8/2010 | Karr et al. |
| 7,780,827 B1 | 8/2010 | Bhullar et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,822,454 B1 | 10/2010 | Alden et al. |
| 7,826,981 B2 | 11/2010 | Goode, Jr. et al. |
| 7,831,310 B2 | 11/2010 | Lebel et al. |
| 7,833,151 B2 | 11/2010 | Khait et al. |
| 7,833,170 B2 | 11/2010 | Matsumoto et al. |
| 7,837,633 B2 | 11/2010 | Conway et al. |
| 7,842,046 B1 | 11/2010 | Nakao |
| 7,846,132 B2 | 12/2010 | Gravesen et al. |
| 7,850,652 B2 | 12/2010 | Liniger et al. |
| 7,860,574 B2 | 12/2010 | Von Arx et al. |
| 7,866,026 B1 | 1/2011 | Wang et al. |
| 7,867,244 B2 | 1/2011 | Lathrop et al. |
| 7,873,299 B2 | 1/2011 | Berner et al. |
| 7,882,611 B2 | 2/2011 | Shah et al. |
| 7,883,464 B2 | 2/2011 | Stafford |
| 7,883,473 B2 | 2/2011 | LeVaughn et al. |
| 7,885,697 B2 | 2/2011 | Brister et al. |
| 7,889,069 B2 | 2/2011 | Fifolt et al. |
| 7,896,844 B2 | 3/2011 | Thalmann et al. |
| 7,899,511 B2 | 3/2011 | Shults et al. |
| 7,899,545 B2 | 3/2011 | John |
| 7,905,833 B2 | 3/2011 | Brister et al. |
| 7,912,655 B2 | 3/2011 | Power et al. |
| 7,912,674 B2 | 3/2011 | Killoren Clark et al. |
| 7,914,450 B2 | 3/2011 | Goode, Jr. et al. |
| 7,914,460 B2 | 3/2011 | Melker et al. |
| 7,916,013 B2 | 3/2011 | Stevenson |
| 7,920,906 B2 | 4/2011 | Goode, Jr. et al. |
| 7,920,907 B2 | 4/2011 | McGarraugh et al. |
| 7,938,797 B2 | 5/2011 | Estes |
| 7,941,200 B2 | 5/2011 | Weinart et al. |
| 7,946,984 B2 | 5/2011 | Brister et al. |
| 7,946,985 B2 | 5/2011 | Mastrototaro et al. |
| 7,955,258 B2 | 6/2011 | Goscha et al. |
| 7,955,297 B2 | 6/2011 | Radmer et al. |
| 7,970,448 B2 | 6/2011 | Shults et al. |
| 7,970,449 B2 | 6/2011 | Ward |
| 7,972,296 B2 | 7/2011 | Braig et al. |
| 7,974,672 B2 | 7/2011 | Shults et al. |
| 7,976,467 B2 | 7/2011 | Young et al. |
| 7,978,063 B2 | 7/2011 | Baldus et al. |
| 7,985,203 B2 | 7/2011 | Haueter et al. |
| 7,985,222 B2 | 7/2011 | Gall et al. |
| 7,996,158 B2 | 8/2011 | Hayter et al. |
| 7,999,674 B2 | 8/2011 | Kamen |
| 8,000,918 B2 | 8/2011 | Fjield et al. |
| 8,005,524 B2 | 8/2011 | Brauker et al. |
| 8,010,174 B2 | 8/2011 | Goode, Jr. et al. |
| 8,010,256 B2 | 8/2011 | Oowada |
| 8,016,774 B2 | 9/2011 | Freeman et al. |
| 8,028,837 B2 | 10/2011 | Gerstle et al. |
| 8,029,441 B2 | 10/2011 | Mazza et al. |
| 8,029,442 B2 | 10/2011 | Funderburk et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,103,471 B2 | 1/2012 | Hayter |
| 8,111,042 B2 | 2/2012 | Bennett |
| 8,112,240 B2 | 2/2012 | Fennell |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,670 B2 | 4/2012 | Quyang et al. |
| 8,160,900 B2 | 4/2012 | Taub et al. |
| 8,172,805 B2 | 5/2012 | Mogensen et al. |
| 8,175,673 B2 | 5/2012 | Say et al. |
| 8,179,266 B2 | 5/2012 | Hermle |

(56) References Cited

U.S. PATENT DOCUMENTS

| 8,180,423 B2 | 5/2012 | Mang et al. |
| 8,192,394 B2 | 6/2012 | Estes et al. |
| 8,216,138 B1 | 7/2012 | McGaraugh et al. |
| 8,221,332 B2 | 7/2012 | Robbins et al. |
| 8,224,410 B2 | 7/2012 | Hadvary et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,262,618 B2 | 9/2012 | Scheurer |
| 8,282,549 B2 | 10/2012 | Brauker et al. |
| 8,333,714 B2 | 12/2012 | Stafford |
| 8,346,335 B2 | 1/2013 | Harper et al. |
| 8,346,337 B2 | 1/2013 | Heller et al. |
| 8,373,544 B2 | 2/2013 | Pitt-Plady |
| 8,374,668 B1 | 2/2013 | Hayter et al. |
| 8,376,945 B2 | 2/2013 | Hayter et al. |
| 8,377,271 B2 | 2/2013 | Mao et al. |
| 8,382,671 B2 | 2/2013 | Anthony et al. |
| 8,398,664 B2 | 3/2013 | Lamps et al. |
| 8,409,093 B2 | 4/2013 | Bugler |
| 8,409,145 B2 | 4/2013 | Raymond et al. |
| 8,439,838 B2 | 5/2013 | Mogensen et al. |
| 8,444,560 B2 | 5/2013 | Hayter et al. |
| 8,461,985 B2 | 6/2013 | Fennell et al. |
| 8,469,986 B2 | 6/2013 | Schraga |
| 8,512,243 B2 | 8/2013 | Stafford |
| 8,515,518 B2 | 8/2013 | Ouyang et al. |
| 8,515,519 B2 | 8/2013 | Brister et al. |
| 8,538,512 B1 | 9/2013 | Bibian et al. |
| 8,545,403 B2 | 10/2013 | Peyser et al. |
| 8,560,038 B2 | 10/2013 | Hayter et al. |
| 8,562,567 B2 | 10/2013 | Gundberg |
| 8,571,808 B2 | 10/2013 | Hayter |
| 8,583,205 B2 | 11/2013 | Budiman et al. |
| 8,585,591 B2 | 11/2013 | Sloan et al. |
| 8,597,570 B2 | 12/2013 | Terashima et al. |
| 8,600,681 B2 | 12/2013 | Hayter et al. |
| 8,602,991 B2 | 12/2013 | Stafford |
| 8,612,163 B2 | 12/2013 | Hayter et al. |
| 8,615,282 B2 | 12/2013 | Brister et al. |
| 8,617,069 B2 | 12/2013 | Bernstein et al. |
| 8,617,071 B2 | 12/2013 | Say et al. |
| 8,622,903 B2 | 1/2014 | Jin et al. |
| 8,628,498 B2 | 1/2014 | Safabach et al. |
| 8,641,674 B2 | 2/2014 | Bobroff et al. |
| 8,652,043 B2 | 2/2014 | Drucker et al. |
| 8,682,408 B2 | 3/2014 | Boock et al. |
| 8,682,615 B2 | 3/2014 | Hayter et al. |
| 8,684,930 B2 | 4/2014 | Feldman et al. |
| 8,692,655 B2 | 4/2014 | Zimman et al. |
| 8,710,993 B2 | 4/2014 | Hayter et al. |
| 8,747,363 B2 | 6/2014 | Nielsen et al. |
| 8,750,955 B2 | 6/2014 | Brister et al. |
| 8,771,183 B2 | 7/2014 | Sloan |
| 8,797,163 B2 | 8/2014 | Finkenzeller |
| 8,808,515 B2 | 8/2014 | Feldman et al. |
| 8,834,366 B2 | 9/2014 | Hayter et al. |
| 8,845,536 B2 | 9/2014 | Brauker et al. |
| 8,870,822 B2 | 10/2014 | Thalmann et al. |
| 8,880,138 B2 | 11/2014 | Cho |
| 8,945,056 B2 | 2/2015 | Lio et al. |
| 8,961,413 B2 | 2/2015 | Teller et al. |
| 9,007,781 B2 | 4/2015 | Moein et al. |
| 9,014,774 B2 | 4/2015 | Mao et al. |
| 9,031,630 B2 | 5/2015 | Hoss et al. |
| 9,060,719 B2 | 6/2015 | Hayter et al. |
| 9,060,805 B2 | 6/2015 | Goodnow et al. |
| 9,066,697 B2 | 6/2015 | Peyser et al. |
| 9,101,302 B2 | 8/2015 | Mace et al. |
| 9,186,098 B2 | 11/2015 | Lee et al. |
| 9,215,992 B2 | 12/2015 | Donnay et al. |
| 9,241,631 B2 | 1/2016 | Valdes et al. |
| 9,259,175 B2 | 2/2016 | Stafford |
| 9,265,453 B2 | 2/2016 | Curry et al. |
| 9,289,179 B2 | 3/2016 | Hayter et al. |
| 9,295,785 B2 | 3/2016 | Gottlieb et al. |
| 9,295,786 B2 | 3/2016 | Gottlieb et al. |
| 9,357,951 B2 | 6/2016 | Simpson et al. |
| 9,398,872 B2 | 7/2016 | Hayter et al. |
| 9,402,544 B2 | 8/2016 | Yee et al. |
| 9,402,570 B2 | 8/2016 | Pace et al. |
| 9,439,586 B2 | 9/2016 | Bugler |
| 9,451,910 B2 | 9/2016 | Brister et al. |
| 9,474,479 B2 | 10/2016 | Pusey et al. |
| 9,480,421 B2 | 11/2016 | Stafford |
| 9,483,608 B2 | 11/2016 | Hayter et al. |
| 9,504,471 B2 | 11/2016 | Vaitekunas et al. |
| 9,558,325 B2 | 1/2017 | Hayter et al. |
| 9,566,384 B2 | 2/2017 | Gyrn et al. |
| 9,636,068 B2 | 5/2017 | Yee et al. |
| 9,668,682 B2 | 6/2017 | Brister et al. |
| 9,743,876 B2 | 8/2017 | Gelfand et al. |
| 9,808,574 B2 | 11/2017 | Yodfat et al. |
| 9,814,414 B2 | 11/2017 | Brister et al. |
| 10,213,139 B2 | 2/2019 | Rao et al. |
| 10,292,632 B2 | 5/2019 | Lee et al. |
| 10,342,489 B2 | 7/2019 | Stafford |
| 10,772,547 B1 | 9/2020 | Lee et al. |
| 10,820,842 B2 | 11/2020 | Harper |
| 10,827,954 B2 | 11/2020 | Hoss et al. |
| 10,874,338 B2 | 12/2020 | Stafford |
| 10,881,340 B2 | 1/2021 | Curry et al. |
| 10,881,341 B1 | 1/2021 | Curry et al. |
| 10,945,647 B2 | 3/2021 | Mazza et al. |
| 10,945,649 B2 | 3/2021 | Lee et al. |
| 10,952,653 B2 | 3/2021 | Harper |
| 10,959,654 B2 | 3/2021 | Curry et al. |
| 10,966,644 B2 | 4/2021 | Stafford |
| 10,973,443 B2 | 4/2021 | Funderburk et al. |
| 10,980,461 B2 | 4/2021 | Simpson et al. |
| 11,000,213 B2 | 5/2021 | Kamath et al. |
| 11,000,216 B2 | 5/2021 | Curry et al. |
| 11,006,870 B2 | 5/2021 | Yee et al. |
| 11,006,871 B2 | 5/2021 | Yee et al. |
| 11,013,440 B2 | 5/2021 | Lee et al. |
| 11,051,724 B2 | 7/2021 | Pace et al. |
| 11,064,917 B2 | 7/2021 | Simpson et al. |
| 11,116,430 B2 | 9/2021 | Funderburk et al. |
| 11,141,084 B2 | 10/2021 | Funderburk et al. |
| 11,166,656 B2 | 11/2021 | Yee et al. |
| 11,179,068 B2 | 11/2021 | Pace et al. |
| 11,197,625 B1 | 12/2021 | Schleicher et al. |
| 11,202,591 B2 | 12/2021 | Yee et al. |
| 11,213,229 B2 | 1/2022 | Yee et al. |
| 11,246,519 B2 | 2/2022 | Donnay et al. |
| 11,266,335 B2 | 3/2022 | Donnay et al. |
| 11,298,056 B2 | 4/2022 | Harper |
| 11,298,058 B2 | 4/2022 | Stafford |
| 11,510,625 B2 | 11/2022 | Gray et al. |
| 2001/0016682 A1 | 8/2001 | Berner et al. |
| 2001/0034479 A1 | 10/2001 | Ring et al. |
| 2001/0037060 A1 | 11/2001 | Thompson et al. |
| 2001/0037366 A1 | 11/2001 | Webb et al. |
| 2001/0039387 A1 | 11/2001 | Rutynowski et al. |
| 2001/0044608 A1 | 11/2001 | Odell et al. |
| 2001/0047127 A1 | 11/2001 | New et al. |
| 2001/0056262 A1 | 12/2001 | Cabiri et al. |
| 2002/0002344 A1 | 1/2002 | Douglas et al. |
| 2002/0010390 A1 | 1/2002 | Guice et al. |
| 2002/0013522 A1 | 1/2002 | Lav et al. |
| 2002/0013538 A1 | 1/2002 | Teller |
| 2002/0016534 A1 | 2/2002 | Trepagnier et al. |
| 2002/0016568 A1 | 2/2002 | Lebel et al. |
| 2002/0019022 A1 | 2/2002 | Dunn et al. |
| 2002/0019584 A1 | 2/2002 | Schulze et al. |
| 2002/0019586 A1 | 2/2002 | Teller et al. |
| 2002/0019606 A1 | 2/2002 | Lebel et al. |
| 2002/0022855 A1 | 2/2002 | Bobroff et al. |
| 2002/0023852 A1 | 2/2002 | McIvor et al. |
| 2002/0029058 A1 | 3/2002 | LeVaughn et al. |
| 2002/0032386 A1 | 3/2002 | Sackner et al. |
| 2002/0039026 A1 | 4/2002 | Stroth et al. |
| 2002/0042090 A1 | 4/2002 | Heller et al. |
| 2002/0045808 A1 | 4/2002 | Ford et al. |

(56) References Cited

U.S. PATENT DOCUMENTS

| | | |
|---|---|---|
| 2002/0049482 A1 | 4/2002 | Fabian et al. |
| 2002/0050250 A1 | 5/2002 | Peterson et al. |
| 2002/0055711 A1 | 5/2002 | Lavi et al. |
| 2002/0057993 A1 | 5/2002 | Maisey et al. |
| 2002/0065454 A1 | 5/2002 | Lebel et al. |
| 2002/0066764 A1 | 6/2002 | Perry et al. |
| 2002/0072720 A1 | 6/2002 | Hague et al. |
| 2002/0072784 A1 | 6/2002 | Sheppard et al. |
| 2002/0074162 A1 | 6/2002 | Su et al. |
| 2002/0076966 A1 | 6/2002 | Carron et al. |
| 2002/0077599 A1 | 6/2002 | Wojcik |
| 2002/0082487 A1 | 6/2002 | Kollias et al. |
| 2002/0084196 A1 | 7/2002 | Liamos et al. |
| 2002/0091796 A1 | 7/2002 | Higginson et al. |
| 2002/0093969 A1 | 7/2002 | Lin et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0111832 A1 | 8/2002 | Judge |
| 2002/0117639 A1 | 8/2002 | Paolini et al. |
| 2002/0118528 A1 | 8/2002 | Su et al. |
| 2002/0119711 A1 | 8/2002 | Van Antwerp et al. |
| 2002/0120186 A1 | 8/2002 | Keimel |
| 2002/0124017 A1 | 9/2002 | Mault |
| 2002/0128594 A1 | 9/2002 | Das et al. |
| 2002/0130042 A1 | 9/2002 | Moerman et al. |
| 2002/0133066 A1 | 9/2002 | Miller et al. |
| 2002/0147135 A1 | 10/2002 | Schnell |
| 2002/0150959 A1 | 10/2002 | Lejeune et al. |
| 2002/0151770 A1 | 10/2002 | Noll et al. |
| 2002/0151796 A1 | 10/2002 | Koulik |
| 2002/0151816 A1 | 10/2002 | Rich et al. |
| 2002/0154050 A1 | 10/2002 | Krupp et al. |
| 2002/0161288 A1 | 10/2002 | Shin et al. |
| 2002/0161290 A1 | 10/2002 | Chance |
| 2002/0161338 A1 | 10/2002 | Peterson |
| 2002/0164836 A1 | 11/2002 | Ho |
| 2002/0165462 A1 | 11/2002 | Westbrook et al. |
| 2002/0169369 A1 | 11/2002 | Ward et al. |
| 2002/0169439 A1 | 11/2002 | Flaherty et al. |
| 2002/0169635 A1 | 11/2002 | Shillingburg |
| 2002/0183604 A1 | 12/2002 | Gowda et al. |
| 2002/0185128 A1 | 12/2002 | Theobald |
| 2002/0185130 A1 | 12/2002 | Wright et al. |
| 2002/0188748 A1 | 12/2002 | Blackwell et al. |
| 2002/0197522 A1 | 12/2002 | Lawrence et al. |
| 2002/0198444 A1 | 12/2002 | Ughigaki et al. |
| 2002/0198543 A1 | 12/2002 | Burdulis et al. |
| 2003/0004403 A1 | 1/2003 | Drinan et al. |
| 2003/0020477 A1 | 1/2003 | Goldstein |
| 2003/0023189 A1 | 1/2003 | Kuo |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0028184 A1 | 2/2003 | Lebel et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0055380 A1 | 3/2003 | Flaherty |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0069509 A1 | 4/2003 | Matzinger et al. |
| 2003/0069510 A1 | 4/2003 | Semler |
| 2003/0076792 A1 | 4/2003 | Theimer |
| 2003/0077642 A1 | 4/2003 | Fritsch et al. |
| 2003/0078481 A1 | 4/2003 | McIvor et al. |
| 2003/0078560 A1 | 4/2003 | Miller et al. |
| 2003/0083686 A1 | 5/2003 | Freeman et al. |
| 2003/0088166 A1 | 5/2003 | Say et al. |
| 2003/0097092 A1 | 5/2003 | Flaherty |
| 2003/0100040 A1 | 5/2003 | Bonnecaze et al. |
| 2003/0100821 A1 | 5/2003 | Heller et al. |
| 2003/0109775 A1 | 6/2003 | O'Neil et al. |
| 2003/0114897 A1 | 6/2003 | Von Arx et al. |
| 2003/0114898 A1 | 6/2003 | Von Arx et al. |
| 2003/0119457 A1 | 6/2003 | Standke |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135127 A1 | 7/2003 | Sackner et al. |
| 2003/0135333 A1 | 7/2003 | Aceti et al. |
| 2003/0144579 A1 | 7/2003 | Buss |
| 2003/0144581 A1 | 7/2003 | Conn et al. |
| 2003/0144608 A1 | 7/2003 | Kojima et al. |
| 2003/0153900 A1 | 8/2003 | Aceti et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0188427 A1 | 10/2003 | Say et al. |
| 2003/0199744 A1 | 10/2003 | Buse et al. |
| 2003/0199790 A1 | 10/2003 | Boecker et al. |
| 2003/0199910 A1 | 10/2003 | Boecker et al. |
| 2003/0204290 A1 | 10/2003 | Sadler et al. |
| 2003/0208113 A1 | 11/2003 | Mault et al. |
| 2003/0208114 A1 | 11/2003 | Ackerman |
| 2003/0212317 A1 | 11/2003 | Kovatchev et al. |
| 2003/0212379 A1 | 11/2003 | Bylund et al. |
| 2003/0212579 A1 | 11/2003 | Brown et al. |
| 2003/0216621 A1 | 11/2003 | Alpert et al. |
| 2003/0216630 A1 | 11/2003 | Jersey-Willuhn et al. |
| 2003/0217966 A1 | 11/2003 | Tapsak et al. |
| 2003/0225361 A1 | 12/2003 | Sabra |
| 2003/0225373 A1 | 12/2003 | Bobroff et al. |
| 2003/0236489 A1 | 12/2003 | Jacobson et al. |
| 2004/0002382 A1 | 1/2004 | Kovelman et al. |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0017300 A1 | 1/2004 | Kotzin et al. |
| 2004/0030226 A1 | 2/2004 | Quy |
| 2004/0030531 A1 | 2/2004 | Miller et al. |
| 2004/0030581 A1 | 2/2004 | Levin et al. |
| 2004/0034289 A1 | 2/2004 | Teller et al. |
| 2004/0039255 A1 | 2/2004 | Simonsen et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0060818 A1 | 4/2004 | Feldman et al. |
| 2004/0061232 A1 | 4/2004 | Shah et al. |
| 2004/0063435 A1 | 4/2004 | Sakamoto et al. |
| 2004/0064068 A1 | 4/2004 | DeNuzzio et al. |
| 2004/0064133 A1 | 4/2004 | Miller et al. |
| 2004/0072357 A1 | 4/2004 | Steine et al. |
| 2004/0073266 A1 | 4/2004 | Haefner et al. |
| 2004/0078215 A1 | 4/2004 | Dahlin et al. |
| 2004/0096959 A1 | 5/2004 | Stiene et al. |
| 2004/0100376 A1 | 5/2004 | Lye et al. |
| 2004/0105411 A1 | 6/2004 | Boatwright et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0111017 A1 | 6/2004 | Say et al. |
| 2004/0116847 A1 | 6/2004 | Wall |
| 2004/0116865 A1 | 6/2004 | Bengtsson |
| 2004/0116866 A1 | 6/2004 | Gorman et al. |
| 2004/0117204 A1 | 6/2004 | Mazar et al. |
| 2004/0119169 A1 | 6/2004 | Hanawa |
| 2004/0122353 A1 | 6/2004 | Shahmirian et al. |
| 2004/0122489 A1 | 6/2004 | Mazar et al. |
| 2004/0133089 A1 | 7/2004 | Kilcoyne et al. |
| 2004/0133164 A1 | 7/2004 | Funderbunk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |

(56) References Cited

U.S. PATENT DOCUMENTS

| | | |
|---|---|---|
| 2004/0140211 A1 | 7/2004 | Broy et al. |
| 2004/0142403 A1 | 7/2004 | Hetzel et al. |
| 2004/0146909 A1 | 7/2004 | Duong et al. |
| 2004/0147872 A1 | 7/2004 | Thompson |
| 2004/0147996 A1 | 7/2004 | Miazga et al. |
| 2004/0152366 A1 | 8/2004 | Schultz et al. |
| 2004/0152622 A1 | 8/2004 | Keith et al. |
| 2004/0158207 A1 | 8/2004 | Hunn et al. |
| 2004/0162521 A1 | 8/2004 | Bengtsson et al. |
| 2004/0162678 A1 | 8/2004 | Hetzel et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204673 A1 | 10/2004 | Flaherty |
| 2004/0204687 A1 | 10/2004 | Mogensen et al. |
| 2004/0204744 A1 | 10/2004 | Penner et al. |
| 2004/0204868 A1 | 10/2004 | Maynard et al. |
| 2004/0206625 A1 | 10/2004 | Bhullar et al. |
| 2004/0206916 A1 | 10/2004 | Colvin, Jr. et al. |
| 2004/0210122 A1 | 10/2004 | Sleburg |
| 2004/0221057 A1 | 11/2004 | Darcey et al. |
| 2004/0223876 A1 | 11/2004 | Kirollos et al. |
| 2004/0223985 A1 | 11/2004 | Dunfield et al. |
| 2004/0225199 A1 | 11/2004 | Evanyk et al. |
| 2004/0225262 A1 | 11/2004 | Fathallah et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0240426 A1 | 12/2004 | Wu et al. |
| 2004/0249253 A1 | 12/2004 | Racchini et al. |
| 2004/0249999 A1 | 12/2004 | Connolly et al. |
| 2004/0254433 A1 | 12/2004 | Bandis et al. |
| 2004/0254434 A1 | 12/2004 | Goodnow et al. |
| 2004/0258564 A1 | 12/2004 | Charlton |
| 2004/0260224 A1 | 12/2004 | Binder et al. |
| 2004/0267300 A1 | 12/2004 | Mace et al. |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0038465 A1 | 2/2005 | Shraga |
| 2005/0038680 A1 | 2/2005 | McMahon |
| 2005/0043598 A1 | 2/2005 | Goode, Jr. et al. |
| 2005/0049179 A1 | 3/2005 | Davidson et al. |
| 2005/0051427 A1 | 3/2005 | Brauker et al. |
| 2005/0051440 A1 | 3/2005 | Simpson et al. |
| 2005/0056552 A1 | 3/2005 | Simpson et al. |
| 2005/0065464 A1 | 3/2005 | Talbot et al. |
| 2005/0070774 A1 | 3/2005 | Addison et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0096520 A1 | 5/2005 | Maekawa et al. |
| 2005/0096587 A1 | 5/2005 | Santini, Jr. et al. |
| 2005/0101912 A1 | 5/2005 | Faust et al. |
| 2005/0101932 A1 | 5/2005 | Cote et al. |
| 2005/0103624 A1 | 5/2005 | Bhullar et al. |
| 2005/0104457 A1 | 5/2005 | Jordan et al. |
| 2005/0106713 A1 | 5/2005 | Phan et al. |
| 2005/0112169 A1 | 5/2005 | Brauker et al. |
| 2005/0112544 A1 | 5/2005 | Xu et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0131347 A1 | 6/2005 | Marano-Ford et al. |
| 2005/0134731 A1 | 6/2005 | Lee et al. |
| 2005/0137488 A1 | 6/2005 | Henry et al. |
| 2005/0137530 A1 | 6/2005 | Campbell et al. |
| 2005/0143635 A1 | 6/2005 | Kamath et al. |
| 2005/0149066 A1 | 7/2005 | Stafford |
| 2005/0151976 A1 | 7/2005 | Toma |
| 2005/0154271 A1 | 7/2005 | Rasdal et al. |
| 2005/0154410 A1 | 7/2005 | Conway et al. |
| 2005/0159678 A1 | 7/2005 | Taniike et al. |
| 2005/0161346 A1 | 7/2005 | Simpson et al. |
| 2005/0165404 A1 | 7/2005 | Miller |
| 2005/0171442 A1 | 8/2005 | Shirasaki et al. |
| 2005/0173245 A1 | 8/2005 | Feldman et al. |
| 2005/0176136 A1 | 8/2005 | Burd et al. |
| 2005/0177398 A1 | 8/2005 | Watanabe et al. |
| 2005/0181010 A1 | 8/2005 | Hunter et al. |
| 2005/0182306 A1 | 8/2005 | Sloan |
| 2005/0182358 A1 | 8/2005 | Veit et al. |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0197793 A1 | 9/2005 | Baker, Jr. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0215871 A1 | 9/2005 | Feldman et al. |
| 2005/0221504 A1 | 10/2005 | Petruno et al. |
| 2005/0222518 A1 | 10/2005 | Dib |
| 2005/0222599 A1 | 10/2005 | Czernecki et al. |
| 2005/0235156 A1 | 10/2005 | Drucker et al. |
| 2005/0236277 A9 | 10/2005 | Imran et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245844 A1 | 11/2005 | Mace et al. |
| 2005/0245904 A1 | 11/2005 | Estes et al. |
| 2005/0247319 A1 | 11/2005 | Berger |
| 2005/0251033 A1 | 11/2005 | Scarantino et al. |
| 2005/0261563 A1 | 11/2005 | Zhou et al. |
| 2005/0267325 A1 | 12/2005 | Bouchier et al. |
| 2005/0267327 A1 | 12/2005 | Iizuka et al. |
| 2005/0269214 A1 | 12/2005 | Lee |
| 2005/0277164 A1 | 12/2005 | Drucker et al. |
| 2005/0277912 A1 | 12/2005 | John |
| 2005/0281234 A1 | 12/2005 | Kawamura et al. |
| 2005/0283114 A1 | 12/2005 | Bresina et al. |
| 2005/0283208 A1 | 12/2005 | Von Arx et al. |
| 2005/0283209 A1 | 12/2005 | Katoozi et al. |
| 2005/0284758 A1 | 12/2005 | Funke et al. |
| 2005/0287620 A1 | 12/2005 | Heller et al. |
| 2006/0001538 A1 | 1/2006 | Kraft et al. |
| 2006/0001551 A1 | 1/2006 | Kraft et al. |

(56) References Cited

U.S. PATENT DOCUMENTS

| | | |
|---|---|---|
| 2006/0004270 A1 | 1/2006 | Bedard et al. |
| 2006/0004272 A1 | 1/2006 | Shah et al. |
| 2006/0004303 A1 | 1/2006 | Weidenhaupt et al. |
| 2006/0006141 A1 | 1/2006 | Ufer et al. |
| 2006/0009727 A1 | 1/2006 | O'Mahony et al. |
| 2006/0010098 A1 | 1/2006 | Goodnow et al. |
| 2006/0012464 A1 | 1/2006 | Nitzan et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0030789 A1 | 2/2006 | Allen |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0040793 A1 | 2/2006 | Martens et al. |
| 2006/0041276 A1 | 2/2006 | Chan |
| 2006/0042080 A1 | 3/2006 | Say et al. |
| 2006/0047220 A1 | 3/2006 | Sakata et al. |
| 2006/0049359 A1 | 3/2006 | Busta et al. |
| 2006/0058588 A1 | 3/2006 | Zdeblick |
| 2006/0064035 A1 | 3/2006 | Wang et al. |
| 2006/0068208 A1 | 3/2006 | Tapsak et al. |
| 2006/0079740 A1 | 4/2006 | Silver et al. |
| 2006/0081469 A1 | 4/2006 | Lee |
| 2006/0086624 A1 | 4/2006 | Tapsak et al. |
| 2006/0091006 A1 | 5/2006 | Wang et al. |
| 2006/0094944 A1 | 5/2006 | Chuang |
| 2006/0095014 A1 | 5/2006 | Ethelfeld |
| 2006/0116607 A1 | 6/2006 | Nakamura et al. |
| 2006/0129173 A1 | 6/2006 | Wilkinson |
| 2006/0129733 A1 | 6/2006 | Solbelman |
| 2006/0135908 A1 | 6/2006 | Liniger et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0155210 A1 | 7/2006 | Beckman et al. |
| 2006/0155317 A1 | 7/2006 | List et al. |
| 2006/0161194 A1 | 7/2006 | Freeman et al. |
| 2006/0161664 A1 | 7/2006 | Mastrototaro et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0181695 A1 | 8/2006 | Sage, Jr. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0189939 A1 | 8/2006 | Gonnelli et al. |
| 2006/0193375 A1 | 8/2006 | Lee et al. |
| 2006/0195029 A1 | 8/2006 | Shults et al. |
| 2006/0195133 A1 | 8/2006 | Freeman et al. |
| 2006/0200020 A1 | 9/2006 | Brister et al. |
| 2006/0200022 A1 | 9/2006 | Brauker et al. |
| 2006/0200181 A1 | 9/2006 | Fukuzawa et al. |
| 2006/0200970 A1 | 9/2006 | Brister et al. |
| 2006/0200981 A1 | 9/2006 | Bhullar et al. |
| 2006/0200982 A1 | 9/2006 | Bhullar et al. |
| 2006/0202805 A1 | 9/2006 | Schulman et al. |
| 2006/0202859 A1 | 9/2006 | Mastrototaro et al. |
| 2006/0211921 A1 | 9/2006 | Brauker et al. |
| 2006/0220839 A1 | 10/2006 | Fifolt et al. |
| 2006/0222566 A1 | 10/2006 | Brauker et al. |
| 2006/0222866 A1 | 10/2006 | Nakamura et al. |
| 2006/0224108 A1 | 10/2006 | Brauker et al. |
| 2006/0224109 A1 | 10/2006 | Steil et al. |
| 2006/0224141 A1 | 10/2006 | Rush et al. |
| 2006/0224171 A1 | 10/2006 | Sakata et al. |
| 2006/0226985 A1 | 10/2006 | Goodnow et al. |
| 2006/0229512 A1 | 10/2006 | Petisce et al. |
| 2006/0233839 A1 | 10/2006 | Jacquet |
| 2006/0247508 A1 | 11/2006 | Fennell |
| 2006/0247710 A1 | 11/2006 | Goetz et al. |
| 2006/0247895 A1 | 11/2006 | Liamos et al. |
| 2006/0248398 A1 | 11/2006 | Neel et al. |
| 2006/0253085 A1 | 11/2006 | Geismar et al. |
| 2006/0253086 A1 | 11/2006 | Moberg et al. |
| 2006/0258929 A1 | 11/2006 | Goode, Jr. et al. |
| 2006/0258939 A1 | 11/2006 | Pesach et al. |
| 2006/0258959 A1 | 11/2006 | Sode |
| 2006/0264785 A1 | 11/2006 | Dring et al. |
| 2006/0264888 A1 | 11/2006 | Moberg et al. |
| 2006/0270922 A1 | 11/2006 | Brauker et al. |
| 2006/0270923 A1 | 11/2006 | Brauker et al. |
| 2006/0271013 A1 | 11/2006 | Triplett et al. |
| 2006/0272652 A1 | 12/2006 | Stocker et al. |
| 2006/0273759 A1 | 12/2006 | Reggiardo |
| 2006/0276714 A1 | 12/2006 | Holt et al. |
| 2006/0276724 A1 | 12/2006 | Freeman et al. |
| 2006/0276771 A1 | 12/2006 | Galley et al. |
| 2006/0281985 A1 | 12/2006 | Ward et al. |
| 2006/0282042 A1 | 12/2006 | Walters et al. |
| 2006/0287591 A1 | 12/2006 | Ocvirk et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016129 A1 | 1/2007 | Liniger et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027384 A1 | 2/2007 | Brister et al. |
| 2007/0027385 A1 | 2/2007 | Brister et al. |
| 2007/0027507 A1 | 2/2007 | Burdett et al. |
| 2007/0030154 A1 | 2/2007 | Aiki et al. |
| 2007/0032706 A1 | 2/2007 | Kamath et al. |
| 2007/0032717 A1 | 2/2007 | Brister et al. |
| 2007/0032718 A1 | 2/2007 | Shults et al. |
| 2007/0033074 A1 | 2/2007 | Nitzan et al. |
| 2007/0038044 A1 | 2/2007 | Dobbles et al. |
| 2007/0045902 A1 | 3/2007 | Brauker et al. |
| 2007/0049865 A1 | 3/2007 | Radmer et al. |
| 2007/0055799 A1 | 3/2007 | Koehler et al. |
| 2007/0056858 A1 | 3/2007 | Chen et al. |
| 2007/0059196 A1 | 3/2007 | Brister et al. |
| 2007/0060801 A1 | 3/2007 | Neinast |
| 2007/0060814 A1 | 3/2007 | Stafford |
| 2007/0060869 A1 | 3/2007 | Tolle et al. |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0088377 A1 | 4/2007 | Levaughn et al. |
| 2007/0090511 A1 | 4/2007 | Borland et al. |
| 2007/0093704 A1 | 4/2007 | Brister et al. |
| 2007/0093754 A1 | 4/2007 | Mogensen et al. |
| 2007/0093786 A1 | 4/2007 | Goldsmith et al. |
| 2007/0095661 A1 | 5/2007 | Wang et al. |
| 2007/0100218 A1 | 5/2007 | Sweitzer et al. |
| 2007/0100222 A1 | 5/2007 | Mastrototaro et al. |
| 2007/0106133 A1 | 5/2007 | Satchwell et al. |

(56) References Cited

U.S. PATENT DOCUMENTS

| | | |
|---|---|---|
| 2007/0106135 A1 | 5/2007 | Sloan et al. |
| 2007/0108048 A1 | 5/2007 | Wang et al. |
| 2007/0110124 A1 | 5/2007 | Zaragoza et al. |
| 2007/0111196 A1 | 5/2007 | Alarcon et al. |
| 2007/0123819 A1 | 5/2007 | Mernoe et al. |
| 2007/0124002 A1 | 5/2007 | Estes et al. |
| 2007/0129621 A1 | 6/2007 | Kellogg et al. |
| 2007/0135696 A1 | 6/2007 | Ward |
| 2007/0135774 A1 | 6/2007 | Turner et al. |
| 2007/0149873 A1 | 6/2007 | Say et al. |
| 2007/0149875 A1 | 6/2007 | Ouyang et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173711 A1 | 7/2007 | Shah et al. |
| 2007/0173741 A1 | 7/2007 | Deshmukh et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179406 A1 | 8/2007 | DeNuzzio et al. |
| 2007/0191701 A1 | 8/2007 | Feldman et al. |
| 2007/0191702 A1 | 8/2007 | Yodfat et al. |
| 2007/0197889 A1 | 8/2007 | Brister et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203539 A1 | 8/2007 | Stone et al. |
| 2007/0203966 A1 | 8/2007 | Brauker et al. |
| 2007/0208244 A1 | 9/2007 | Brauker et al. |
| 2007/0208245 A1 | 9/2007 | Brauker et al. |
| 2007/0208246 A1 | 9/2007 | Brauker et al. |
| 2007/0213611 A1 | 9/2007 | Simpson et al. |
| 2007/0219480 A1 | 9/2007 | Kamen et al. |
| 2007/0219496 A1 | 9/2007 | Kamen et al. |
| 2007/0222609 A1 | 9/2007 | Duron et al. |
| 2007/0227911 A1 | 10/2007 | Wang et al. |
| 2007/0228071 A1 | 10/2007 | Kamen et al. |
| 2007/0231846 A1 | 10/2007 | Cosentino et al. |
| 2007/0232877 A1 | 10/2007 | He |
| 2007/0232878 A1 | 10/2007 | Kovatchev et al. |
| 2007/0232879 A1 | 10/2007 | Brister et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244368 A1 | 10/2007 | Bayloff et al. |
| 2007/0244379 A1 | 10/2007 | Boock et al. |
| 2007/0244383 A1 | 10/2007 | Talbot et al. |
| 2007/0244398 A1 | 10/2007 | Lo et al. |
| 2007/0249922 A1 | 10/2007 | Peyser et al. |
| 2007/0253021 A1 | 11/2007 | Mehta et al. |
| 2007/0255116 A1 | 11/2007 | Mehta et al. |
| 2007/0255125 A1 | 11/2007 | Moberg et al. |
| 2007/0255302 A1 | 11/2007 | Koeppel et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2008/0004512 A1 | 1/2008 | Funderburk et al. |
| 2008/0004515 A1 | 1/2008 | Jennewine et al. |
| 2008/0004573 A1 | 1/2008 | Kaufmann et al. |
| 2008/0004601 A1 | 1/2008 | Jennewine et al. |
| 2008/0004904 A1 | 1/2008 | Tran |
| 2008/0009304 A1 | 1/2008 | Fry |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0018433 A1 | 1/2008 | Pitt-Pladdy |
| 2008/0021543 A1 | 1/2008 | Shrivastava |
| 2008/0021666 A1 | 1/2008 | Goode, Jr. et al. |
| 2008/0027296 A1 | 1/2008 | Hadvary et al. |
| 2008/0027474 A1 | 1/2008 | Curry et al. |
| 2008/0029391 A1 | 2/2008 | Mao et al. |
| 2008/0030369 A1 | 2/2008 | Mann et al. |
| 2008/0031941 A1 | 2/2008 | Pettersson |
| 2008/0033254 A1 | 2/2008 | Kamath et al. |
| 2008/0033268 A1 | 2/2008 | Stafford |
| 2008/0033273 A1 | 2/2008 | Zhou et al. |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0046038 A1 | 2/2008 | Hill et al. |
| 2008/0055070 A1 | 3/2008 | Bange et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0058830 A1 | 3/2008 | Cole et al. |
| 2008/0059227 A1 | 3/2008 | Clapp |
| 2008/0060955 A1 | 3/2008 | Goodnow |
| 2008/0061961 A1 | 3/2008 | John |
| 2008/0062055 A1 | 3/2008 | Cunningham et al. |
| 2008/0064437 A1 | 3/2008 | Chambers et al. |
| 2008/0064937 A1 | 3/2008 | McGarraugh et al. |
| 2008/0064941 A1 | 3/2008 | Funderburk et al. |
| 2008/0064943 A1 | 3/2008 | Talbot et al. |
| 2008/0064944 A1 | 3/2008 | VanAntwerp et al. |
| 2008/0065646 A1 | 3/2008 | Zhang et al. |
| 2008/0066305 A1 | 3/2008 | Wang et al. |
| 2008/0067627 A1 | 3/2008 | Boeck et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0092911 A1 | 4/2008 | Schulman et al. |
| 2008/0097246 A1 | 4/2008 | Stafford |
| 2008/0097289 A1 | 4/2008 | Steil et al. |
| 2008/0097908 A1 | 4/2008 | Dicks et al. |
| 2008/0099332 A1 | 5/2008 | Scott et al. |
| 2008/0102441 A1 | 5/2008 | Chen et al. |
| 2008/0108942 A1 | 5/2008 | Brister et al. |
| 2008/0112848 A1 | 5/2008 | Huffstodt et al. |
| 2008/0114228 A1 | 5/2008 | McCluskey et al. |
| 2008/0114280 A1 | 5/2008 | Stafford |
| 2008/0119705 A1 | 5/2008 | Patel et al. |
| 2008/0119707 A1 | 5/2008 | Stafford |
| 2008/0119710 A1 | 5/2008 | Reggiardo et al. |
| 2008/0125636 A1 | 5/2008 | Ward et al. |
| 2008/0127052 A1 | 5/2008 | Rostoker |
| 2008/0129486 A1 | 6/2008 | Jeckelmann et al. |
| 2008/0133059 A1 | 6/2008 | Trippel et al. |
| 2008/0133702 A1 | 6/2008 | Sharma et al. |
| 2008/0139910 A1 | 6/2008 | Mastrototaro et al. |
| 2008/0146904 A1 | 6/2008 | Hunn |
| 2008/0148873 A1 | 6/2008 | Wang |
| 2008/0154205 A1 | 6/2008 | Wojcik |
| 2008/0154286 A1 | 6/2008 | Abbott et al. |
| 2008/0154513 A1 | 6/2008 | Kovatchev et al. |
| 2008/0161664 A1 | 7/2008 | Mastrototaro et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0167578 A1 | 7/2008 | Bryer et al. |
| 2008/0172205 A1 | 7/2008 | Breton et al. |
| 2008/0177149 A1 | 7/2008 | Weinart et al. |
| 2008/0177165 A1 | 7/2008 | Blomquist et al. |
| 2008/0179187 A1 | 7/2008 | Ouyang |
| 2008/0182537 A1 | 7/2008 | Manku et al. |
| 2008/0183060 A1 | 7/2008 | Steil et al. |

(56)        References Cited

U.S. PATENT DOCUMENTS

| | | |
|---|---|---|
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0188796 A1 | 8/2008 | Steil et al. |
| 2008/0189051 A1 | 8/2008 | Goode, Jr. et al. |
| 2008/0194926 A1 | 8/2008 | Goh et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214481 A1 | 9/2008 | Challoner et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0215035 A1 | 9/2008 | Yodfat et al. |
| 2008/0228051 A1 | 9/2008 | Shults et al. |
| 2008/0228054 A1 | 9/2008 | Shults et al. |
| 2008/0234561 A1 | 9/2008 | Roesicke et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242962 A1 | 10/2008 | Roesicke et al. |
| 2008/0242963 A1 | 10/2008 | Essenpreis et al. |
| 2008/0243051 A1 | 10/2008 | DeStefano |
| 2008/0252459 A1 | 10/2008 | Butler et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255440 A1 | 10/2008 | Eilerson et al. |
| 2008/0255808 A1 | 10/2008 | Hayter |
| 2008/0256048 A1 | 10/2008 | Hayter |
| 2008/0262300 A1 | 10/2008 | Reynolds et al. |
| 2008/0262469 A1 | 10/2008 | Brister et al. |
| 2008/0267823 A1 | 10/2008 | Wang et al. |
| 2008/0269584 A1 | 10/2008 | Shekalim |
| 2008/0269673 A1 | 10/2008 | Butoi et al. |
| 2008/0269683 A1 | 10/2008 | Bikovsky |
| 2008/0269687 A1 | 10/2008 | Chong et al. |
| 2008/0269714 A1 | 10/2008 | Mastrototaro et al. |
| 2008/0275313 A1 | 11/2008 | Brister et al. |
| 2008/0275327 A1 | 11/2008 | Faarbaek et al. |
| 2008/0278333 A1 | 11/2008 | Fennell et al. |
| 2008/0281178 A1 | 11/2008 | Chuang et al. |
| 2008/0281179 A1 | 11/2008 | Fennell et al. |
| 2008/0283396 A1 | 11/2008 | Wang et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0308523 A1 | 12/2008 | Krulevitch et al. |
| 2008/0312518 A1 | 12/2008 | Jina et al. |
| 2008/0312601 A1 | 12/2008 | Cane |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0312859 A1 | 12/2008 | Skyggebjerg et al. |
| 2008/0319085 A1 | 12/2008 | Wright et al. |
| 2008/0319295 A1 | 12/2008 | Bernstein et al. |
| 2008/0319296 A1 | 12/2008 | Bernstein et al. |
| 2008/0319414 A1 | 12/2008 | Yodfat et al. |
| 2008/0319416 A1 | 12/2008 | Yodfat et al. |
| 2009/0005659 A1 | 1/2009 | Kollias et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0028824 A1 | 1/2009 | Chiang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0036915 A1 | 2/2009 | Karbowniczek et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048499 A1 | 2/2009 | Glejbol |
| 2009/0048503 A1 | 2/2009 | Dalal et al. |
| 2009/0048563 A1 | 2/2009 | Ethelfeld et al. |
| 2009/0054737 A1 | 2/2009 | Magar et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054753 A1 | 2/2009 | Robinson et al. |
| 2009/0054866 A1 | 2/2009 | Teisen-Simony et al. |
| 2009/0055149 A1 | 2/2009 | Hayter et al. |
| 2009/0058635 A1 | 3/2009 | LaLonde et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063187 A1 | 3/2009 | Johnson et al. |
| 2009/0063402 A1 | 3/2009 | Hayter |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub |
| 2009/0088787 A1 | 4/2009 | Koike et al. |
| 2009/0093687 A1 | 4/2009 | Telfort et al. |
| 2009/0099436 A1 | 4/2009 | Brister et al. |
| 2009/0099521 A1 | 4/2009 | Gravesen et al. |
| 2009/0102678 A1 | 4/2009 | Mazza et al. |
| 2009/0105554 A1 | 4/2009 | Stahmann et al. |
| 2009/0105560 A1 | 4/2009 | Solomon |
| 2009/0105568 A1 | 4/2009 | Bugler |

(56) References Cited

U.S. PATENT DOCUMENTS

| | | |
|---|---|---|
| 2009/0105569 A1 | 4/2009 | Stafford |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0108992 A1 | 4/2009 | Shafer |
| 2009/0112123 A1 | 4/2009 | Freeman et al. |
| 2009/0112478 A1 | 4/2009 | Mueller, Jr. et al. |
| 2009/0118592 A1 | 5/2009 | Klitgaard |
| 2009/0124877 A1 | 5/2009 | Shariati et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielson |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0150454 A1 | 6/2009 | Gejdos et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0171182 A1 | 7/2009 | Stafford |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0198186 A1 | 8/2009 | Mernoe et al. |
| 2009/0198215 A1 | 8/2009 | Chong et al. |
| 2009/0203981 A1 | 8/2009 | Brauker et al. |
| 2009/0204340 A1 | 8/2009 | Feldman et al. |
| 2009/0204341 A1 | 8/2009 | Brauker et al. |
| 2009/0210249 A1 | 8/2009 | Rasch-Menges et al. |
| 2009/0212766 A1 | 8/2009 | Olson et al. |
| 2009/0216100 A1 | 8/2009 | Ebner et al. |
| 2009/0216103 A1 | 8/2009 | Brister et al. |
| 2009/0216215 A1 | 8/2009 | Thalmann et al. |
| 2009/0234200 A1 | 9/2009 | Husheer |
| 2009/0240120 A1 | 9/2009 | Mensinger et al. |
| 2009/0240121 A1 | 9/2009 | Bickoff |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0259118 A1 | 10/2009 | Feldman et al. |
| 2009/0259201 A1 | 10/2009 | Hwang et al. |
| 2009/0259202 A1 | 10/2009 | Leeflang et al. |
| 2009/0267765 A1 | 10/2009 | Greene et al. |
| 2009/0270765 A1 | 10/2009 | Ghesquire et al. |
| 2009/0277242 A1 | 11/2009 | Crane et al. |
| 2009/0281406 A1 | 11/2009 | McGarraugh et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292184 A1 | 11/2009 | Funderburk et al. |
| 2009/0292185 A1 | 11/2009 | Funderburk et al. |
| 2009/0294277 A1 | 12/2009 | Thomas et al. |
| 2009/0298182 A1 | 12/2009 | Schulat et al. |
| 2009/0299152 A1 | 12/2009 | Taub et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2009/0299301 A1 | 12/2009 | Gottlieb et al. |
| 2010/0004597 A1 | 1/2010 | Gryn et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0014626 A1 | 1/2010 | Fennell et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022863 A1 | 1/2010 | Mogensen et al. |
| 2010/0022988 A1 | 1/2010 | Wochner et al. |
| 2010/0025238 A1 | 2/2010 | Gottlieb et al. |
| 2010/0030038 A1 | 2/2010 | Brauker et al. |
| 2010/0030053 A1 | 2/2010 | Goode, Jr. et al. |
| 2010/0030111 A1 | 2/2010 | Perriere |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0036281 A1 | 2/2010 | Doi |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0049129 A1 | 2/2010 | Yokoi et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0076379 A1 | 3/2010 | Matusch |
| 2010/0081905 A1 | 4/2010 | Bommakanti et al. |
| 2010/0081906 A1 | 4/2010 | Hayter et al. |
| 2010/0081908 A1 | 4/2010 | Dobbles et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0105999 A1 | 4/2010 | Dixon et al. |
| 2010/0106088 A1 | 4/2010 | Yodfat et al. |
| 2010/0113894 A1 | 5/2010 | Brenneman et al. |
| 2010/0113897 A1 | 5/2010 | Brenneman et al. |
| 2010/0119693 A1 | 5/2010 | Tapsak et al. |
| 2010/0119881 A1 | 5/2010 | Patel et al. |
| 2010/0121167 A1 | 5/2010 | McGarraugh et al. |
| 2010/0121169 A1 | 5/2010 | Petisce et al. |
| 2010/0137695 A1 | 6/2010 | Yodfat et al. |
| 2010/0141656 A1 | 6/2010 | Krieftewirth |
| 2010/0145229 A1 | 6/2010 | Perez et al. |
| 2010/0145377 A1 | 6/2010 | Lai et al. |
| 2010/0146300 A1 | 6/2010 | Brown |
| 2010/0151987 A1 | 6/2010 | Notsu |
| 2010/0152548 A1 | 6/2010 | Koski |
| 2010/0152554 A1 | 6/2010 | Steine et al. |
| 2010/0152674 A1 | 6/2010 | Kavazov et al. |
| 2010/0160757 A1 | 6/2010 | Weinert et al. |

(56) References Cited

U.S. PATENT DOCUMENTS

| | | |
|---|---|---|
| 2010/0160759 A1 | 6/2010 | Celentano et al. |
| 2010/0160760 A1 | 6/2010 | Shults et al. |
| 2010/0161269 A1 | 6/2010 | Kamath et al. |
| 2010/0168538 A1 | 7/2010 | Keenan et al. |
| 2010/0168540 A1 | 7/2010 | Kamath et al. |
| 2010/0168541 A1 | 7/2010 | Kamath et al. |
| 2010/0168542 A1 | 7/2010 | Kamath et al. |
| 2010/0168543 A1 | 7/2010 | Kamath et al. |
| 2010/0168544 A1 | 7/2010 | Kamath et al. |
| 2010/0168545 A1 | 7/2010 | Kamath et al. |
| 2010/0168546 A1 | 7/2010 | Kamath et al. |
| 2010/0168547 A1 | 7/2010 | Kamath et al. |
| 2010/0168660 A1 | 7/2010 | Galley et al. |
| 2010/0168677 A1 | 7/2010 | Gabriel et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode, Jr. et al. |
| 2010/0174266 A1 | 7/2010 | Estes |
| 2010/0179399 A1 | 7/2010 | Goode, Jr. et al. |
| 2010/0179400 A1 | 7/2010 | Brauker et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179405 A1 | 7/2010 | Goode, Jr. et al. |
| 2010/0179407 A1 | 7/2010 | Goode, Jr. et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode, Jr. et al. |
| 2010/0185073 A1 | 7/2010 | Goode, Jr. et al. |
| 2010/0185074 A1 | 7/2010 | Goode, Jr. et al. |
| 2010/0185075 A1 | 7/2010 | Brister et al. |
| 2010/0185175 A1 | 7/2010 | Kamen et al. |
| 2010/0186069 A1 | 7/2010 | Brister et al. |
| 2010/0186070 A1 | 7/2010 | Brister et al. |
| 2010/0186071 A1 | 7/2010 | Simpson et al. |
| 2010/0186072 A1 | 7/2010 | Goode, Jr. et al. |
| 2010/0186075 A1 | 7/2010 | Brister et al. |
| 2010/0190435 A1 | 7/2010 | Cook et al. |
| 2010/0191082 A1 | 7/2010 | Brister et al. |
| 2010/0191087 A1 | 7/2010 | Talbot et al. |
| 2010/0191472 A1 | 7/2010 | Doniger et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198042 A1 | 8/2010 | Sloan et al. |
| 2010/0198142 A1 | 8/2010 | Sloan et al. |
| 2010/0198314 A1 | 8/2010 | Wei |
| 2010/0204557 A1 | 8/2010 | Kiaie et al. |
| 2010/0204653 A1 | 8/2010 | Gryn et al. |
| 2010/0212583 A1 | 8/2010 | Brister et al. |
| 2010/0213057 A1 | 8/2010 | Feldman et al. |
| 2010/0213080 A1 | 8/2010 | Celentano et al. |
| 2010/0214104 A1 | 8/2010 | Goode, Jr. et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228111 A1 | 9/2010 | Friman et al. |
| 2010/0228497 A1 | 9/2010 | Kamath et al. |
| 2010/0230285 A1 | 9/2010 | Hoss et al. |
| 2010/0235439 A1 | 9/2010 | Goodnow et al. |
| 2010/0240975 A1 | 9/2010 | Goode, Jr. et al. |
| 2010/0240976 A1 | 9/2010 | Goode, Jr. et al. |
| 2010/0256471 A1 | 10/2010 | Say et al. |
| 2010/0259543 A1 | 10/2010 | Tarassenko et al. |
| 2010/0261987 A1 | 10/2010 | Kamath et al. |
| 2010/0262183 A1 | 10/2010 | Abbott et al. |
| 2010/0262201 A1 | 10/2010 | He et al. |
| 2010/0267161 A1 | 10/2010 | Wu et al. |
| 2010/0274107 A1 | 10/2010 | Boock et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0324403 A1 | 12/2010 | Brister et al. |
| 2010/0325868 A1 | 12/2010 | Wang et al. |
| 2010/0326842 A1 | 12/2010 | Mazza et al. |
| 2010/0331642 A1 | 12/2010 | Bruce et al. |
| 2010/0331644 A1 | 12/2010 | Neale et al. |
| 2010/0331647 A1 | 12/2010 | Shah et al. |
| 2010/0331648 A1 | 12/2010 | Kamath et al. |
| 2010/0331651 A1 | 12/2010 | Groll |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0004276 A1 | 1/2011 | Blair et al. |
| 2011/0009727 A1 | 1/2011 | Mensinger et al. |
| 2011/0015509 A1 | 1/2011 | Peyser |
| 2011/0016691 A1 | 1/2011 | Alden et al. |
| 2011/0021889 A1 | 1/2011 | Hoss et al. |
| 2011/0022411 A1 | 1/2011 | Hjelm et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0040163 A1 | 2/2011 | Telson et al. |
| 2011/0040256 A1 | 2/2011 | Bobroff et al. |
| 2011/0040263 A1 | 2/2011 | Hordum et al. |
| 2011/0046456 A1 | 2/2011 | Hordum et al. |
| 2011/0046467 A1 | 2/2011 | Simpson et al. |
| 2011/0046977 A1 | 2/2011 | Goodnow et al. |
| 2011/0054275 A1 | 3/2011 | Stafford |
| 2011/0054282 A1 | 3/2011 | Nekoomaram et al. |
| 2011/0060196 A1 | 3/2011 | Stafford |
| 2011/0060530 A1 | 3/2011 | Fennell |
| 2011/0070633 A1 | 3/2011 | Matsumoto et al. |
| 2011/0073475 A1 | 3/2011 | Kastanos et al. |
| 2011/0077469 A1 | 3/2011 | Blocker et al. |
| 2011/0077490 A1 | 3/2011 | Simpson et al. |
| 2011/0077494 A1 | 3/2011 | Doniger et al. |
| 2011/0077659 A1 | 3/2011 | Mandecki et al. |
| 2011/0081726 A1 | 4/2011 | Berman et al. |
| 2011/0082484 A1 | 4/2011 | Saravia et al. |
| 2011/0087196 A1 | 4/2011 | Hunn et al. |
| 2011/0097090 A1 | 4/2011 | Cao |
| 2011/0106126 A1 | 5/2011 | Love et al. |
| 2011/0112696 A1 | 5/2011 | Yodfat et al. |
| 2011/0118579 A1 | 5/2011 | Goode, Jr. et al. |
| 2011/0118580 A1 | 5/2011 | Goode, Jr. et al. |
| 2011/0123971 A1 | 5/2011 | Berkowitz et al. |
| 2011/0124992 A1 | 5/2011 | Brauker et al. |
| 2011/0124997 A1 | 5/2011 | Goode, Jr. et al. |
| 2011/0125040 A1 | 5/2011 | Crawford et al. |
| 2011/0125410 A1 | 5/2011 | Goode, Jr. et al. |
| 2011/0130970 A1 | 6/2011 | Goode, Jr. et al. |
| 2011/0130971 A1 | 6/2011 | Goode, Jr. et al. |
| 2011/0130998 A1 | 6/2011 | Goode, Jr. et al. |
| 2011/0137257 A1 | 6/2011 | Gyrn et al. |
| 2011/0137571 A1 | 6/2011 | Power et al. |
| 2011/0144465 A1 | 6/2011 | Shults et al. |
| 2011/0148905 A1 | 6/2011 | Simmons et al. |

(56) References Cited

U.S. PATENT DOCUMENTS

| | | |
|---|---|---|
| 2011/0152637 A1 | 6/2011 | Kateraas et al. |
| 2011/0172510 A1 | 7/2011 | Chickering, III et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0184482 A1 | 7/2011 | Eberman et al. |
| 2011/0184752 A1 | 7/2011 | Ray et al. |
| 2011/0190603 A1 | 8/2011 | Stafford |
| 2011/0190614 A1 | 8/2011 | Brister et al. |
| 2011/0191044 A1 | 8/2011 | Stafford |
| 2011/0193704 A1 | 8/2011 | Harper et al. |
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0213225 A1 | 9/2011 | Bernstein et al. |
| 2011/0218414 A1 | 9/2011 | Kamath et al. |
| 2011/0218490 A1 | 9/2011 | Ocvirk et al. |
| 2011/0230741 A1 | 9/2011 | Liang et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |
| 2011/0257495 A1 | 10/2011 | Hoss et al. |
| 2011/0257521 A1 | 10/2011 | Fraden |
| 2011/0257895 A1 | 10/2011 | Brauker et al. |
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0282327 A1 | 11/2011 | Kellogg et al. |
| 2011/0287528 A1 | 11/2011 | Fern et al. |
| 2011/0288574 A1 | 11/2011 | Curry et al. |
| 2011/0289497 A1 | 11/2011 | Kiaie et al. |
| 2011/0290645 A1 | 12/2011 | Brister et al. |
| 2011/0313543 A1 | 12/2011 | Brauker et al. |
| 2011/0319729 A1* | 12/2011 | Donnay ............. A61B 5/15186 |
| | | 600/309 |
| 2011/0319733 A1 | 12/2011 | Stafford |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0088995 A1 | 4/2012 | Fennell et al. |
| 2012/0095406 A1 | 4/2012 | Gyrn et al. |
| 2012/0108934 A1 | 5/2012 | Valdes et al. |
| 2012/0108983 A1 | 5/2012 | Banet et al. |
| 2012/0116322 A1 | 5/2012 | Brink et al. |
| 2012/0123385 A1 | 5/2012 | Edwards et al. |
| 2012/0143135 A1 | 6/2012 | Cole et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0179113 A1 | 7/2012 | Yokota et al. |
| 2012/0184909 A1 | 7/2012 | Gyrn et al. |
| 2012/0190943 A1 | 7/2012 | Donnay et al. |
| 2012/0190989 A1 | 7/2012 | Kaiser et al. |
| 2012/0197098 A1 | 8/2012 | Donnay et al. |
| 2012/0197222 A1 | 8/2012 | Donnay et al. |
| 2012/0245447 A1 | 9/2012 | Karan et al. |
| 2012/0265042 A1 | 10/2012 | Neinast et al. |
| 2012/0296327 A1 | 11/2012 | Hutchins et al. |
| 2012/0303043 A1* | 11/2012 | Donnay ............... A61B 5/6849 |
| | | 606/129 |
| 2013/0035575 A1 | 2/2013 | Mayou et al. |
| 2013/0047981 A1 | 2/2013 | Bacon |
| 2013/0109940 A1 | 5/2013 | Yang et al. |
| 2013/0111248 A1 | 5/2013 | Ghesquiere et al. |
| 2013/0150691 A1 | 6/2013 | Pace et al. |
| 2013/0184547 A1 | 7/2013 | Taub et al. |
| 2013/0199312 A1 | 8/2013 | Wilmer et al. |
| 2013/0225959 A1 | 8/2013 | Bugler |
| 2013/0235166 A1 | 9/2013 | Jones et al. |
| 2013/0253289 A1 | 9/2013 | Hadvary et al. |
| 2013/0267811 A1 | 10/2013 | Pryor et al. |
| 2013/0317323 A1 | 11/2013 | Fujiwara et al. |
| 2014/0031655 A1 | 1/2014 | Stafford |
| 2014/0121480 A1 | 5/2014 | Budiman et al. |
| 2014/0148667 A1 | 5/2014 | Boock et al. |
| 2014/0171771 A1 | 6/2014 | Feldman et al. |
| 2014/0188053 A1 | 7/2014 | Lundquist |
| 2014/0228760 A1 | 8/2014 | Ethelfeld |
| 2014/0275907 A1 | 9/2014 | Feldman et al. |
| 2015/0005601 A1 | 1/2015 | Hoss et al. |
| 2015/0018643 A1 | 1/2015 | Cole et al. |
| 2015/0025338 A1 | 1/2015 | Lee et al. |
| 2015/0073238 A1 | 3/2015 | Matsumoto et al. |
| 2015/0105644 A1 | 4/2015 | Yang et al. |
| 2015/0141776 A1 | 5/2015 | Hadvary et al. |
| 2015/0164545 A1 | 6/2015 | Gyrn |
| 2015/0173661 A1 | 6/2015 | Myles |
| 2015/0241407 A1 | 8/2015 | Ou et al. |
| 2015/0326072 A1 | 11/2015 | Petras et al. |
| 2016/0058342 A1 | 3/2016 | Maiz-Aguinaga et al. |
| 2016/0058470 A1 | 3/2016 | Peterson et al. |
| 2016/0058474 A1 | 3/2016 | Peterson et al. |
| 2016/0128615 A1 | 5/2016 | Curry et al. |
| 2016/0157759 A1 | 6/2016 | Yang |
| 2016/0256106 A1 | 9/2016 | Krasnow et al. |
| 2016/0331283 A1 | 11/2016 | Rao et al. |
| 2016/0331284 A1 | 11/2016 | Pace |
| 2016/0338733 A1 | 11/2016 | Shah et al. |
| 2016/0338734 A1 | 11/2016 | Shah et al. |
| 2016/0354555 A1 | 12/2016 | Gibson et al. |
| 2017/0112531 A1 | 4/2017 | Schoonmaker et al. |
| 2017/0112533 A1 | 4/2017 | Schoonmaker et al. |
| 2017/0112534 A1 | 4/2017 | Schoonmaker et al. |
| 2017/0127985 A1 | 5/2017 | Thompson et al. |
| 2017/0128011 A1 | 5/2017 | Frey et al. |
| 2017/0165451 A1 | 6/2017 | Frey et al. |
| 2017/0188908 A1 | 7/2017 | Hoss et al. |
| 2017/0188910 A1 | 7/2017 | Halac et al. |
| 2017/0188912 A1* | 7/2017 | Halac ................... A61B 5/6848 |
| 2017/0216536 A1 | 8/2017 | Scott |
| 2017/0265791 A1 | 9/2017 | Pace et al. |
| 2017/0290533 A1 | 10/2017 | Antonio et al. |
| 2017/0290534 A1 | 10/2017 | Antonio et al. |
| 2017/0290535 A1 | 10/2017 | Rao et al. |
| 2017/0290546 A1 | 10/2017 | Antonio et al. |
| 2017/0319137 A1 | 11/2017 | Tsubouchi et al. |
| 2017/0367630 A1 | 12/2017 | Arita et al. |
| 2017/0368268 A1 | 12/2017 | Chopra |
| 2018/0116572 A1 | 5/2018 | Simpson et al. |
| 2018/0125464 A1 | 5/2018 | Kolb et al. |
| 2018/0235520 A1 | 8/2018 | Rao et al. |
| 2018/0360493 A1 | 12/2018 | Baker et al. |
| 2018/0368771 A1 | 12/2018 | Gray et al. |
| 2019/0133501 A1 | 5/2019 | Rao et al. |
| 2019/0133638 A1 | 5/2019 | Ii et al. |
| 2019/0298240 A1 | 10/2019 | Lee et al. |
| 2020/0077928 A1 | 3/2020 | Brister et al. |
| 2020/0100712 A1 | 4/2020 | Stafford |
| 2020/0113494 A1 | 4/2020 | Akiyama |
| 2020/0178899 A1 | 6/2020 | Chae et al. |
| 2020/0196919 A1 | 6/2020 | Rao et al. |
| 2020/0397356 A1 | 12/2020 | Yee et al. |
| 2021/0030969 A1 | 2/2021 | Huang et al. |
| 2021/0113124 A1 | 4/2021 | Yee et al. |
| 2021/0161437 A1 | 6/2021 | Thomas et al. |
| 2021/0177315 A1 | 6/2021 | Thomas et al. |
| 2021/0204841 A1 | 7/2021 | Thomas et al. |
| 2021/0204843 A1 | 7/2021 | Mazza et al. |
| 2021/0378592 A1 | 12/2021 | Rodriguez et al. |
| 2022/0007973 A1 | 1/2022 | Rao et al. |
| 2022/0079475 A1 | 3/2022 | Cole et al. |
| 2022/0125480 A1 | 4/2022 | Rao et al. |

(56) References Cited

U.S. PATENT DOCUMENTS

| | | | |
|---|---|---|---|
| 2022/0273240 | A1 | 9/2022 | Hopcroft |
| 2023/0108476 | A1 | 4/2023 | Rao |
| 2024/0293615 | A1 | 9/2024 | Lanigan |

FOREIGN PATENT DOCUMENTS

| | | |
|---|---|---|
| CA | 2468577 | 6/2003 |
| CA | 2495648 | 2/2004 |
| CA | 2143172 | 7/2005 |
| CA | 2498682 | 9/2005 |
| CA | 2555749 | 9/2005 |
| CA | 2632709 | 6/2007 |
| CA | 2396613 | 3/2008 |
| CA | 2678336 | 5/2008 |
| CA | 2615575 | 6/2008 |
| CA | 2626349 | 9/2008 |
| CA | 2701374 | 4/2009 |
| CA | 2413148 | 8/2010 |
| CA | 2728831 | 7/2011 |
| CA | 2766693 A1 | 9/2011 |
| CA | 2617965 | 10/2011 |
| CA | 2766685 A1 | 12/2011 |
| CA | 3050721 | 7/2018 |
| CA | 3050721 A1 | 7/2018 |
| CA | 3120335 | 3/2023 |
| CA | 3182961 | 3/2023 |
| CN | 1202872 | 5/2005 |
| CN | 101163440 | 4/2008 |
| CN | 101268932 | 9/2008 |
| CN | 101296650 | 10/2008 |
| CN | 201370857 | 12/2009 |
| DE | 44 01 400 | 7/1995 |
| DE | 201 10 059 | 8/2002 |
| DE | 101 17 285 | 11/2002 |
| DE | 10 2008 053 216 | 5/2010 |
| EP | 0 010 375 | 4/1980 |
| EP | 0 026 995 | 4/1981 |
| EP | 0 048 090 | 3/1982 |
| EP | 0 078 636 | 5/1983 |
| EP | 0 096 288 | 12/1983 |
| EP | 0098592 | 1/1984 |
| EP | 0 125 139 | 11/1984 |
| EP | 0127958 | 12/1984 |
| EP | 0 136 362 | 4/1985 |
| EP | 0 170 375 | 2/1986 |
| EP | 0 177 743 | 4/1986 |
| EP | 0 080 304 | 5/1986 |
| EP | 0 184 909 | 6/1986 |
| EP | 0 206 218 | 12/1986 |
| EP | 0 230 472 | 8/1987 |
| EP | 0 241 309 | 10/1987 |
| EP | 0 245 073 | 11/1987 |
| EP | 0 255 291 | 2/1988 |
| EP | 0 278 647 | 8/1988 |
| EP | 0 319 277 A1 | 6/1989 |
| EP | 0320109 | 6/1989 |
| EP | 0353328 | 2/1990 |
| EP | 0 359 831 | 3/1990 |
| EP | 0 368 209 | 5/1990 |
| EP | 0390390 | 10/1990 |
| EP | 0396788 | 11/1990 |
| EP | 0 400 918 | 12/1990 |
| EP | 0 453 283 | 10/1991 |
| EP | 0 470 290 | 2/1992 |
| EP | 0 567 725 | 11/1993 |
| EP | 0286118 | 1/1995 |
| EP | 0680727 | 11/1995 |
| EP | 0724859 | 8/1996 |
| EP | 0805574 | 11/1997 |
| EP | 0973289 | 1/2000 |
| EP | 0678308 | 5/2000 |
| EP | 1 048 264 | 11/2000 |
| EP | 1 177 802 | 2/2002 |
| EP | 0 729 366 | 7/2002 |
| EP | 1292218 | 3/2003 |
| EP | 1077634 | 7/2003 |
| EP | 1 092 390 | 7/2004 |
| EP | 1568309 | 8/2005 |
| EP | 1 630 898 | 3/2006 |
| EP | 1 669 020 | 6/2006 |
| EP | 1666091 | 6/2006 |
| EP | 1 704 889 | 9/2006 |
| EP | 1703697 | 9/2006 |
| EP | 1704893 | 9/2006 |
| EP | 1 729 128 | 12/2006 |
| EP | 0 987 982 | 1/2007 |
| EP | 1956371 | 8/2008 |
| EP | 1 972 270 A1 | 9/2008 |
| EP | 2031534 | 3/2009 |
| EP | 2060284 | 5/2009 |
| EP | 1897487 | 11/2009 |
| EP | 1897492 | 11/2009 |
| EP | 2113864 | 11/2009 |
| EP | 1897488 | 12/2009 |
| EP | 1681992 | 4/2010 |
| EP | 2201969 | 6/2010 |
| EP | 1448489 | 8/2010 |
| EP | 1971396 | 8/2010 |
| EP | 1725163 | 12/2010 |
| EP | 2260757 | 12/2010 |
| EP | 2 327 362 | 6/2011 |
| EP | 1413245 | 6/2011 |
| EP | 2327984 | 6/2011 |
| EP | 2335587 | 6/2011 |
| EP | 2153382 | 2/2012 |
| EP | 2284773 | 2/2012 |
| EP | 1 789 116 B1 | 5/2013 |
| EP | 3 251 597 B1 | 11/2019 |
| EP | 3 632 314 | 4/2020 |
| EP | 3 632 315 A1 | 4/2020 |
| EP | 3 851 045 A1 | 7/2021 |
| EP | 3 730 044 B1 | 12/2021 |
| EP | 3 730 045 B1 | 3/2022 |
| EP | 3 766 408 B1 | 4/2022 |
| EP | 3 928 688 B1 | 6/2022 |
| EP | 20177703.4 | 6/2023 |
| EP | 20177712.5 | 6/2023 |
| EP | 20195922.8 | 6/2023 |
| EP | 4 111 949 B1 | 7/2023 |
| EP | 3 300 658 B1 | 1/2024 |
| EP | 4 344 633 | 4/2024 |
| EP | 4 203 819 | 7/2024 |
| GB | 1 394 171 | 5/1975 |
| GB | 1 599 241 | 9/1981 |
| GB | 2 073 891 | 10/1981 |
| GB | 2 067 764 | 1/1984 |
| GB | 2 154 003 | 8/1985 |
| GB | 2 204 408 | 11/1988 |
| GB | 2 254 436 | 10/1992 |
| GB | 2409951 | 7/2005 |
| JP | 54-041191 | 4/1979 |
| JP | 55-010581 | 1/1980 |
| JP | 55-010583 | 1/1980 |
| JP | 55-010584 | 1/1980 |
| JP | 55-012406 | 1/1980 |
| JP | 56-163447 | 12/1981 |
| JP | 57-070448 | 4/1982 |
| JP | 60-173457 | 9/1985 |
| JP | 60-173458 | 9/1985 |
| JP | 60-173459 | 9/1985 |
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 01-114746 | 5/1989 |
| JP | 01-114747 | 5/1989 |
| JP | 01-124060 | 5/1989 |
| JP | 01-134244 | 5/1989 |
| JP | 01-156658 | 6/1989 |
| JP | 02-062958 | 3/1990 |

(56) References Cited

FOREIGN PATENT DOCUMENTS

| | | |
|---|---|---|
| JP | 02-120655 | 5/1990 |
| JP | 02-287145 | 11/1990 |
| JP | 02-310457 | 12/1990 |
| JP | 03-020752 | 1/1991 |
| JP | 03-026956 | 2/1991 |
| JP | 03-028752 | 2/1991 |
| JP | 03-500940 | 2/1991 |
| JP | 03-194458 | 8/1991 |
| JP | 03-202764 | 9/1991 |
| JP | 05-072171 | 3/1993 |
| JP | 05-196595 | 8/1993 |
| JP | 06-190050 | 7/1994 |
| JP | 07-055757 | 3/1995 |
| JP | 07-072585 | 3/1995 |
| JP | 07-182462 | 7/1995 |
| JP | 07-311196 | 11/1995 |
| JP | 08-285814 | 11/1996 |
| JP | 08-285815 | 11/1996 |
| JP | 09-021778 | 1/1997 |
| JP | 09-101280 | 4/1997 |
| JP | 09-285459 | 4/1997 |
| JP | 10-170471 | 6/1998 |
| JP | 10-305016 | 11/1998 |
| JP | 11-506629 | 6/1999 |
| JP | 11-225359 | 8/1999 |
| JP | 2003-144417 | 5/2003 |
| JP | 2004-033438 | 2/2004 |
| JP | 2004-214014 | 7/2004 |
| JP | 2004-520103 | 7/2004 |
| JP | 2004-520898 | 7/2004 |
| JP | 2004-358016 | 12/2004 |
| JP | 2006-021031 | 1/2006 |
| JP | 2006-280464 | 10/2006 |
| JP | 2006-527036 | 11/2006 |
| JP | 2007-510499 | 4/2007 |
| JP | 2007-152037 | 6/2007 |
| JP | 2008-506468 | 3/2008 |
| JP | 2021-531135 | 2/2023 |
| KR | 10-2017-0068694 | 6/2017 |
| SU | 1281988 | 1/1987 |
| WO | WO 89/05119 | 6/1989 |
| WO | WO 89/08713 | 9/1989 |
| WO | WO 90/05300 | 5/1990 |
| WO | WO 90/05910 | 5/1990 |
| WO | WO 91/01680 | 2/1991 |
| WO | WO 91/04704 | 4/1991 |
| WO | WO 91/15993 | 10/1991 |
| WO | WO-1992/013271 | 8/1992 |
| WO | WO-1994/020602 | 9/1994 |
| WO | WO-95/28878 | 2/1995 |
| WO | WO 96/25089 | 8/1996 |
| WO | WO-96/35370 | 11/1996 |
| WO | WO 96/39977 | 12/1996 |
| WO | WO 97/02847 | 1/1997 |
| WO | WO 97/19344 | 5/1997 |
| WO | WO 97/21457 | 6/1997 |
| WO | WO-97/33513 | 9/1997 |
| WO | WO 97/42882 | 11/1997 |
| WO | WO 97/42883 | 11/1997 |
| WO | WO 97/42886 | 11/1997 |
| WO | WO 97/42888 | 11/1997 |
| WO | WO 97/43962 | 11/1997 |
| WO | WO-98/04902 | 2/1998 |
| WO | WO 98/35053 | 8/1998 |
| WO | WO 98/56293 | 12/1998 |
| WO | WO-99/27849 | 6/1999 |
| WO | WO-99/28736 | 6/1999 |
| WO | WO 99/33504 | 7/1999 |
| WO | WO 99/56613 | 11/1999 |
| WO | WO 00/40159 | 7/2000 |
| WO | WO 00/49940 | 8/2000 |
| WO | WO-00/60350 | 10/2000 |
| WO | WO-2000/059370 | 10/2000 |
| WO | WO-00/74753 | 12/2000 |
| WO | WO 00/78992 | 12/2000 |
| WO | WO 01/17875 A1 | 3/2001 |
| WO | WO 01/52727 A1 | 7/2001 |
| WO | WO-2001/052935 | 7/2001 |
| WO | WO 01/58348 | 8/2001 |
| WO | WO-2001/054753 | 8/2001 |
| WO | WO 02/15778 | 2/2002 |
| WO | WO 02/16905 | 2/2002 |
| WO | WO 02/50534 | 6/2002 |
| WO | WO 02/058537 | 8/2002 |
| WO | WO 02/100457 | 12/2002 |
| WO | WO-03/026728 | 4/2003 |
| WO | WO 03/028784 | 4/2003 |
| WO | WO 03/056319 | 7/2003 |
| WO | WO-03/057027 | 7/2003 |
| WO | WO 03/072164 | 9/2003 |
| WO | WO 03/073936 | 9/2003 |
| WO | WO 03/076893 | 9/2003 |
| WO | WO-03/085372 | 10/2003 |
| WO | WO-2003/082091 | 10/2003 |
| WO | WO 2004/006982 | 1/2004 |
| WO | WO-2004/015539 | 2/2004 |
| WO | WO 2004/028337 | 4/2004 |
| WO | WO 2004/030726 | 4/2004 |
| WO | WO 2004/034024 | 4/2004 |
| WO | WO-2004/047445 | 6/2004 |
| WO | WO 2004/049237 | 6/2004 |
| WO | WO 2004/054445 | 7/2004 |
| WO | WO 2004/060436 | 7/2004 |
| WO | WO 2004/061420 | 7/2004 |
| WO | WO-2004/090503 | 10/2004 |
| WO | WO-2004/098405 | 11/2004 |
| WO | WO 2004/098682 A2 | 11/2004 |
| WO | WO-2004/098683 | 11/2004 |
| WO | WO 2004/098684 | 11/2004 |
| WO | WO 2004/098685 | 11/2004 |
| WO | WO 2004/107971 | 12/2004 |
| WO | WO 2004/112602 | 12/2004 |
| WO | WO 2005/011779 A1 | 2/2005 |
| WO | WO 2005/018450 | 3/2005 |
| WO | WO 2005/037184 | 4/2005 |
| WO | WO-2005/041766 | 5/2005 |
| WO | WO 2005/044116 | 5/2005 |
| WO | WO-2005/045744 | 5/2005 |
| WO | WO-2005/046780 | 5/2005 |
| WO | WO-2005/051170 | 6/2005 |
| WO | WO-2005/057175 | 6/2005 |
| WO | WO-2005/065538 | 7/2005 |
| WO | WO 2005/084534 | 9/2005 |
| WO | WO 2005/089103 | 9/2005 |
| WO | WO 2005/092177 | 10/2005 |
| WO | WO-2005/121785 | 12/2005 |
| WO | WO-2005/123186 | 12/2005 |
| WO | WO 2006/001024 | 1/2006 |
| WO | WO 2006/015922 | 2/2006 |
| WO | WO-2006/017358 | 2/2006 |
| WO | WO-2006/020212 | 2/2006 |
| WO | WO 2006/024671 | 3/2006 |
| WO | WO-2006/026741 | 3/2006 |
| WO | WO-2006/032653 | 3/2006 |
| WO | WO 2006/036145 | 4/2006 |
| WO | WO 2006/040083 | 4/2006 |
| WO | WO 2006/042811 | 4/2006 |
| WO | WO 2006/061354 | 6/2006 |
| WO | WO-2006/064397 | 6/2006 |
| WO | WO-2006/072035 | 7/2006 |
| WO | WO-2006/079114 | 7/2006 |
| WO | WO-2006/086423 | 8/2006 |
| WO | WO 2006/094513 | 9/2006 |
| WO | WO 2006/108809 | 10/2006 |
| WO | WO 2006/110742 | 10/2006 |
| WO | WO 2006/114297 | 11/2006 |
| WO | WO-2006/118947 | 11/2006 |
| WO | WO-2006/121921 | 11/2006 |
| WO | WO-2006/124099 | 11/2006 |
| WO | WO 2007/002189 | 1/2007 |
| WO | WO 2007/002189 A2 | 1/2007 |
| WO | WO-2007/007459 | 1/2007 |
| WO | WO-2007/016399 | 2/2007 |
| WO | WO-2007/019289 | 2/2007 |

(56)　　　　References Cited

FOREIGN PATENT DOCUMENTS

| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/065285 | 6/2007 |
| WO | WO 2007/089738 | 8/2007 |
| WO | WO-2007/092618 | 8/2007 |
| WO | WO 2007/097754 | 8/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO 2007/140783 | 12/2007 |
| WO | WO-2007/143225 | 12/2007 |
| WO | WO-2007/149319 | 12/2007 |
| WO | WO/2008-001366 | 1/2008 |
| WO | WO/2008-014792 | 2/2008 |
| WO | WO-2008/021913 | 2/2008 |
| WO | WO 2008/031106 | 3/2008 |
| WO | WO 2008/031110 | 3/2008 |
| WO | WO 2008/039944 | 4/2008 |
| WO | WO-2008/042760 | 4/2008 |
| WO | WO-2008/048452 | 4/2008 |
| WO | WO 2008/051920 | 5/2008 |
| WO | WO 2008/051924 | 5/2008 |
| WO | WO-2008/052374 | 5/2008 |
| WO | WO 2008/061552 A1 | 5/2008 |
| WO | WO-2008/062099 | 5/2008 |
| WO | WO 2008/065646 | 6/2008 |
| WO | WO 2008/073813 | 6/2008 |
| WO | WO 2008/073813 A1 | 6/2008 |
| WO | WO-2008/086541 | 7/2008 |
| WO | WO 2008/103620 | 8/2008 |
| WO | WO 2008/114223 | 9/2008 |
| WO | WO-2008/115409 | 9/2008 |
| WO | WO-2008/128210 | 10/2008 |
| WO | WO-2008/129532 | 10/2008 |
| WO | WO-2008/130896 | 10/2008 |
| WO | WO-2008/130897 | 10/2008 |
| WO | WO-2008/130898 | 10/2008 |
| WO | WO 2008/133702 | 11/2008 |
| WO | WO 2008/138006 | 11/2008 |
| WO | WO-2008/143943 | 11/2008 |
| WO | WO-2008/144445 | 11/2008 |
| WO | WO 2008/147921 | 12/2008 |
| WO | WO 2008/147921 A1 | 12/2008 |
| WO | WO 2008/150917 | 12/2008 |
| WO | WO-2008/153693 | 12/2008 |
| WO | WO 2008/155377 | 12/2008 |
| WO | WO-2008/157821 | 12/2008 |
| WO | WO 2009/007287 | 1/2009 |
| WO | WO 2009/007287 A1 | 1/2009 |
| WO | WO 2009/010396 | 1/2009 |
| WO | WO 2009/016635 | 2/2009 |
| WO | WO 2009/016638 | 2/2009 |
| WO | WO-2009/018058 | 2/2009 |
| WO | WO-2009/035773 | 3/2009 |
| WO | WO 2009/039013 | 3/2009 |
| WO | WO 2009/062674 | 5/2009 |
| WO | WO 2009/062675 | 5/2009 |
| WO | WO 2009/066288 A1 | 5/2009 |
| WO | WO-2009/068661 | 6/2009 |
| WO | WO-2009/086216 | 7/2009 |
| WO | WO-2009/096992 | 8/2009 |
| WO | WO-2009/097594 | 8/2009 |
| WO | WO-2010/062898 | 6/2010 |
| WO | WO-2010/077329 | 7/2010 |
| WO | WO 2010/091005 | 8/2010 |
| WO | WO 2010/099507 | 9/2010 |
| WO | WO 2010/112521 | 10/2010 |
| WO | WO 2010/141922 | 12/2010 |
| WO | WO-2011/000528 | 1/2011 |
| WO | WO 2011/002815 | 1/2011 |
| WO | WO 2011/015659 | 2/2011 |
| WO | WO-2011/022418 | 2/2011 |
| WO | WO 2011/025549 | 3/2011 |
| WO | WO-2011/104616 | 9/2011 |
| WO | WO 2011/119896 | 9/2011 |
| WO | WO 2011/119898 A1 | 9/2011 |
| WO | WO 2012/103429 | 8/2012 |
| WO | PCT/US2012/062551 | 1/2013 |
| WO | WO 2013/090215 | 6/2013 |
| WO | WO 2016/183493 A1 | 11/2016 |
| WO | WO 2017/027749 | 2/2017 |
| WO | WO 2017/116915 | 7/2017 |
| WO | WO 2017/134227 | 8/2017 |
| WO | WO 2018/136898 | 7/2018 |
| WO | WO 2018/166963 | 9/2018 |
| WO | WO 2019/005627 A1 | 1/2019 |
| WO | WO 2019/236850 | 12/2019 |
| WO | WO 2019/236859 | 12/2019 |
| WO | WO 2019/236876 | 12/2019 |
| WO | WO 2022/046416 | 3/2022 |
| WO | WO 2022/060677 | 3/2022 |
| WO | PCT/US2023/010054 | 5/2023 |

OTHER PUBLICATIONS

AU, 2007309066 Examiner's Report, dated Aug. 16, 2013.
AU, 2008265541 Examiner's Report, dated Oct. 15, 2012.
AU, 2008265541 Examiner's Report, dated Nov. 29, 2013.
AU, 2010286917 Examiner's Report, dated Sep. 8, 2014.
AU, 2011230596 Examiner's Report, dated Feb. 28, 2014.
AU, 2016201703 Examiner's Report, dated Mar. 22, 2017.
AU, 2017254903 Examiner's Report, dated Dec. 11, 2018.
AU, 2018200899 Examiner's Report, dated Dec. 6, 2018.
CA, 2,765,712 Examiner's Report, dated Apr. 10, 2017.
CA, 2,765,712 Examiner's Report, dated Mar. 27, 2018.
CN, 200780045373.9 Notice of Allowance, dated May 18, 2011.
CN, 200780045373.9 Office Action, dated Apr. 14, 2010.
CN, 201080027344.1 Office Action, dated Jun. 5, 2014.
CN, 201080027344.1 Office Action, dated Feb. 6, 2015.
CN, 201080006480.2 Office Action, dated May 6, 2013.
CN, 201080006480.2 Office Action, dated Dec. 11, 2013.
CN, 201080006481.7 Office Action, dated Dec. 2, 2014.
CN, 201180002616.7 Office Action, dated Apr. 24, 2014.
CN, 201180002617.1 Office Action, dated Jul. 3, 2014.
CN, 20160144860.1 Office Action, dated Mar. 23, 2018.
CN, 20160144860.1 Office Action, dated Dec. 10, 2018.
CN, 20160144860.1 Office Action, dated May 23, 2019.
EP, 06804122.7 Decision to Refuse the Application, dated Feb. 25, 2013.
EP, 06804122.7 Examination Report, dated Nov. 30, 2011.
EP, 06804122.7 Examination Report, dated Jan. 25, 2011.
EP, 06815715.5 Extended Search Report, dated Oct. 30, 2009.
EP, 07842173.2 Examination Report, dated Mar. 21, 2013.
EP, 07842173.2 Extended Search Report, dated Dec. 29, 2010.
EP, 07842180.7 Examination Report, dated Oct. 23, 2012.
EP, 07842180.7 Examination Report, dated Dec. 14, 2011.
EP, 07842180.7 Examination Report, dated Feb. 23, 2011.
EP, 07842180.7 Extended Search Report, dated Sep. 28, 2009.
EP, 10739031.2 Extended Search Report, dated May 7, 2013.
EP, 10739031.2 Examination Report, dated Oct. 28, 2016.
EP, 10739031.2 Notice of Opposition, dated Dec. 20, 2018.
EP, 10739031.2 Reply to Notice of Opposition, dated May 21, 2019.
EP, 10739031.2 Reply to Notice of Opposition Reply, dated Aug. 8, 2019.
EP, 10739031.2 Summons to Attend Oral Proceedings, dated Sep. 17, 2019.
EP, 10739031.2 Written Submissions, dated Dec. 3, 2019.
EP, 10739031.2 Response to Written Submissions, dated Jan. 24, 2020.
EP, 10739031.2 Summons to Attend Oral Proceedings, dated May 20, 2020.
EP, 10739031.2 Written Submissions, dated Nov. 20, 2020.
EP, 10739031.2 Response to Written Submissions, dated Jan. 7, 2021.

(56)                 References Cited

OTHER PUBLICATIONS

EP, 10739031.2 Decision and Grounds for Revoking Patent, dated Jun. 9, 2021.
EP, 10739031.2 Grounds of Appeal, dated Oct. 19, 2021.
EP, 10739031.2 Response to Grounds of Appeal, dated Mar. 1, 2022.
EP, 10739031.2 Response to Response to Grounds of Appeal, dated Jul. 29, 2022.
EP, 10812438.9 Extended Search Report, dated Dec. 10, 2013.
EP, 11760268.0 Minutes of Oral Proceedings, dated Aug. 11, 2022.
EP, 11760268.0 Communication from Board of Appeals, dated Mar. 31, 2022.
EP, 11760268.0 Response to Written Submissions, dated Jan. 14, 2020.
EP, 11760268.0 Response to Notice of Appeal, dated Sep. 15, 2019.
EP, 11760268.0 Statement of Grounds of Appeal, dated Apr. 23, 2019.
EP, 11760268.0 Grounds of Appeal, dated Apr. 18, 2019.
EP, 11760268.0 Notice of Appeal ADC, dated Feb. 25, 2019.
EP, 11760268.0 Notice of Appeal Dexcom, dated Feb. 22, 2019.
11760268.0 Interlocutory Decision, dated Dec. 13, 2018.
EP, 11760268.0 Response to Summons to Attend Oral Proceedings, dated Sep. 13, 2018.
EP, 11760268.0 Letter Regarding the Opposition Procedure, dated Sep. 12, 2018.
EP, 11760268.0 Summons to Attend Oral Proceedings, dated Mar. 22, 2018.
EP, 11760268.0 Comments on Reply to Notice of Opposition, dated Dec. 27, 2017.
EP, 11760268.0 Reply to Notice of Opposition, dated Sep. 4, 2017.
EP, 11760268.0 Notice of Opposition, dated Mar. 29, 2017.
EP, 13000105.0 Examination Report, dated Oct. 18, 2016.
EP, 13000105.0 Minutes of the Oral Proceedings, dated Oct. 18, 2016.
EP, 13000105.0 Notice of Opposition, dated Jan. 4, 2019.
EP, 15184320.8 Examination Report, dated Apr. 18, 2017.
EP, 16176370.1 Extended Search Report, dated Dec. 7, 2016.
EP, 16793637.6 Extended Search Report, dated Oct. 9, 2018.
EP, 17182379.2 Extended Search Report, dated Feb. 21, 2018.
EP, 17201183.5 Extended Search Report, dated May 7, 2018.
EP, 17201183.5 Examination Report, dated May 7, 2019.
EP, 18192278.2 Extended Search Report, dated Mar. 13, 2019.
EP, 18208224.8 Extended Search Report, dated Oct. 11, 2019.
EP, 19151577.4 Extended Search Report, dated Aug. 16, 2019.
EP, 19151577.4 Examination Report, dated May 27, 2022.
EP, 19184881.1 Extended Search Report, dated Nov. 21, 2019.
EP, 20177703.4 Extended Search Report, dated Sep. 25, 2020.
EP, 20177712.5 Extended Search Report, dated Sep. 30, 2020.
EP, 20195922.8 Extended Search Report, dated Dec. 16, 2020.
EP, 21152231.3 Extended Search Report, dated May 11, 2021.
EP, 21192910.4 Extended Search Report, dated Mar. 31, 2022.
EP, 21211041.5 Extended Search Report, dated Mar. 3, 2022.
IL, 198329 Office Action, dated Mar. 5, 2012.
JP, 2009-534798 Office Action, dated Sep. 25, 2012.
JP, 2012-526736 Office Action, dated Apr. 15, 2014.
JP, 2012-526736 Office Action, dated Dec. 16, 2014.
JP, 2013-501503 Office Action, dated Mar. 3, 2015.
JP, 2015-159805 Office Action, dated Aug. 9, 2016.
JP, 2016-44196 Office Action, dated Apr. 11, 2017.
MX, MX/a/2009/004398 Office Action, dated Sep. 24, 2012.
US, Institution Decision, IPR No. 2022-00605, dated Jul. 27, 2022.
US, Patent Owner's Preliminary Sur-Reply, IPR No. 2022-00605, dated Jun. 28, 2022.
US, Petitioner's Preliminary Reply to Patent Owner's Preliminary Response, IPR No. 2022-00605, dated Jun. 21, 2022.
US, Patent Owner's Preliminary Response, IPR No. 2022-00605, dated May 24, 2022.
US, Petition for Inter Partes Review of U.S. Pat. No. 10,945,649, IPR No. 2022-00605, dated Feb. 15, 2022.
US, Institution Decision, IPR No. 2022-00637, dated Jul. 27, 2022.

US, Patent Owner's Preliminary Sur-Reply, IPR No. 2022-00637, dated Jun. 28, 2022.
US, Petitioner's Preliminary Reply to Patent Owner's Preliminary Response, IPR No. 2022-00637, dated Jun. 21, 2022.
US, Patent Owner's Preliminary Response, IPR No. 2022-00637, dated Jun. 9, 2022.
US, Petition for Inter Partes Review of U.S. Pat. No. 11,013,440, IPR No. 2022-00637, dated Feb. 8, 2022.
US, Reexamination U.S. Appl. No. 95/002,162 Request to Review Order Denying Request for Reexamination, dated Dec. 13, 2012.
US, Reexamination U.S. Appl. No. 95/002,162 Order Denying Request for Reexamination, dated Nov. 13, 2012.
US, Request for Reexamination U.S. Appl. No. 95/002,162 of U.S. Pat. No. 8,175,673, dated Sep. 7, 2012.
US, Reexamination U.S. Appl. No. 95/002,113 Request to Review Order Denying Request for Reexamination, dated Dec. 13, 2012.
US, Reexamination U.S. Appl. No. 95/002,113 Order Denying Request for Reexamination, dated Nov. 13, 2012.
US, Request for Reexamination U.S. Appl. No. 95/002,113 of U.S. Pat. No. 6,990,366, dated Aug. 30, 2012.
US, Reexamination U.S. Appl. No. 90/011,730 Notice of Intent to Issue Ex Parte Reexamination Certificate, dated Apr. 5, 2012.
US, Reexamination U.S. Appl. No. 90/011,730 Office Action, dated Jan. 11, 2012.
US, Reexamination U.S. Appl. No. 90/011,730 Order Granting Request for Reexamination, dated Aug. 24, 2011.
US, Request for Reexamination U.S. Appl. No. 90/011,730 of U.S. Pat. No. 6,990,366, dated Jun. 3, 2011.
US, Reexamination U.S. Appl. No. 90/010,791 Ex Parte Reexamination Certificate, dated May 17, 2011.
US, Reexamination U.S. Appl. No. 90/010,791 Office Action, dated Dec. 17, 2010.
US, Reexamination U.S. Appl. No. 90/010,791 Office Action, dated May 28, 2010.
US, Reexamination U.S. Appl. No. 90/010,791 Order Granting Request for Reexamination, dated Feb. 22, 2010.
US, Request for Reexamination U.S. Appl. No. 90/010,791 of U.S. Pat. No. 6,990,366, dated Dec. 22, 2009.
US, Reexamination U.S. Appl. No. 90/009,328 Notice of Intent to Issue Ex Parte Reexamination Certificate, dated Nov. 20, 2009.
US, Reexamination U.S. Appl. No. 90/009,328 Office Action, dated Sep. 30, 2009.
US, Reexamination U.S. Appl. No. 90/009,328 Office Action, dated Aug. 4, 2009.
US, Reexamination U.S. Appl. No. 90/009,328 Order Granting Request for Reexamination, dated Dec. 9, 2008.
US, Request for Reexamination U.S. Appl. No. 90/009,328 of U.S. Pat. No. 6,990,366, dated Nov. 10, 2008.
US, Reexamination U.S. Appl. No. 90/009,104 Notice of Intent to Issue Ex Parte Reexamination Certificate, dated Nov. 20, 2009.
US, Reexamination U.S. Appl. No. 90/009,104 Office Action, dated Sep. 30, 2009.
US, Reexamination U.S. Appl. No. 90/009,104 Office Action, dated Aug. 4, 2009.
US, Reexamination U.S. Appl. No. 90/009,104 Office Action, dated Oct. 16, 2008.
US, Reexamination U.S. Appl. No. 90/009,104 Order Granting Request for Reexamination, dated Jun. 5, 2008.
US, Request for Reexamination U.S. Appl. No. 90/009,104 of U.S. Pat. No. 6,990,366, dated Apr. 8, 2008.
US, Reexamination U.S. Appl. No. 90/008,457 Notice of Intent to Issue Ex Parte Reexamination Certificate, dated Mar. 13, 2008.
US, Reexamination U.S. Appl. No. 90/008,457 Order Granting Request for Reexamination, dated Feb. 23, 2007.
US, Request for Reexamination U.S. Appl. No. 90/008,457 of U.S. Pat. No. 6,990,366, dated Jan. 23, 2007.
US, Request for Reexamination U.S. Appl. No. 90/008,172 of U.S. Pat. No. 6,990,366, dated Aug. 16, 2006.
US, Reexamination U.S. Appl. No. 90/007,910 Patent Board Decision, dated May 17, 2013.
US, Reexamination U.S. Appl. No. 90/007,910 Decision on Appeal, dated Jan. 18, 2011.

(56)　　　　　References Cited

OTHER PUBLICATIONS

US, Reexamination U.S. Appl. No. 90/007,910 Advisory Action, dated Jul. 30, 2009.
US, Reexamination U.S. Appl. No. 90/007,910 Advisory Action, dated Feb. 6, 2009.
US, Reexamination U.S. Appl. No. 90/007,910 Examiner's Answer to Appeal Brief, dated Nov. 19, 2009.
US, Reexamination U.S. Appl. No. 90/007,910 Office Action, dated Oct. 2, 2008.
US, Reexamination U.S. Appl. No. 90/007,910 Office Action, dated Feb. 13, 2008.
US, Reexamination U.S. Appl. No. 90/007,910 Order Granting Request for Reexamination, dated Mar. 27, 2006.
US, Request for Reexamination U.S. Appl. No. 90/007,910 of U.S. Pat. No. 6,175,752, dated Feb. 1, 2006.
US, Reexamination U.S. Appl. No. 90/009,270 Order Denying Request for Reexamination, dated Dec. 1, 2008.
US, Request for Reexamination U.S. Appl. No. 90/009,270 of U.S. Pat. No. 6,175,752, dated Sep. 8, 2008.
US, Reexamination U.S. Appl. No. 90/009,497 Notice of Intent to Issue Reexamination Certificate, dated Aug. 23, 2010.
US, Reexamination U.S. Appl. No. 90/009,497 Order Granting Request, dated Jul. 30, 2009.
US, Request for Reexamination U.S. Appl. No. 90/009,497 of U.S. Pat. No. 6,175,752, dated Jun. 17, 2009.
WO, PCT/US2006/037312 ISR and Written Opinion, dated Apr. 17, 2007.
WO, PCT/US2006/037928 ISR and Written Opinion, dated Jul. 11, 2008.
WO, PCT/US2007/078065 ISR and Written Opinion, dated Apr. 11, 2008.
WO, PCT/US2007/078073 ISR and Written Opinion, dated Apr. 11, 2008.
WO, PCT/US2007/082114 ISR and Written Opinion, dated May 9, 2008.
WO, PCT/US2010/002401 ISR and Written Opinion, dated Nov. 12, 2010.
WO, PCT/US2010/022860 ISR and Written Opinion, dated Mar. 23, 2010.
WO, PCT/US2010/022928 ISR and Written Opinion, dated Mar. 21, 2010.
WO, PCT/US2010/047381 ISR and Written Opinion, dated Oct. 15, 2010.
WO, PCT/US2010/050772 ISR and Written Opinion, dated Dec. 3, 2010.
WO, PCT/US2010/050888 ISR, and Written Opinion, dated Nov. 29, 2010.
WO, PCT/US2010/051861 ISR and Written Opinion, dated Nov. 30, 2010.
WO, PCT/US2011/029881 ISR and Written Opinion, dated May 20, 2011.
WO, PCT/US2011/029883 ISR and Written Opinion, dated Jun. 2, 2011.
WO, PCT/US2011/029884 ISR and Written Opinion, dated Jun. 1, 2011.
WO, PCT/US2013/052397 ISR and Written Opinion, dated Dec. 2, 2013.
WO, PCT/US2019/035843 ISR and Written Opinion, dated Sep. 18, 2019.
WO, PCT/US2021/040541 ISR and Written Opinion, dated Dec. 20, 2021.
WO, PCT/US2021/045576 ISR and Written Opinion, dated Jan. 27, 2022.
WO, PCT/US2021/048086 ISR and Written Opinion, dated Feb. 28, 2022.
WO, PCT/US2021/050672 ISR and Written Opinion, dated Jan. 5, 2022.
Abruna, H. D., et al., "Rectifying Interfaces Using Two-Layer Films of Electrochemically Polymerized Vinylpyridine and Vinylbipyridine Complexes of Ruthenium and Iron on Electrodes", Journal of the American Chemical Society, 1981, vol. 103, No. 1, pp. 1-5.
ACCU-CHEK Compact Plus Owner's Booklet, 2008, pp. 1-100.
ACCU-CHEK Softclix Plus Lancet Device retrieved from https://web.archive.org/web/20061018055737/http://www.accu-check.com/us/rewrite/content/en_US/2.1.7.1:10/article/ACCM_general_article_3303.htm, 2006, pp. 1-2.
Ahson, S., et al., "RFID Handbook: Applications, Technology, Security, and Privacy", 2008, Chapter 4, Far-Field Tag Antenna Design Methodology, and Chapter 13, RFID Tags for Metallic Object Identification, pp. 71 and 253-254.
Albery, W.J., et al., "Amperometric Enzyme Electrodes Part II: Conducting Salts as Electrode Materials for the Oxidation of Glucose Oxidase", Journal of ElectroAnalytical Chemistry, 1985, vol. 194, pp. 223-235.
Albery, W.J., et al., "Amperometric Enzyme Electrodes", Philosophical Transactions of the Royal Society of London, 1987, vol. 316, pp. 107-119.
Ambade, V. N., et al., "Methods for Estimation of Blood Glucose: A Comparative Evaluation", Medical Journal Armed Forces India, 1998, vol. 54, No. 2, pp. 131-133.
Anderson, L. B., et al., "Thin-Layer Electrochemistry: Steady-State Methods of Studying Rate Processes", Journal of ElectroAnalytical Chemistry, 1965, vol. 10, pp. 295-305.
Application Note AN048, Antenna Part No. FR05-S1-N-0-102, Compact Reach Xtend™, Bluetooth®, 802.11b/g WLAN Chip Antenna, 2008, pp. 1-13.
Application Note AVR2023—AT86RF231 PCB reference design for antenna diversity, Atmel Corporation, 2008, pp. 1-15.
Application Note nRF9E5 RF and antenna layout, Nordic Semiconductor, 2006, pp. 1-13.
ASTM International, Designation D2240-05, 2010, pp. 1-13.
Bartlett, P. N., et al., "Covalent Binding of Electron Relays to Glucose Oxidase", Journal of the Chemical Society, Chemical Communications, 1987, pp. 1603-1604.
Bartlett, P. N., et al., "Modification of Glucose Oxidase by Tetrathiafulvalene", Journal of the Chemical Society, Chemical Communications, 1990, pp. 1135-1136.
Benkič, K., et al., "Using RSSI value for distance estimation in Wireless sensor networks based on ZigBee", 15th International Conference on Systems, Signals and Image Processing, Bratislava, Slovakia, 2008, pp. 1-4.
Biosensors: Fundamentals and Applications, Turner et al., Eds., 1987, pp. 1-786.
"Bluetooth Antenna Design", National Semiconductor Application Note, 2005, pp. 1-16.
Bluetooth Core Specification 4.0, Jun. 30, 2010, Master Table of Contents & Compliance Requirements, pp. 1-89.
Bonnett, A. H., et al., "Squirrel-Cage Rotor Options for AC Induction Motors", IEEE Transactions on Industry Applications, 2001, vol. 37, No. 4, pp. 1197-1209.
Brandt, J., et al., "Covalent Attachment of Proteins to Polysaccharide Carriers by Means of Benzoquinone", Biochimica et Biophysica Acta, 1975, vol. 386, pp. 196-202.
Brownlee, M., et al., "A Glucose-Controlled Insulin-Delivery System: Semisynthetic Insulin Bound to Lectin", Science, 1979, vol. 206, pp. 1190-1191.
Bühling, K. J., et al., "Optimal timing for postprandial glucose measurement in pregnant women with diabetes and a non-diabetic pregnant population evaluated by the Continuous Glucose Monitoring System (CGMS®)", Journal of Perinatal Medicine, 2005, vol. 33, No. 2, pp. 125-131.
Callaway, Jr., E. H., "Wireless Sensor Networks: Architectures and Protocols", 2004, Chapter 8, Antennas and the Definition of RF Performance, pp. 201-202.
Cass, A.E.G. et al., "Ferricinium Ion as an Electron Acceptor for Oxido-Reductases", Journal of ElectroAnalytical Chemistry, 1985, vol. 190, pp. 117-127.
Castner, J. F., et al., "Mass Transport and Reaction Kinetic Parameters Determined Electrochemically for Immobilized Glucose Oxidase", Biochemistry, 1984, vol. 23, No. 10, pp. 2203-2210.

(56) References Cited

OTHER PUBLICATIONS

Cheyne, E.H., et al., "Performance of a Continuous Glucose Monitoring System During Controlled Hypoglycaemia in Healthy Volunteers", Diabetes Technology & Therapeutics, 2002, vol. 4, No. 5, pp. 607-613.

Clark Jr., L. C., et al., "Differential Anodic Enzyme Polarography for the Measurement of Glucose", Oxygen Transport to Tissue: Instrumentation, Methods, and Physiology, 1973, pp. 127-133.

Clarke, W. L., et al., "Evaluating Clinical Accuracy of Systems for Self-Monitoring of Blood Glucose", Diabetes Care, 1987, vol. 10, No. 5, pp. 622-628.

Clarke, W., et al., "Statistical Tools to Analyze Continuous Glucose Monitor Data", Diabetes Technology & Therapeutics, 2009, vol. 11, Suppl. 1, pp. S-45-S-54.

Compact Plus Blood Glucose Meter retrieved from https://web.archive.org/web/20090316065810/http://www.accu-check.com/us/rewrite/content/en_US/2.1.9:0/article/ACCM_general_article_5136.htm, 2009, pp. 1-3.

Complaint Abbott Diabetes Care Inc. v. Dexcom, Inc. U.S. District Court Delaware C.A. No. 05-590 filed Aug. 11, 2005.

Complaint, Amended, Abbott Diabetes Care Inc. v. Dexcom, Inc. U.S. District Court Delaware C.A. No. 05-590 filed Jun. 27, 2006.

Complaint Abbott Diabetes Care Inc. v. Dexcom, Inc. U.S. District Court Delaware C.A. No. 06-514 filed Aug. 17, 2006.

Cox, M., "An Overview of Continuous Glucose Monitoring Systems", Journal of Pediatric Health Care, 2009, vol. 23, No. 5, pp. 344-347.

Csoregi, E., et al., "On-Line Glucose Monitoring by Using Microdialysis Sampling and Amperometric Detection Based on 'Wired' Glucose Oxidase in Carbon Paste", Mikrochimica Acta, 1995, vol. 121, pp. 31-40.

Cullen, M.T., et al., "The Changing Presentations of Diabetic Ketoacidosis During Pregnancy", Amer. J. Perinatol, 1996, vol. 13, No. 7, pp. 449-451 (abstract only).

In Vivo Glucose Sensing, Cunningham et al., Eds., 2010, Chemical Analysis, vol. 174, pp. 1-466.

Darley, J., "Is your user experience as good as your technology?", 2019, retrieved from https://www.massdevice.com/is-your-user-experience-as-good-as-your-technology/, pp. 1-16.

Davis, G., "Electromechanical Techniques for the Development of Amperometric Biosensors", Biosensors, 1985, vol. 1, pp. 161-178.

IPR2022-00605 (Ex. 2001) Declaration of Michael Cima, Ph.D dated May 24, 2022, pp. 1-70.

IPR2022-00637 (Ex. 2001) Declaration of Michael Cima, Ph.D dated Jun. 9, 2022, p. 1-79.

IPR2022-00605 (Ex. 1003) Declaration of Gary D. Fletcher, Ph.D dated Feb. 15, 2022, pp. 1-122.

IPR2022-00605 (Ex. 1003) Corrected Declaration of Gary D. Fletcher, Ph.D dated Feb. 18, 2022, pp. 1-124.

IPR2022-00637 (Ex. 1035) Second Declaration of Gary D. Fletcher, Ph.D dated Feb. 28, 2022, pp. 1-136.

Decuir, J., "Bluetooth 4.0: Low Energy", IEEE SCV Consultants' Network of Silicon Valley, 2012, pp. 1-68.

Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", The Journal of Physical Chemistry, 1987, vol. 91, No. 6, pp. 1285-1289.

Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", Journal of the American Chemical Society, 1988, vol. 110, No. 8, pp. 2615-2620.

Degani, Y., et al., "Electrical Communication Between Redox Centers of Glucose Oxidase and Electrodes via Electrostatically and Covalently Bound Redox Polymers", Journal of the American Chemical Society, 1989, vol. 111, pp. 2357-2358.

Dehez, B., et al., "Development of a Spherical Induction Motor With Two Degrees of Freedom", IEEE Transactions on Magnetics, 2006, vol. 42, No. 8, pp. 2077-2089.

Dementyev, A., et al., "Power Consumption Analysis of Bluetooth Low Energy, ZigBee and ANT Sensor Nodes in a Cyclic Sleep Scenario", IEEE International Wireless Symposium (IWS), 2013, Beijing, China, pp. 1-4.

Denisevich, P., et al., "Unidirectional Current Flow and Charge State Trapping at Redox Polymer Interfaces on Bilayer Electrodes: Principles, Experimental Demonstration, and Theory", Journal of the American Chemical Society, 1981, vol. 103, pp. 4727-4737.

"Dexcom CEO tells investors not to fear new competition from Abbott's Freestyle Libre", 2017, retrieved from https://www.mobihealthnews.com/content/dexcom-ceo-tells-investors-not-to-fear-new-competition-abbotts-freestyle-libre, pp. 1-3.

Dexcom G5 Mobile System User Guide, 2020, pp. 1-410.

Dexcom G6, Winner Health & Wellness Award, Core77 Design Awards, 2019, retrieved from https://designawards.core77.com/health-wellness/85111/Dexcom-G6, pp. 1-8.

DexCom™ STS™ Continuous Glucose Monitoring System User's Guide, 2006, pp. 1-57.

Dicks, J.M., et al., "Ferrocene Modified Polypyrrole with Immobilised Glucose Oxidase and its Application in Amperometric Glucose Microbiosensors", Annales de Biologie Clinique, 1989, vol. 47, pp. 607-619.

ECMA International Standard ECMA-340, Near Field Communication Interface and Protocol (NFCIP-1), 2nd Edition, 2004, pp. 1-65.

Ellis, C. D., et al., "Selectivity and Directed Charge Transfer through an Electroactive Metallopolymer Film", Journal of the American Chemical Society, 1981, vol. 103, No. 25, pp. 7480-7483.

Engstrom, R. C., "Electrochemical Pretreatment of Glassy Carbon Electrodes", Analytical Chemistry, 1982, vol. 54, No. 13, pp. 2310-2314.

Engstrom, R. C., et al., "Characterization of Electrochemically Pretreated Glassy Carbon Electrodes", Analytical Chemistry, 1984, vol. 56, No. 2, pp. 136-141.

Facchinetti, A., et al., "A New Index to Optimally Design and Compare Continuous Glucose Monitoring Glucose Prediction Algorithms", Diabetes Technology & Therapeutics, 2011, vol. 13, No. 2, pp. 111-119.

Feldman, B., et al., "Electron Transfer Kinetics at Redox Polymer/Solution Interfaces Using Microelectrodes and Twin Electrode Thin Layer Cells", Journal of ElectroAnalytical Chemistry, 1985, vol. 194, pp. 63-81.

File History of U.S. Pat. No. 10,292,632.

File History of U.S. Pat. No. 10,945,649.

File History of U.S. Pat. No. 11,013,440.

File Wrapper of U.S. Appl. No. 60/587,787.

File Wrapper of U.S. Appl. No. 12/250,760.

Fischer, H., et al., "Intramolecular Electron Transfer Medicated by 4,4'-Bypyridine and Related Bridging Groups", Journal of the American Chemical Society, 1976, vol. 98, No. 18, pp. 5512-5517.

Foulds, N. C., et al., "Enzyme Entrapment in Electrically Conducting Polymers: Immobilisation of Glucose Oxidase in Polypyrrole and its Application in Amperometric Glucose Sensors", Journal of the Chemical Society, Faraday Transactions 1, 1986, vol. 82, pp. 1259-1264.

Foulds, N. C., et al., "Immobilization of Glucose Oxidase in Ferrocene-Modified Pyrrole Polymers", Analytical Chemistry, 1988, vol. 60, No. 22, pp. 2473-2478.

Freedman, D., et al., Statistics: Second Edition, 1991, Chapter 5, p. 74.

Freestyle Navigator Continuous Glucose Monitor FDA Premarket Approval (PMA), May 2022, pp. 1-6.

Freestyle Navigator Summary of Safety and Effectiveness Data, 2008, pp. 1-27.

Freestyle Navigator User's Guide, 2008, pp. 1-195.

Frenzel, L. E., "Printed-Circuit-Board Antennas, retrieved from https://www.electronicdesign.com/technologies/boards/article/21751417/printedcircuitboard-antennasprint/3266", Electronic Design, 2005, pp. 1-4.

Frew, J. E., et al., "Electron-Transfer Biosensors", Philosophical Transactions of the Royal Society of London, 1987, vol. 316, pp. 95-106.

(56) References Cited

OTHER PUBLICATIONS

Fujipoly Silver ZEBRA® Connector Data Sheet FSDS 01-34, Version 5, 2006, pp. 1-7.

Gilligan, B. J., et al., "Evaluation of a Subcutaneous Glucose Sensor out to 3 Months in a Dog Model", Diabetes Care, 1994, vol. 17, No. 8, pp. 882-887.

Gonzales, W. V., et al., "The Progress of Glucose Monitoring—A Review of Invasive to Minimally and Non-Invasive Techniques, Devices and Sensors", Sensors, 2019, vol. 19, No. 800, pp. 1-45.

Gonzalez, O. L., et al., "Low-Cost Wireless Sensors—Designer Reference Manual", Freescale Semiconductor, 2007, pp. 1-146.

Gorton, L., et al., "Selective Detection in Flow Analysis Based on the Combination of Immobilized Enzymes and Chemically Modified Electrodes", Analytica Chimica Acta, 1991, vol. 250, pp. 203-248.

Gregg, B. A., et al., "Redox Polymer Films Containing Enzymes. 1. A Redox-Conducting Epoxy Cement: Synthesis, Characterization, and Electrocatalytic Oxidation of Hydroquinone", Journal of Physical Chemistry, 1991, vol. 95, No. 15, pp. 5970-5975.

Gregg, T. H., "How Continuous Glucose Monitoring is Transforming Diabetes Treatment", Qualcomm Life Connect, 2013, pp. 1-33.

Guardian® RT Continuous Glucose Monitoring System REF MMT-7900 User Guide, 2005, pp. 1-128.

Guerra, S., et al., "A Dynamic Risk Measure from Continuous Glucose Monitoring Data", Diabetes Technology & Therapeutics, 2011, vol. 13, No. 8, pp. 843-852.

Güler, N. F., et al., "Theory and Applications of Biotelemetry", Journal of Medical Systems, 2002, vol. 26, No. 2, pp. 159-178.

Hale, P. D., et al., "A New Class of Amperometric Biosensor Incorporating a Polymeric Electron-Transfer Mediator", Journal of the American Chemical Society, 1989, vol. 111, No. 9, pp. 3482-3484.

Hao, Y., "Wireless body sensor networks for health-monitoring applications", Physiol. Meas., 2008, vol. 29, R27-R56.

Hawkridge, F. M., et al., "Indirect Coulometric Titration of Biological Electron Transport Components", Analytical Chemistry, 1973, vol. 45, No. 7, pp. 1021-1027.

Heftman, G., "Chip Antenna Reduces Cell-Phone Dimensions", Microwaves & RF, 1999, p. 182.

Heise, T., et al., "Hypoglycemia Warning Signal and Glucose Sensors: Requirements and Concepts", Diabetes Technology & Therapeutics, 2003, vol. 5, No. 4, pp. 563-571.

Heller, A., et al., "Amperometric Biosensors Based on Three-Dimensional Hydrogel-Forming Epoxy Networks", Sensors and Actuators B, 1993, vol. 13-14, pp. 180-183.

Heller, A., "Implanted Electrochemical Glucose Sensors for the Management of Diabetes", Annnu. Rev. Biomed. Eng., 1999, vol. 1, pp. 153-175.

Hirsch, I. B., "Introduction: History of Glucose Monitoring", Clinical Compendia, 2018, vol. 2018, No. 1, 1 page.

Hoel, P. G., Elementary Statistics: Fourth Edition, 1976, Chapter 5, pp. 113-114.

Howe, D., "Comparing the Dexcom G6 to the G5", 2018, retrieved from https://beyondtype1.org/comparing-the-dexcom-g6-to-the-g5/, pp. 1-10.

Huang, Y., et al., "Antennas from Theory to Practice", 2008, Chapter 8, Antenna Diversity, pp. 322-325.

Ianniello, R. M., et al., "Immobilized Enzyme Chemically Modified Electrode as an Amperometric Sensor", Analytical Chemistry, 1981, vol. 53, No. 13, pp. 2090-2095.

Ianniello, R. M., et al., "Differential Pulse Voltammetric Study of Direct Electron Transfer in Glucose Oxidase Chemically Modified Graphite Electrodes", Analytical Chemistry, 1982, vol. 54, No. 7, pp. 1098-1101.

Ikeda, T., et al., "Kinetics of Outer-Sphere Electron Transfers Between Metal Complexes in Solutions and Polymeric Films on Modified Electrodes", Journal of the American Chemical Society, 1981, vol. 103, No. 25, pp. 7422-7425.

Ikeda, T., et al., "Glucose Oxidase- Immobilized Benzoquinone-Carbon Paste Electrode as a Glucose Sensor", Agricultural and Biological Chemistry, 1985, vol. 49, No. 2, pp. 541-543.

"In Vitro Diagnostic Products for Human Use", Federal Register, 1974, vol. 39, No. 126, pp. 24136-24147.

Jain, A.K., et al., "Wound Rotor Induction Generator With Sensorless Control and Integrated Active Filter for Feeding Nonlinear Loads in a Stand-Alone Grid", IEEE Transactions on Industrial Electronics, 2008, vol. 55, No. 1, pp. 218-228.

James, Jr., et al., "Handbook of Microstrip Antennas", 1969, pp. 1038-1047.

Johnson, J. M., et al., "Potential-Dependent Enzymatic Activity in an Enzyme Thin-Layer Cell", Analytical Chemistry, 1982, vol. 54, No. 8, pp. 1377-1383.

Johnson, K. W., "Reproducible Electrodeposition of Biomolecules for the Fabrication of Miniature Electroenzymatic Biosensors", Sensors and Actuators B, 1991, vol. 5, pp. 85-89.

Jönsson, G., et al., "An Amperometric Glucose Sensor Made by Modification of a Graphite Electrode Surface With Immobilized Glucose Oxidase and Adsorbed Mediator", Biosensors, 1985, vol. 1, pp. 355-368.

Josowicz, M., et al., "Electrochemical Pretreatment of Thin Film Platinum Electrodes", Journal of the Electrochemical Society, 1988, vol. 135, No. 1, pp. 112-115.

Jovanovic, L., "The Role of Continuous Glucose Monitoring in Gestational Diabetes Mellitus", Diabetes Technology & Therapeutics, 2000, vol. 2, Supplement 1, pp. S-67-S-71.

Katakis, I., et al., "L-$\alpha$-Glycerophosphate and $_L$-Lactate Electrodes Based on the Electrochemical 'Wiring' of Oxidases", Analytical Chemistry, 1992, vol. 64, No. 9, pp. 1008-1013.

Katakis, I., et al., "Electrostatic Control of the Electron Transfer Enabling Binding of Recombinant Glucose Oxidase and Redox Polyelectrolytes", Journal of the American Chemical Society, 1994, vol. 116, No. 8, pp. 3617-3618.

Kenausis, G., et al., "'Wiring' of Glucose Oxidase and Lactate Oxidase Within a Hydrogel Made with Poly(vinyl pyridine) complexed with $[Os(4,4'$-dimethoxy-2,2'-bipyridine)$_2Cl]^{+/2+}$", Journal of the Chemical Society, Faraday Transactions, 1996, vol. 92, No. 20, pp. 4131-4136.

Klonoff, D. C., "A Review of Continuous Glucose Monitoring Technology", Diabetes Technology & Therapeutics, 2005, vol. 7, No. 5, pp. 770-775.

Kulys, J., et al., "Mediatorless Peroxidase Electrode and Preparation of Bienzyme Sensors", Bioelectrochemistry and Bioenergetics, 1990, vol. 24, pp. 305-311.

León, L. P., et al., "Continuous-Flow Analysis for Glucose in Serum, with Use of Hexokinase and Glucose-6-Phosphate Dehydrogenase Co-Immobilized in Tubular Form", Clinical Chemistry, 1980, vol. 26, No. 1, pp. 123-129.

Lindner, E., et al., "Flexible (Kapton-Based) Microsensor Arrays of High Stability for Cardiovascular Applications", Journal of the Chemical Society, Faraday Transactions, 1993, vol. 89, No. 2, pp. 361-367.

Loy, M., et al., "ISM-Band and Short Range Device Antennas", Texas Instruments Application Report, 2005, pp. 1-38.

McNeil, C. J., et al., "Thermostable Reduced Nicotinamide Adenine Dinucleotide Oxidase: Application to Amperometric Enzyme Assay", Analytical Chemistry, 1989, vol. 61, No. 1, pp. 25-29.

Medtronic Guardian® REAL-Time Continuous Glucose Monitoring System User Guide, 2006, pp. 1-184.

IPR2022-00605 (Ex. 1027) The Merriam-Webster Dictionary, Merriam Webster, Incorporated (2005), pp. 66, 403, and 415.

Microchip Technology Inc., MRF24J40MA Data Sheet, 2008, pp. 1-30.

Miyawaki, O., et al., "Electrochemical and Glucose Oxidase Coenzyme Activity of Flavin Adenine Dinucleotide Covalently Attached to Glassy Carbon at the Adenine Amino Group", Biochimica et Biophysica Acta, 1985, vol. 838, pp. 60-68.

Moore, B., "The Potential Use of Radio Frequency Identification Devices for Active Monitoring of Blood Glucose Levels", Journal of Diabetes Science and Technology, 2009, vol. 3, No. 1, pp. 180-183.

(56) References Cited

OTHER PUBLICATIONS

Morak, J., et al., "Design and Evaluation of a Telemonitoring Concept Based on NFC-Enabled Mobile Phones and Sensor Devices", IEEE Transactions on Information Technology in Biomedicine, 2012, vol. 16, No. 1, pp. 17-23.

Morbiducci, U., et al., "Improved Usability of the Minimal Model of Insulin Sensitivity Based on an Automated Approach and Genetic algorithms for Parameter Estimation", Clinical Science, vol. 112, 2007, pp. 257-263.

Mougiakakou, S. G., et al., "A Real Time Simulation Model of Glucose-Insulin Metabolism for Type 1 Diabetes Patients", Proceedings of the 2005 IEEE, 2005, pp. 298-301.

Movassaghi, S., et al., "Wireless Technologies for Body Area Networks: Characteristics and Challenges", 2012 International Symposium on Communications and Information Technologies (ISCIT), 2012, Gold Coast, QLD, Australia, pp. 42-47.

"Murata Puts Antenna on a Chip", Passives, 1999, vol. 44, 1 page.

Nagy, G., et al., "A New Type of Enzyme Electrode: The Ascorbic Acid Eliminator Electrode", Life Sciences, 1982, vol. 31, No. 23, pp. 2611-2616.

Nakamura, S., et al., "Effect of Periodate Oxidation on the Structure and Properties of Glucose Oxidase", Biochimica et Biophysica Acta., 1976, vol. 445, pp. 294-308.

Narasimham, K., et al., "p-Benzoquinone Activation of Metal Oxide Electrodes for Attachment of Enzymes", Enzyme and Microbial Technology, 1985, vol. 7, pp. 283-286.

Ohara, T. J., et al., "'Wired' Enzyme Electrodes for Amperometric Determination of Glucose or Lactate in the Presence of Interfering Substances", Analytical Chemistry, 1994, vol. 66, No. 15, pp. 2451-2457.

Ohara, T. J., "Osmium Bipyridyl Redox Polymers Used in Enzyme Electrodes", Platinum Metals Review, 1995, vol. 39, No. 2, pp. 54-62.

OmniPod Insulet UST400 User Manual, 2011, pp. 1-190.

Opinion of the Court, Supreme Court of the United States, No. 04-1350, KSR International co., Petitioner v. Teleflex Inc, et al., Apr. 30, 2007.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", Journal of ElectroAnalytical Chemistry, 1989, vol. 260, pp. 487-494.

Palleschi, G., et al., "A Study of Interferences in Glucose Measurements in Blood by Hydrogen Peroxide Based Glucose Probes", Analytical Biochemistry, 1986, vol. 159, pp. 114-121.

Pankratov, I., et al., "Sol-Gel Derived Renewable-Surface Biosensors", Journal of ElectroAnalytical Chemistry, 1995, vol. 393, pp. 35-41.

Parker, R., et al., "Robust H∞ Glucose Control in Diabetes Using a Physiological Model", AlChE Journal, 2000, vol. 46, No. 12, 2000, pp. 2537-2549.

Passey, R. B., et al., "Evaluation and Comparison of 10 Glucose Methods and the Reference Method Recommendation in the Proposed Product Class Standard (1974)", Clinical Chemistry, 1977, vol. 23, No. 1, pp. 131-139.

Pathak, C., et al., "Rapid Photopolymerization of Immunoprotective Gels in Contact with Cells and Tissue", Journal of the American Chemical Society, 1992, vol. 114, No. 21, pp. 8311-8312.

Patton, S. R., et al., "Continuous Glucose Monitoring Versus Self-monitoring of Blood Glucose in Children with Type 1 Diabetes—Are there Pros and Cons for Both?", US Endocrinol., 2012, vol. 8, No. 1, pp. 27-29.

Pollak, A., et al., "Enzyme Immobilization by Condensation Copolymerization into Cross-Linked Polyacrylamide Gels", Journal of the American Chemical Society, 1980, vol. 102, No. 20, pp. 6324-6336.

IPR2022-00605 (Ex. 1024) "Rotor," Dictionary of Mechanical Engineering, Fourth Ed., G.H.F. Nayler, Society of Automotive Engineers, Inc., 1996, p. 328.

IPR2022-00605 (Ex. 1025) "Rotor," Random House Kernerman Webster's College Dictionary, K Dictionaries Ltd. (2010), available at https://www.thefreedictionary.com/rotor.

IPR2022-00605 (Ex. 1026) "Rotate," Random House Kernerman Webster's College Dictionary, K Dictionaries Ltd. (2010), available at https://www.thefreedictionary.com/rotate.

Samuels, G. J., et al., "An Electrode-Supported Oxidation Catalyst Based on Ruthenium (IV). pH "Encapsulation" in a Polymer Film", Journal of the American Chemical Society, 1981, vol. 103, No. 2, pp. 307-312.

Sandham, W., et al., "Blood Glucose Prediction for Diabetes Therapy Using a Recurrent Artificial Neural Network", 9th European Signal Processing Conference, 1998, Rhodes, Greece, pp. 1-4.

Sasso, S. V., et al., "Electropolymerized 1,2-Diaminobenzene as a Means to Prevent Interferences and Fouling and to Stabilize Immobilized Enzyme in Electrochemical Biosensors", Analytical Chemistry, 1990, vol. 62, No. 11, pp. 1111-1117.

IPR2022-00605 (Ex. 1013) Scheduling Order in Abbott Diabetes Care Inc., et al. v. Dexcom, Inc., 1:21-cv-00977 (D. Del.), dated Dec. 2, 2021.

Schmehl, R. H., et al., "The Effect of Redox Site Concentration on the Rate of Mediated Oxidation of Solution Substrates by a Redox Copolymer Film", Journal of ElectroAnalytical Chemistry, 1983, vol. 152, pp. 97-109.

Schoepke, E., "Chip Antenna Layout Considerations for 802.11 Applications", Johanson Technology, 2006, retrieved from https://www.johansontechnology.com/chip-antenna-layout-considerations-for-802-11-applications, pp. 1-7.

Sharawi, M. S., "Use of low-cost patch antennas in modern wireless technology", IEEE Potentials, 2006, pp. 35-38 and 47.

Sittampalam, G., et al., "Surface-Modified Electrochemical Detector for Liquid Chromatography", Analytical Chemistry, 1983, vol. 55, No. 9, pp. 1608-1610.

Soegijoko, S., et al., "External Artificial Pancreas: A New Control Unit Using Microprocessor", Hormone and Metabolic Research Supplement Series, 1982, vol. 12, pp. 165-169.

Sparacino, G., et al., "Glucose Concentration Can Be Predicted Ahead in Time from Continuous Glucose Monitoring Sensor Time-Series", IEEE Transactions on Biomedical Engineering, 2007, vol. 54, No. 5, pp. 931-937.

Sprules, S. D., et al., "Evaluation of a New Disposable Screen-Printed Sensor Strip for the Measurement of NADH and Its Modification to Produce a Lactate Biosensor Employing Microliter Volumes", Electroanalysis, 1996, vol. 8, No. 6, pp. 539-543.

Sternberg, F., et al., "Calibration Problems of Subcutaneous Glucosensors when Applied "In-Situ" in Man", Hormone and Metabolic Research, 1994, vol. 26, pp. 523-526.

Sternberg, R., et al., "Covalent Enzyme Coupling on Cellulose Acetate Membranes for Glucose Sensor Development", Analytical Chemistry, 1988, vol. 60, No. 24, pp. 2781-2786.

Suekane, M., et al., "Immobilization of Glucose Isomerase", Zettschrift fur Allgemeine Mikrobiologie, 1982, vol. 22, No. 8, pp. 565-576.

Tajima, S., et al., "Simultaneous Determination of Glucose and 1,5-Anydroglucitol", Chemical Abstracts, 1989, vol. 111, No. 25, p. 394.

Tarasevich, M. R., "Bioelectrocatalysis", Comprehensive Treatise of Electrochemistry, 1985, vol. 10, pp. 231-295.

Tatsuma, T., et al., "Enzyme Monolayer- and Bilayer-Modified Tin Oxide Electrodes for the Determination of Hydrogen Peroxide and Glucose", Analytical Chemistry, 1989, vol. 61, No. 21, pp. 2352-2355.

Taylor, C., et al., ""Wiring" of Glucose Oxidase Within a Hydrogel Made with Polyvinyl Imidazole Complexed with [(Os-4,4'-dimethoxy-2,2'-bipyridine)Cl]+/2+", Journal of ElectroAnalytical Chemistry, 1995, vol. 396, pp. 511-515.

Townsend, K., et al., "Getting Started with Bluetooth Low Energy—Chapter 1", 2014, pp. 1-26.

Trojanowicz, M., et al., "Enzyme Entrapped Polypyrrole Modified Electrode for Flow-Injection Determination of Glucose", Biosensors & Bioelectronics, 1990, vol. 5, pp. 149-156.

Turner, R.F.B., et al., "A Biocompatible Enzyme Electrode for Continuous in vivo Glucose Monitoring in Whole Blood", Sensors and Actuators B, 1990, vol. 1, pp. 561-564.

(56)        References Cited

OTHER PUBLICATIONS

Tuzhi, P., et al., "Constant Potential Pretreatment of Carbon Fiber Electrodes for in Vivo Electrochemistry", Analytical Letters, 1991, vol. 24, No. 6, pp. 935-945.

Umana, M., "Protein-Modified Electrochemically Active Biomaterial Surface", U.S. Army Research Office, Analytical and Chemical Sciences Research Triangle Institute, 1988, pp. 1-9.

United States Court of Appeals for the Federal Circuit, No. 06-1402, Leapfrog Enterprises, Inc. v. Fisher-Price, Inc. and Mattel, Inc., May 9, 2007.

Urban, G., et al., "Miniaturized Thin-Film Biosensors Using Covalently Immobilized Glucose Oxidase", Biosensors & Bioelectronics, 1991, vol. 6, pp. 555-562.

Vreeke, M. S., et al., "Hydrogen Peroxide Electrodes Based on Electrical Connection of Redox Centers of Various Peroxidases to Electrodes through a Three-Dimensional Electron-Relaying Polymer Network", Diagnostic Biosensors Polymers, Chapter 15, 1993, pp. 180-193.

Vreeke, M., et al., "Hydrogen Peroxide and $\beta$-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry, 1992, vol. 64, No. 24, pp. 3084-3090.

Wang, D. L., et al., "Miniaturized Flexible Amperometric Lactate Probe", Analytical Chemistry, 1993, vol. 65, No. 8, pp. 1069-1073.

Wang, J., et al., "Activation of Glassy Carbon Electrodes by Alternating Current Electrochemical Treatment", Analytica Chimica Acta, 1985, vol. 167, pp. 325-334.

Wang, J., et al., "Amperometric Biosensing of Organic Peroxides with Peroxidase-Modified Electrodes", Analytica Chimica Acta, 1991, vol. 254, pp. 81-88.

Wang, J., et al., "Screen-Printable Sol-Gel Enzyme-Containing Carbon Inks", Analytical Chemistry, 1996, vol. 68, No. 15, pp. 2705-2708.

Wang, J., et al., "Sol-Gel-Derived Metal-Dispersed Carbon Composite Amperometric Biosensors", Electroanalysis, 1997, vol. 9, No. 1, pp. 52-55.

Wang, X.H., et al., "Bluetooth: Opening a blue sky for healthcare", Mobile Information Systems, 2006, vol. 2, pp. 151-167.

Waterhouse, R., "Printed Antennas for Wireless Communications," 2007, pp. 116-129 and 284-289.

Williams, D. L., et al., "Electrochemical-Enzymatic Analysis of Blood Glucose and Lactate", Analytical Chemistry, 1970, vol. 42, No. 1, pp. 118-121.

Wong, KL, "Planar Antennas for Wireless Communications," 2003, Chapter 1, Introduction and Overview, pp. 4-17, 38-45, and 218-221.

Yabuki, S., et al., "Electro-Conductive Enzyme Membrane", Journal of the Chemical Society, Chemical Communications, 1989, pp. 945-946.

Yang, L., et al., "Determination of Oxidase Enzyme Substrates Using Cross-Flow Thin-Layer Amperometry", Electroanalysis, 1996, vol. 8, No. 8-9, pp. 716-721.

Yao, S. J., et al., "The Interference of Ascorbate and Urea in Low-Potential Electrochemical Glucose Sensing", Proceedings of the Twelfth Annual International Conference of the IEEE Engineering in Medicine and Biology Society, 1990, vol. 12, Part 2, pp. 487-489.

Yao, T., "A Chemically-Modified Enzyme Membrane Electrode as an Amperometric Glucose Sensor", Analytica Chimica Acta, 1983, vol. 148, pp. 27-33.

Yildiz, A., et al., "Evaluation of an Improved Thin-Layer Electrode", Analytical Chemistry, 1968, vol. 40, No. 7, pp. 1018-1024.

Zamzow, K., et al., "New Wearable Continuous Blood Glucose Monitor (BGM) and Artificial Pancreas (AP)", Diabetes, 1990, vol. 39, pp. 5A-20.

Z-Carbon Connector, retrieved from http://www.zaxisconnector.com/SS_zc.shtml, 2004, 2 pages.

Zhang, Y., et al., "Application of Cell Culture Toxicity Tests to the Development of Implantable Biosensors", Biosensors & Bioelectronics, 1991, vol. 6, pp. 653-661.

Zhang, Y., et al., "Elimination of the Acetaminophen Interference in an Implantable Glucose Sensor", Analytical Chemistry, 1994, vol. 66, No. 7, pp. 1183-1188.

Zhu, J., et al., "Fabrication and Characterization of Glucose Sensors Based on a Microarray $H_2O_2$ electrode", Biosensors & Bioelectronics, 1994, vol. 9, pp. 295-300.

Zisser, H. C., "The OmniPod Insulin Management System: the Latest Innovation in Insulin Pump Therapy", Diabetes Ther, 2010, vol. 1, No. 1, pp. 10-24.

Z-Silver Connector, retrieved from http://www.zaxisconnector.com/SS_zs.shtml, 2004, 2 pages.

AU, 2011269796 Examination Report, dated Apr. 3, 2014.

EP, 10739015.5 Extended Search Report, dated May 10, 2013.

EP, 11760268.0 Extended Search Report, dated Apr. 14, 2014.

EP, 18741791.0 Extended Search Report, dated Sep. 23, 2020.

WO, PCT/US2016/032485 ISR and Written Opinion, dated Sep. 12, 2016.

WO, PCT/US2018/014745 ISR and Written Opinion, dated Jun. 4, 2018.

Alcock, S. J., et al., "Continuous Analyte Monitoring to Aid Clinical Practice", IEEE Engineering in Medicine and Biology Magazine, 1994, pp. 319-325.

Armour, J. C., et al., "Application of Chronic Intravascular Blood Glucose Sensor in Dogs", Diabetes, vol. 39, 1990, pp. 1519-1526.

Aussedat, B., et al., "A User-Friendly Method for Calibrating a Subcutaneous Glucose Sensor-Based Hypoglycaemic Alarm", Biosensors & Bioelectronics, vol. 12, No. 11, 1997, pp. 1061-1071.

Bennion, N., et al., "Alternate Site Glucose Testing: A Crossover Design", Diabetes Technology & Therapeutics, vol. 4, No. 1, 2002, pp. 25-33.

Bindra, D. S., et al., "Design and in Vitro Studies of a Needle-Type Glucose Sensor for Subcutaneous Monitoring", Analytical Chemistry, vol. 63, No. 17, 1991, pp. 1692-1696.

Bindra, D. S., et al., "Pulsed Amperometric Detection of Glucose in Biological Fluids at a Surface-Modified Gold Electrode", Analytical Chemistry, vol. 61, No. 22, 1989, pp. 2566-2570.

Bobbioni-Harsch, E., et al., "Lifespan of Subcutaneous Glucose Sensors and Their Performances During Dynamic Glycaemia Changes in Rats", Journal of Biomedical Engineering, vol. 15, 1993, pp. 457-463.

Cass, A. E., et al., "Ferrocene-Medicated Enzyme Electrode for Amperometric Determination of Glucose", Analytical Chemistry, vol. 56, No. 4, 1984, pp. 667-671.

Claremont, D. J., et al., "Biosensors for Continuous In Vivo Glucose Monitoring", Proceedings of the Annual International Conference of the IEEE Engineering in Medicine and Biology Society, vol. 10, 1988.

Clark Jr., L. C., et al., "Electrode Systems for Continuous Monitoring in Cardiovascular Surgery", Annals New York Academy of Sciences, 1962, pp. 29-45.

Clark Jr., L. C., et al., "Long-term Stability of Electroenzymatic Glucose Sensors Implanted in Mice", American Society of Artificial Internal Organs Transactions, vol. XXXIV, 1988, pp. 259-265.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.

Csoregi, E., et al., "Design, Characterization, and One-Point in Vivo Calibration of a Subcutaneously Implanted Glucose Electrode", Analytical Chemistry, vol. 66, No. 19, 1994, pp. 3131-3138.

Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.

Feldman, B., et al., "Correlation of Glucose Concentrations in Interstitial Fluid and Venous Blood During Periods of Rapid Glucose Change", Abbott Diabetes Care Inc. Freestyle Navigator Continuous Glucose Monitor Pamphlet, 2004.

(56)     References Cited

OTHER PUBLICATIONS

Gregg, B. A., et al., "Cross-Linked Redox Gels Containing Glucose Oxidase for Amperometric Biosensor Applications", Analytical Chemistry, vol. 62, No. 3, 1990, pp. 258-263.

Gunasingham, et al., "Electrochemically Modulated Optrode for Glucose", Biosensors & Bioelectronics, vol. 7, 1992, pp. 353-359.

Harrison, D. J., et al., "Characterization of Perfluorosulfonic Acid Polymer Coated Enzyme Electrodes and a Miniatureized Integrated Potentiostat for Glucose Analysis in Whole Blood", Analytical Chemistry, vol. 60, No. 19, 1988, pp. 2002-2007.

Heller, A., "Electrical Wiring of Redox Enzymes", Accounts of Chemical Research, 1990, vol. 23, No. 5, pp. 128-134.

Heller, A., "Electrical Connection Enzyme Redox Centers to Electrodes", Journal of Physical Chemistry, vol. 96, No. 9, 1990, pp. 3579-3587.

Ikeda, T., et al., "Artificial Pancreas—Investigation of the Stability of Glucose Sensors Using a Telemetry System" (English translation of abstract), Jpn. J. Artif. Organs, vol. 19, No. 2, 1990, pp. 889-892.

Isermann, R., "Supervision, Fault-Detection and Fault-Diagnosis Methods—An Introduction", Control Engineering Practice, vol. 5, No. 5, 1997, pp. 639-652.

Isermann, R., et al., "Trends in the Application of Model-Based Fault Detection and Diagnosis of Technical Processes", Control Engineering Practice, vol. 5, No. 5, 1997, pp. 709-719.

Johnson, K. W., "Peripheral Circulation", John Wiley & Sons, 1978, pp. 19889.

Johnson, K. W., et al., "In vivo Evaluation of an Electroenzymatic Glucose Sensor Implanted in Subcutaneous Tissue", Biosensors & Bioelectronics, vol. 7, 1992, pp. 709-714.

Jungheim, K., et al., "How Rapid Does Glucose Concentration Change in Daily Life of Patients with Type 1 Diabetes?", Diabetologia, 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Koudelka, M., et al., "In-Vivo Behaviour of Hypodermically Implanted Microfabricated Glucose Sensors", Biosensors & Bioelectronics, vol. 6, 1991, pp. 31-36.

Lager, W., et al., "Implantable Electrocatalytic Glucose Sensor", Hormone Metabolic Research, vol. 26, 1994, pp. 526-530.

Maidan, R., et al., "Elimination of Electrooxidizable Interferant-Produced Currents in Amperometric Biosensors", Analytical Chemistry, vol. 64, No. 23, 1992, pp. 2889-2896.

Mastrototaro, J. J., et al., "An Electroenzymatic Glucose Sensor Fabricated on a Flexible Substrate", Sensors and Actuators B, vol. 5, 1991, pp. 139-144.

McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.

Minimed Technologies, "Tape Tips and Other Infusion Site Information", 1995.

Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, vol. 7, 1992, pp. 345-352.

Moatti-Sirat, D., et al., "Reduction of Acetaminophen Interference in Glucose Sensors by a Composite Nafion Membrane: Demonstration in Rats and Man", Diabetologia, vol. 37, 1994, pp. 610-616.

Moatti-Sirat, D., et al., "Towards Continuous Glucose Monitoring: In Vivo Evaluation of a Miniaturized Glucose Sensor Implanted for Several Days in Rat Subcutaneous Tissue", Diabetologia, vol. 35, 1992, pp. 224-330.

Ohara, T. J., et al., "Glucose Electrodes Based on Cross-Linked [Os(bpy)$_2$Cl]$^{+/2+}$Complexed Poly(1-Vinylimidazole) Films", Analytical Chemistry, vol. 65, No. 23, 1993, pp. 3512-3517.

Olievier, C. N., et al., "In Vivo Measurement of Carbon Dioxide Tension with a Miniature Electrodes", Pflugers Archiv: European Journal of Physiology, vol. 373, 1978, pp. 269-272.

Pickup, J., et al., "Implantable Glucose Sensors: Choosing the Appropriate Sensing Strategy", Biosensors, vol. 3, 1987/88, pp. 335-346.

Pickup, J., "Developing Glucose Sensors for In Vivo Use", Tibtech, vol. 11, 1993, pp. 285-291.

Pickup, J., et al., "Potentially-Implantable, Amperometric Glucose Sensors with Mediated Electron Transfer: Improving the Operating Stability", Biosensors, vol. 4, 1989, pp. 109-119.

Pickup, J., et al., "In Vivo Molecular Sensing in Diabetes Mellitus: An Implantable Glucose Sensor with Direct Electron Transfer", Diabetologia, vol. 32, 1989, pp. 213-217.

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.

Poitout, V., et al., "A Glucose Monitoring System for on Line Estimation in Man of Blood Glucose Concentration Using a Miniaturized Glucose Sensor Implanted in the Subcutaneous Tissue and a Wearable Control Unit", Diabetolgia, vol. 36, 1993, pp. 658-663.

Poitout, V., et al., "Calibration in Dogs of a Subcutaneous Miniaturized Glucose Sensor Using a Glucose Meter for Blood Glucose Determination", Biosensors & Bioelectronics, vol. 7, 1992, pp. 587-592.

Poitout, V., et al., "In Vitro and In Vivo Evaluation in Dogs of a Miniaturized Glucose Sensor", ASAIO Transactions, vol. 37, No. 3, 1991, pp. M298-M300.

Quinn, C. P., et al., "Kinetics of Glucose Delivery to Subcutaneous Tissue in Rats Measured with 0.3-mm Amperometric Microsensors", The American Physiological Society, 1995, pp. E155-E161.

Ratner, B. D., "Reducing Capsular Thickness and Enhancing Angeiogenesis Around Implant Drug Release Systems", Journal of Controlled Release, vol. 78, 2002, pp. 211-218.

Reach, G., et al., "Can Continuous Glucose Monitoring Be Used for the Treatment of Diabetes?", Analytical Chemistry, vol. 64, No. 6, 1992, pp. 381-386.

Rebrin, K., et al., "Automated Feedback Control of Subcutaneous Glucose Concentration in Diabetic Dogs", Diabetologia, vol. 32, 1989, pp. 573-576.

Roe, J. N., et al., "Bloodless Glucose Measurements", Critical Review in Therapeutic Drug Carrier Systems, vol. 15, No. 3, 1998, pp. 199-241.

Sakakida, M., et al., "Development of Ferrocene-Mediated Needle-Type Glucose Sensor as a Measure of True Subcutaneous Tissue Glucose Concentrations," Artificial Organs Today, vol. 2, No. 2, 1992, pp. 145-158.

Sakakida, M., et al., "Ferrocene-Mediated Needle-Type Glucose Sensor Covered with Newly Designed Biocompatible Membrane", Sensors and Actuators B, vol. 13-14, 1993, pp. 319-322.

Salehi, C., et al., "A Telemetry-Instrumentation System for Long-Term Implantable Glucose and Oxygen Sensors", Analytical Letters, vol. 29, No. 13, 1996, pp. 2289-2308.

Scheller, F., et al., "Enzyme Electrodes and Their Application", Philosophical Transactions of the Royal Society of London B, vol. 316, 1987, pp. 85-94.

Schmidt, F. J., et al., "Calibration of a Wearable Glucose Sensor", The International Journal of Artificial Organs, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.

Shichiri, M., et al., "Wearable Artificial Endocrine Pancreas With Needle-Type Glucose Sensor", The Lancet, 1982, pp. 1129-1131.

Shichiri, M., et al., "Glycaemic Control in Pancreatectomized Dogs with a Wearable Artificial Endocrine Pancreas", Diabetologia, vol. 24, 1983, pp. 179-184.

Shichiri, M., et al., "In Vivo Characteristics of Needle-Type Glucose Sensor-Measurements of Subcutaneous Glucose Concentrations in Human Volunteers", Hormone and Metabolic Research Supplement Series, vol. 20, 1988, pp. 17-20.

(56) References Cited

OTHER PUBLICATIONS

Shichiri, M., et al., "Membrane design for extending the long-life of an implantable glucose sensor", Diabetes Nutrition and Metabolism, vol. 2, 1989, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.

Sternberg, R., et al., "Study and Development of Multilayer Needle-type Enzyme-based Glucose Microsensors", Biosensors, vol. 4, 1988, pp. 27-40.

Thompson, M., et al., "In Vivo Probes: Problems and Perspectives", Clinical Biochemistry, vol. 19, 1986, pp. 255-261.

Turner, A.P.F., et al., "Diabetes Mellitus: Biosensors for Research and Management", Biosensors, vol. 1, 1985, pp. 85-115.

Updike, S. J., et al., "Principles of Long-term Fully Implanted Sensors with Emphasis on Radiotelemetric Monitoring of Blood Glucose from inside a Subcutaneous Foreign Body Capsule (FBC)", Biosensors in the Body: Continuous in vivo Monitoring, Chapter 4, 1997, pp. 117-137.

Updike, S. J., et al., "A Subcutaneous Glucose Sensor With Improved Longevity, Dynamic Range, and Stability of Calibration", Diabetes Care, 2000, vol. 23, pp. 208-214.

Velho, G., et al., "Strategies for calibrating a subcutaneous glucose sensor", Biomedica Biochimica Acta, vol. 48, 1989, pp. 957-964.

Velho, G., et al., "In Vitro and In Vivo Stability of Electrode Potentials in Needle-Type Glucose Sensors", Diabetes, vol. 38, No. 2, 1989, pp. 164-171.

Von Woedtke, T., et al., "In Situ Calibration of Implanted Electrochemical Glucose Sensors", Biomedica Biochimica Acta, vol. 48, 1989, pp. 943-952.

Wilson, G. S., et al., "Progress toward the Development of an Implantable Sensor for Glucose", Clinical Chemistry, vol. 38, No. 9, 1992, pp. 1613-1617.

Ye, L., et al., "High Current Density 'Wired' Quinoprotein Glucose Dehydrogenase Electrode", Analytical Chemistry, vol. 65, No. 3, 1993, pp. 238-241.

PCT/US2012/068839 ISR and Written Opinion dated Feb. 22, 2013.

NL 2009963 Search Report and Written Opinion dated Aug. 12, 2013.

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.

Brooks, S. L., et al., "Development of an On-Line Glucose Sensor for Fermentation Monitoring", Biosensors, vol. 3, 1987/88, pp. 45-56.

Diem, P., et al., "Clinical Performance of a Continuous Viscometric Affinity Sensor for Glucose", Diabetes Technology & Therapeutics, vol. 6, 2004, pp. 790-799.

El-Khatib, F. H, et al., "Adaptive Closed-Loop Control Provides Blood-Glucose Regulation Using Subcutaneous Insulin and Glucagon Infusion in Diabetic Swine", Journal of Diabetes Science and Technology, vol. 1, No. 2, 2007, pp. 181-192.

Garg, S., et al., "Improvement in Glycemic Excursions with a Transcutaneous, Real-Time Continuous Glucose Sensor", Diabetes Care, vol. 29, No. 1, 2006, pp. 44-50.

Kaplan, S. M., "Wiley Electrical and Electronics Engineering Dictionary", IEEE Press, 2004, pp. 141, 142, 548, 549.

Kondepati, V., et al., "Recent Progress in Analytical Instrumentation for Glycemic Control in Diabetic and Critically Ill Patients", Analytical Bioanalytical Chemistry, vol. 388, 2007, pp. 545-563.

Lo, B., et al., "Key Technical Challenges and Current Implementations of Body Sensor Networks", Body Sensor Networks, 2005, pp. 1-5.

Lodwig, V., et al., "Continuous Glucose Monitoring with Glucose Sensors: Calibration and Assessment Criteria", Diabetes Technology & Therapeutics, vol. 5, No. 4, 2003, pp. 573-587.

Lortz, J., et al., "What is Bluetooth? We Explain the Newest Short-Range Connectivity Technology", Smart Computing Learning Series, Wireless Computing, vol. 8, Issue 5, 2002, pp. 72-74.

Malin, S. F., et al., "Noninvasive Prediction of Glucose by Near-Infrared Diffuse Reflectance Spectoscopy", Clinical Chemistry, vol. 45, No. 9, 1999, pp. 1651-1658.

McGarraugh, G., et al., "Glucose Measurements Using Blood Extracted from the Forearm and the Finger", TheraSense, Inc., 2001, 16 Pages.

McGarraugh, G., et al., "Physiological Influences on Off-Finger Glucose Testing", Diabetes Technology & Therapeutics, vol. 3, No. 3, 2001, pp. 367-376.

Rodriguez, N., et al., "Flexible Communication and Control Protocol for Injectable Neuromuscular Interfaces", IEEE Transactions on Biomedical Circuits and Systems, IEEE, vol. 1, No. 1, 2007, pp. 19-27.

Roe, J. N., et al., "Bloodless Glucose Measurements", Critical Review in Therapeutic Drug Carrier Systems, vol. 15, Issue 3, 1998, pp. 199-241.

Salditt, P., "Trends in Medical Device Design and Manufacturing", SMTA News and Journal of Surface Mount Technology, vol. 17, 2004, pp. 19-24.

Tung, S., "Layers of Security for Active RFID Tags", RFID Handbook: Applications, Technology, Security, and Privacy, Edited by Ehson, et al., Chapter 33, 2008, pp. 1-28.

Affidavit of Richard Paragas signed on May 18, 2016, pp. 1-4.

Affidavit of Paul Neale signed on May 18, 2016, pp. 1-2.

Choleau, C., et al., "Calibration of a Subcutaneous Amperometric Glucose Sensor Implanted for 7 Days in Diabetic Patients Part 2. Superiority of the One-Point Calibration Method", Biosensor & Bioelectronics, 2002, vol. 17, No. 8, pp. 647-654.

Choleau, C., et al., "Calibration of a Subcutaneous Amperometric Glucose Sensor Part 1. Effect of Measurement Uncertainties on the Determination of Sensor Sensitivity and Background Current", Biosensor & Bioelectronics, 2002, vol. 17, No. 8, pp. 641-646.

Cleo™ 90 Infusion Set, 510(k) Summary of Safety and Effectiveness, Aug. 10, 2004, pp. 1-618.

Cleo® 90 Infusion Set Training Guide, 2011, 1 page.

De Block, C., et al., "Minimally-Invasive and Non-Invasive Continuous Glucose Monitoring Systems: Indications, Advantages, Limitations and Clinical Aspects", Current Diabetes Reviews, 2008, vol. 4, No. 3, pp. 159-168.

Delve Talks: Jake Leach, Dexcom, retrieved from https://www.delve.com/podcasts/delve-talks-jake-leach-dexcom, 2019, pp. 1-9.

File Wrapper of U.S. Appl. No. 10/633,367.

Garibotto, J., et al., "An Innovative Application of Shape Memory Alloy Technology Yields a Novel Therapeutic Approach to Diabetes Management", Insulet Corporation, 2006, p. A41.

Guerci, B., et al., "Clinical Performance of CGMS in Type 1 Diabetic Patients Treated by Continuous Subcutaneous Insulin Infusion Using Insulin Analogs", Diabetes Care, 2003, vol. 26, No. 3, pp. 582-589.

Kovatchev, B. P., et al., "Evaluating the Accuracy of Continuous Glucose-Monitoring Sensors", Diabetes Care, 2004, vol. 27, No. 8, pp. 1922-1928.

Mauras, N., et al., "Lack of Accuracy of Continuous Sensors in Healthy, Nondiabetic Children: Results of the Diabetes Research in Children Network (DirecNet) Accuracy Study", Journal of Pediatrics, 2004, pp. 770-775.

IPR2022-00605 (Ex. 2008) MiniMed® Glucose Sensor, REF MMT-7002, Instructions for Use, May 1999, pp. 1-4.

MINIMED Quick-set™ retrieved from https://web.archive.org/web/20010412224824/http://www.minimed.com/patientfam/pf_ipt_pumpinfusion_quickset.shtml, Apr. 12, 2001, pp. 1-2.

(56)    References Cited

OTHER PUBLICATIONS

MINIMED Sof-set Micro QR® Sof-set Ultimate QR® retrieved from https://web.archive.org/web/20010412225617/http://www.minimed.com/patientfam/pf_ipt_pumpinfusion_sofset.shtml, Apr. 12, 2001, pp. 1-2.

IPR2022-00605 (Ex. 2003) "Monitoring Your Blood Sugar", retrieved from https://www.cdc.gov/diabetes/managing/managing-blood-sugar/bloodglucosemonitoring.html, 2021, pp. 1-3.

Osmonics, Poretics® Polycarbonate Membrane; Product Leaflet; Engineering Purity, 2002, pp. 1-2.

Repas, R., "Sensor Sense: RFID for smart position sensing", retrieved from https://www/machinedesign/com/automation-iiot/article/21818777/sensor-sense-rfid-for-smart-position-sensing, 2010, pp. 1-2.

Schmidtke, D. W., et al., "Accuracy of the One-Point in Vivo Calibration of "Wired" Glucose Oxidase Electrodes Implanted in Jugular Veins of Rats in Periods of Rapid Rise and Decline of the Glucose Concentration", Analytical Chemistry, 1998, vol. 70, No. 10, pp. 2149-2155.

Tierney, M. J., et al., "Effect of Acetaminophen on the Accuracy of Glucose Measurements Obtained with the GlucoWatch Biographer", Diabetes Technology & Therapeutics, 2000, vol. 2, No. 2, pp. 199-207.

Tsalikian, e., et al., "Accuracy of the GlucoWatch G2® Biographer and the Continuous Glucose Moninitoring System During Hypoglycemia: Experience of the Diabetes Research in Children Network", Diabetes Care, 2004, vol. 27, No. 3, pp. 722-726.

Ward, W. K., et al., "Rise in Background Current Over Time in a Subcutaneous Glucose Sensor in the Rabbit: Relevance to Calibration and Accuracy", Biosensors & Bioelectronics, 2000, vol. 15, pp. 53-61.

CA, 2,872,576 Examiner's Report, dated Feb. 17, 2015.

CA, 2,872,576 Examiner's Report, dated Feb. 19, 2016.

CN, 201980082748.1 First Office Action, dated Jan. 10, 2023.

EP, 06851063.5 Extended Search Report, dated Sep. 21, 2009.

EP, 07843396.8 Extended Search Report, dated Dec. 22, 2010.

EP, 10739031.2 Response to Response to Response to Grounds of Appeal, dated Jan. 18, 2023.

EP, 11760268.0 Decision of the Oral Proceedings, dated Sep. 27, 2022.

EP, 13000104.3 Extended Search Report, dated Mar. 12, 2013.

EP, 14179905.6 Summons to Attend Oral Proceedings, dated Apr. 10, 2017.

EP, 14179905.6 Notice of Opposition, dated May 19, 2016.

EP, 14179905.6 Extended Search Report, dated Dec. 23, 2014.

EP, 15002441.2 Extended Search Report, dated Dec. 18, 2015.

EP, 19900891.3 Extended Search Report, dated Sep. 26, 2022.

EP, 20177703.4 Reply to Opposition, dated Feb. 22, 2023.

EP, 20177703.4 Grounds of Opposition, dated Sep. 28, 2022.

EP, 20177703.4 Notice of Opposition, dated Sep. 28, 2022.

EP, 20177703.4 Examination Report, dated Jun. 25, 2021.

EP, 20177712.5 Grounds of Opposition Gulde & Partner Patent, dated Dec. 22, 2022.

EP, 20177712.5 Grounds of Opposition Dexcom, dated Dec. 22, 2022.

EP, 20177712.5 Notice of Opposition Gulde & Partner Patent, dated Dec. 22, 2022.

EP, 20177712.5 Notice of Opposition Dexcom, dated Dec. 22, 2022.

EP, 20195922.8 Grounds of Opposition Dexcom, dated Jan. 26, 2023.

EP, 20195922.8 Notice of Opposition Dexcom, dated Jan. 26, 2023.

EP, 22168031.7 Extended Search Report, dated Aug. 17, 2022.

EP, 22169853.3 Extended Search Report, dated Sep. 2, 2022.

JP, 2021-531135 Office Action, dated Feb. 22, 2023.

MY, PI2021004760 Examination Report, dated Mar. 30, 2022.

MY, PI2021005830 Examination Report, dated Sep. 30, 2022.

MY, PI2021005830 Examination Report, dated Aug. 29, 2022.

WO, PCT/US2006/062690 ISR and Written Opinion, dated Jan. 2, 2008.

WO, PCT/US2007/079774 ISR and Written Opinion, dated Apr. 1, 2008.

WO, PCT/US2022/037291 ISR and Written Opinion, dated Nov. 22, 2022.

WO, PCT/US2022/037291 Invitation to Pay Additional Fees, dated Sep. 29, 2022.

Certified Copy of U.S. Appl. No. 60/424,099, filed Nov. 5, 2002.

Medtronic MiniMed Sen-Serter® User Guide, 2006, pp. 1-96.

"Abbott Receives CE Mark for Freestyle® Libre, A Revolutionary Glucose Monitoring System for People With Diabetes", 2014, 7 pages.

"Alcove", Webster's New College Dictionary, 2001, p. 26.

Anderson, A. J., "Foundations of Computer Technology", 1994, pp. 55-57.

Boise, M., "Dexcom CEO Kevin Sayer Explains G6", 2018, retrieved from https://beyondtype1.org/dexcom-ceo-kevin-sayer-explains-g6/, 9 pages.

Certified True Copy of Preliminary Amendment filed on Apr. 20, 2018 for U.S. Pat. No. 10,827,954, 7 pages.

Certified True Copy of Excerpts of the File History of U.S. Pat. No. 10,973,443, 22 pages.

CGMs Changing Diabetes Management: Kevin Sayer, DIC Interview Transcript, 2019, retrieved from https://www.diabetesincontrol.com/cgms-changing-diabetes-management- kevin-sayer-dic-interview-transcript/, 10 pages.

"Deciding When to Submit a 510(k) for a Change to an Existing Device, Guidance for Industry and Food and Drug Administration Staff", 2017, pp. 1-77.

"Deciding When to Submit a 510(k) for a Software Change to an Existing Device, Guidance for Industry and Food and Drug Administration Staff", 2017, pp. 1-31.

Dexcom CEO- Prime Position in Our Market - Mad Money - CNBC.mp4, Transcript 2023 by Sonix, 2 pages.

DexCom (DXCM) 2017 Q4 Earnings Call Transcript, 2017, retrieved from https://docoh.com/transcript/1093557/2017Q4/DXCM, 11 pages.

DexCom (DXCM) Q1 2018 Results—Earnings Call Transcript, 2018, retrieved from https://seekingalpha.com/article/4168949-dexcom-dxcm-q1-2018-results-earnings-call-transcript, 4 pages.

Dexcom, Inc. NasdaqGS:DXCM Company Conference Presentation, 2019, 10 pages.

Dexcom, Inc. NasdaqGS:DXCM Company Conference Presentation, 2020, 9 pages.

Dexcom, Inc. NasdaqGS:DXCM Company Conference Presentation, 2021, 16 pages.

Dexcom G6 Continuous Glucose Monitoring System User Guide, pp. 1-22.

Dexcom G6 Start Here Set up Guide, pp. 1-8.

Dexcom G6 Using Your G6 Guide, Mar. 2020, pp. 1-7.

Dexcom Seven® Plus Continuous Glucose Monitoring System User's Guide, 2011, pp. 1-144.

DexCom™ STS™ Continuous Glucose Monitoring System FDA Premarket Approval (PMA), 2006, pp. 1-7.

DexCom™ STS™ Continuous Glucose Monitoring System Summary of Safety and Effectiveness Data, 2006, 20 pages.

DexCom™ STS™ Sensor Instructions for Use, 2006, pp. 1-6.

Dexcom STS-7 Continuous Glucose Monitoring System FDA Premarket Approval (PMA), 2007, pp. 1-7.

Dexcom STS®-7 Continuous Glucose Monitoring System Summary of Safety and Effectiveness Data, 2007, 14 pages.

Dexcom STS®-7 Continuous Glucose Monitoring System User's Guide, 2007, pp. 1-74.

Diglas, J., et al., "Reduced pain perception with Pen Mate™, an automatic needle insertion device for use with an insulin pen", Practical Diabetes International, 1999, vol. 16, No. 2, pp. 39-41.

"Does Dexcom Really Have a Future If It Can't Match Abbott's Scale", 2019, retrieved from https://www.sprucepointcap.com/reports/dxcm_research_thesis_3-21-2019.pdf, p. 46.

Email chain from Sophie Hood, oldest email dated Jan. 24, 2023, 5 pages.

European Standard, ISO 11607-1, Packaging for terminally sterilized medical devices - Part 1: Requirements for materials, sterile barrier systems and packaging systems, 2006, 32 pages.

(56) References Cited

OTHER PUBLICATIONS

European Standard, ISO 13485, Medical devices - Quality management systems - Requirement for regulatory purposes, 2003, 69 pages.
European Standard, ISO 15197, In vitro diagnostic test systems - Requirements for blood glucose monitoring systems for self-testing in managing diabetes mellitus, 2003, 43 pages.
Explore The Monroe Street Market Community, Retrieved from https://www.monroestreetmarket.com/floor-plans/apartment/B-231, 2 pages.
"FDA authorizes first fully interoperable continuous glucose monitoring system, streamlines review pathway for similar devices", FDA News Release, 2018, retrieved from https://www.fda.gov/news-events/press-announcements/fda-authorizes-first-fully-interoperable-continuous-glucose-monitoring-system-streamlines-review, 3 pages.
Food and Drug Administration, HHS, 2009, Code of Federal Regulation § 820.30, Subpart C-Design Controls, pp. 147-148.
Freestyle Libre Pro Flash Glucose Monitoring System Summary of Safety and Effectiveness Data, 2016, 31 pages.
FreeStyle Lite Blood Glucose Monitoring System Owner's Booklet, 2006, 15 pages.
FreeStyle Navigator Continuous Glucose Monitoring System FDA Premarket Approval (PMA), 2008, pp. 1-7.
Hemmerich, K. J., et al., "Sterilization Methods Stand the Test of Time", 2004, retrieved from https://www.mddionline.com/sterilization/sterilization-methods-stand-test-time, pp. 1-8.
Hirsch, I. B., "Realistic Expectations and Practical Use of Continuous Glucose Monitoring for the Endocrinologist", The Journal of Clinical Endocrinology & Metabolism, 2009, VI. 94, No. 7, pp. 2232-2238.
Hoss, U., et al., "Continuous glucose monitoring in the tissue: Do we really need to calibrate in-vivo?", pp. 1-21.
Hoss, U., et al., "Continuous Glucose Monitoring in Subcutaneous Tissue Using Factory-Calibrated Sensors: A Pilot Study", Diabetes Technology & Therapeutics, 2010, vol. 12, No. 8, pp. 591-597.
Hoss, U., et al., "Feasibility of Factory Calibration for Subcutaneous Glucose Sensors in Subjects With Diabetes", Journal of Diabetes Science and Technology, 2014, vol. 8, No. 1, pp. 89-94.
"Housing", "recess", "release", and "retain", Merriam-Webster's Collegiate Dictionary, Tenth Edition, 1999, pp. 563, 975, 987, and 999.
"Housing" and "recess", The New Penguin English Dictionary, 2000, pp. 678 and 1167.
Hughes, M. D., "The Business of Self-Monitoring of Blood Glucose: A Market Profile", Journal of Diabetes Science and Technology, 2009, vol. 3, No. 5, pp. 1219-1223.
IEEE 100 The Authoritative Dictionary of IEEE Standards Terms, Seventh Edition, 2000, 3 pages.
International Standard, ISO 14971, Medical devices—Application of risk management to medical devices, 2007, 90 pages.
"An Interview with Kevin Sayer, President and CEO of Dexcom, About The New G6", 2021, 5 pages.
Kal, S., "Basic Electronics—Devices, Circuits and IT Fundamentals", 2006, Chapter 13, Microcomputers and Microprocessors, p. 412.
Klueh, U., et al., "Inflammation and Glucose Sensors: Use of Dexamethasone to Extend Glucose Sensor Function and Life Span in Vivo", Journal of Diabetes Science and Technology, 2007, vol. 1, No. 4, pp. 496-504.
Klueh, U., et al., "Blood-Induced Interference of Glucose Sensor Function in Vitro: Implications for in Vivo Sensor Function", Journal of Diabetes Science and Technology, 2007, vol. 1, No. 6, pp. 842-849.
Medtronic Guardian® REAL-Time Continuous Glucose Monitoring System User Guide, 2006, pp. 1-181.
Medtronic MiniMed Guardian Rt Fda Premarket Approval (PMA), 2005, pp. 1-6.
Medtronic MiniMed Guardian RT Summary of Safety and Effectiveness Data, 2005, 13 pages.

Medtronic MiniMed Paradigm® REAL-Time 522 and 722 Insulin Pumps User Guide, 2008, pp. 1-262.
Occupational Safety and Health Admin., Labor, 2003, 29 CFR § 1910.1030 Bloodborne pathogens, pp. 260-273.
Omnipod image, Exhibit 182 of ADC Reply Brief SJ, Daubert, Sep. 22, 2022, 2 pages.
One Touch® Ultra™ Blood Glucose Monitoring System Owner's Booklet, 2000, 23 pages.
OneTouch Ultra2 Blood Glucose Monitoring System Owner's Booklet, 2005, 34 pages.
Order, Federal Communications Commission, 2006, pp. 1-8.
Program, 2nd International Conference on Advanced Technologies & Treatments for Diabetes, Athens, Greece, 2009, 3 pages.
"Recess", Cambridge Dictionary of American English, 2000, pp. 710-711.
"Retract", The Chambers Dictionary, 1998, p. 1410.
"Retract", The New Oxford American Dictionary, 2001, p. 1455.
"Retract", Webster's Third New International Dictionary, 1993, pp. 1939-1940.
"Submission and Review of Sterility Information in Premarket Notification (510(k)) Submissions for Devices Labeled as Sterile, Guidance for Industry and Food and Drug Administration Staff", 2016, pp. 1-11.
Tegnestedt, C., et al., "Levels and sources of sound in the intensive care unit - an observational study of three room types", Acta Anaesthiesiologica Scandinavica, 2013, pp. 1-10.
Watkin, J., "An Introduction to Flash Glucose Monitoring", 14 pages. For Inter Partes Review Of U.S. Pat. No. 11,202,591, IPR No. 2023-01409 For Inter Partes Review Of U.S. Pat. No. 11,266,335, IPR No. 2023-01397 For Inter Partes Review Of U.S. Pat. No. 11,266,335, IPR No. 2023-01396 Final Written Decision, IPR No. 2022-00605 Petitioner's Reply to Patent Owner's Response to Petition, IPR No. 2022-00605 Supplemental Declaration of Gary D. Fletcher, Ph.D, IPR No. 2022-00605.
201980082748.1 Second Office Action Jul. 10, 2023.
20177703.4 Reply to Reply to Notice of Opposition Jun. 29, 2023.
20177712.5 Reply to Reply to Notice of Opposition Dexcom Sep. 27, 2023.
20177712.5 Reply to Reply to Notice of Opposition Guide & Partner Patent Aug. 30, 2023.
20195922.8 Summons to Attend Oral Proceedings Sep. 21, 2023.
20195922.8 Reply to Notice of Intervention Aug. 29, 2023.
20195922.8 Reply to Reply to Notice of Oppositon Aug. 21, 2023.
2021-531135 Office Action Aug. 9, 2023.
PI2022007295 Examination Report Jul. 11, 2023.
Petition for Inter Partes Review of U.S. Pat. No. 11,202,591, IPR No. 2023-01409 Oct. 11, 2023.
Petition for Inter Partes Review of U.S. Pat. No. 11,266,335, IPR No. 2023-01397 Oct. 6, 2023.
Final Written Decision, IPR No. 2022-00605 Jul. 10, 2023.
Petitioner's Reply to Patent Owner's Response to Petition, IPR No. 2022-00605 Jan. 11, 2023.
Supplemental Declaration of Gary D. Fletcher, Ph.D, IPR No. 2022-00605 Jan. 11, 2023.
Breton, M. D., et al., "Optimum Subcutaneous Glucose Sampling and Fourier Analysis of Continuous Glucose Monitors", Journal of Diabetes Science and Technology, 2008, vol. 2, No. 3, pp. 495-500.
Dexcom G6 Continuous Glucose Monitoring System User Guide, 2019, pp. 1-27.
Email from John Shaw of Shaw & Keller dated May 16, 2023, 2 pages.
Hoss, U., et al., "Continuous glucose monitoring in the tissue: Do we really need to calibrate in-vivo?", Feb. 28, 2009, pp. 1-21.
Panteleon, A. E., et al., "The Role of the Independent Variable to Glucose Sensor Calibration", Diabetes Technology & Therapeutics, 2003, vol. 5, No. 3, pp. 401-410.
Parker, S. P., ed., McGraw-Hill Dictionary of Mechanical and Design Engineering, 1984 (excerpted), pp. 1-4.
Shenoi, B. A., ed., Introduction to Digital Signal Processing and Filter Design, 2006, "Introduction", Chapter 1, pp. 1-30.
Smith, S. S., ed., The Scientist and Engineer's Guide to Digital Signal Processing, Second Edition, 1997-1999, "Digital Signal Processors", Chapter 28, pp. 503-534.

(56) References Cited

OTHER PUBLICATIONS

U.S. Pat. No. 2,617,192 Examiner's Report Oct. 22, 2012.
U.S. Pat. No. 2,984,939 Examiner's Report Nov. 15, 2023.
U.S. Pat. No. 3,182,961 Examiner's Report Dec. 6, 2023.
200780039416.2 Second Office Action Apr. 25, 2012.
200780039416.2 First Office Action Mar. 30, 2011.
200880005388.7 Second Office Action May 16, 2012.
200880005388.7 First Office Action Jul. 25, 2011.
201980082748.1 Final Office Action Nov. 27, 2023.
06813967.4 Extended Search Report Mar. 4, 2010.
0678869.3 Examination Report Sep. 25, 2012.
06788869.3 Extended Search Report Mar. 18, 2010.
07854298.2 Extended Search Report Mar. 29, 2010.
08730066.1 Extended Search Report Oct. 5, 2012.
18741791.0 Examination Report Dec. 15, 2023.
20177703.4 Reply to Reply to Reply to Notice of Opposition ADC Dec. 18, 2023.
20177703.4 Reply to Notice of Intervention Nov. 17, 2023.
20177712.5 Reply to Reply to Reply to Notice of Oppsition ADC Dec. 18, 2023.
20177712.5 Reply to Notice of Intervention Nov. 17, 2023.
20195922.8 Written Submissions Dexcom Dec. 12, 2023.
20195922.8 Written Submission ADC Oct. 23, 2023.
23166498.8 Extended Search Report Nov. 17, 2023.
2009-534799 Final Office Action Feb. 19, 2013.
2009-534799 Office Action Sep. 27, 2011.
MX/a/2009/004322 Office Action Mar. 11, 2013.
MX/a/2009/004322 Office Action Sep. 19, 2012.
PI2023005466 Examination Report Dec. 29, 2023
2009135048 Office Action Dec. 20, 2011.
2009119430 Office Action Jun. 5, 2011.
Petitioner's Explanation of Material Differences Between Petitions, IPR No. 2023-01397 Oct. 6, 2023.
Declaration of Gary D. Fletcher, Ph.D, IPR No. 2023- 01396 and IPR No. 2023-01397 Oct. 6, 2023.
Petitioner's Explanation of Material Differences Between Petitions, IPR No. 2023-01396 Oct. 6, 2023.
Notice of Final Written Decision re Inter Partes Review of the '649 Patent, IPR No. 2022-00605 Jul. 13, 2023.
Record of Oral Hearing, IPR No. 2022-00605 Apr. 26, 2023.
Second Declaration by Dr. Michael Cima in Support of Patent Owner's Response, IPR No. 2022-00605 Oct. 19, 2022
Patent Owner's Response, IPR No. 2022-00605 Oct. 19, 2022.
Request for Ex Parte Reexamination Under 35.U.S.C. §§ 302-307 and 37 C.F.R. § 1.510 of U.S. Pat. No. 11,013,440 Dec. 11, 2023.
Reexamination U.S. Appl. No. 90/019,331 Order Granting Request for Reexamination of U.S. Pat. No. 11,000,216 Jan. 23, 2024.
Request for Ex Parte Reexamination Under 35.U.S.C. §§ 302-307 and 37 C.F.R. § 1.510 of U.S. Pat. No. 11,000,216 Dec. 11, 2023.
Reexamination U.S. Appl. No. 90/019,307 Order Granting Request for Reexamination of U.S. Pat. No. 10,973,443 Dec. 22, 2023.
Request for Ex Parte Reexamination Under 35.U.S.C. §§ 302-307 and 37 C.F.R. § 1.510 of U.S. Pat. No. 10,973,443 Nov. 27, 2023.
Request for Ex Parte Reexamination Under 35.U.S.C. §§ 302-307 and 37 C.F.R. § 1.510 of U.S. Pat. No. 10,959,654.
WO PCT/US2006/029541 ISR and Written Opinion Apr. 24, 20207.
WO PCT/US2006/033885 ISR and Written Opinion Aug. 3, 2007.
WO PCT/US2007/082121 ISR and Written Opinion May 9, 2008.
WO PCT/US2008/054186 ISR and Written Opinion Aug. 8, 2008.
WO PCT/US2008/065154 ISR and Written Opinion Sep. 3, 2008.
WO PCT/US2010/047065 ISR and Written Opinion Dec. 21, 2010.
WO PCT/US2010/047414 ISR and Written Opinion Dec. 27, 2010.
WO PCT/US2010/047415 ISR and Written Opinion Oct. 25, 2010.
10739031.2 Minutes of Oral Proceedings May 10, 2024.
10739031.2 Communication from Board of Appeals Feb. 21, 2024.
10739031.2 Summons to Attend Oral Proceedings Oct. 26, 2023.
20177703.4 Summons to Attend Oral Proceedings Apr. 29, 2024.
20177712.5 Response to Written Submissions Dexcom Feb. 26, 2024.
20177712.5 Written Submissions ADC Jan. 26, 2024.
20195922.8 Decision Revoking the European Patent May 8, 2024.
20195922.8 Minutes of the Oral Proceedings May 8, 2024.
20195922.8 Written Submissions Dexcom Mar. 15, 2024.
20195922.8 Response to Summons to Attend Oral Proceedings Feb. 15, 2024.
21211041.5 Grounds of Opposition Dexcom Mar. 28, 2024.
21211041.5 Notice of Opposition Dexcom Mar. 28, 2024.
Claim No. HP-2021-000025 Approved Judgement, Oct. 18, 2023.
Third Declaration of Gary Fletcher, Ph.D., IPR No. 2024-00520 Jan. 31, 2024.
Petition For Inter Partes Review Of U.S. Pat. No. 11,266,335, IPR No. 2024-00520 Jan. 31, 2024.
Patent Owner's Preliminary Response, IPR No. 2023-01409 Jan. 18, 2024.
Notice of Filing Date Accorded to Petition and Time for Filing Patent Owner Preliminary Response, IPR No. 2023-01409. Oct. 18, 2023.
Patent Owner's Preliminary Response, IPR No. 2023-01397.
Patent Owner's Response to Petitioner's Explanation of Material Differences Between Petitions, IPR Nos. 2023-01396 and 2023-01397.
Patent Owner's Preliminary Response, IPR No. 2023-01396.
Notice of Filing Date Accorded to Petition and Time for Filing Patent Owner Preliminary Response, IPR No. 2023-01396.
Reexamination U.S. Appl. No. 90/019,330 Order Granting Request for Reexamination of U.S. Pat. No. 10,959,654.
PCT/US2024/011756 Invitation to Pay Additional Fees.
Blum, A., "Freestyle Libre Glucose Monitoring System", Clinical Pharmacology Update, 2018. Vol. 36, No. 2, pp. 203-204.
Brown, A., et al., "Abbott debuts Flash Glucose Monitoring, A New Alternative to Fingersticks", 2021, retrieved from https://diatribe.org/diabetes-technology/abbott-debuts-flash-glucose-monitoring-new-alternative-fingersticks, 6 pages.
Chen, T. L., et al., "A Novel Fault-Tolerant Sensor System for Sensor Drift Compensation", Sensors and Actuators A: Physical, 2008, vol. 147, No. 2, pp. 623-632.
Continuous Glucose Monitoring Systems Product Reference Guide, Diabetes Health, 2006- 2007, pp. 50-51.
Das, S. D., et al., "Review - Electrochemistry and Other Emerging Technologies for Continuous Glucose Monitoring Devices", ECS Sensors Plus, 2022, 19 pages.
Dexcom G6 Continuous Glucose Monitoring System User Guide, 2022, 346 pages.
Dexcom G7 Inserting Sensor Instructions for Use, 2021, pp. 1-2.
Dexcom G7, Start Here, Operational Manual, 2022, pp. 1-9 (English Abstract).
Dexcom G7, User Guide, 2022, p. 1-179 (English Abstract).
Englert, K., et al., "Skin and Adhesive Issues With Continuous Glucose Monitors: A Sticky Situation", Journal of Diabetes Science and Technology, 2014, vol. 8, No. 4, pp. 745-751.
"Extending G6 sensors beyond 10 days. Can this be done?", 2021, retrieved from https://www.reddit.com/r/dexcom/comments/la83hi/extending_g6_sensors_beyond_10_days can_this_be/, 6 pages.
File Wrapper of U.S. Appl. No. 61/317,243.
File Wrapper of U.S. Appl. No. 61/345,562.
File Wrapper of U.S. Appl. No. 61/361,374.
File Wrapper of U.S. Appl. No. 61/411,262.
Freckmann, G., et al., "Performance Evaluation of Three Continuous Glucose Monitoring Systems: Comparison of Six Sensors per Subject in Parallel", Journal of Diabetes Science and Technology, 2013, vol. 7, No. 4, pp. 842-853.
Freestyle Libre Brochure, 2016, 10 pages.
Freestyle Libre Fact Sheet, 2016, retrieved from www.FreeStyleLibre.de, 2 pages.
Guardian™ Connect System User Guide, 2020, 99 pages.
Harris, J. M., et al., "Common Causes of Glucose Oxidase Instability in In Vivo Biosensing: A Brief Review", Journal of Diabetes Science and Technology. 2013, vol. 7, No. 4, pp. 1030-1038.
Heller, A., et al., "Electrochemical Glucose Sensors and Their Applications in Diabetes Management", Chemical Reviews, 2008, vol. 108, No. 7, pp. 2482-2505.

(56)                  References Cited

OTHER PUBLICATIONS

Hoogma, RPLM, et al., "Comparison of the Effects of Continuous Subcutaneous Inulin Infusion", Diabetic Medicine, 2006, vol. 23, No. 2, pp. 141-147.
Hoss, U., et al., "Factory-Calibrated Continuous Glucose Sensors: The Science Behind the Technology", Diabetes Technology & Therapeutics, 2017. Vol. 19, Suppl. 2, pp. S-44 - S-50.
"How to Extend the Dexcom G6 Sensor Beyond the Ten Day Hard Stop", Diabetes Daily Staff, 2021, retrieved from https://www.diabetesdaily.com/blog/how-to-extend-the-dexcom-g6- sensor-goes-beyond-the-ten-day-hard-stop-580510/, 11 pages.
Klonoff, D. C., "Continuous Glucose Monitoring: Roadmap for 21st Century Diabetes Therapy", Diabetes Care, 2005, vol. 28, No. 5, pp. 1231-1239.
Medtronic MiniMed iPro2 User Guide, 2010, pp. 1-99.
Migneault, I., et al., "Glutaraldehyde: Behavior in Aqueous Solution, Reaction With Proteins, and Application to Enzyme Crosslinking", Biotechniques, 2004, vol. 37, No. 5, pp. 790-802.
Nichols, S. P., et al., "Biocompatible Materials for Continuous Glucose Monitoring Devices", Chem Rev., 2013, vol. 113, No. 4, pp. 2528-2549.
Rice, M. J., et al., "Continuous Measurement of Glucose: Facts and Challenges", Anesthesiology, 2012, vol. 116, No. 1, pp. 199-204.
Rigo, R. S., et al., "Cutaneous Reactions to Continuous Glucose Monitoring and Continuous Subcutaneous Insulin Infusion Devices in Type 1 Diabetes Mellitus", Journal of Diabetes Science and Technology, 2021, vol. 15, No. 4, pp. 786-791.
Rocchitta, G., et al., "Enzyme Biosensors for Biomedical Applications: Strategies for Safeguarding Analytical Performances in Biological Fields", Sensors, 2016. Vol. 16, No. 6, 21 pages.
"Transcutaneous", Webster's Third New International Dictionary, 2002, p. 2426.
Xu, J., et al., "Anti-Biofouling Strategies for Long-Term Continuous Use of Implantable Sensors", Chemosensors, 2020, vol. 20 No. 3, 29 pages.
2,984,939 Examiner's Report Aug. 7, 2024.
3,120,335 Examiner's Report May 27, 2024.
200880005149.1 Notice of Allowance Jun. 21, 2013.
200880005149.1 Fourth Office Action Dec. 3, 2012.
200880005149.1 Third Office Action Feb. 16, 2012.
200880005149.1 Second Office Action Aug. 17, 2011.
200880005149.1 First Office Action Jul. 29, 2010.
Complaint in Litigation of EP 3300658 Mar. 20, 2024.
10739031.2 Decision of Oral Proceedings Jun. 11, 2024.
17182379.2 Grounds of Opposition Jul. 12, 2024.
17182379.2 Notice of Opposition Jul. 12, 2024.
17182379.2 Reply to Examination Report Apr. 9, 2021.
17182379.2 Reply to Search Report Oct. 3, 2018.
19900891.3 Extended Search Report Sep. 26, 2022.
20177712.5 Summons to Attend Oral Proceedings Jul. 2, 2024.
20195922.8 Notice of Appeal Jul. 4, 2024.
20195922.8 Written Submissions Dexcom Feb. 9, 2024.
21211041.5 Reply to Notice of Opposition Jul. 17, 2024.
24152079.0 Partial Search Report Jun. 14, 2024.
MX/a/2021/007294 Office Action Aug. 20, 2024.
2009134334 Office Action Feb. 7, 2012.
First Expert Opinion of Dr Michael Schoemaker of Litigation of EP 3977921 Jun. 11, 2024.
Notice of Filing Date Accorded to Petition and Time for Filing Patent Owner Preliminary Response, IPR No. 2024-00860 May 23, 2024.
Declaration of Dr. Cameron Riviere, Ph.D., IPR No. 2024-00860 May 9, 2024.
Petition For Inter Partes Review Of U.S. Pat. No. 11,510,625, IPR No. 2024-00860 May 8, 2024.
Decision Denying Institution of Inter Partes Review, IPR No. 2024-00520 Aug. 8, 2024.
Patent Owner's Authorized Sur-Reply to Petitioner's Reply to Patent Owner's Preliminary Response, IPR No. 2024-00520 Jun. 11, 2024.

Petitioner's Authorized Reply to Patent Owner's Preliminary Response, IPR No. 2024-00520, May 31, 2024.
Patent Owner's Preliminary Response, IPR No. 2024-00520 Mar. 25, 2024.
Patent Owner's Exhibit List, IPR No. 2024-00520, Mar. 25, 2024.
Telephonic Hearing, IPR No. 2024-00520 Mar. 13, 2024.
Petitioner's Explanation of Material Differences Between the Petition in IPR2024-00520 and Previously Filed Petitions in IPR2023-01396 and IPR2023-01397, IPR No. 2024-00520 Jan. 31, 2024.
Order, IPR No. 2023-01409 May 30, 2024.
Notice of Stipulation, IPR No. 2023-01409 May 29, 2024.
Patent Owner's Objections to Petitioner's Exhibits to the Petition, IPR No. 2023-01409 Apr. 29, 2024.
Patent Owner's Request for Rehearing by the Director, IPR 2023-01409 Apr. 29, 2024.
Email of Peter McAndrews, IPR 2023-01409 Apr. 29, 2024.
Decision Granting Institution of Inter Partes Review, IPR No. 2023-01409 Apr. 15, 2024.
Scheduling Order, IPR 2023-01409 Apr. 15, 2024.
Order Conduct of the Proceeding 37 C.F.R. § 42.5, IPR No. 2023-01409 Feb. 6, 2024.
Petitioner's Updated Exhibit List, IPR No. 2023-01409 Feb. 5, 2024.
Telephonic Conference Call, IPR No. 2023-01409 Feb. 2, 2024.
Patent Owner's Updated Mandatory Notices, IPR No. 2023-01409 Feb. 2, 2024.
Email of Andrew M. Mason, IPR 2023-01409. Jan. 30, 2024.
Decision Denying Institution of Inter Partes Review, IPR No. 2023-01397 Apr. 16, 2024.
Patent Owner's Updated Exhibit List, IPR No. 2023-01397 Mar. 25, 2024.
Telephonic Hearing, IPR No. 2023-01397 Mar. 13, 2024.
Petitioner's Updated Mandatory Notices Pursuant to 37 C.F.R. § 42.8(a)(3), IPR No. 2023-01397 Feb. 19, 2024.
Patent Owner's Updated Mandatory Notices, IPR No. 2023-01397 Feb. 2, 2024.
Petitioner's Request for Rehearing of Decision Denying Institution, IPR No. 2023-01396 May 16, 2024.
Decision Denying Institution of Inter Partes Review, IPR No. 2023-01396 Apr. 16, 2024.
Patent Owner's Updated Exhibit List, IPR No. 2023-01396 Mar. 25, 2024.
Telephonic Hearing, IPR No. 2023-01396 Mar. 13, 2024.
Petitioner's Updated Mandatory Notices Pursuant to 37 C.F.R. § 42.8(a)(3), IPR No. 2023-01396 Feb. 19, 2024.
Reexamination U.S. Appl. No. 90/019,329 Notification of Concurrent Proceedings May 15, 2024.
Petition Under 37 CFR § 1.181 and/or § 1.182 to Terminate Reexamination No. U.S. Appl. No. 90/019,329 Apr. 26, 2024.
Reexamination U.S. Appl. No. 90/019,329 Order Granting Request for Reexamination of U.S. Pat. No. 11,013,440 Jan. 30, 2024.
Reexamination U.S. Appl. No. 90/019,329 Declaration of Gary D. Fletcher, Ph.D Dec. 11, 2023.
Reexamination U.S. Appl. No. 90/019,331 Decision Granting Petition Aug. 26, 2024.
Reexamination U.S. Appl. No. 90/019,331 Petition to Withdraw From Issue and Reopen the Proceeding Jul. 26, 2024.
Reexamination U.S. Appl. No. 90/019,331 Notice of Intent to Issue Ex Parte Reexamination Certificate Jul. 10, 2024.
Reexamination U.S. Appl. No. 90/019,331 Notification of Concurrent Proceedings May 15, 2024.
Reexamination U.S. Appl. No. 90/019,330 Decision Granting Petition and Vacating a Reexamination Certificate Aug. 26, 2024.
Ex Parte Reexamination Certificate of U.S. Pat. No. 10,959,654 Aug. 5, 2024.
Reexamination U.S. Appl. No. 90/019,330 Petition to Withdraw From Issue and Reopen the Proceeding Jul. 26, 2024.
Reexamination U.S. Appl. No. 90/019,330 Notice of Intent to Issue Ex Parte Reexamination Certificate of U.S. Pat. No. 10,959,654 Jul. 1, 2024.
Reexamination U.S. Appl. No. 90/019,330 Notification of Concurrent Proceedings May 15, 2024.

(56) References Cited

OTHER PUBLICATIONS

Reexamination U.S. Appl. No. 90/019,330 Declaration of John Mastrototaro, Ph.D Dec. 11, 2023.

PCT/US2008/054165 ISR and Written Opinion Jun. 5, 2008.

PCT/US2008/067791 ISR and Written Opinion Sep. 30, 2008.

PCT/US24/11756 ISR and Written Opinion Jun. 28, 2024.

PCT/US24/16127 Invitation to Pay Additional Fees Jun. 4, 2024.

PCT/US24/18665 ISR and Written Opinion Jun. 21, 2024.

"27 Winners Announced at the 19th Annual Medical Design Excellence Awards (MDEA) Award Ceremony", UBM Americas, 2017, 4 pages.

"55 Chosen as Winners in Annual BIG Innovation Awards", 2018, retrieved from https://www.bintelligence.com/posts/55-chosen-as-winners-in-annual-big-innovation-awards, 2 pages.

2017 Good Design Award, retrieved from https://www.g-mark.org/gallery/winners/9dda01a3-803d-11ed-af7e-0242ac130002, 9 pages.

"2019 Top 10 Innovations", The Scientist, retrieved from https://www.the-scientist.com/2019-top-10-innovations-66738, 7 pages.

Abbott 2023 Annual Report, retrieved from https://www.abbottinvestor.com/static-files/6cb09c09-2422-40e0-a24b-6545ffcf5267, pp. 1-82.

Abbott Clinical Trials Competitor and Ecosystem Players, 2020, 28 pages.

"Abbott's Freestyle Libre® Is Named Best Medical Technology In Last 50 Years By The Galien Foundation", 2022, PRNewswire, 1 page.

"Abbott's Freestyle® Libre 2 ICGM Cleared in U.S. for Adults and Children With Diabetes, Achieving Highest Level of Accuracy and Performance Standards", retrieved from https://abbott.mediaroom.com/2020-06-15-Abbotts-FreeStyle-R-Libre-2-iCGM-Cleared-in-U-S-for-Adults-and-Children-with-Diabetes-Achieving-Highest-Level-of-Accuracy-and-Performance-tandards#:~:text=FDA%20clears%20Abbott's%20FreeStyle%20Libre,high%20or%20low%20Without%20scanning, on Jul. 7, 2024, 3 pages.

"Abbott's Freestyle LibreR 3 Receives U.S. Fda Clearance—Features World's Smallest, Thinnest and Most Accurate 14-Day Glucose Sensor", 2022, PRNewswire, 3 pages.

"Abbott's Freestyle Libre Flash Glucose Monitoring System Wins the IMSTA Most Innovative Product Multi-National Award 2017", retrieved from https://www.ie.abbott/media-center/news/abbotts-freestyle-libre-flash-glucose-monitoring-system-wins-the-imsta-award-2017.html, 2 pages.

"Abbott's Freestyle® Libre 14 Day Flash Glucose Monitoring System Now Approved in U.S.", 2018, PRNewswire, 2 pages.

About the Edison Awards retrieved from https://edisonawards.com/about/, 2024, 3 pages.

Ahn, D., "Abbott's Euro approved wearable glucose monitor is different than anything on the market", 2014, retrieved from https://www.imedicalapps.com/2014/09/abbotts-wearable-glucose-monitor/, 6 pages.

"BinaxNOW, FreeStyle Libre 2 win BIG innovation honors", 2021, retrieved from https://www.abbott.com/corpnewsroom/strategy-and-strength/binaxnow-freestyle-libre-win-big-innovation-honors.html, 6 pages.

Cather, D. E., "Cgm Frustrations Survey", 2020, 36 pages.

Certified Copy of U.S. Appl. No. 61/149,639, filed Feb. 3, 2009.

CES 2022 Innovation Award Honorees, retrieved from https://www.ces.tech/innovation-awards/honorees/2022/best-of/f/freestyle-libre-3-system.aspx, 1 page.

2019 Chicago Innovation Award Winner Abbott Laboratories, retrieved from https://chicagoinnovation.com/winners/abbott-laboratories/, 4 pages.

Design Concepts Project Status Update, Glucose Sensor Applicator Dexcom (project #2554), 2014, 5 pages.

Dexcom G5 Quick Start Guide, 2020, pp. 1-31.

Dexcom G6 Start Here Set up Guide, 2022, p. 18 p. .

"The Dexcom G7. The most accurate CGM system.1" retrieved from https://www.dexcom.com/g7-cgm-system on Jun. 27, 2024, 20 pages.

Dexcom G7 Continuous Glucose Monitoring (CGM) System Section 510(k) Approval, 2022, 10 pages.

Dexcom G7 User Guide, 2024, p. i-186.

Edison Awards Announces 2016 Gold, Silver, and Bronze Awards Winners, Edison Awards, 9 pages.

Edison Best New Product Awards™ 2021 Winners retrieved from https://edisonawards.com/2021-winners/, 19 pages.

Edison Best New Product Awards™ 2022 Winners retrieved from https://edisonawards.com/2022-winners/, 52 pages.

Email from Christopher M Dougherty dated Dec. 17, 2019, 68 pages.

File Wrapper of U.S. Appl. No. 62/524,247.

Freestyle Libre FAQ, 2024, retrieved from https://www.freestyle.abbott/uk-en/support/faq/question-answer.html?q=UKFaqquestion-55#, 2 pages.

"FreeStyle Libre Honored by Prix Galien", 2019, 4 pages.

FreeStyle Libre In-Service Guide, 2021, 28 pages.

FreeStyle Libre 2 Get Started Guide, 2023, pp. 1-28.

Freestyle Libre 2 HCP Pulse Report, 2021, 13 pages.

"FreeStyle Libre 2—Zucker messen ohne stechen per Sensor und App", German Innovation Awards Gold Winner, 2020, retrieved from https://www.german-innovation-award.de/preistraeger/preis/gewinner/freestyle-libre-2-zucker-messen-ohne-stechen-per-sensor-und-app/#:~:text=Beschreibung%20Die%20kontinuierliche%20Glukosemessung%20mit, um%20di e%20Glukosewerte%20kontinuierlich%20aufzuzeichnen, 1 page.

FreeStyle Libre 3 Get Started Guide, 2023, pp. 1-20.

FreeStyle Libre 3 User's Manual, 2022-2023, pp. iv-241.

The Galien Foundation is proud to announce the laureates of the best-of-the-best from the half century 1970-2020, The 2022 Galien Golden Jubilee Winners, retrieved from https://www.galienfoundation.org/galien-golden-jubilee, 3 pages.

Gough, D. A., et al., "Development of the Implantable Glucose Sensor: What Are the Prospects and Why Is It Taking So Long?", Diabetes, 1995, vol. 44, pp. 1005-1009.

Hermanides, J., et al., "Current Application of Continuous Glucose Monitoring in the Treatment of Diabetes", Diabetes Care, 2011, vol. 34, Suppl. 2, pp. S197-S201.

Hovorka, R., "Continuous glucose monitoring and closed-loop systems", Diabetic Medicine, 2005, vol. 23, pp. 1-12.

Insert Molding, 1996, retrieved from https://www.mddionline.com/equipment/insert-molding, 4 pages.

International Diabetes Device 2022 Blue Book, Seagrove Partners, 142 pages.

Joseph, J. I., et al., "Glucose Sensing in the Subcutaneous Tissue: Attempting to Correlate the Immune Response with Continuous Glucose Monitoring Accuracy", Diabetes Technology.

Lomas, P., "Dexcom G7 Release: The Most Exciting New Features", 2024, retrieved from https://notjustapatch.com/dexcom-g7-features/, 13 pages.

Lovett, L., "What's next for Dexcom? Ceo, Cto talk G6 for inpatient use, expanding CGMs for patients without diabetes", 2020, retrieved from https://www.mobihealthnews.com/news/whats-next-dexcom-ceo-cto-talk-g6-inpatient-use-expanding-cgms-patients-without-diabetes, 6 pages.

Medtronic Enlite Serter User Guide, 2014, 26 pages.

Meltsner, M A, et al., "Observations on rotating needle insertions using a brachytherapy robot", Phys. Med. Biol., 2007, vol. 52, pp. 6027-6037.

Ólafsdóttir, A. F., et al., "A Clinical Trial of the Accuracy and Treatment Experience of the Flash Glucose Monitor FreeStyle Libre in Adults with Type 1 Diabetes", Diabetes Technology & Therapeutics, 2017, vol. 19, No. 3, pp. 164-172.

"Periphery", Cambridge Dictionary of American English, 2000, p. 631.

"Product Review: Abbott FreeStyle Libre Flash Glucose Monitor", DiabetesMine Team, 2021, retrieved from https://www.healthline.com/diabetesmine/abbott-freestyle-libre-review#bottom-line, 6 pages.

"Real-World Data Show Abbott's Freestyle LibreR Systems And GLP-1 Medicines Work Better Together For People With Type 2 Diabetes", 2024, PRNewswire, 2 pages.

Sclater, N., et al., eds., Mechanisms and Mechanical Devices Sourcebook, Fourth Edition, 2007, Chapter 12 - Shaft Couplings and Connections, pp. 290-307.

(56) References Cited

OTHER PUBLICATIONS

Tsumura, R., et al., "Histological Evaluation of Tissue Damage Caused by Rotational Needle Insertion", Proceedings of the Annual International Conference of the IEEE Engineering in Medicine and Biology Society, 2016, pp. 5120-5123.
Van Den Boom, L., et al., "Changes in the utilization of blood glucose test strips among patients using intermittent-scanning continuous glucose monitoring in Germany", Diabetes, Obesity and Metabolism, 2020, vol. 22, pp. 922-928.
19151577.4 Examination Report Oct. 7, 2024.
20177712.5 Summons to Attend Oral Proceedings Oct. 1, 2024.
20177712.5 Response to Summons to Attend Oral Proceedings Aug. 30, 2024.
20195922.8 Grounds of Appeal Sep. 6, 2024.
21211041.5 Summons to Attend Oral Proceedings, Sep. 23, 2024.
23166498.8 Examination Report Sep. 2, 2024.
24152079.0 Extended Search Report Sep. 4, 2024.
24183336.7 Extended Search Report Oct. 11, 2024.
24187206.8 Extended Search Report Oct. 9, 2024.
Reexamination No. U.S. Appl. No. 90/019,307 Petition Under 37 CFR § 1.181 to Terminate Aug. 15, 2024.
Reexamination No. U.S. Appl. No. 90/019,307 Decision on Petitions Aug. 7, 2024.
Reexamination No. U.S. Appl. No. 90/019,307 Petition Under 37 CFR § 1.59 to Expunge Application Papers Aug. 1, 2024.
Reexamination No. U.S. Appl. No. 90/019,307 Petition Under 37 CFR § 1.59 to Expunge Application Papers Jun. 12, 2024.
Reexamination U.S. Appl. No. 90/019,307 Notification of Concurrent Proceedings May 15, 2024.
Reexamination No. U.S. Appl. No. 90/019,307 Petition Under 37 CFR §§ 1.182 and/or § 1.183 to Allow Filing and Consideration of Response to Patent Owner's Extraordinary Petition to Suspend Mar. 19, 2024.
Reexamination No. U.S. Appl. No. 90/019,307 Petition Under 37 CFR § 1.181 and/or § 1.183 to Suspend Mar. 1, 2024.
Reexamination U.S. Appl. No. 90/019,329 Notice of Intent to Issue Ex Parte Reexamination Certificate Oct. 8, 2024.
Reexamination U.S. Appl. No. 90/019,329 Decision on Petition Under 37 C.F.R. § 1.59 Sep. 16, 2024.
Reexamination U.S. Appl. No. 90/019,329 Statutory disclaimer per Manual of Patent Examining Procedure (MPEP) 1490 Sep. 3, 2024.
Reexamination U.S. Appl. No. 90/019,329 Petition Under 37 C.F.R. § 1.182 to Seal Document Versions Filed via IDS and Substitute Redacted Document Versions Therfor Aug. 1, 2024.
Reexamination No. U.S. Appl. No. 90/019,329 Petition Under 37 CFR § 1.59 to Expunge Application Papers Aug. 1, 2024.
Reexamination No. U.S. Appl. No. 90/019,329 Ex Parte Reexamination Interview Summary Jul. 25, 2024.
Reexamination U.S. Appl. No. 90/019,329 Decision on Petition Under 37 C.F.R. § 1.59 Jul. 22, 2024.
Reexamination No. U.S. Appl. No. 90/019,329 Decision Sua Sponte Vacating Notice of Intent to Issue Ex Parte Reexamination Certificat Jul. 3, 2024.
Reexamination No. U.S. Appl. No. 90/019,329 Petition Under 37 CFR § 1.59 to Expunge Application Papers Jun. 12, 2024.
Reexamination U.S. Appl. No. 90/019,331 Notice of Intent to Issue Ex Parte Reexamination Certificate Oct. 15, 2024.
Reexamination U.S. Appl. No. 90/019,331 Decision on Petition Under 37 C.F.R. § 1.59 Sep. 16, 2024.
Reexamination U.S. Appl. No. 90/019,331 Petition Under 37 C.F.R. § 1.182 to Seal Document Versions Filed via IDS and Substitute Redacted Document Versions Therfor Aug. 1, 2024.
Reexamination No. U.S. Appl. No. 90/019,331 Petition Under 37 CFR § 1.59 to Expunge Application Papers Aug. 1, 2024.
Reexamination U.S. Appl. No. 90/019,331 Decision on Petition Under 37 C.F.R. § 1.59 Jul. 16, 2024.
Reexamination No. U.S. Appl. No. 90/019,331 Petition Under 37 CFR § 1.59 to Expunge Application Papers Jun. 12, 2024.
Reexamination U.S. Appl. No. 90/019,330 Notice of Intent to Issue Ex Parte Reexamination Certificate Oct. 7, 2024.
Reexamination U.S. Appl. No. 90/019,330 Decision on Petition Under 37 C.F.R. § 1.59 Sep. 16, 2024.
Reexamination U.S. Appl. No. 90/019,330 Petition Under 37 C.F.R. § 1.182 to Seal Document Versions Filed via IDS and Substitute Redacted Document Versions Therfor Aug. 1, 2024.
Reexamination No. U.S. Appl. No. 90/019,330 Petition Under 37 CFR § 1.59 to Expunge Application Papers Aug. 1, 2024.
Reexamination U.S. Appl. No. 90/019,330 Decision on Petition Under 37 C.F.R. § 1.59 Jul. 16, 2024.
Reexamination No. U.S. Appl. No. 90/019,330 Petition Under 37 CFR § 1.59 to Expunge Application Papers Jun. 12, 2024.
WO PCT/US24/16127 ISR and Written Opinion Sep. 11, 2024.
ACCU-CHEK® Softclix Lancet Device retrieved from file:///C:/Users/afredericks/Downloads/softclix-user-manual.pdf, 2007, 2 pages.
American National Standard, Ansi/Aami HE75:2009, Human factors engineering - Design of medical devices, 2010, 465 pages.
Automated Retractable VanishPoint Syringe 510(k) Safety and Effectiveness Summary, 1998, 5 pages.
"Bluetooth rival unveiled by Nokia", 2006, retrieved from news.bbc.co.uk/1/hi/technology/5403564.stm, 2 pages.
Breton, M., et al., "Fully Integrated Artificial Pancreas in Type 1 Diabetes: Modular Closed-Loop Glucose Control Maintains Near Normoglycemia", Diabetes, 2012, vol. 61, No. 9, pp. 2230-2237.
Dexcom G5 Mobile System User Guide, 2015, pp. 1-260.
U.S. Appl. No. 61/569,287, filed Dec. 11, 2011.
International Standard, IEC 62366, Medical devices - Application of usability engineering to medical devices, 2007, 214 pages.
Kaye, R., et al., "Medical Device Use-Safety: Incorporating Human Factors Engineering into Risk Management", 2000, retrieved from https://www.qualysinnova.com/download/files/MD-Use-Safety.pdf, pp. 1-33.
Medtronic MiniMed One-press Serter User Guide, 2015, 26 pages.
Medtronic MiniMed Paradigm® 512 and 712 Insulin Pumps User Guide, 2005, pp. 1-136.
Microlet® 2 Lancing Device, 2008, retrieved from https://image.tigermedical.com/Manuals/BAY6606-20141216010820833.pdf, 1 page.
3,050,721 Examiner's Report Nov. 8, 2024.
20177703.4 Response to Withdrawals Jan. 7, 2025.
20177703.4 Withdrawal of Intervention Dec. 27, 2024.
20177703.4 Withdrawal of Opposition Dec. 27, 2024.
20177703.4 Written Submissions Dexcom Nov. 22, 2024.
20195922.8 Withdrawal of Intervention Dec. 27, 2024.
20195922.8 Withdrawal of Opposition Dec. 27, 2024.
21211041.5 Withdrawal of Opposition Dec. 27, 2024.
21211041.5 Notice of Appeal Dec. 17, 2024.
21211041.5 Response to Summons to Attend Oral Proceedings Dexcom Nov. 12, 2024.
21211041.5 Response to Summons to Attend Oral Proceedings Nov. 12, 2024.
24152079.0 Examination Report Dec. 2, 2024.
24194029.5 Extended Search Report Nov. 18, 2024.
EP 24201435.5 Extended Search Report Jan. 27, 2025
JP 2024-31538 Office Action Oct. 16, 2024.
MY PI2022002786 Examination Report Jan. 8, 2025.
UP Second Expert Opinion of Dr Michael Schoemaker in Litigation of EP 3977921 Nov. 8, 2024.
Decision Denying Institution of Inter Partes Review, IPR No. 2024-00860 Nov. 20, 2024.
Patent Owner Preliminary Response Pursuant to 37 C.F.R. § 42.107, IPR No. 2024-00860 Aug. 23, 2024.
Declaration of Julia Castellano, IPR No. 2024-00860 Aug. 21, 2024.
Declaration of Scott E. Davis, IPR No. 2024-00860 Jun. 5, 2024.
Patent Owner's Request For Oral Argument, IPR No. 2023-01409 Dec. 3, 2024.
Petitioner's Request For Oral Argument, IPR No. 2023-01409 Dec. 3, 2024.
Patent Owner's Objections to Petitioner's Exhibits Submitted With Its Reply, IPR No. 2023-01409 With Its Reply, IPR No. 2023-01409 Nov. 1, 2024.
Petitioner's Updated Exhibit List, IPR No. 2023-01409 Oct. 25, 2024.
Second Declaration of Gary Fletcher, Ph.D., IPR No. 2023-01409 Oct. 25, 2024.

(56) References Cited

OTHER PUBLICATIONS

Petitioner's Reply to Patent Owner's Response, IPR No. 2023-01409 Oct. 25, 2024.
Deposition of Karl R. Leinsing, MSME, PE, IPR No. 2023-01409 Oct. 17, 2024.
Conference Call Before The Patent Trial And Appeal Board • Before Judge Cynthia Hardman, IPR No. 2023-01409 Oct. 17, 2024.
Notice of Joint Stipulation to Modify Schedule, IPR No. 2023-01409 Sep. 26, 2024.
Declaration of Karl R. Leinsing, MSME, PE, IPR No. 2023-01409 Jul. 19, 2024.
Patent Owner's Response, IPR No. 2023-01409 Jul. 19, 2024.
Deposition of Gary Fletcher, Ph.D., IPR No. 2023-01409 Jun. 26, 2024.
Decision Denying Patent Owner's Request on Rehearing of Decision Denying Institution, IPR No. 2023-01396 Aug. 9, 2024.
Ex Parte Reexamination Certificate of U.S. Pat. No. 11,013,440 Oct. 30, 2024.
Reexamination U.S. Appl. No. 90/019,329 Notice of Intent to Issue Ex Parte Reexamination Certificate Oct. 8, 2023.
Ex Parte Reexamination Certificate of U.S. Pat. No. 11,000,216 Nov. 14, 2024.
Ex Parte Reexamination Certificate of U.S. Pat. No. 10,959,654 Nov. 5, 2024.
Abbott Patent Marking Diabetes, 2024, retrieved from https://www.abbott.com/patents/diabetes-patents.html, 6 pages.
Using your ACCU-CHEK® Multiclix Lancet Device, 2005, retrieved from https://www.northcoastmed.com/wp-content/uploads/2023/03/multiclix_userguide.pdf, 2 pages.
"The Advantages of the Cleo® 90 Infusion Set Are Clear", 2019, retrieved from https://web.archive.org/web/20220816002119/https://smiths-medical.com/-/media/M/Smiths-medical_com//Files/Import-Files/Product-Literature/IN193873GB-092019_LR.pdf, 2 pages.
Burge, M. R., et al., "Continuous Glucose Monitoring: The Future of Diabetes Management", Diabetes Spectrum, 2008, vol. 21, No. 2, pp. 112-119.
Clancy, N. T., et al., "A new device for assessing changes in skin viscoelasticity using indentation and optical measurement", Skin Research and Technology, 2010, vol. 16, pp. 210-228.
Cleo® 90 Infusion Set 510(k) Premarket Notification, 2004, 1 page.
Dexcom G6 Continuous Glucose Monitoring (CGM) System Section 510(k) Approval, 2022, pages.
Dexcom STS Continuous Monitors FDA Premarket Approval (PMA), 2006, 2 pages.
Freestyle Navigator Answers to Frequently Asked Questions, 2007, retrieved from https://web.archive.org/web/20080917183534/http://www.freestylenavigator.com/ab_nav/url/c ontent/en_US/3 0.10.10:1 O/general_content/General_ContenL0000004.htm, 2 pages.
"The Future is Bright for Veteran-centric Rehabilitation Research Publications", Journal of Rehabilitation Research & Development (JRRD), 2013, retrieved from https://www.rehab.research.va.gov/jrrd/index.html, 2 pages.
Mazze, R. S., et al., "Evaluating the Accuracy, Reliability, and Clinical Applicability of Continuous Glucose Monitoring (CGM): Is CGM Ready for Real Time?", Diabetes Technology & Therapeutics, 2009, vol. 11, No. 1., pp. 11-18.
Medtronic MiniMed Guardian® Real-Time Components, 2007, retrieved from https://web.archive.org/20071013095335/http:/www.medtronicdiabetes.com/products/guardian/components.html, 2 pages.
Medtronic MiniMed Guardian® Real-Time Features, 2007, retrieved from https://web.archive.org/20071025084715/http:/www.medtronicdiabetes.com/products/guardian/features.html, 2 pages.
Piper, H. G., et al., "Real-Time Continuous Glucose Monitoring in Pediatric Patients During and After Cardiac Surgery", Pediatrics, 2006, vol. 118, No. 3, pp. 1176-1184.
Rabiee, A., et al., "Numerical and Clinical Accuracy of a Continuous Glucose Monitoring System during Intravenous Insulin Therapy in the Surgical and Burn Intensive Care Units", Journal of Diabetes Science and Technology, 2009, vol. 3, No. 4, pp. 951-959.

Sacks, A. H., et al., "Skin blood flow changes and tissue deformations produced by cylindrical indentors", Journal of Rehabilitation Research and Development, 1985, vol. 22, No. 3, pp. 1-6.
Schneider, M., et al., "Evaluating the use of the Cleo® 90 infusion set for patients on a palliative care unit", International Journal of Palliative Nursing, 2009, vol. 15,. No. 8, pp. 372-376.
AU 2019404908 Examiner's Report Feb. 17, 2025.
CA 3,228,738 Examiner's Report May 8, 2025.
CN 202211091194.1 Notification of Filing Divisional Application Mar. 27, 2025.
EP 17182379.2 Reply to Reply to Opposition May 16, 2025.
EP 17182379.2 Reply to Opposition Feb. 27, 2025.
EP 19900891.3 Examination Report May 8, 2025.
EP 21211041.5 Grounds of Appeal Apr. 23, 2025.
EP 21211041.5 Minutes of Oral Proceedings Dec. 13, 2024.
EP 23190032.5 Examination Report May 19, 2025.
JP 2023-516522 Office Action Mar. 5, 2025.
JP 2023-514023 Office Action Apr. 16, 2025.
MX MX/a/2021/007294 Second Office Action Feb. 19, 2025.
MY PI2021003022 Examination Report Mar. 5, 2025.
Patent Owner's Response To Petitioner's Explanation Of Parallel Petitions Challenging U.S. Pat. No. 11,510,325, IPR No. 2024-00860 Aug. 23, 2024.
Petitioner's Explanation Of Parallel Petitions Challenging U.S. Pat. No. 11,510,325, IPR No. 2024-00860 May 9, 2024.
Termination Due to Settlement After Institution of Trial, IPR No. 2023-01409 Jan. 7, 2025.
Joint Motion to Treat Settlement Agreement as Business Confidential Information. IPR No. 2023-01409 Jan. 3, 2025.
Joint Motion to Terminate Proceeding Under 35 U.S.C. § 317(a), IPR No. 2023-01409 Jan. 3, 2025.
Order Setting Oral Argument, IPR No. 2023-01409 Dec. 11, 2024.
Patent Owner's Sur-Reply, IPR No. 2023-01409 Dec. 10, 2024.
Deposition of Gary D. Fletcher, Ph.D., IPR No. 2023-01409 Dec. 4, 2024.
Reexamination No. U.S. Appl. No. 90/019,307 Office Action Mar. 18, 2025.
Reexamination No. U.S. Appl. No. 90/019,307 Decision on Petition Feb. 13, 2025.
Reexamination U.S. Appl. No. 90/019,329 Decision on Petition Under 37 C.F.R. § 1.181 Mar. 18, 2025.
WO PCT/US25/13698 Invitation to Pay Additional Fees Apr. 15, 2025.
CN 202180063087.5 First Office Action Aug. 14, 2025.
EP 17182379.2 Written Submissions Aug. 6, 2025.
EP 17182379.2 Summons to Attend Oral Proceedings Jul. 4, 2025.
EP 19151577.4 Examination Report Sep. 3, 2025.
EP 20177712.5 Written Submissions Gulde Aug. 21, 2025.
EP 20177712.5 Response to Summons to Attend Oral Proceedings Aug. 21, 2025.
EP 21192910.4 Notice of Opposition Stolmar Sep. 10, 2025.
EP 21192910.4 Notice of Opposition Strawman Sep. 10, 2025.
EP 24218309.3 Extended Search Report Jul. 9, 2025.
EP 24194029.5 Examination Report Aug. 26, 2025.
EP 24220160.6 Extended Search Report Jun. 17, 2025.
JP 2023-514023 Final Office Action Aug. 20, 2025.
JP 2023-514024 Office Action Apr. 30, 2025.
JP 2023-532327 Office Action Jul. 23, 2025.
JP 2025-026588 Office Action Aug. 27, 2025.
Reexamination No. U.S. Appl. No. 90/019,307 Final Office Action Jul. 8, 2025.
WO PCT/US25/13698 ISR and Written Opinion Jun. 5, 2025.
WO PCT/US25/27260 Invitation to Pay Additional Fees Jul. 24, 2025.
EP 17182379.2 Decision Revoking the European Patent Nov. 24, 2025.
EP 17182379.2 Minutes of the Oral Proceedings Nov. 24, 2025.
EP 20177712.5 Decision Revoking the European Patent Nov. 28, 2025.
EP 20177712.5 Minutes of the Oral Proceedings Nov. 28, 2025.
EP 21192910.4 Notice of Intervention Nov. 14, 2025.
EP 23166498.8 Examination Report Dec. 10, 2025.
EP 23190032.5 Examination Report Dec. 10, 2025.

(56)          References Cited

OTHER PUBLICATIONS

EP 24201435.5 Examination Report Oct. 26, 2025.
WO PCT/US2025/027260 Isr and Written Opinion Sep. 16, 2025.

* cited by examiner

SYSTEMS, DEVICES AND METHODS FOR ANALYTE SENSOR INSERTION

CROSS-REFERENCE TO RELATED APPLICATIONS

The present application is a continuation of U.S. patent application Ser. No. 17/357,090, filed Jun. 24, 2021, which is a continuation of U.S. patent application Ser. No. 15/877,331, filed Jan. 22, 2018, now U.S. Pat. No. 11,071,478, which claims priority to and the benefit of U.S. Provisional Patent Application No. 62/449,570, filed Jan. 23, 2017, both of which are incorporated by reference herein in their entireties for all purposes.

FIELD

The subject matter described herein relates generally to systems, devices, and methods for using an applicator and a sensor control unit in an in vivo analyte monitoring system.

BACKGROUND

The detection and/or monitoring of analyte levels, such as glucose, ketones, lactate, oxygen, hemoglobin A1C, or the like, can be vitally important to the health of an individual having diabetes. Patients suffering from diabetes mellitus can experience complications including loss of consciousness, cardiovascular disease, retinopathy, neuropathy, and nephropathy. Diabetics are generally required to monitor their glucose levels to ensure that they are being maintained within a clinically safe range, and may also use this information to determine if and/or when insulin is needed to reduce glucose levels in their bodies, or when additional glucose is needed to raise the level of glucose in their bodies.

Growing clinical data demonstrates a strong correlation between the frequency of glucose monitoring and glycemic control. Despite such correlation, however, many individuals diagnosed with a diabetic condition do not monitor their glucose levels as frequently as they should due to a combination of factors including convenience, testing discretion, pain associated with glucose testing, and cost.

To increase patient adherence to a plan of frequent glucose monitoring, in vivo analyte monitoring systems can be utilized, in which a sensor control device may be worn on the body of an individual who requires analyte monitoring. To increase comfort and convenience for the individual, the sensor control device may have a small form-factor, and can be assembled and applied by the individual with a sensor applicator. The application process includes inserting a sensor, such as a dermal sensor that senses a user's analyte level in a bodily fluid located in the dermal layer of the human body, using an applicator or insertion mechanism, such that the sensor comes into contact with a bodily fluid. The sensor control device may also be configured to transmit analyte data to another device, from which the individual or her health care provider ("HCP") can review the data and make therapy decisions.

While current sensors can be convenient for users, they are also susceptible to malfunctions due to improper insertion. These malfunctions can be caused by user error, lack of proper training, poor user coordination, overly complicated procedures, and other issues. This can be particularly true for analyte monitoring systems having dermal sensors, which are typically of smaller scale relative to sensors used to measure an analyte level in an interstitial fluid ("ISF"), and which are inserted using sharps (also known as "introducers" or "needles") that are shorter than those used for ISF sensors. Some prior art systems, for example, may rely too much on the precision assembly and deployment of a sensor control device and an applicator by the individual user. Other prior art systems may utilize sharp insertion and retraction mechanisms that are susceptible to premature withdrawal before the sensor can be properly implanted. In addition, with respect to dermal sensors, some prior art systems may utilize sharps that are not optimally configured to create an insertion path in the dermal layer without creating trauma to surrounding tissue. These challenges and others described herein can lead to improperly inserted or damaged sensors, and consequently, a failure to properly monitor the patient's analyte level.

Thus, a need exists for more reliable sensor insertion devices, systems and methods, particularly for use in conjunction with dermal sensors, that are easy to use by the patient and less prone to error.

SUMMARY

Provided herein are example embodiments of systems, devices and methods for the assembly and use of an applicator and a sensor control device of an in vivo analyte monitoring system, and in particular, where dermal sensors are utilized. An applicator can be provided to the user in a sterile package with an electronics housing of the sensor control device contained therein. A structure separate from the applicator, such as a container, can also be provided to the user as a sterile package with a sensor module and a sharp module contained therein. The user can couple the sensor module to the electronics housing, and can couple the sharp to the applicator with an assembly process that involves the insertion of the applicator into the container in a specified manner. After assembly, the applicator can be used to position the sensor control device on a human body with a sensor in contact with the wearer's bodily fluid (e.g., dermal fluid). The embodiments provided herein are improvements to prevent or reduce the likelihood that a sensor is improperly inserted or damaged. Other improvements and advantages are provided as well. The various configurations of these devices are described in detail by way of the embodiments which are only examples.

Other systems, devices, methods, features and advantages of the subject matter described herein will be or will become apparent to one with skill in the art upon examination of the following figures and detailed description. It is intended that all such additional systems, devices, methods, features, and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 17-1 is a call-out that enlarges a portion of FIG. 17.

DETAILED DESCRIPTION

Figure 1:
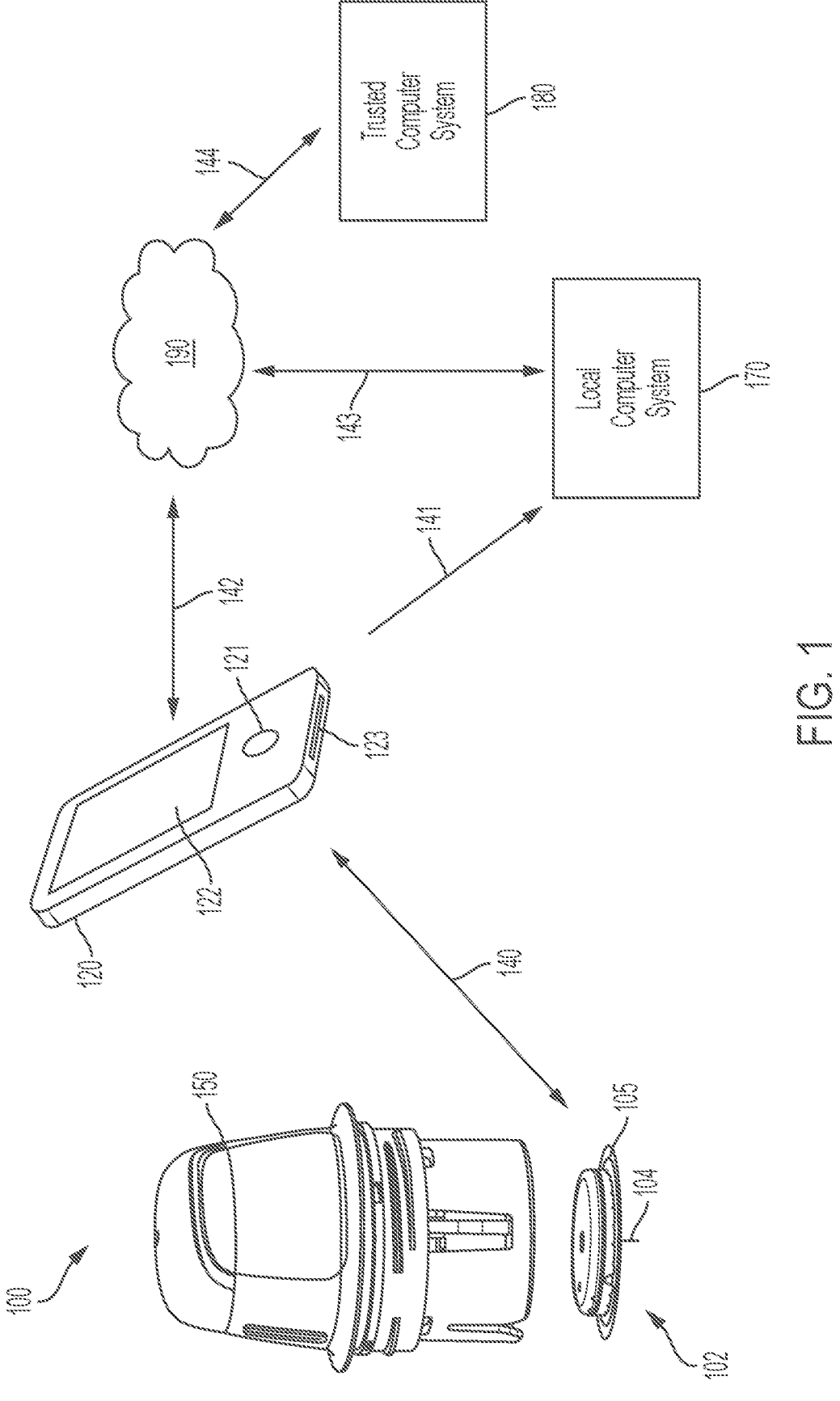
FIG. 1 is a system overview of a sensor applicator, reader device, monitoring system, network, and remote system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a," "an," and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Generally, embodiments of the present disclosure include systems, devices, and methods for the use of dermal sensor insertion applicators for use with in vivo analyte monitoring systems. Accordingly, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including systems that are entirely non-invasive.

Furthermore, for each and every embodiment of a method disclosed herein, systems and devices capable of performing each of those embodiments are covered within the scope of the present disclosure. For example, embodiments of sensor control devices are disclosed, and these devices can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

As mentioned, a number of embodiments of systems, devices, and methods are described herein that provide for the improved assembly and use of dermal sensor insertion devices for use with in vivo analyte monitoring systems. In particular, several embodiments of the present disclosure are designed to improve the method of sensor insertion with respect to in vivo analyte monitoring systems and, in particular, to prevent the premature retraction of an insertion sharp during a sensor insertion process. Some embodiments, for example, include a dermal sensor insertion mechanism with an increased firing velocity and a delayed sharp retraction. In other embodiments, the sharp retraction mechanism can be motion-actuated such that the sharp is not retracted until the user pulls the applicator away from the skin. Consequently, these embodiments can reduce the likelihood of prematurely withdrawing an insertion sharp during a sensor insertion process; decrease the likelihood of improper sensor insertion; and decrease the likelihood of damaging a sensor during the sensor insertion process, to name a few advantages. Several embodiments of the present disclosure also provide for improved insertion sharp modules to account for the small scale of dermal sensors and the relatively shallow insertion path present in a subject's dermal layer. In addition, several embodiments of the present disclosure are designed to prevent undesirable axial and/or rotational movement of applicator components during sensor insertion. Accordingly, these embodiments can reduce the likelihood of instability of a positioned dermal sensor, irritation at the insertion site, damage to surrounding tissue, and breakage of capillary blood vessels resulting in fouling of the dermal fluid with blood, to name a few advantages. In addition, to mitigate inaccurate sensor readings which can be caused by trauma at the insertion site, several embodiments of the present disclosure can reduce the end-depth penetration of the needle relative to the sensor tip during insertion.

Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "handheld reader device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. Other devices such as personal computers have also been utilized with or incorporated into in vivo and in vitro monitoring systems.

Example Embodiment of In Vivo Analyte Monitoring System

FIG. 1 is a conceptual diagram depicting an example embodiment of an analyte monitoring system 100 that includes a sensor applicator 150, a sensor control device 102, and a reader device 120. Here, sensor applicator 150 can be used to deliver sensor control device 102 to a monitoring location on a user's skin where a sensor 104 is maintained in position for a period of time by an adhesive patch 105. Sensor control device 102 is further described in FIGS. 2B and 2C, and can communicate with reader device 120 via a communication path 140 using a wired or wireless technique. Example wireless protocols include Bluetooth, Bluetooth Low Energy (BLE, BTLE, Bluetooth SMART, etc.), Near Field Communication (NFC) and others. Users can monitor applications installed in memory on reader device 120 using screen 122 and input 121 and the device battery can be recharged using power port 123. More detail about reader device 120 is set forth with respect to FIG. 2A below. Reader device 120 can communicate with local computer system 170 via a communication path 141 using a wired or wireless technique. Local computer system 170 can include one or more of a laptop, desktop, tablet, phablet, smartphone, set-top box, video game console, or other computing device and wireless communication can include any of a number of applicable wireless networking protocols including Bluetooth, Bluetooth Low Energy (BTLE), Wi-Fi or others. Local computer system 170 can communicate via communications path 143 with a network 190 similar to how reader device 120 can communicate via a communications path 142 with network 190, by wired or wireless technique as described previously. Network 190 can be any of a number of networks, such as private networks and public networks, local area or wide area networks, and so forth. A trusted computer system 180 can include a server and can provide authentication services and secured data storage and can communicate via communications path 144 with network 190 by wired or wireless technique.

Example Embodiment of Reader Device

Figure 2A:
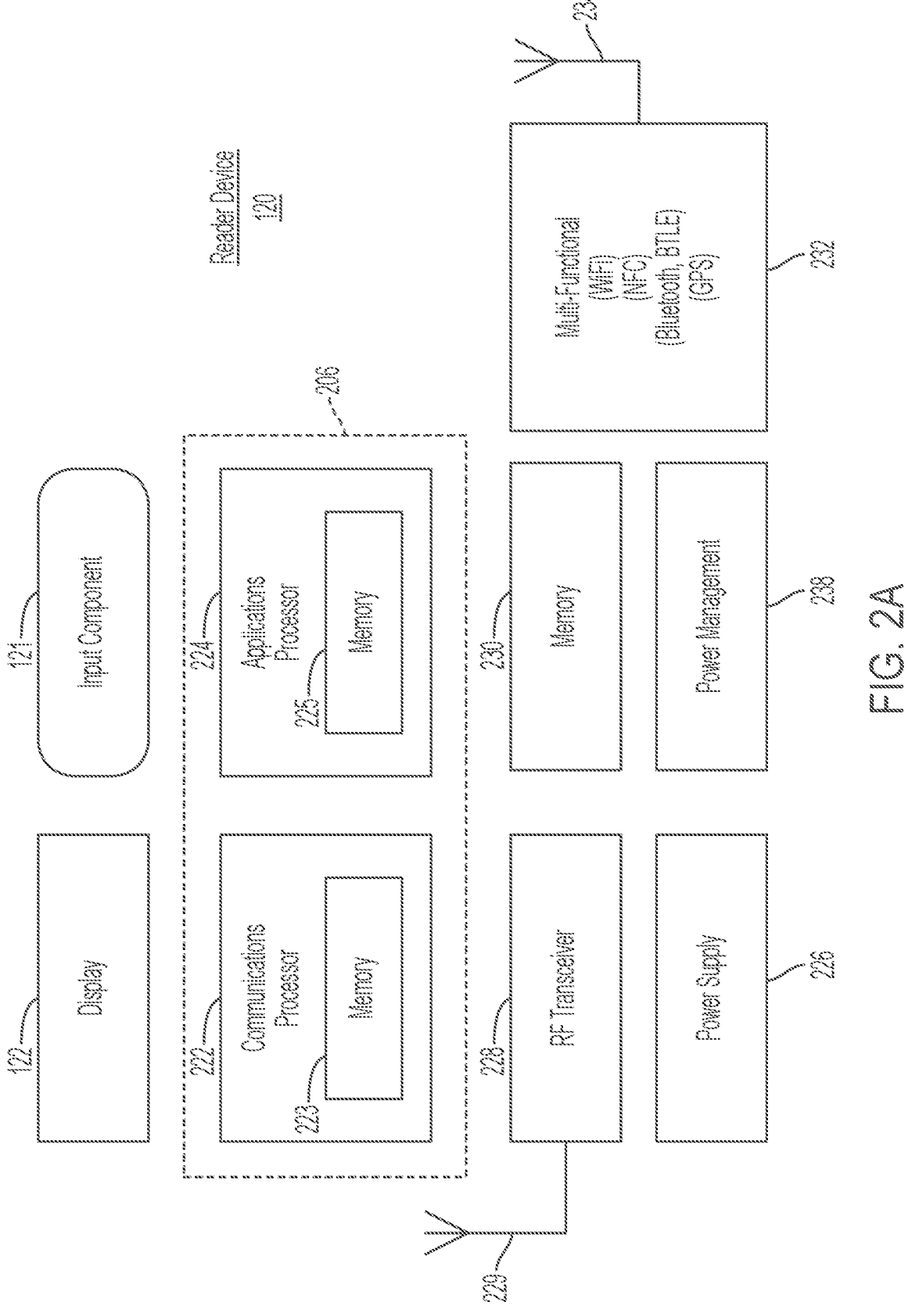
FIG. 2A is a block diagram depicting an example embodiment of a reader device.

FIG. 2A is a block diagram depicting an example embodiment of a reader device configured as a smartphone. Here, reader device 120 can include a display 122, input component 121, and a processing core 206 including a communications processor 222 coupled with memory 223 and an applications processor 224 coupled with memory 225. Also included can be separate memory 230, RF transceiver 228 with antenna 229, and power supply 226 with power management module 238. Further included can be a multi-functional transceiver 232 which can communicate over Wi-Fi, NFC, Bluetooth, BTLE, and GPS with an antenna 234. As understood by one of skill in the art, these components are electrically and communicatively coupled in a manner to make a functional device.

Example Embodiments of Sensor Control Device

Figures 2B, 2C:
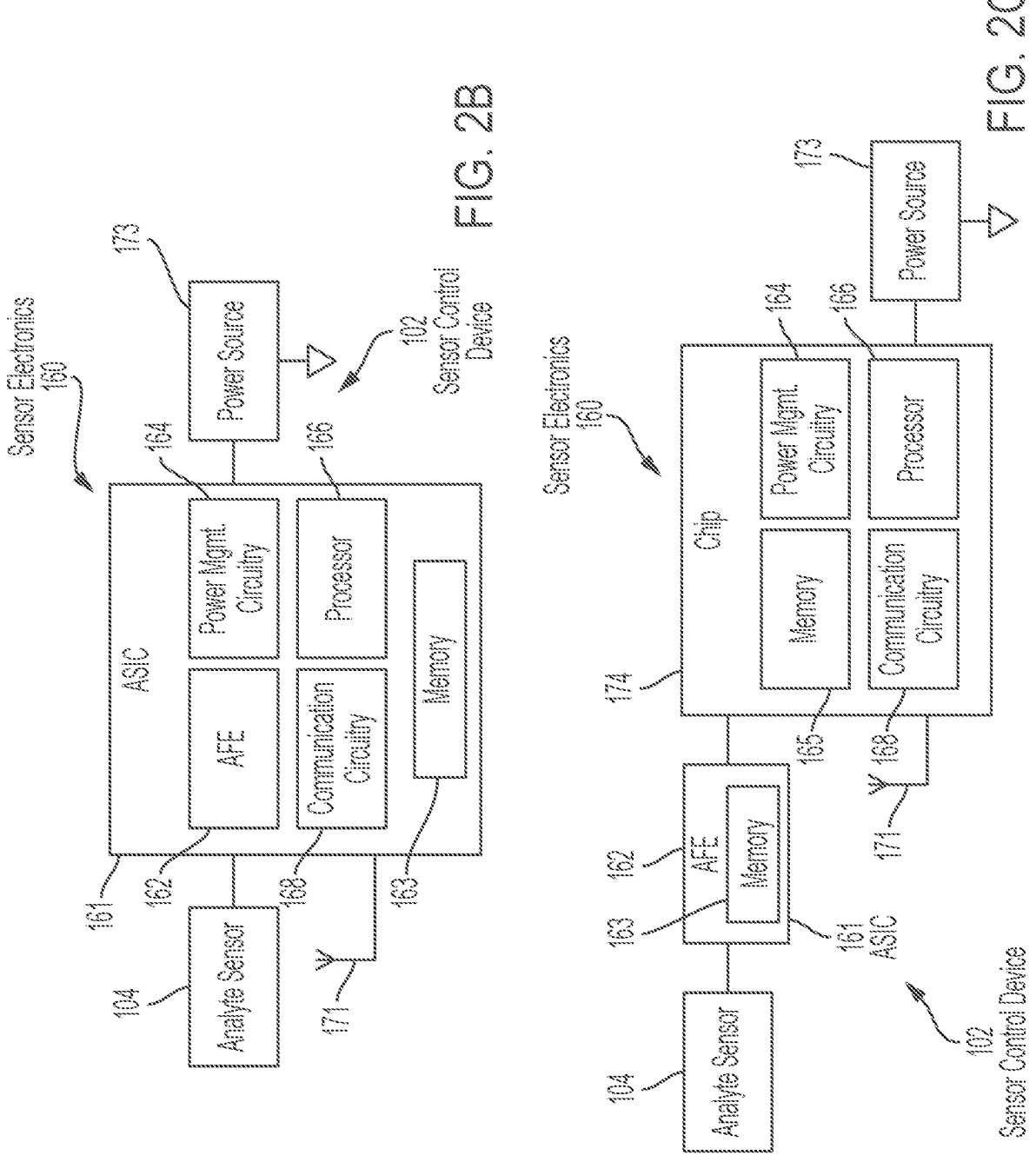
FIGS. 2B and 2C are block diagrams depicting example embodiments of sensor control devices.

FIGS. 2B and 2C are block diagrams depicting example embodiments of sensor control device 102 having analyte sensor 104 and sensor electronics 160 (including analyte monitoring circuitry) that can have the majority of the processing capability for rendering end-result data suitable for display to the user. In FIG. 2B, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as analyte monitoring circuitry, but in other embodiments either circuit can perform the analyte monitoring function. Processor 166 can include one or more processors, microprocessors, controllers, and/or microcontrollers, each of which can be a discrete chip or distributed amongst (and a portion of) a number of different chips.

A memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 173, which can be a coin cell battery, or the like. AFE 162 interfaces with in vivo analyte sensor 104 and receives measurement data therefrom and outputs the data to processor 166 in digital form, which in turn processes the data to arrive at the end-result glucose discrete and trend values, etc. This data can then be provided to communication circuitry 168 for sending, by way of antenna 171, to reader device 120 (not shown), for example, where minimal further processing is needed by the resident software application to display the data.

FIG. 2C is similar to FIG. 2B but instead includes two discrete semiconductor chips 162 and 174, which can be packaged together or separately. Here, AFE 162 is resident on ASIC 161. Processor 166 is integrated with power management circuitry 164 and communication circuitry 168 on chip 174. AFE 162 includes memory 163 and chip 174 includes memory 165, which can be isolated or distributed within. In one example embodiment, AFE 162 is combined with power management circuitry 164 and processor 166 on one chip, while communication circuitry 168 is on a separate chip. In another example embodiment, both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

Example Embodiment of Assembly Process for Sensor Control Device

Figures 3A, 3B, 3C, 3D, 3E, 3F:
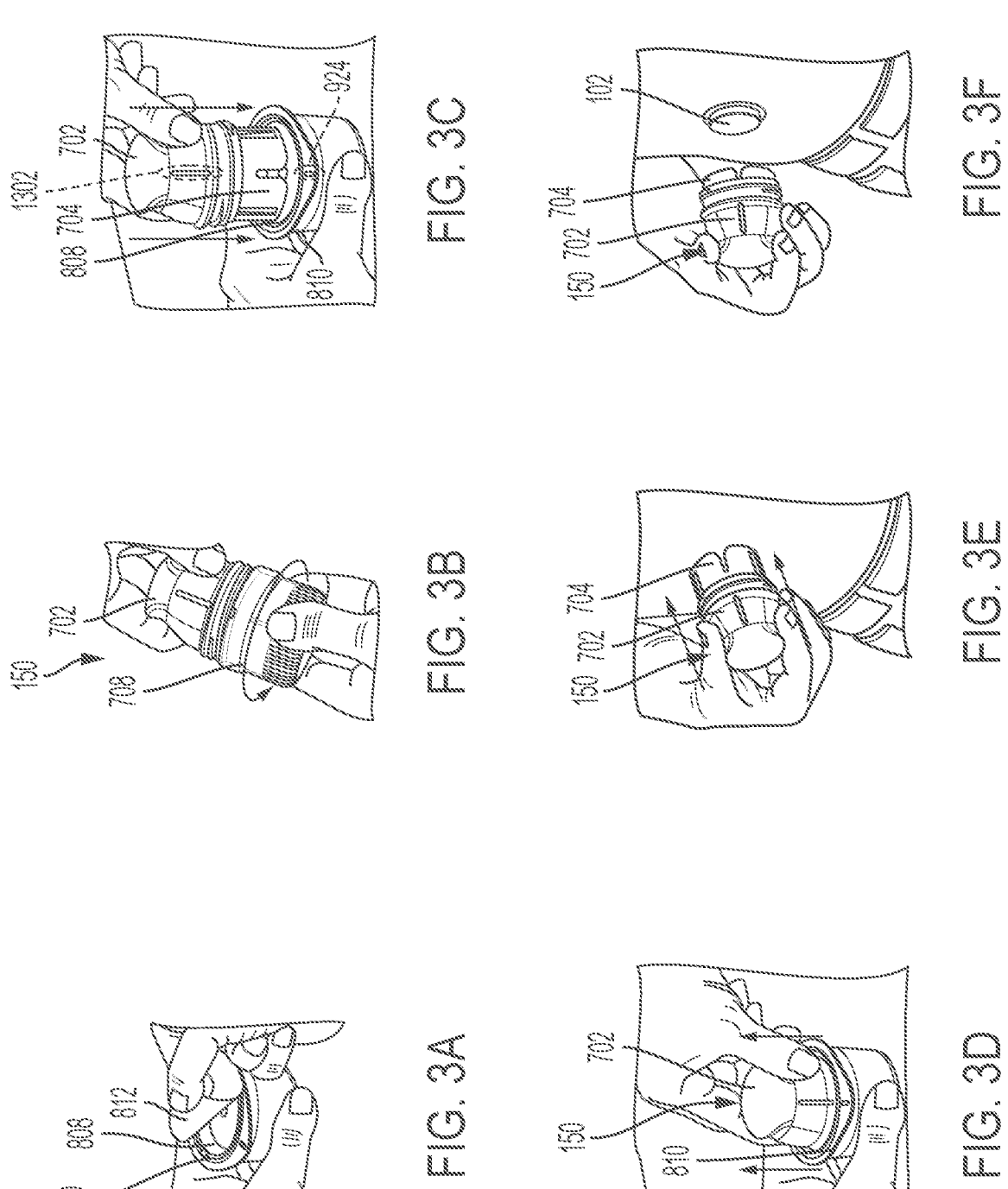
FIG. 3A is a proximal perspective view depicting an example embodiment of a user preparing a tray for an assembly.
FIG. 3B is a side view depicting an example embodiment of a user preparing an applicator device for an assembly.
FIG. 3C is a proximal perspective view depicting an example embodiment of a user inserting an applicator device into a tray during an assembly.
FIG. 3D is a proximal perspective view depicting an example embodiment of a user removing an applicator device from a tray during an assembly.
FIG. 3E is a proximal perspective view depicting an example embodiment of a patient applying a sensor using an applicator device.
FIG. 3F is a proximal perspective view depicting an example embodiment of a patient with an applied sensor and a used applicator device.

The components of sensor control device 102 can be acquired by a user in multiple packages requiring final assembly by the user before delivery to an appropriate user location. FIGS. 3A-3D depict an example embodiment of an assembly process for sensor control device 102 by a user, including preparation of separate components before coupling the components in order to ready the sensor for delivery. FIGS. 3E-3F depict an example embodiment of delivery of sensor control device 102 to an appropriate user location by selecting the appropriate delivery location and applying device 102 to the location.

FIG. 3A is a proximal perspective view depicting an example embodiment of a user preparing a container 810, configured here as a tray (although other packages can be used), for an assembly process. The user can accomplish this preparation by removing lid 812 from tray 810 to expose platform 808, for instance by peeling a non-adhered portion of lid 812 away from tray 810 such that adhered portions of lid 812 are removed. Removal of lid 812 can be appropriate in various embodiments so long as platform 808 is adequately exposed within tray 810. Lid 812 can then be placed aside.

FIG. 3B is a side view depicting an example embodiment of a user preparing an applicator device 150 for assembly.

Applicator device 150 can be provided in a sterile package sealed by a cap 708. Preparation of applicator device 150 can include uncoupling housing 702 from cap 708 to expose sheath 704 (FIG. 3C). This can be accomplished by unscrewing (or otherwise uncoupling) cap 708 from housing 702. Cap 708 can then be placed aside.

FIG. 3C is a proximal perspective view depicting an example embodiment of a user inserting an applicator device 150 into a tray 810 during an assembly. Initially, the user can insert sheath 704 into platform 808 inside tray 810 after aligning housing orienting feature 1302 (or slot or recess) and tray orienting feature 924 (an abutment or detent). Inserting sheath 704 into platform 808 temporarily unlocks sheath 704 relative to housing 702 and also temporarily unlocks platform 808 relative to tray 810. At this stage, removal of applicator device 150 from tray 810 will result in the same state prior to initial insertion of applicator device 150 into tray 810 (i.e., the process can be reversed or aborted at this point and then repeated without consequence).

Sheath 704 can maintain position within platform 808 with respect to housing 702 while housing 702 is distally advanced, coupling with platform 808 to distally advance platform 808 with respect to tray 810. This step unlocks and collapses platform 808 within tray 810. Sheath 704 can contact and disengage locking features (not shown) within tray 810 that unlock sheath 704 with respect to housing 702 and prevent sheath 704 from moving (relatively) while housing 702 continues to distally advance platform 808. At the end of advancement of housing 702 and platform 808, sheath 704 is permanently unlocked relative to housing 702. A sharp and sensor (not shown) within tray 810 can be coupled with an electronics housing (not shown) within housing 702 at the end of the distal advancement of housing 702. Operation and interaction of the applicator device 150 and tray 810 are further described below.

FIG. 3D is a proximal perspective view depicting an example embodiment of a user removing an applicator device 150 from a tray 810 during an assembly. A user can remove applicator 150 from tray 810 by proximally advancing housing 702 with respect to tray 810 or other motions having the same end effect of uncoupling applicator 150 and tray 810. The applicator device 150 is removed with sensor control device 102 (not shown) fully assembled (sharp, sensor, electronics) therein and positioned for delivery.

FIG. 3E is a proximal perspective view depicting an example embodiment of a patient applying sensor control device 102 using applicator device 150 to a target area of skin, for instance, on an abdomen or other appropriate location. Advancing housing 702 distally collapses sheath 704 within housing 702 and applies the sensor to the target location such that an adhesive layer on the bottom side of sensor control device 102 adheres to the skin. The sharp is automatically retracted when housing 702 is fully advanced, while the sensor (not shown) is left in position to measure analyte levels.

FIG. 3F is a proximal perspective view depicting an example embodiment of a patient with sensor control device 102 in an applied position. The user can then remove applicator 150 from the application site.

System 100, described with respect to FIGS. 3A-3F and elsewhere herein, can provide a reduced or eliminated chance of accidental breakage, permanent deformation, or incorrect assembly of applicator components compared to prior art systems. Since applicator housing 702 directly engages platform 808 while sheath 704 unlocks, rather than indirect engagement via sheath 704, relative angularity between sheath 704 and housing 702 will not result in breakage or permanent deformation of the arms or other components. The potential for relatively high forces (such as in conventional devices) during assembly will be reduced, which in turn reduces the chance of unsuccessful user assembly.

Example Embodiment of Sensor Applicator Device

Figures 4A, 4B, 4C:
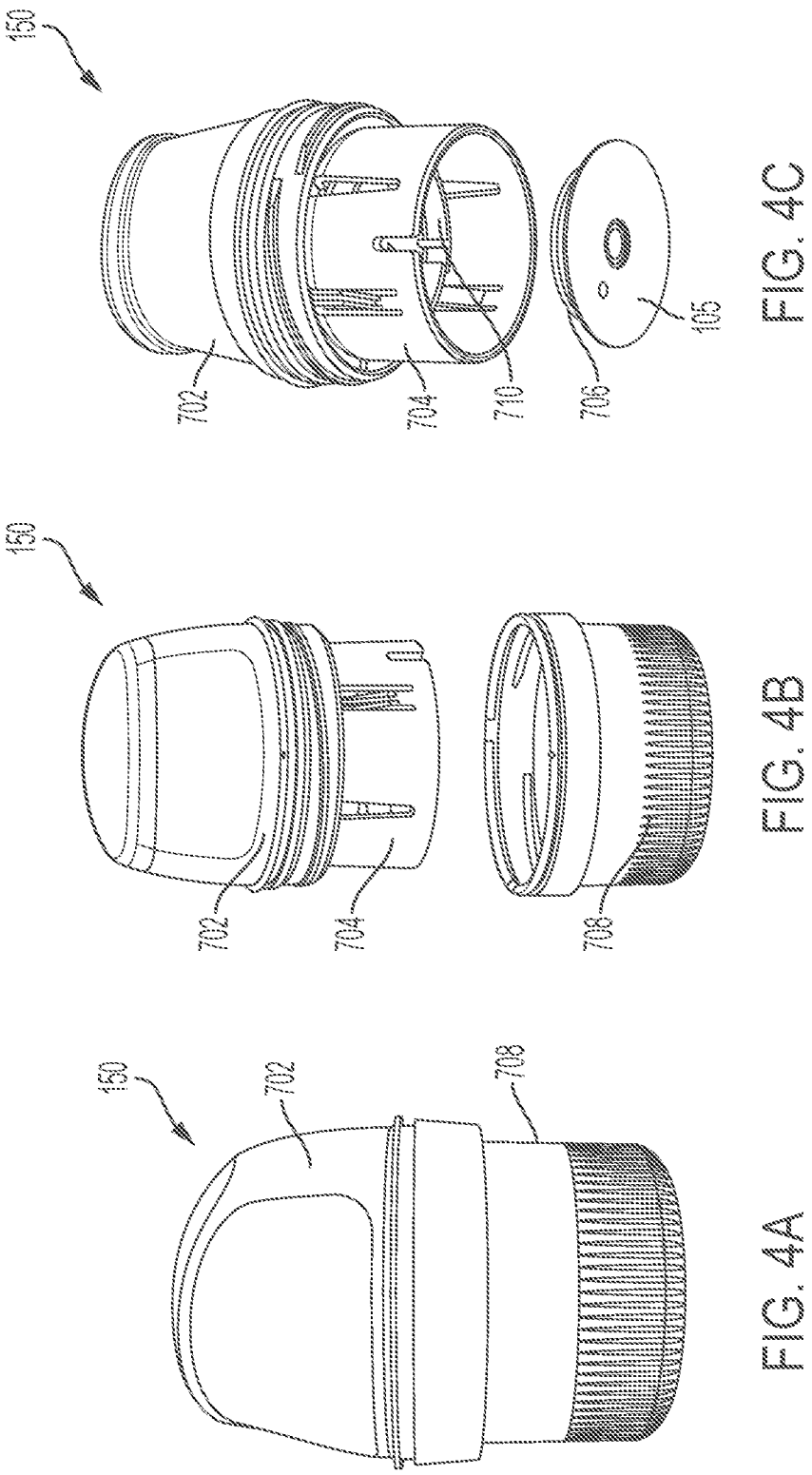
FIG. 4A is a side view depicting an example embodiment of an applicator device coupled with a cap.
FIG. 4B is a side perspective view depicting an example embodiment of an applicator device and cap decoupled.
FIG. 4C is a perspective view depicting an example embodiment of a distal end of an applicator device and electronics housing.

FIG. 4A is a side view depicting an example embodiment of an applicator device 150 coupled with screw cap 708. This is an example of how applicator 150 is shipped to and received by a user, prior to assembly by the user with a sensor. FIG. 4B is a side perspective view depicting applicator 150 and cap 708 after being decoupled. FIG. 4C is a perspective view depicting an example embodiment of a distal end of an applicator device 150 with electronics housing 706 and adhesive patch 105 removed from the position they would have retained within sensor electronics carrier 710 of sheath 704, when cap 708 is in place.

Example Embodiment of Tray and Sensor Module Assembly

Figure 5:
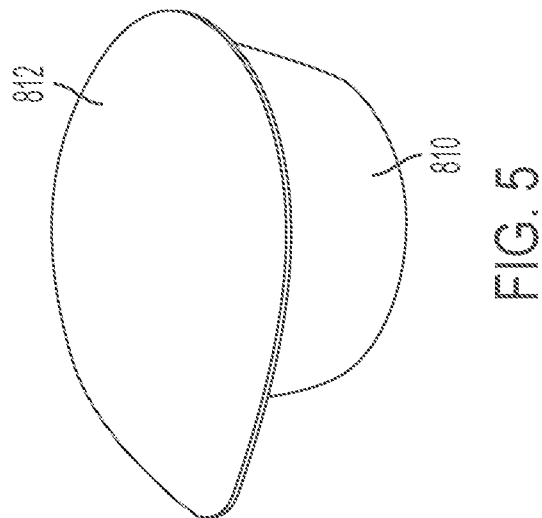
FIG. 5 is a proximal perspective view depicting an example embodiment of a tray with sterilization lid coupled.

FIG. 5 is a proximal perspective view depicting an example embodiment of a tray 810 with sterilization lid 812 removably coupled thereto, which may be representative of how the package is shipped to and received by a user prior to assembly.

Figure 6A:
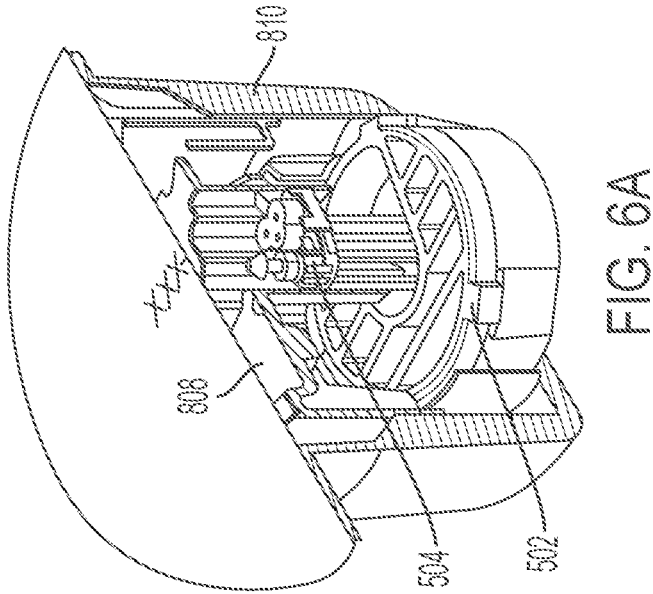
FIG. 6A is a proximal perspective cutaway view depicting an example embodiment of a tray with sensor delivery components.

FIG. 6A is a proximal perspective cutaway view depicting sensor delivery components within tray 810. Platform 808 is slidably coupled within tray 810. Desiccant 502 is stationary with respect to tray 810. Sensor module 504 is mounted within tray 810.

Figure 6B:
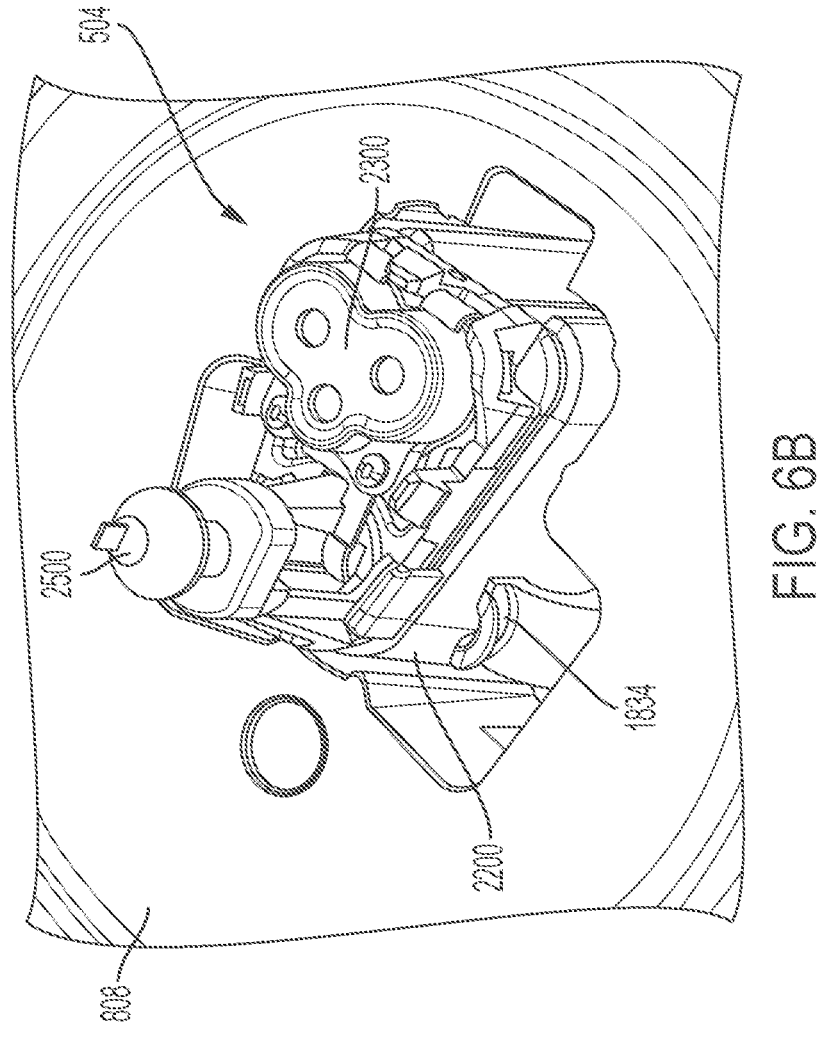
FIG. 6B is a proximal perspective view depicting sensor delivery components.

FIG. 6B is a proximal perspective view depicting sensor module 504 in greater detail. Here, retention arm extensions 1834 of platform 808 releasably secure sensor module 504 in position. Module 2200 is coupled with connector 2300, sharp module 2500 and sensor (not shown) such that during assembly they can be removed together as sensor module 504.

Example Embodiment of Applicator Housing

Figure 7A:
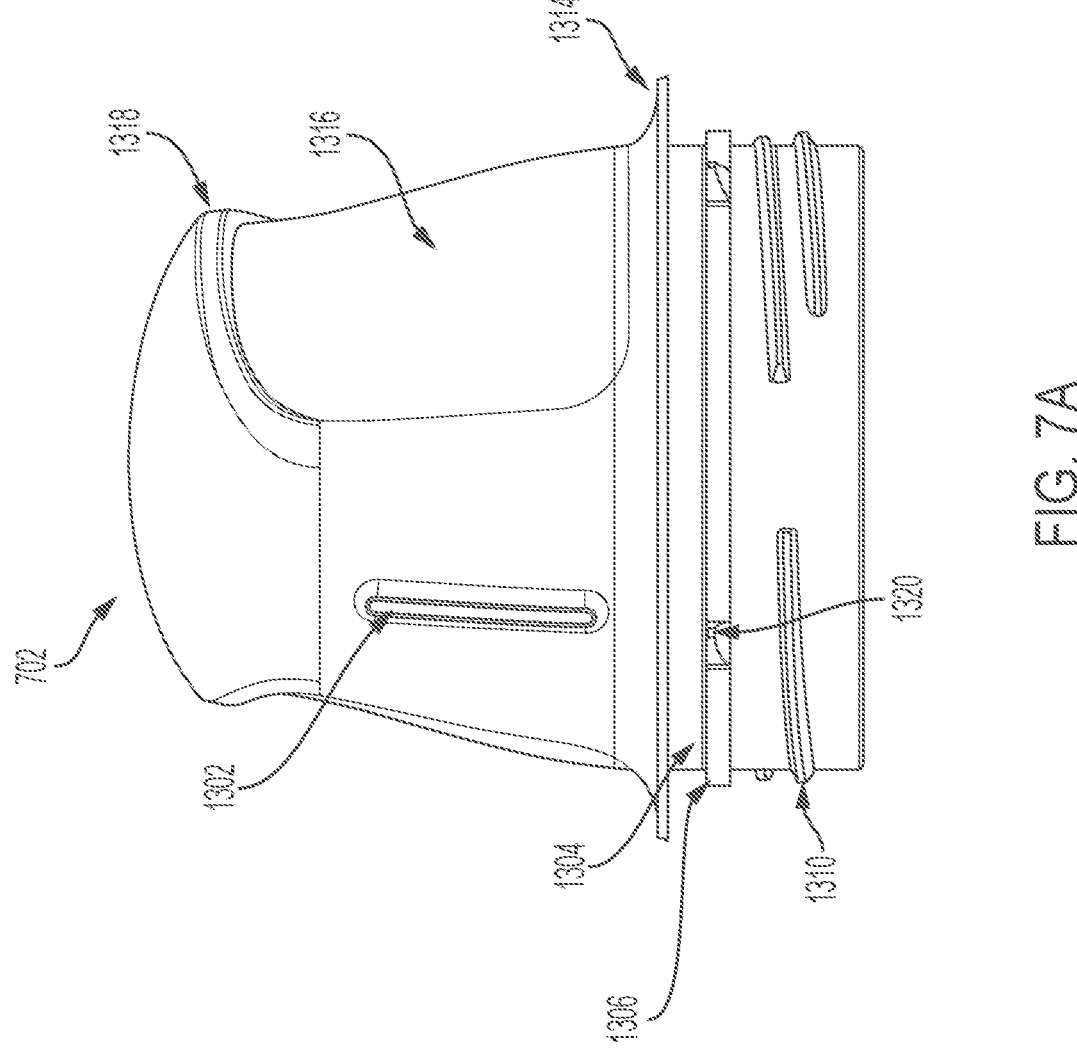
FIG. 7A is side view depicting an example embodiment of a housing.

FIG. 7A is side view depicting an example embodiment of the applicator housing 702 that can include an internal cavity with support structures for applicator function. A user can push housing 702 in a distal direction to activate the applicator assembly process and then also to cause delivery of sensor control device 102, after which the cavity of housing 702 can act as a receptacle for a sharp. In the example embodiment, various features are shown including housing orienting feature 1302 for orienting the device during assembly and use. Tamper ring groove 1304 can be a recess located around an outer circumference of housing 702, distal to a tamper ring protector 1314 and proximal to a tamper ring retainer 1306. Tamper ring groove 1304 can retain a tamper ring so users can identify whether the device has been tampered with or otherwise used. Housing threads 1310 can secure housing 702 to complimentary threads on cap 708 (FIGS. 4A and 4B) by aligning with complimentary cap threads and rotating in a clockwise or counterclockwise direction. A side grip zone 1316 of housing 702 can provide an exterior surface location where a user can grip housing 702 in order to use it. Grip overhang 1318 is a slightly raised ridge with respect to side grip zone 1316 which can aid in ease of removal of housing 702 from cap 708. A shark tooth 1320 can be a raised section with a flat side located on a clockwise edge to shear off a tamper ring (not shown), and hold tamper ring in place after a user has unscrewed cap 708 and housing 702. In the example embodiment four shark teeth 1320 are used, although more or less can be used as desired.

Figure 7B:
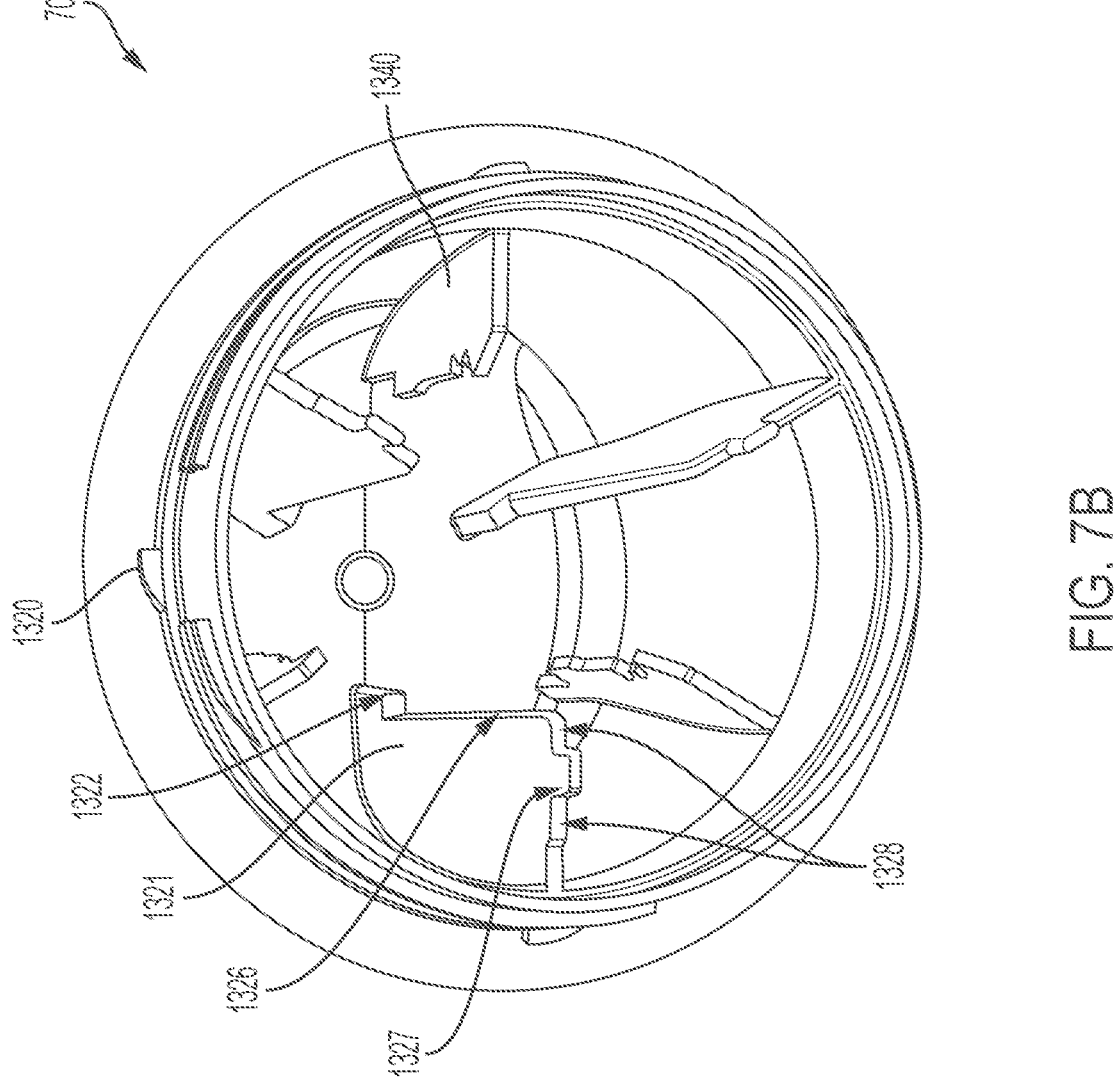
FIG. 7B is a perspective view depicting an example embodiment of a distal end of a housing.

FIG. 7B is a perspective view depicting a distal end of housing 702. Here, three housing guide structures (or "guide ribs") 1321 are located at 120 degree angles with respect to each other and at 60 degree angles with respect to locking structures (or "locking ribs") 1340, of which there are also three at 120 degree angles with respect to each other. Other angular orientations, either symmetric or asymmetric, can be used, as well as any number of one or more structures 1321 and 1340. Here, each structure 1321 and 1340 is configured as a planar rib, although other shapes can be used. Each guide rib 1321 includes a guide edge (also called a "sheath guide rail") 1326 that can pass along a surface of sheath 704 (e.g., guide rail 1418 described with respect to FIG. 8A). An insertion hard stop 1322 can be a flat, distally facing surface of housing guide rib 1321 located near a proximal end of housing guide rib 1321. Insertion hard stop 1322 provides a surface for a sensor electronics carrier travel limiter face 1420 of a sheath 704 (FIG. 8B) to abut during use, preventing sensor electronics carrier travel limiter face 1420 from moving any further in a proximal direction. A carrier interface post 1327 passes through an aperture 1510 (FIG. 9A) of sensor electronics carrier 710 during an assembly. A sensor electronics carrier interface 1328 can be a rounded, distally facing surface of housing guide ribs 1321 which interfaces with sensor electronics carrier 710.

Figure 7C:
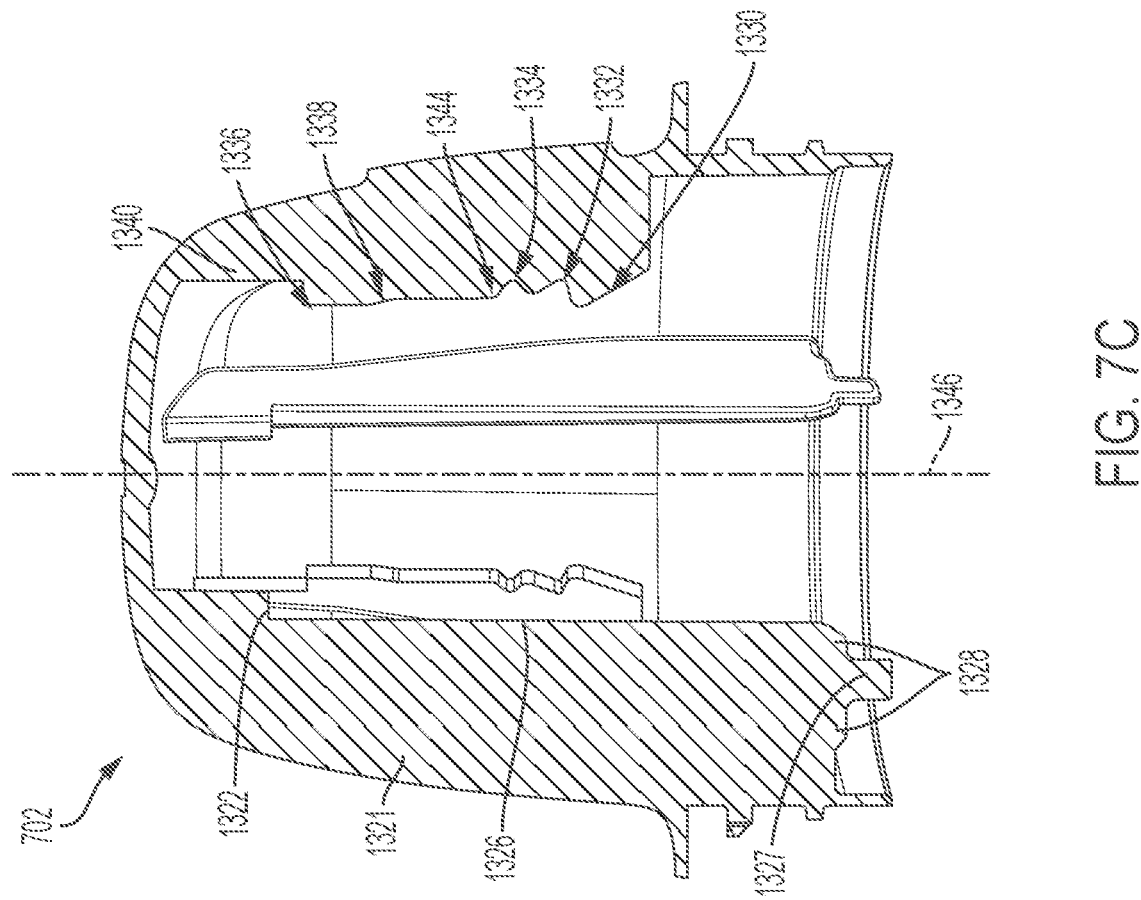
FIG. 7C is a side cross-sectional view depicting an example embodiment of a housing.

FIG. 7C is a side cross-section depicting an example embodiment of a housing. In the example embodiment, side cross-sectional profiles of housing guide rib 1321 and locking rib 1340 are shown. Locking rib 1340 includes sheath snap lead-in feature 1330 near a distal end of locking rib 1340 which flares outward from central axis 1346 of housing 702 distally. Each sheath snap lead-in feature 1330 causes detent snap round 1404 of detent snap 1402 of sheath 704 as shown in FIG. 8C to bend inward toward central axis 1346 as sheath 704 moves towards the proximal end of housing 702. Once past a distal point of sheath snap lead-in feature 1330, detent snap 1402 of sheath 704 is locked into place in locked groove 1332. As such, detent snap 1402 cannot be easily moved in a distal direction due to a surface with a near perpendicular plane to central axis 1346, shown as detent snap flat 1406 in FIG. 8C.

As housing 702 moves further in a proximal direction toward the skin surface, and as sheath 704 advances toward the distal end of housing 702, detent snaps 1402 shift into the unlocked grooves 1334, and applicator 150 is in an "armed" position, ready for use. When the user further applies force to the proximal end of housing 702, while sheath 704 is pressed against the skin, detent snap 1402 passes over firing detent 1344. This begins a firing sequence (as described, for example, with respect to FIGS. 12A-12D) due to release of stored energy in the deflected detent snaps 1402, which travel in a proximal direction relative to the skin surface, toward sheath stopping ramp 1338 which is slightly flared outward with respect to central axis 1346 and slows sheath 704 movement during the firing sequence. The next groove encountered by detent snap 1402 after unlocked groove 1334 is final lockout groove 1336 which detent snap 1402 enters at the end of the stroke or pushing sequence performed by the user. Final lockout recess 1336 can be a proximally-facing surface that is perpendicular to central axis 1346 which, after detent snap 1402 passes, engages a detent snap flat 1406 and prevents reuse of the device by securely holding sheath 704 in place with respect to housing 702. Insertion hard stop 1322 of housing guide rib 1321 prevents sheath 704 from advancing proximally with respect to housing 702 by engaging sensor electronics carrier travel limiter face 1420.

Figure 7E:
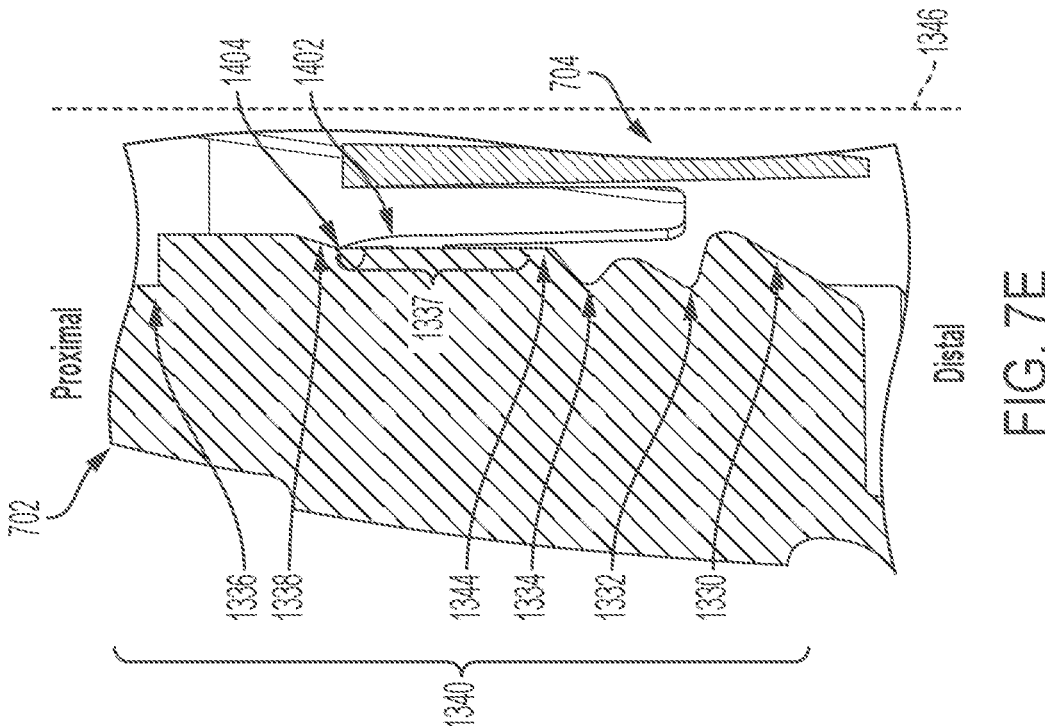
FIGS. 7D and 7E are side cross-sectional views depicting a locking rib portion of an example embodiment of a housing with a portion of a sheath.
Figure 7D:
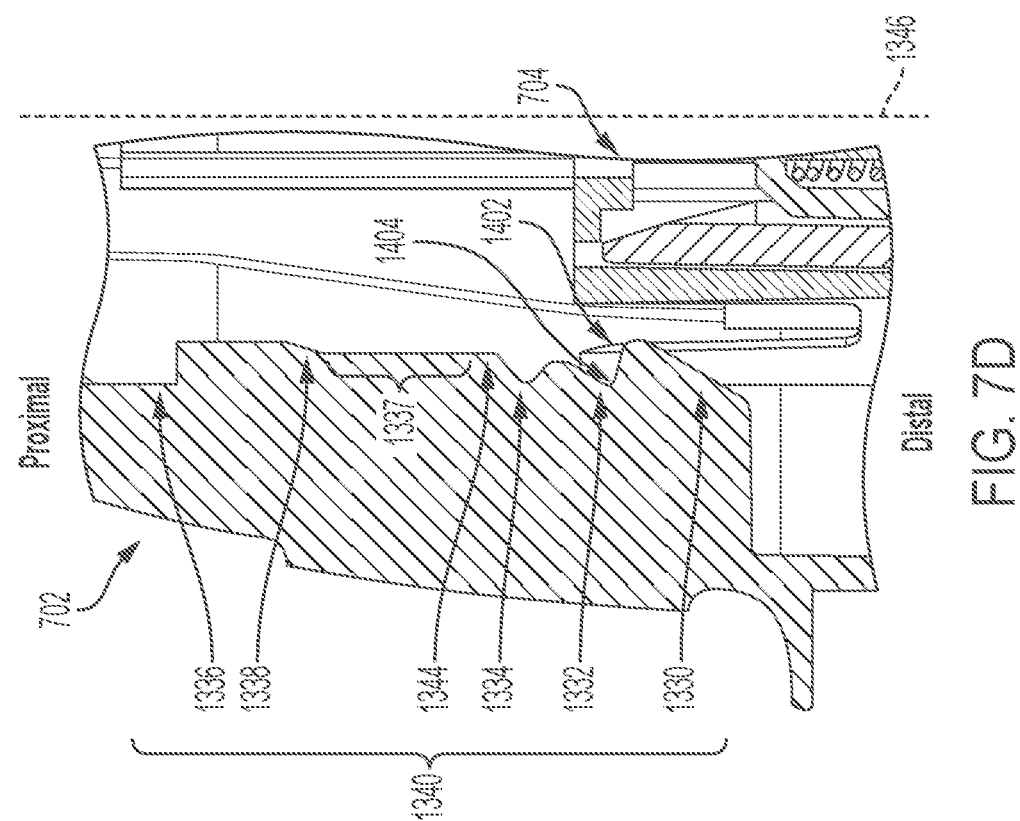

FIGS. 7D and 7E are close-up side views of an example embodiment of locking rib 1340 of applicator housing 702, as detent snap 1402 of sheath 704 moves toward the proximal end of housing 702. FIG. 7D shows sheath 704 in a "locked" state, in which detent round 1404 of detent snap 1402 has already passed over sheath snap lead-in feature 1330 and is positioned in locked groove 1332 of locking rib 1340. As force is applied to the proximal end of housing 702, detent round 1404 is advanced proximally into unlocked groove 1334, placing applicator 150 into an "armed" position. When force is further applied to the proximal end of housing 702, applicator 150 is "fired," as detent round 1404 is advanced proximally from the unlocked groove 1334 and passes over firing detent 1344. Thereafter, sheath 704 is further advanced proximally such that detent round 1404 is slidably advanced over firing surface 1337, as shown in FIG. 7E. In this embodiment, firing surface 1337 is substantially parallel to central axis 1346. As sheath 704 continues to advance proximally, detent round 1404 reaches sheath stopping ramp 1338 which slows the movement of sheath 704. Upon detent round 1404 reaching final lockout recess 1336, detent snap flat 1406 (not shown) is engaged and securely holds sheath 704 in place with respect to housing 702.

Figure 7G:
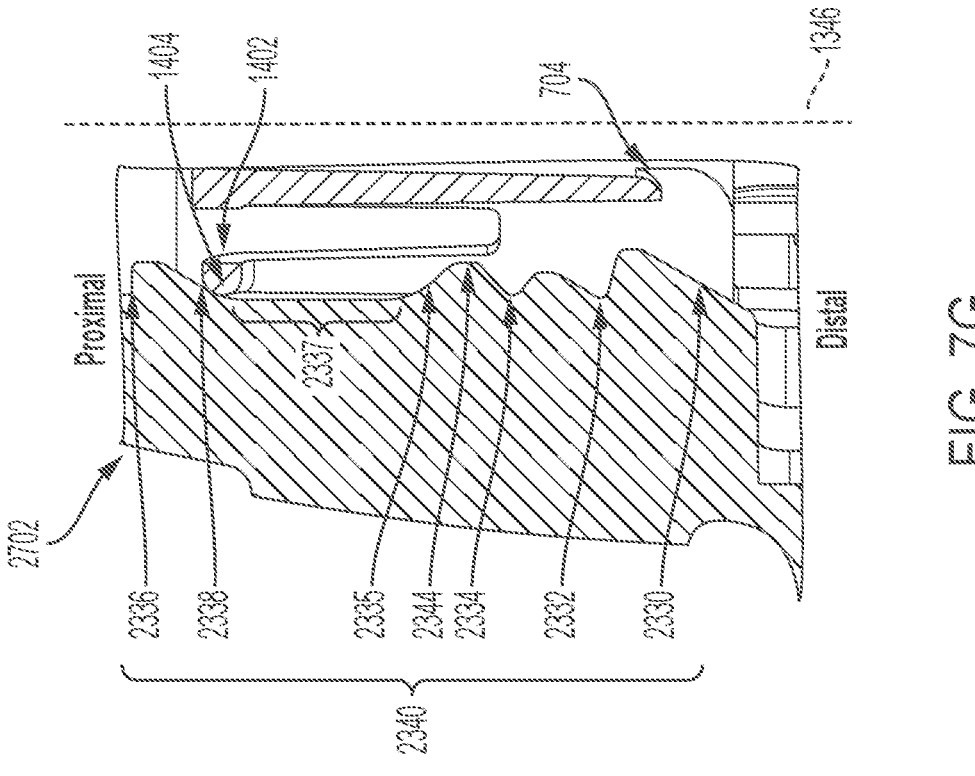
FIGS. 7F and 7G are side cross-sectional views depicting a locking rib portion of another example embodiment of a housing and a portion of a sheath.
Figure 7F:
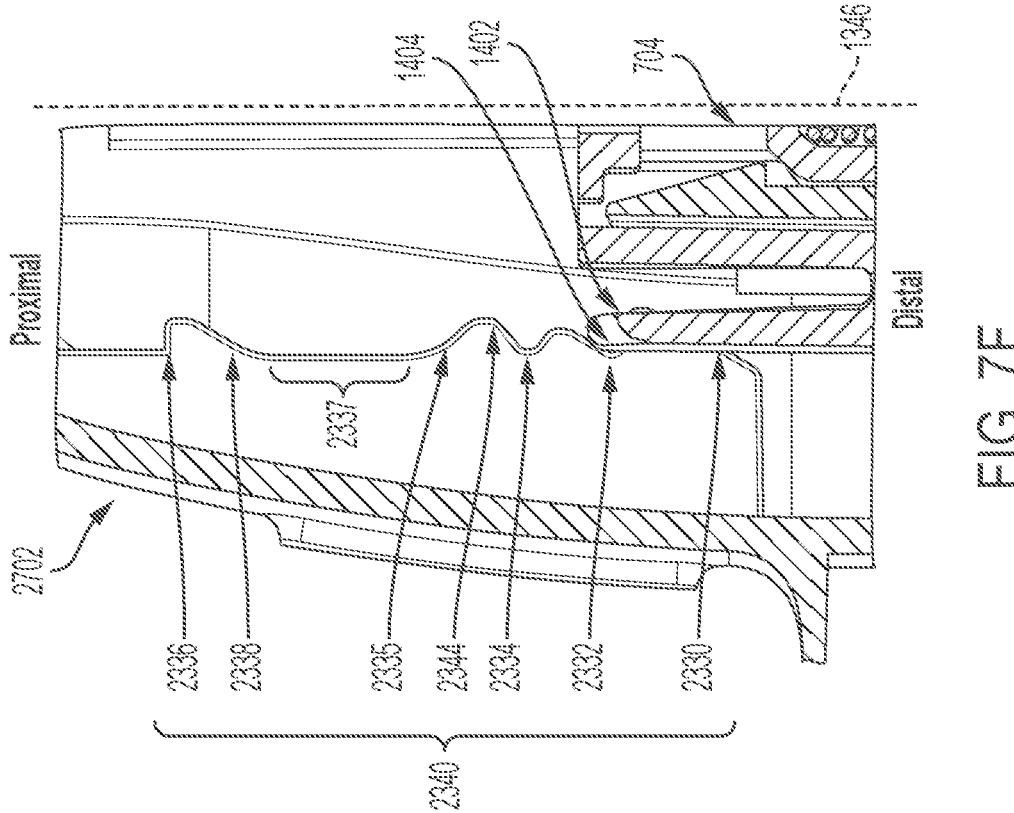

FIGS. 7F and 7G are close-up side views of an alternative embodiment of locking rib 2340 that is designed to improve the firing velocity of the sharp from the sensor applicator. Here, locking rib 2340 includes an inward detent ramp 2335 to reduce friction between sheath 704 and housing 2702 during firing. Locking rib 2340 also includes a sheath stopping ramp 2338 at the proximal end of firing surface 2337. In FIG. 7F, sheath 704 is initially shown in a "locked" state, in which detent round 1404 of detent snap 1402 has already passed over sheath snap lead-in feature 2330, and is positioned in locked groove 2332. As force is applied to the proximal end of housing 2702, detent round 1404 is advanced into unlocked groove 2334, placing applicator 150 into the "armed" position. When force is further applied to the proximal end of housing 2702, applicator 150 is "fired," as detent round 1404 passes over firing detent 2344.

As shown in FIG. 7G, detent round 1404 then advances toward the proximal end of housing 2702 in a "free flight" state, in which detent round 1404 passes over inward detent ramp 2335. While advancing proximally in the "free flight" state, detent round 1404 can be in non-continuous, or have no contact with, inward detent ramp 2335 and firing surface 2337. In this regard, detent round 1404 can be easily and quickly advanced, as there is little to no frictional force between detent round 1404 and inward detent ramp 2335 and firing surface 2337, and as such, improves upon the firing velocity of the sharp from the applicator. Sheath stopping ramp 2338, which is positioned proximally further along the locking rib 2340 relative to the embodiment shown in FIGS. 7D and 7E, provides an edge portion to frictionally engage the detent round 1404 and slow the movement of sheath 704. The sheath stopping ramp 2338 can have a sloped shape and provide for increasing frictional contact as the detent round 1404 advances in a proximal direction. Finally, upon detent round 1404 reaching final lockout recess 2336, detent snap flat 1406 (not shown) is engaged and securely holds sheath 704 in place with respect to housing 2702. Lockout recess 2336 prevents detent round 1404 and sheath 704 from backwards, or distal movement. This embodiment reflects a higher firing velocity relative to the embodiment depicted in FIGS. 7D and 7E, which also assists in prevention of a premature withdrawal of sharp.

Figure 7I:
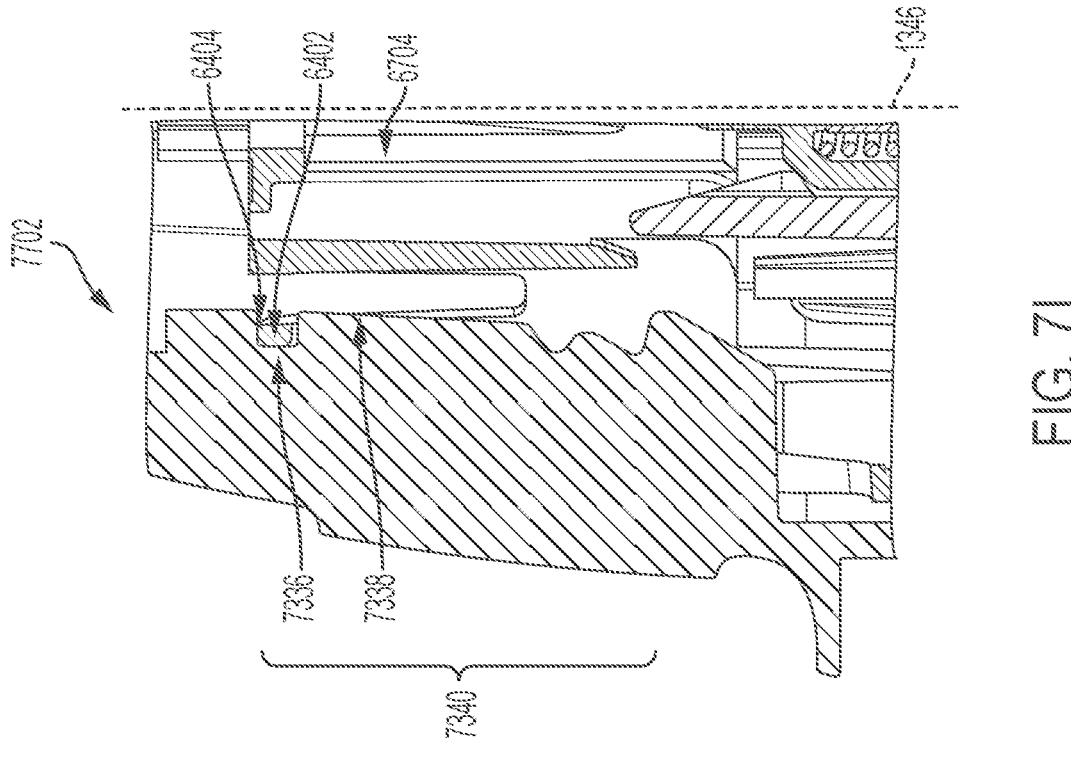
FIG. 7I is a side cross-sectional view depicting a locking rib portion of another example embodiment of a housing and a portion of a sheath.
Figure 7H:
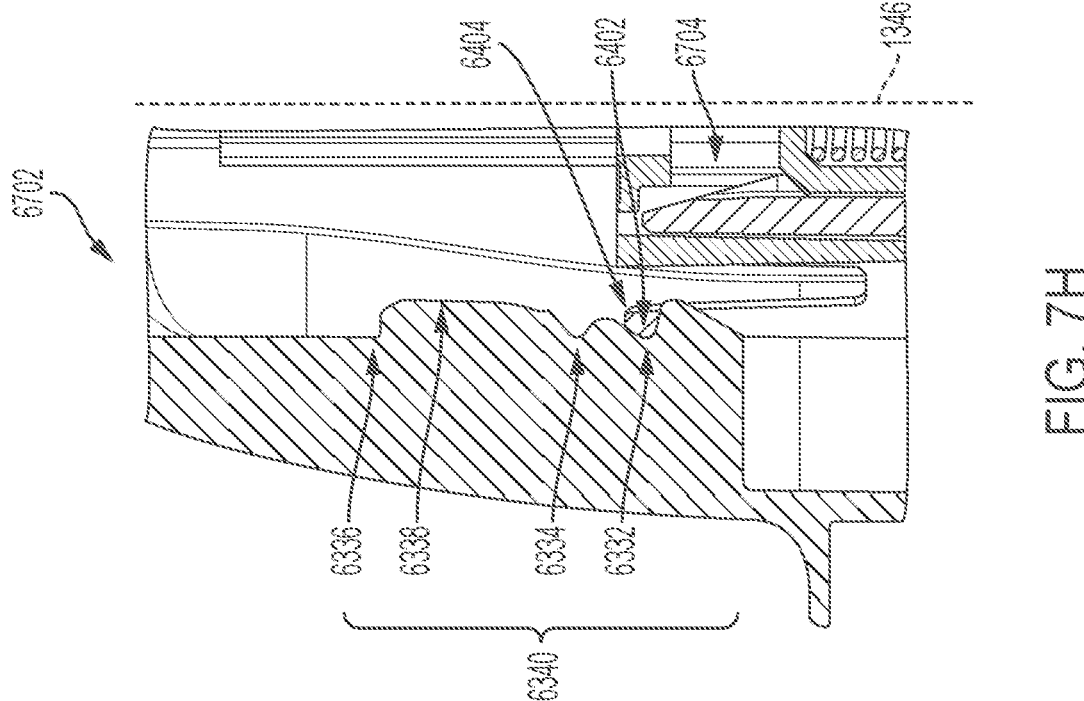
FIG. 7H is a side cross-sectional view depicting a locking rib portion of another example embodiment of a housing and a portion of a sheath.

FIG. 7H is a close-up side view of an alternative embodiment of locking rib 6340 designed to maintain a downward force on sheath 6704 during firing which, in turn, can prevent sheath 6704 from unwanted movement during the sensor insertion process. Here, sheath 6704 is shown in a "locked" state, in which detent round 6404 of detent snap 6402 is positioned in locked groove 6332. As force is applied to the proximal end of housing 6702, detent round 6404 is advanced into unlocked groove 6334, placing applicator in the "armed" position. When force is further applied to the proximal end of housing 6702, applicator is "fired," and detent round 6404 advances over sloped firing surface 6338 toward the proximal end of housing 6702. Sloped firing surface 6338 can be angled toward central axis 1346 such that the resulting downward force upon sheath 6704 increases as detent round 6404 advances in a proximal direction. In the depicted embodiment, detent round 6404 is in continuous contact with sloped firing surface 6338. Lock-out recess 6336 prevents detent round 6404 and sheath 6704 from backwards, or distal movement. This embodiment reflects a slower firing velocity relative to the previously described embodiments, and can be used, for example, with the motion-actuated sharp retraction process that is described with respect to FIGS. 14A-14C and 15A-15B.

FIG. 7I is a close-up side view of still another alternative embodiment of locking rib 7340, also designed to maintain a downward force on sheath 6704 during firing which, in turn, can prevent sheath 6704 from unwanted movement during a sensor insertion process. Here, sheath 6704 is shown in a "fired" state, in which detent round 6404 of detent snap 6402 is positioned in a two-way lockout recess 7336. Upon detent round 6404 advancing into two-way lockout recess 7336, sheath 6704 can be prevented from further movement in either a proximal or distal direction. This can reduce unwanted movement of sheath 6704 during the sensor insertion process. Furthermore, in some embodiments, as described with respect to FIGS. 14A-14C and 15A-15B, two-way lockout recess 7336 can provide for the immobilization of sheath 6704 during a motion-actuated sharp retraction process. As can be seen in FIG. 7I, sloped firing surface 7338 is angled toward central axis 1346 such that a resulting downward force upon sheath 6704 increases as detent round 6404 advances in a proximal direction. In the depicted embodiment, detent round 6404 is in continuous contact with sloped firing surface 7338. This embodiment reflects a slower firing velocity and can be used, for example, with the motion-actuated sharp retraction process that is described with respect to FIGS. 14A-14C and 15A-15B.

Example Embodiment of Applicator Sheath

Figure 8A:
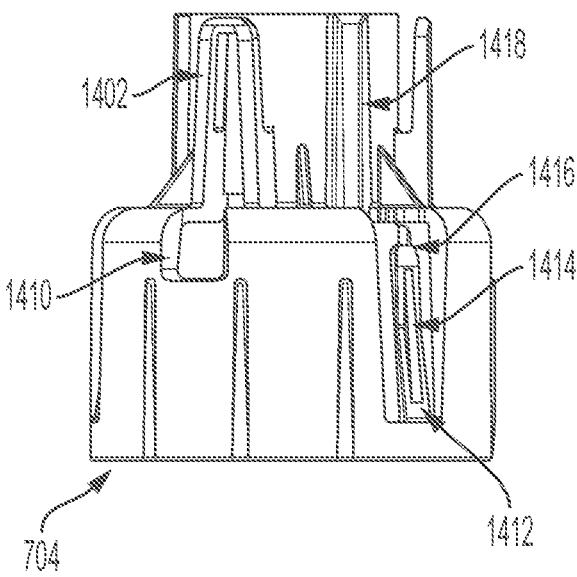
FIG. 8A is a side view depicting an example embodiment of a sheath.
Figure 8B:
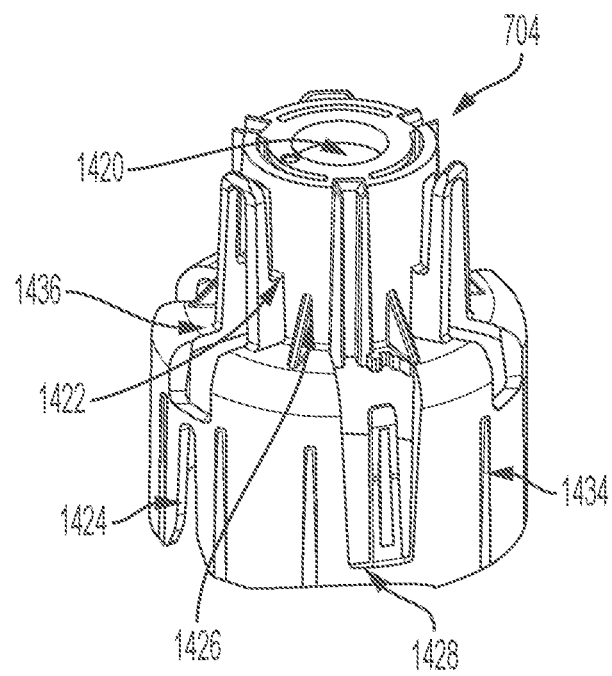
FIG. 8B is a perspective view depicting an example embodiment of a proximal end of a sheath.

FIGS. 8A and 8B are a side view and perspective view, respectively, depicting an example embodiment of sheath 704. In this example embodiment, sheath 704 can stage sensor control device 102 above a user's skin surface prior to application. Sheath 704 can also contain features that help retain a sharp in a position for proper application of a sensor, determine the force required for sensor application, and guide sheath 704 relative to housing 702 during application. Detent snaps 1402 are near a proximal end of sheath 704, described further with respect to FIG. 8C below. Sheath 704 can have a generally cylindrical cross section with a first radius in a proximal section (closer to top of figure) that is shorter than a second radius in a distal section (closer to bottom of figure). Also shown are a plurality of detent clearances 1410, three in the example embodiment. Sheath 704 can include one or more detent clearances 1410, each of which can be a cutout with room for sheath snap lead-in feature 1330 to pass distally into until a distal surface of locking rib 1340 contacts a proximal surface of detent clearance 1410.

Guide rails 1418 are disposed between sensor electronics carrier traveler limiter face 1420 at a proximal end of sheath 704 and a cutout around lock arms 1412. Each guide rail 1418 can be a channel between two ridges where the guide edge 1326 of housing guide rib 1321 can slide distally with respect to sheath 704.

Lock arms 1412 are disposed near a distal end of sheath 704 and can include an attached distal end and a free proximal end, which can include lock arm interface 1416. Lock arms 1412 can lock sensor electronics carrier 710 to sheath 704 when lock arm interface 1416 of lock arms 1412 engage lock interface 1502 of sensor electronics carrier 710. Lock arm strengthening ribs 1414 can be disposed near a central location of each lock arm 1412 and can act as a strengthening point for an otherwise weak point of each lock arm 1412 to prevent lock arm 1412 from bending excessively or breaking.

Detent snap stiffening features 1422 can be located along the distal section of detent snaps 1402 and can provide reinforcement to detent snaps 1402. Alignment notch 1424 can be a cutout near the distal end of sheath 704, which provides an opening for user alignment with sheath orientation feature of platform 808. Stiffening ribs 1426 can include buttresses, that are triangularly shaped here, which provide support for detent base 1436. Housing guide rail clearance 1428 can be a cutout for a distal surface of housing guide rib 1321 to slide during use. Tilt reducing ribs 1434 are also located in a distal region of sheath 704.

FIG. 8C is a close-up perspective view depicting an example embodiment of detent snap 1402 of sheath 704. Detent snap 1402 can include a detent snap bridge 1408 located near or at its proximal end. Detent snap 1402 can also include a detent snap flat 1406 on a distal side of detent snap bridge 1408. An outer surface of detent snap bridge 1408 can include detent snap rounds 1404 which are rounded surfaces that allow for easier movement of detent snap bridge 1408 across interior surfaces of housing 702 such as, for example, locking rib 1340.

Figure 8D:
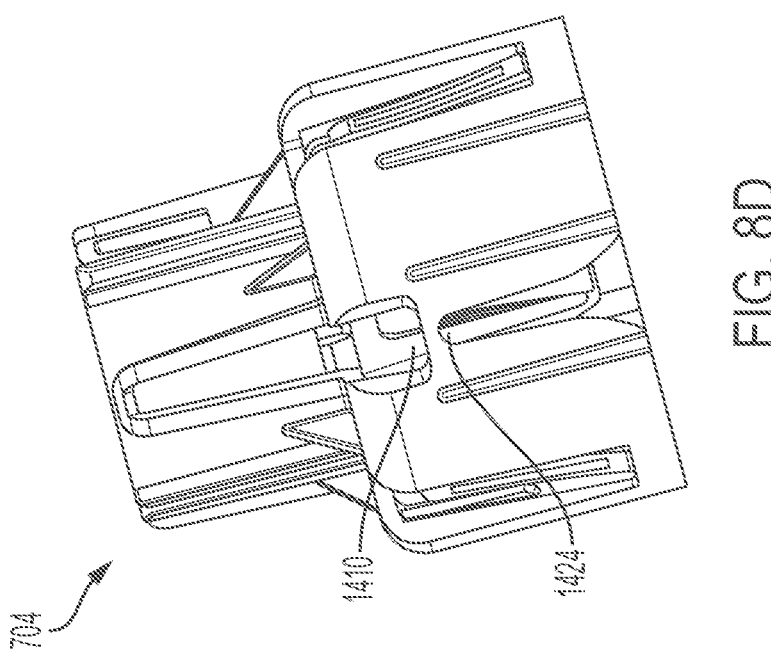
FIG. 8D is a side view depicting an example embodiment of features of a sheath.
Figure 8C:
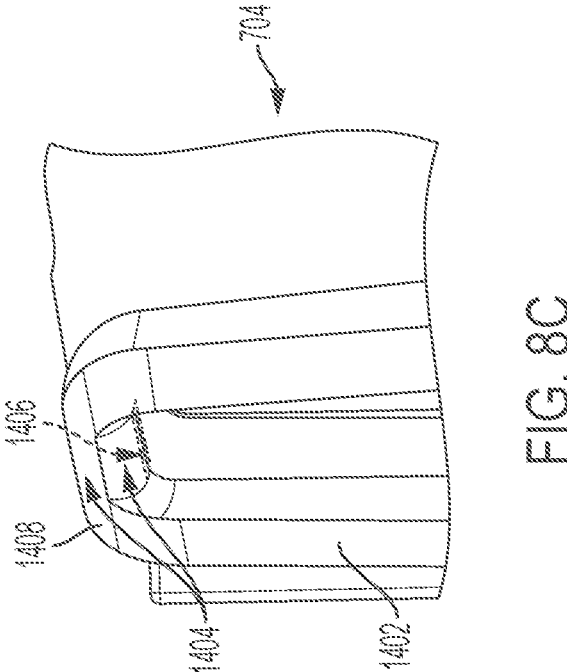
FIG. 8C is a close-up perspective view depicting an example embodiment of a distal side of a detent snap of a sheath.

FIG. 8D is a side view depicting an example embodiment of sheath 704. Here, alignment notch 1424 can be relatively close to detent clearance 1410. Detent clearance 1410 is in a relatively proximal location on distal portion of sheath 704.

Figure 8E:
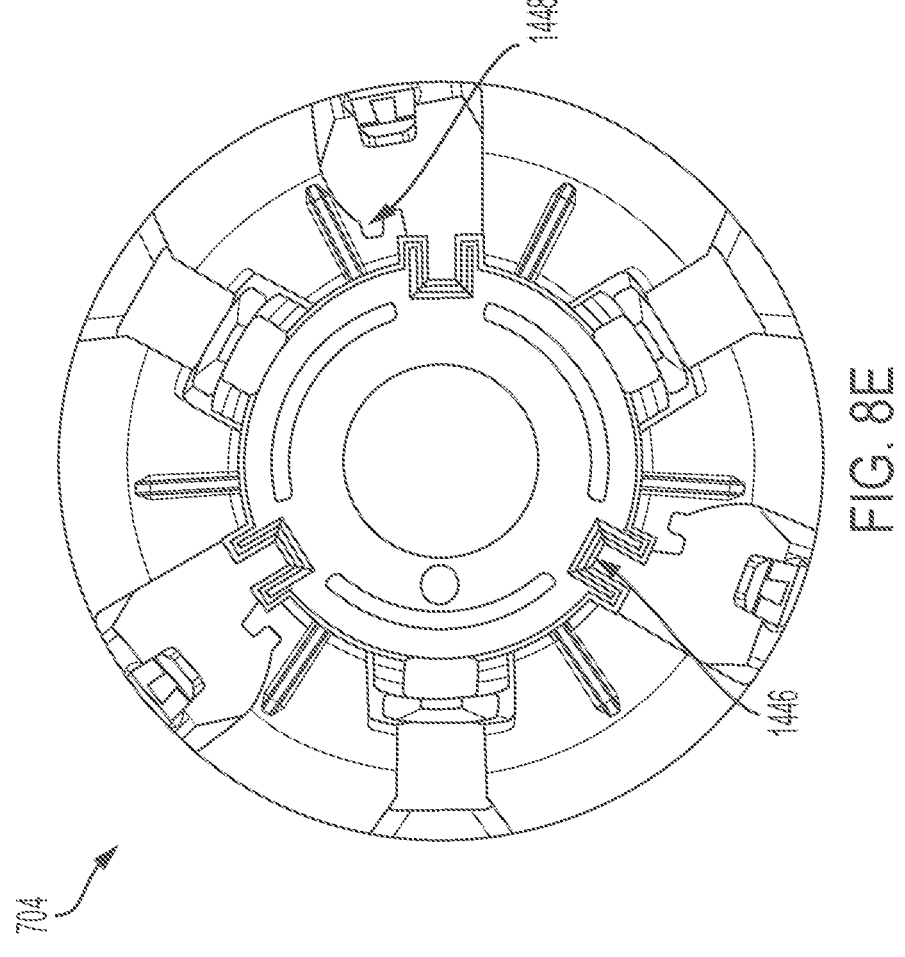
FIG. 8E is an end view of an example embodiment of a proximal end of a sheath.

FIG. 8E is an end view depicting an example embodiment of a proximal end of sheath 704. Here, a back wall for guide rails 1446 can provide a channel to slidably couple with housing guide rib 1321 of housing 702. Sheath rotation limiter 1448 can be notches which reduce or prevent rotation of the sheath 704.

Figures 8F, 8G, 8H:
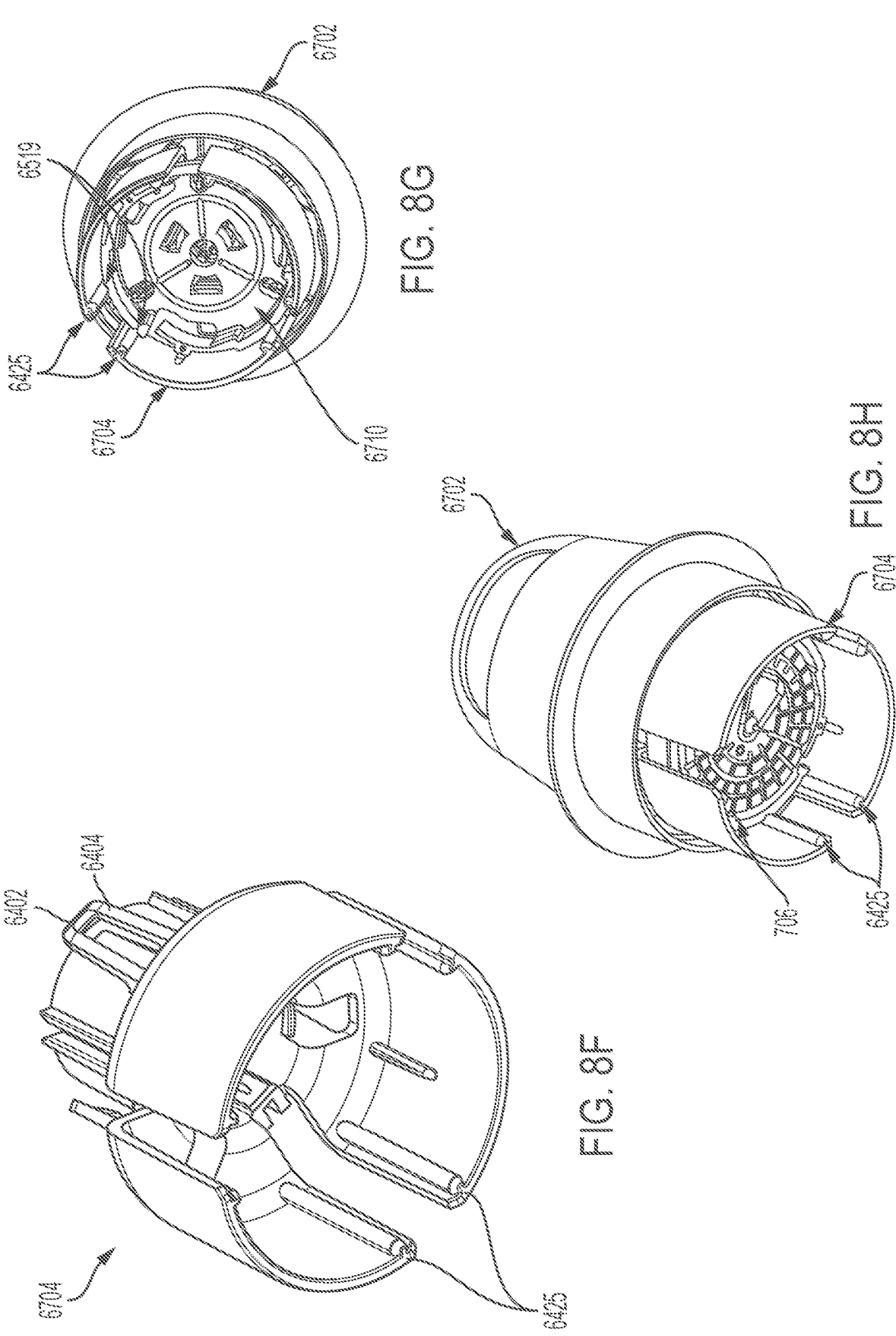
FIGS. 8F to 8H are perspective views depicting another example embodiment of a sheath in various stages of assembly with other applicator components.

FIGS. 8F-8H are perspective views of an alternative example embodiment of sheath 6704 in various stages of assembly with other components of the applicator. As shown in FIG. 8F, sheath 6704 can have many of the same features as sheath 704, previously described with respect to FIGS. 8A-8C. Sheath 6704, for example, can include one or more detent snaps 6404 having one or more detent rounds 6402 attached thereto. Sheath 6704, however, can be shorter in overall length as compared to sheath 702. In addition, sheath 6704 can include one or more inner sheath ribs 6425 disposed on the inner surface of sheath 6704, and which protrude in an inward direction towards the central axis of sheath 6704.

Turning to FIG. 8G, sheath 6704 is shown in perspective view in a stage of assembly with applicator housing 6702 and sensor electronics carrier 6710. One or more inner sheath ribs 6425 of sheath 6704 can interface with one or more corresponding rib notches 6519 in sensor electronics carrier 6710. The fitted interface between corresponding ribs 6425 and notches 6519 can help maintain axial alignment of the sheath 6704 and sensor electronics carrier 6710 during the sensor insertion process. Furthermore, the interface between ribs 6425 and notches 6519 can reduce lateral and rotational movement between the applicator components, which can, in turn, reduce the chance of improper sensor insertion.

Turning to FIG. 8H, sheath 6704 is shown in perspective view in a stage of assembly with applicator housing 6702 and sensor electronics housing 706, which has been inserted into sensor electronics carrier 6710. Inner sheath ribs 6425 are also shown.

It should be noted that although six inner sheath ribs 6425 and six corresponding rib notches 6519 are depicted, any number of ribs and notches are fully within the scope of the present disclosure. Moreover, while ribs 6425 are depicted with a rounded surface edge, in other embodiments, ribs 6425 can have a rectangular or triangular shape, and rib notches 6519 can have a corresponding receiving shape for interfacing with ribs 6425. In addition, although ribs 6425 are depicted as being disposed on an inner circumferential surface of sheath 6704, ribs 6425 can also be disposed on any other surface of sheath 6704, or portion thereof, that comes into contact with sensor electronics carrier 6710.

Example Embodiments of Sensor Electronics Carriers

Figure 9A:
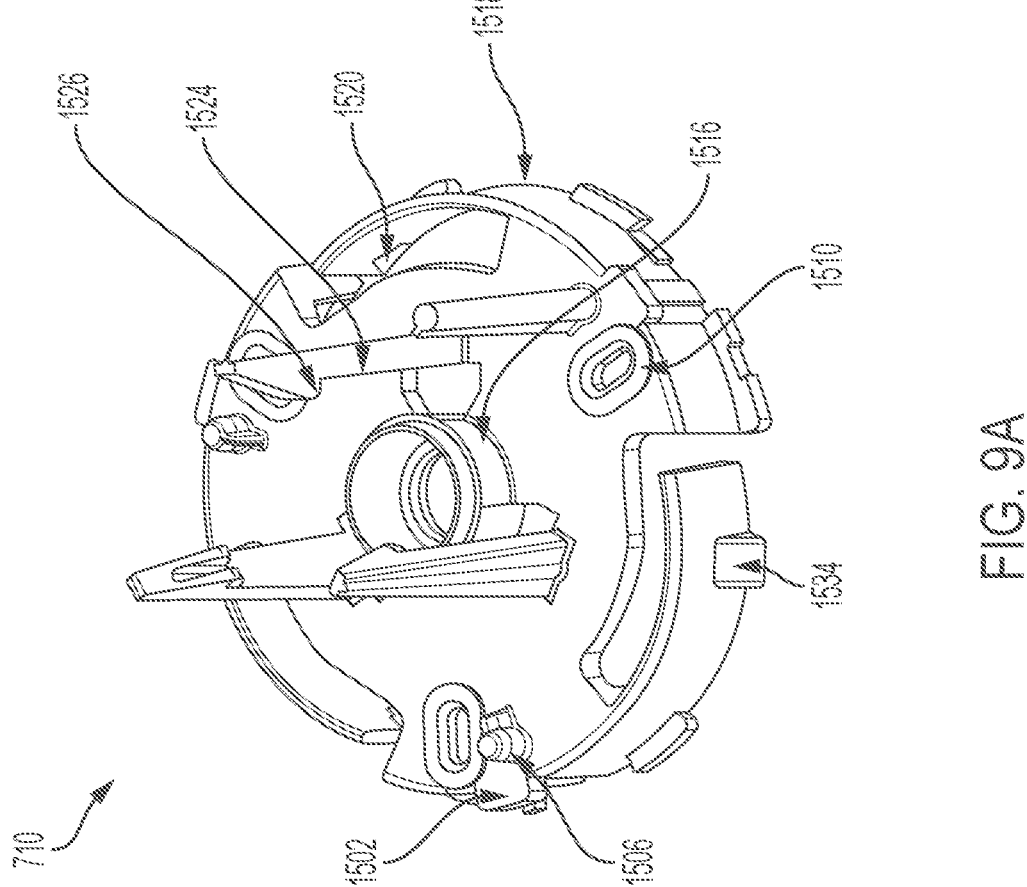
FIG. 9A is a proximal perspective view depicting an example embodiment of a sensor electronics carrier.

FIG. 9A is a proximal perspective view depicting an example embodiment of sensor electronics carrier 710 that can retain sensor electronics within applicator 150. It can also retain sharp carrier 1102 with sharp module 2500. In this example embodiment, sensor electronics carrier 710 generally has a hollow round flat cylindrical shape, and can include a sensor electronics retention feature 1520 and one or more deflectable sharp carrier lock arms 1524 (e.g., three) extending proximally from a proximal surface surrounding a centrally located spring alignment ridge 1516 for maintaining alignment of spring 1104. Each lock arm 1524 has a detent or retention feature 1526 located at or near its proximal end. Shock lock 1534 can be a tab located on an outer circumference of sensor electronics carrier 710 extending outward and can lock sensor electronics carrier 710 for added safety prior to firing. Rotation limiter 1506 can be a proximally extending relatively short protrusion on a proximal surface of sensor electronics carrier 710 which limits rotation of carrier 710. Sharp carrier lock arms 1524 can interface with sharp carrier 1102 as described with reference to FIGS. 10A-10E below.

Figure 9C:
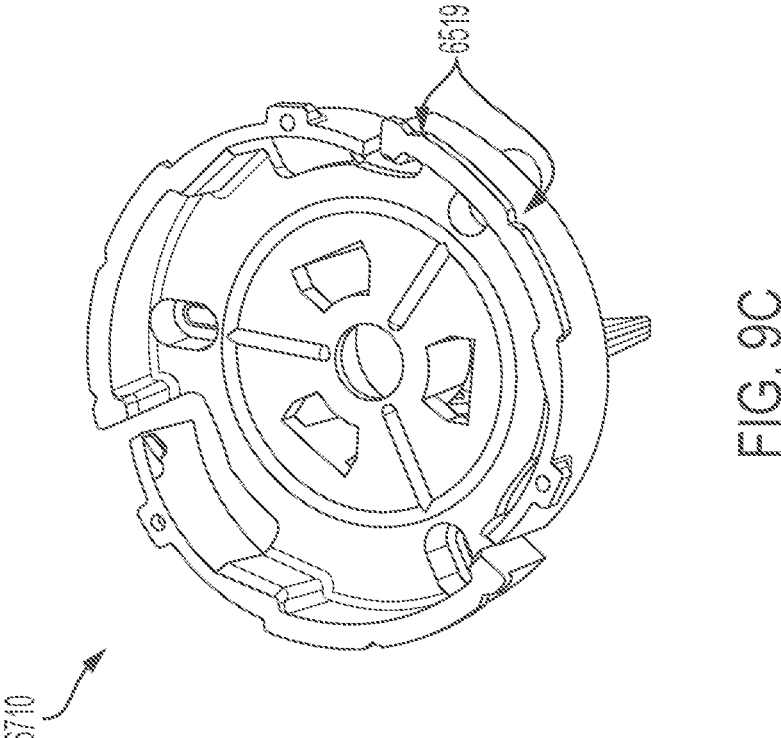
FIG. 9C is a distal perspective view depicting another example embodiment of a sensor electronics carrier.
Figure 9B:
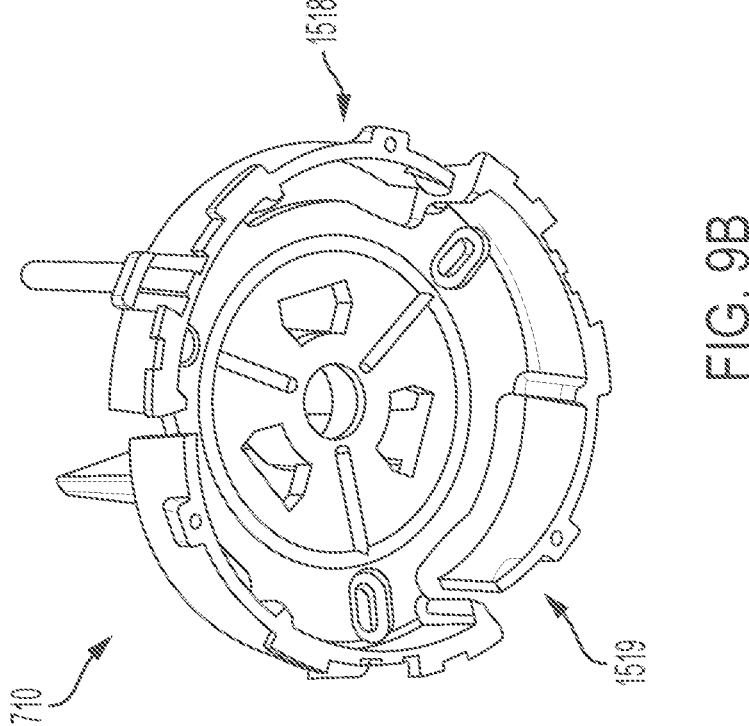
FIG. 9B is a distal perspective view depicting an example embodiment of a sensor electronics carrier.

FIG. 9B is a distal perspective view of sensor electronics carrier 710. Here, one or more sensor electronics retention spring arms 1518 (e.g., three) are normally biased towards the position shown and include a detent 1519 that can pass over the distal surface of electronics housing 706 of device 102 when housed within recess or cavity 1521. In certain embodiments, after sensor control device 102 has been adhered to the skin with applicator 150, the user pulls applicator 150 in a proximal direction, i.e., away from the skin. The adhesive force retains sensor control device 102 on the skin and overcomes the lateral force applied by spring arms 1518. As a result, spring arms 1518 deflect radially outwardly and disengage detents 1519 from sensor control device 102 thereby releasing sensor control device 102 from applicator 150.

FIG. 9C is a perspective view of an alternative example embodiment of sensor electronics carrier 6710. As shown in FIG. 9C, sensor electronics carrier 6710 can have many of the same features as sensor electronics carrier 710, previously described with respect to FIGS. 9A-9B. In addition, sensor electronics carrier 6710 also includes one or more notch ribs 6519 disposed along an outer circumferential surface. As best seen in FIGS. 8F-8H, notch ribs 6519 are configured to interface with inner sheath ribs 6425 in order to maintain axial alignment of the sheath and sensor electronics carrier, and reduce lateral and rotational movement between applicator components during the sensor insertion process.

Figure 9D:
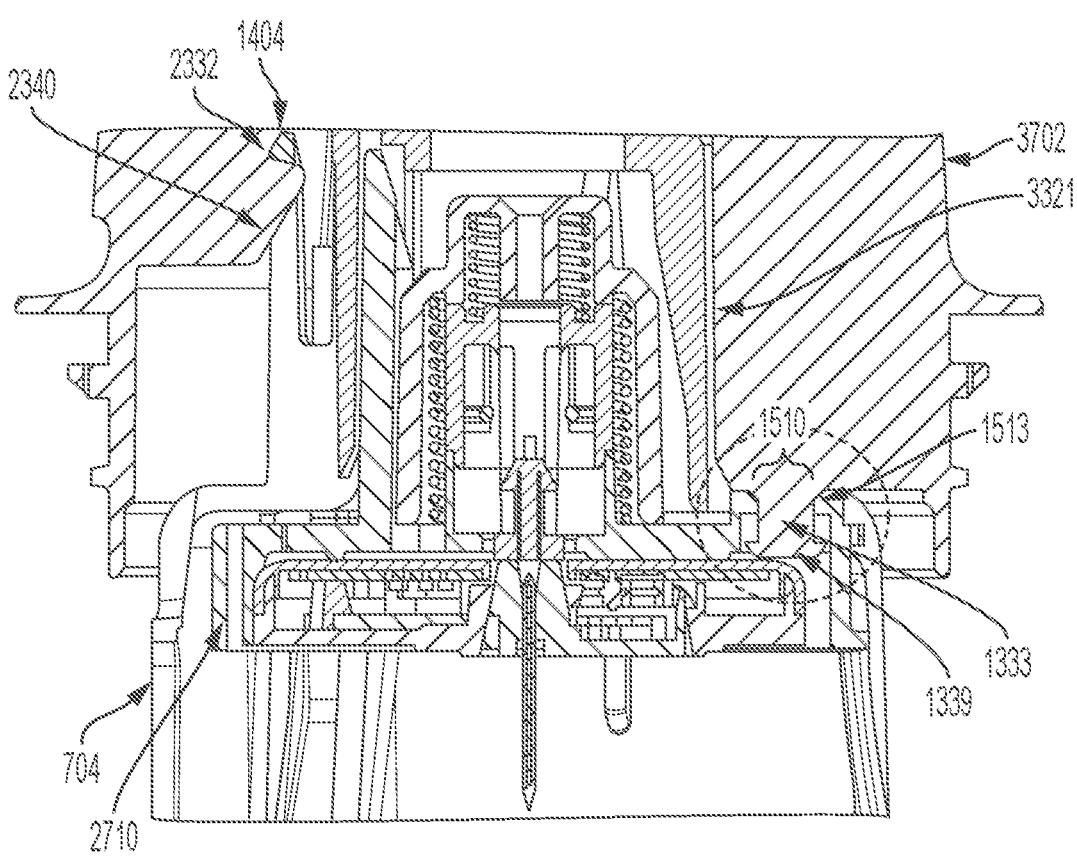
FIG. 9D is a side cross-sectional view depicting another example embodiment of a sensor electronics carrier along with housing and sheath.
Figure 9E:
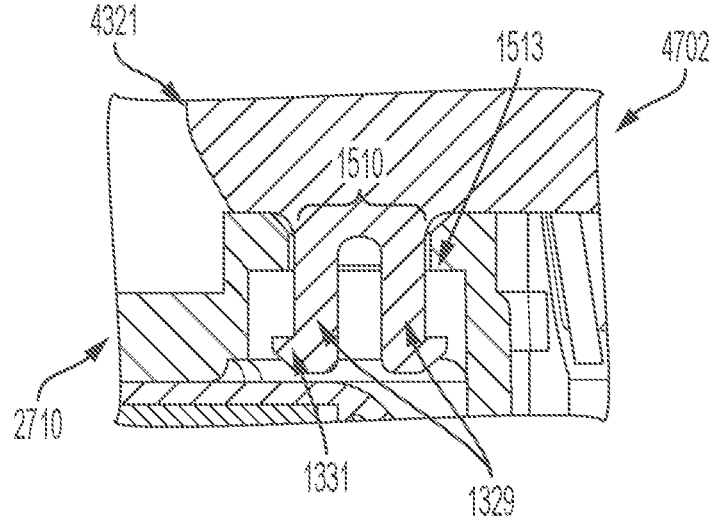
FIG. 9E is a close-up side cross-sectional view depicting another example embodiment of a sensor electronics carrier along with housing.

FIGS. 9D and 9E depict alternative embodiments of sensor electronics carriers for use with the insertion of dermal sensors. These embodiments include a retention mechanism to couple the applicator housing with the sensor electronics carrier, while also allowing for the sensor electronics carrier to advance a limited distance in a proximal-to-distal direction while the sharp is inserted into the skin. The retention mechanism can operate to further increase the velocity of sharp insertion during firing, while delaying the sharp retraction, as further described below and with respect to FIGS. 13A-13D. In other embodiments (e.g., as shown in FIGS. 14A-14C and 15A-15B), the retention mechanism can also provide for a displacement area between the sensor electronics carrier and sheath, through which a motion-actuated sharp retention mechanism can be initiated.

FIG. 9D is a side cross-sectional view of an alternative embodiment of sensor electronics carrier 2710, shown here with applicator housing 3702 and sheath 704. Here, applicator 150 is depicted in a "locked state," in which detent round 1404 of sheath 704 is positioned in locked groove 2332 of locking rib 2340 of housing 3702. At a distal end of housing guide rib 3321 of housing 3702, a heat stake post 1333 is provided. Heat stake post 1333 can protrude in a distal direction through aperture 1510 of sensor electronics carrier 2710. Distal portion 1339 of heat stake post 1333 can be flared such that the distal portion is larger than aperture 1510 of sensor electronics carrier 2710, and prevents heat stake post 1333 from sliding out of aperture 1510 due to impedance of aperture ledge 1513. Heat stake post 1333 can have a length greater than the thickness of aperture ledge 1513, allowing for spaced movement between sensor electronics carrier 2710 and housing 3702 along a longitudinal axis through the center of heat stake post 1333 (as further depicted in FIGS. 13A-13D). As shown in FIG. 9D, when applicator 150 is depicted in the "locked state," the proximal end (or base) of heat stake post 1333 is near to, or flush against, sensor electronics carrier 2710, aperture 1510 and aperture ledge 1513. During a firing sequence, sensor electronics carrier 2710 is displaced in a distal direction, creating a spaced relation between the proximal end (or base) of heat stake post 1333 and sensor electronics carrier 2710, aperture 1510 and aperture ledge 1513.

FIG. 9E is a side cross-sectional view of sensor electronics carrier 710 and an alternative embodiment of housing 4702. At a distal end of housing guide rib 4321 of housing 4702, one or more snap-in arms 1329 are provided. Snap-in arms 1329 can protrude in a distal direction through aperture 1510 of sensor electronics carrier 2710. A snap-in detent 1331 is provided at the end of each snap-in arm 1329. Snap-in detents 1331 can be flared such that the distal ends of snap-in arms 1329 are larger than the aperture 1510 of sensor electronics carrier 2710, and prevent snap-in arms 1329 from completely exiting out of aperture 1510 due to aperture ledge 1513. Snap-in arms 1329 can also have a length greater than the thickness of ledge 1513, allowing for spaced movement between sensor electronics carrier 2710 and housing 4702 along a longitudinal axis. The movement of the embodiments depicted in FIG. 9E during the "locked" and "firing" stages are similar to the movement of the embodiments shown in FIG. 9D, and further illustrated in FIGS. 12A-12D and 13A-13D. Additionally, the embodiments described with respect to FIGS. 9D and 9E can also be implemented with a motion-actuated sharp retraction mechanism, which is further described with respect to FIGS. 14A-14C and 15A-15B.

Example Embodiments of Sharp Carriers

Figure 10B:
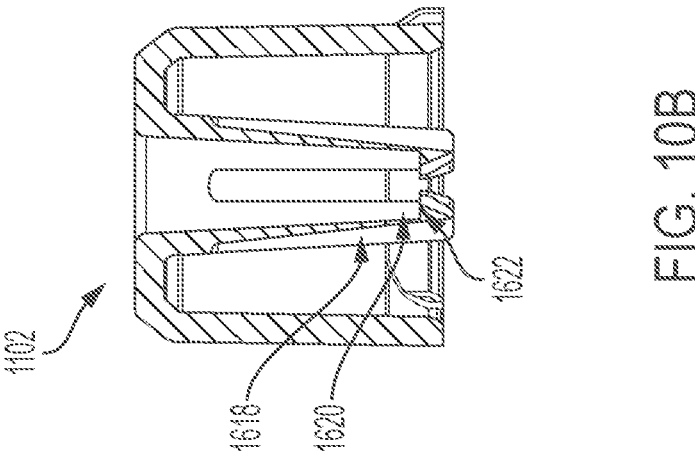
FIG. 10B is a side cross-section depicting an example embodiment of a sharp carrier.
Figure 10A:
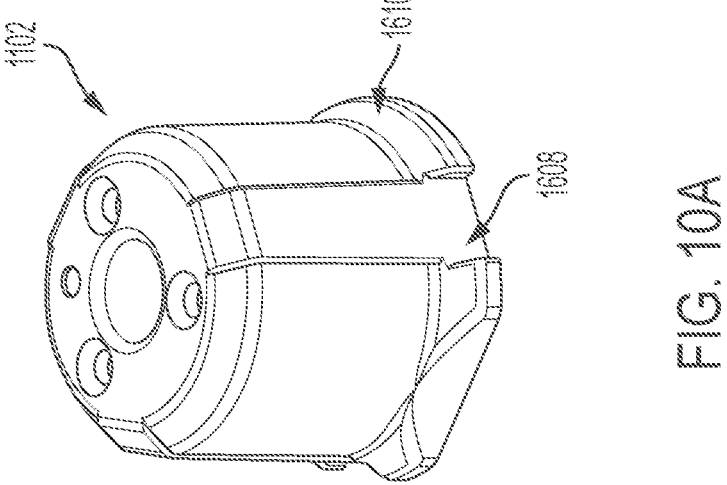
FIG. 10A is a proximal perspective view of an example embodiment of a sharp carrier.

FIGS. 10A and 10B are a proximal perspective view and a side cross-sectional view, respectively, depicting an example embodiment of sharp carrier 1102. Sharp carrier 1102 can grasp and retain sharp module 2500 within applicator 150. It can also automatically retract as a result of one or more springs changing from a preloaded, compressed state to an expanded state during an insertion process, as described with respect to FIGS. 12A-12D and 13A-13D. Near a distal end of sharp carrier 1102 can be anti-rotation slots 1608 which prevent sharp carrier 1102 from rotating when located within a central area of sharp carrier lock arms 1524 (as shown in FIG. 9A). Anti-rotation slots 1608 can be located between sections of sharp carrier base chamfer 1610, which can ensure full retraction of sharp carrier 1102 through sheath 704 upon retraction of sharp carrier 1102 at the end of the deployment procedure.

Figure 11A:
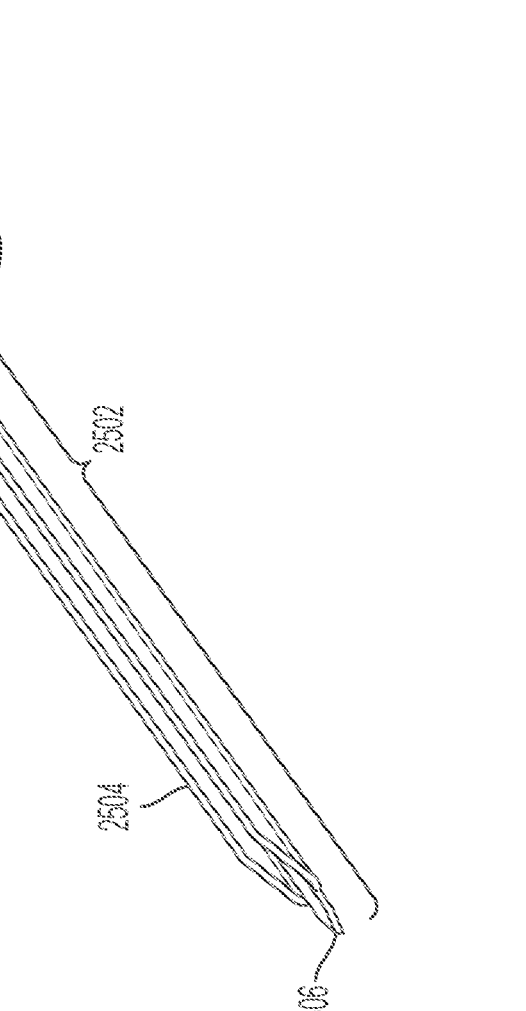
FIG. 11A is a perspective view depicting an example embodiment of a sharp module.

As shown in FIG. 10B, sharp retention arms 1618 can be located in an interior of sharp carrier 1102 about a central axis and can include a sharp retention clip 1620 at a distal end of each arm 1618. Sharp retention clip 1620 can have a proximal surface which can be nearly perpendicular to the central axis and can abut a distally facing surface of sharp hub 2516 (FIG. 11A).

Figure 10C:
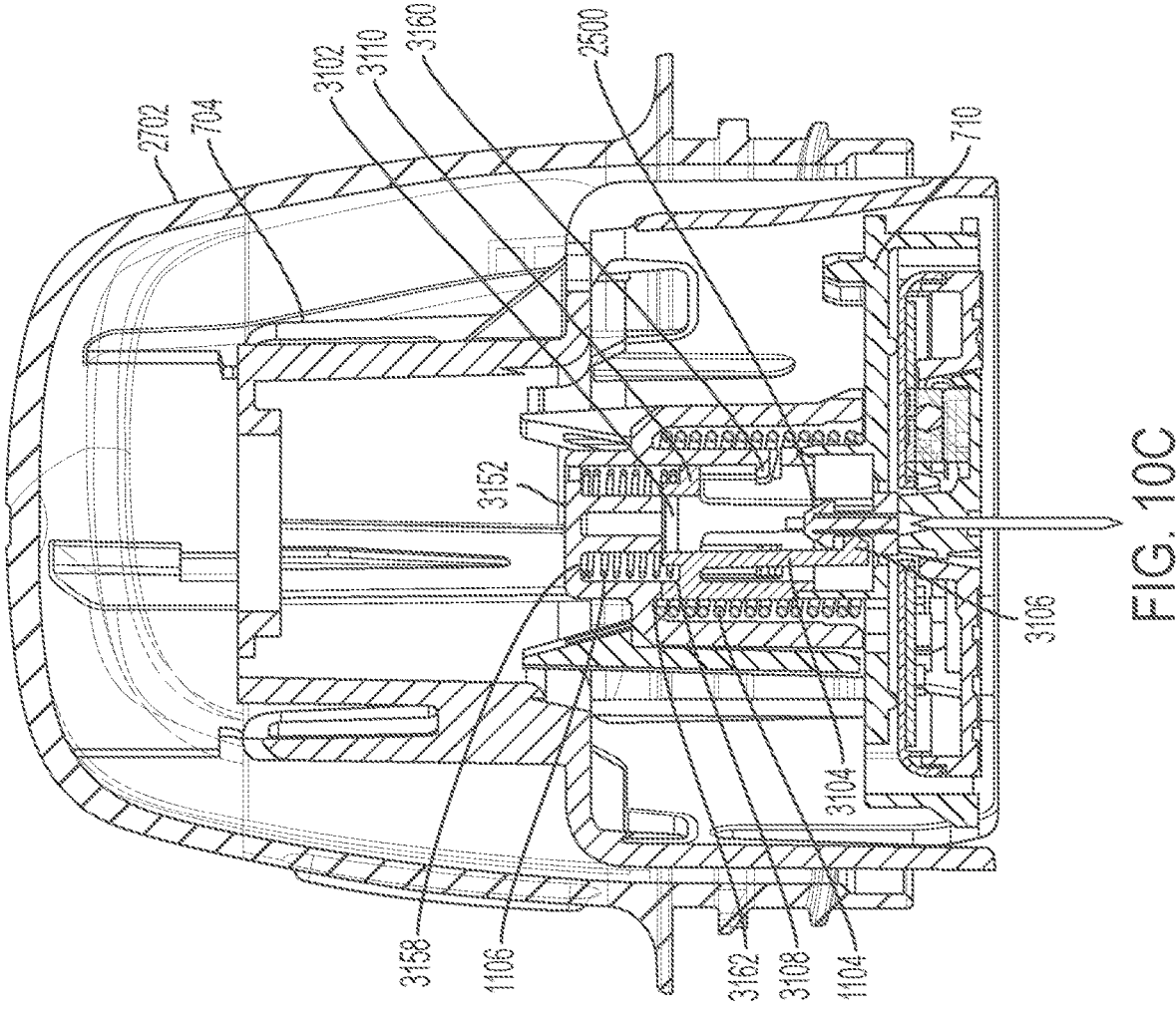
FIG. 10C is a side cross-sectional view depicting another example embodiment of a sharp carrier assembly within an applicator.
Figure 10D:
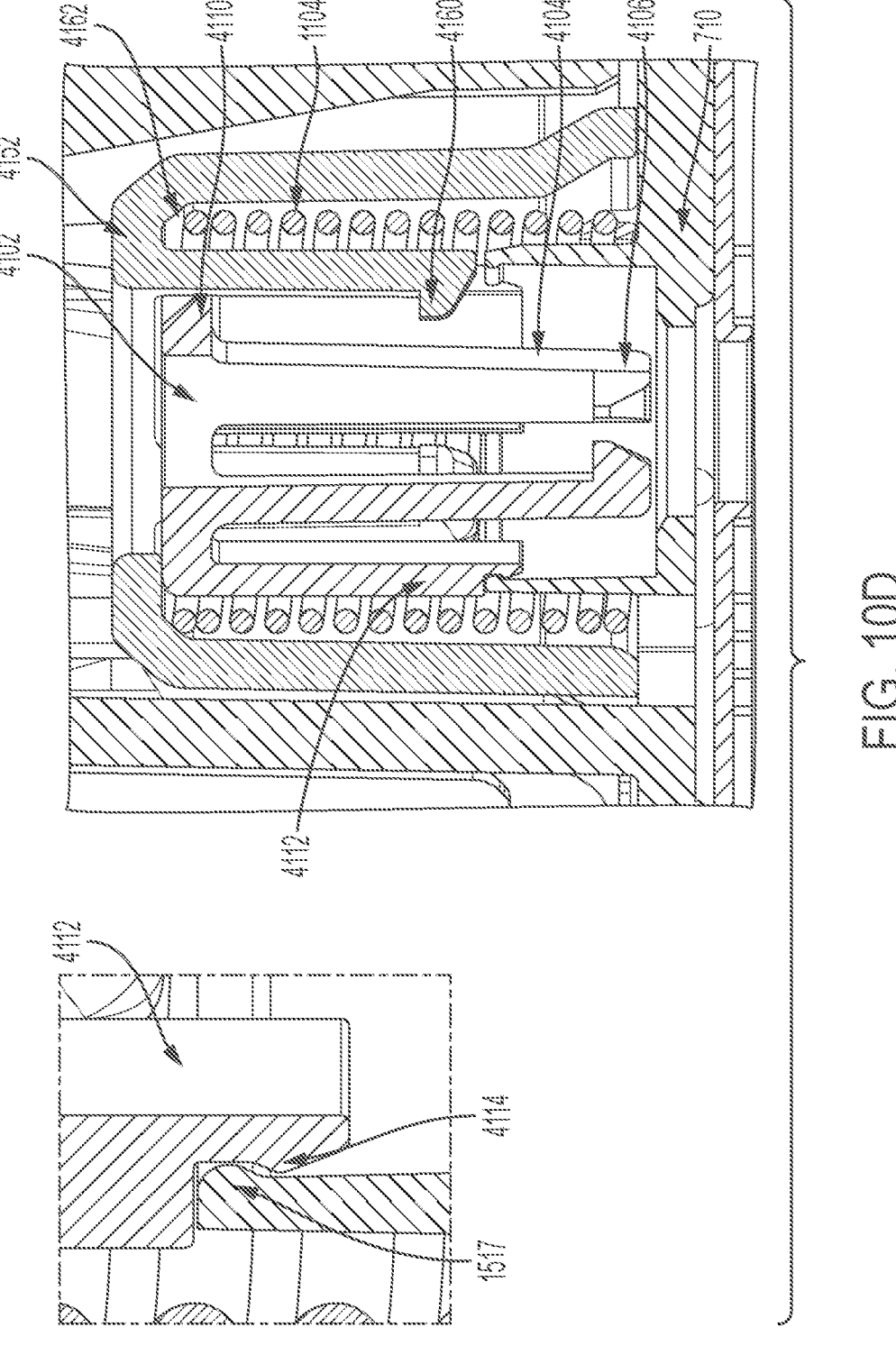
FIG. 10D is a side cross-sectional view with a call-out depicting another example embodiment of a sharp carrier assembly along with a portion of a sensor electronics carrier.
Figure 10E:
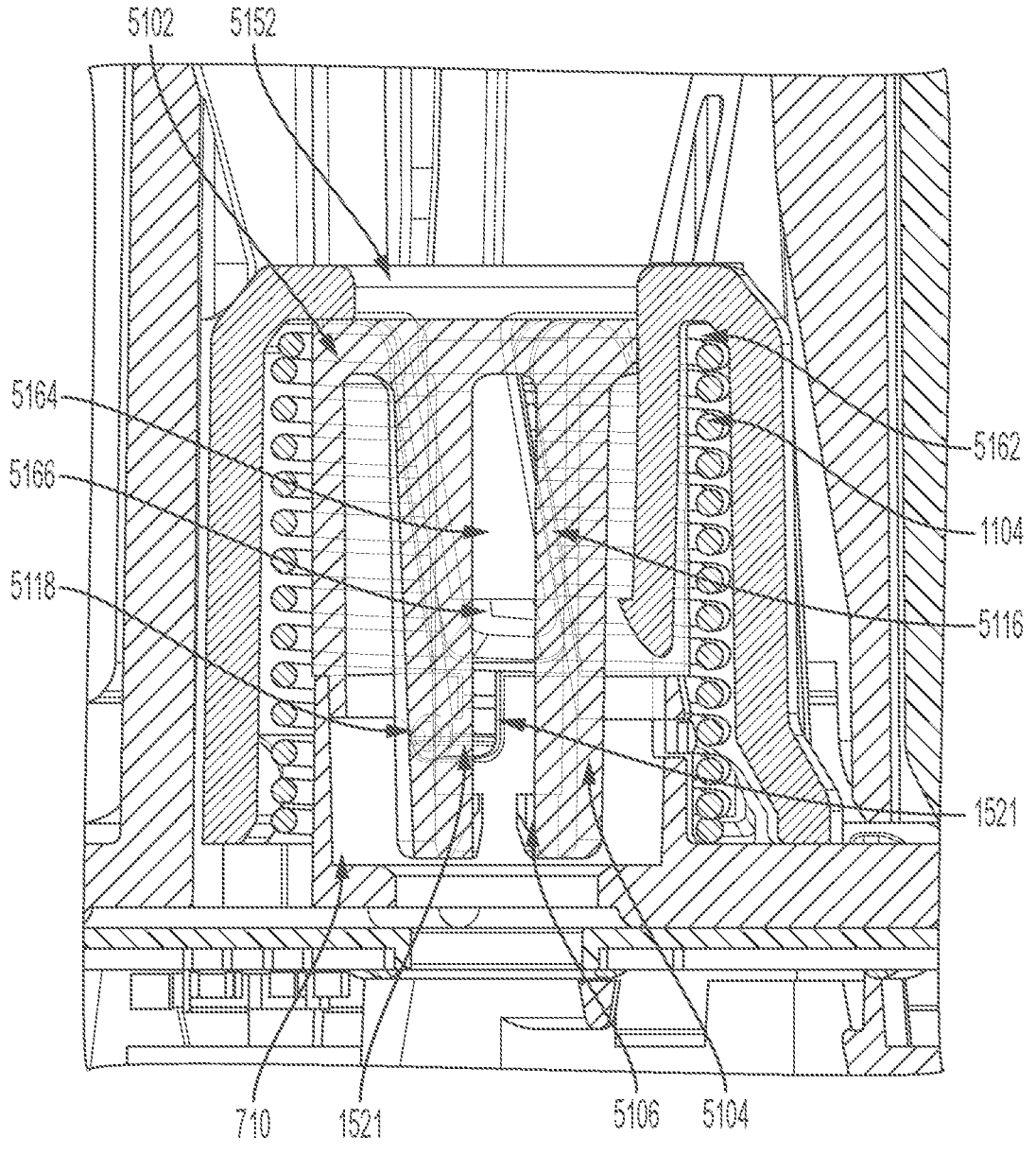
FIG. 10E is a side cross-sectional view depicting another example embodiment of a sharp carrier assembly along with a portion of a sensor electronics carrier.

FIGS. 10C to 10E depict alternative embodiments of sharp carrier assemblies, each of which consists of an inner sharp carrier and an outer sharp carrier. These embodiments provide for a delay, created by a separate retraction process for each sharp carrier, occurs during a firing sequence in which a dermal sensor is implanted into a subject's dermal layer prior to retraction of the sharp. The introduction of the delay can significantly reduce the likelihood of premature withdrawal of the sharp during the insertion process.

FIG. 10C is a side view of an alternative embodiment of a two-piece sharp carrier assembly consisting of inner sharp carrier 3102 and outer sharp carrier 3152, along with sensor electronics carrier 710, sheath 704, and housing 2702. Inner sharp carrier 3102 can include one or more sharp retention arms 3104 for retaining sharp module 2500. Sharp retention arms 3104 can further include a sharp retention clip 3106 located at a distal end of each arm 3104. Sharp retention clips 3106 can have a proximal surface that can be nearly perpendicular to a central axis and can abut a distally facing surface of sharp hub 2516, as shown in FIG. 11A. At a proximal end surface of inner sharp carrier 3102, a bottom inner spring retention channel 3108 is provided which can retain a distal end of inner spring 1106, which is shown in a preloaded and compressed state prior to retraction of the sharp carrier assembly. One or more inner carrier latches 3110 are also provided at or near a proximal end of inner sharp carrier 3102. Inner carrier latch 3110 can include a substantially flat surface that faces towards the distal end of applicator 150 and protrudes radially outward from a central longitudinal axis of inner sharp carrier 3102.

Still referring to FIG. 10C, outer sharp carrier 3152 can be external to and surround inner sharp carrier 3102. At a proximal end of outer sharp carrier 3152, a top inner spring retention channel 3158 is provided, which can retain a proximal end of inner spring 1106. Top inner spring retention channel 3158 of outer sharp carrier 3152 and bottom inner spring retention channel 3108 of inner sharp carrier 3102 each provide a surface to retain an end of inner spring 1106. Outer sharp carrier 3152 can also include an outer spring retention channel 3162 for retaining a proximal end of outer spring 1104, which is also shown in a preloaded and compressed state prior to the retraction of the sharp carrier assembly. As seen in FIG. 10C, outer spring 1104 is shown as having both a greater length and radius than inner spring 1106. However, springs 1104, 1106 can be of equal size and/or radius, or, in the alternative, inner spring 1106 may have a greater radius and/or length than outer spring 1104. In some embodiments, outer spring 1104 has an equal or greater stiffness than inner spring 1106.

Referring again to FIG. 10C, outer sharp carrier 3152 can also include one or more outer carrier latches 3160. Outer carrier latch 3160 can include a substantially flat surface that faces towards the proximal end of applicator 150 and protrudes radially inward towards a central longitudinal axis of outer sharp carrier 3152. The flat surface of outer carrier latch 3160 and the flat surface of inner carrier latch 3110 can be facing each other and aligned along a longitudinal axis extending from the proximal end to the distal end of applicator 150. As described in FIGS. 12A-12D and 13A-13D, inner carrier latch 3110 is positioned proximally to outer carrier latch 3160 in a spaced relation while applicator 150 is in a "locked" state. As sheath 704 is advanced in a proximal direction, applicator 150 is "fired," and sharp carrier lock arms 1524 of sensor electronics carrier 710 are released into their biased outward position. Subsequently, forces generated by expansion of inner spring 1106 and outer spring 1104 cause outer sharp carrier 3152 to advance in a proximal direction. In addition, an opposing force generated by the expansion of inner spring 1106 causes the inner sharp carrier 3102 to remain in relatively the same position, thereby preventing premature retraction of sharp. Similarly, an opposing force generated by the expansion of outer spring 1104 causes sensor electronics carrier 710 to remain in relatively the same position (or displaced in a distal direction toward the skin surface). As outer sharp carrier 3152 further advances in a proximal direction, outer carrier latch 3160 engages inner carrier latch 3110. Proximal forces caused by the carrier latches 3160, 3110 cause inner sharp carrier 3102 to move in a proximal direction into applicator 150, thereby retracting the sharp (not shown).

FIG. 10D is a side view of another embodiment of a two-piece sharp carrier assembly, consisting of inner sharp carrier 4102 and outer sharp carrier 4152. Similar to the previous embodiment, inner sharp carrier 4102 can include one or more sharp retention arms 4104 with sharp retention clips 4106, and one or more inner carrier latches 4110 at or near a proximal end of inner sharp carrier 4102. Outer sharp carrier 4152 can also include a spring retention channel 4162 for retaining spring 1104, as well as outer carrier latch 4160 for interfacing with inner carrier latch 4110. These structures operate in a similar fashion as the embodiment described with respect to FIG. 10C.

Figures 12A, 12B:
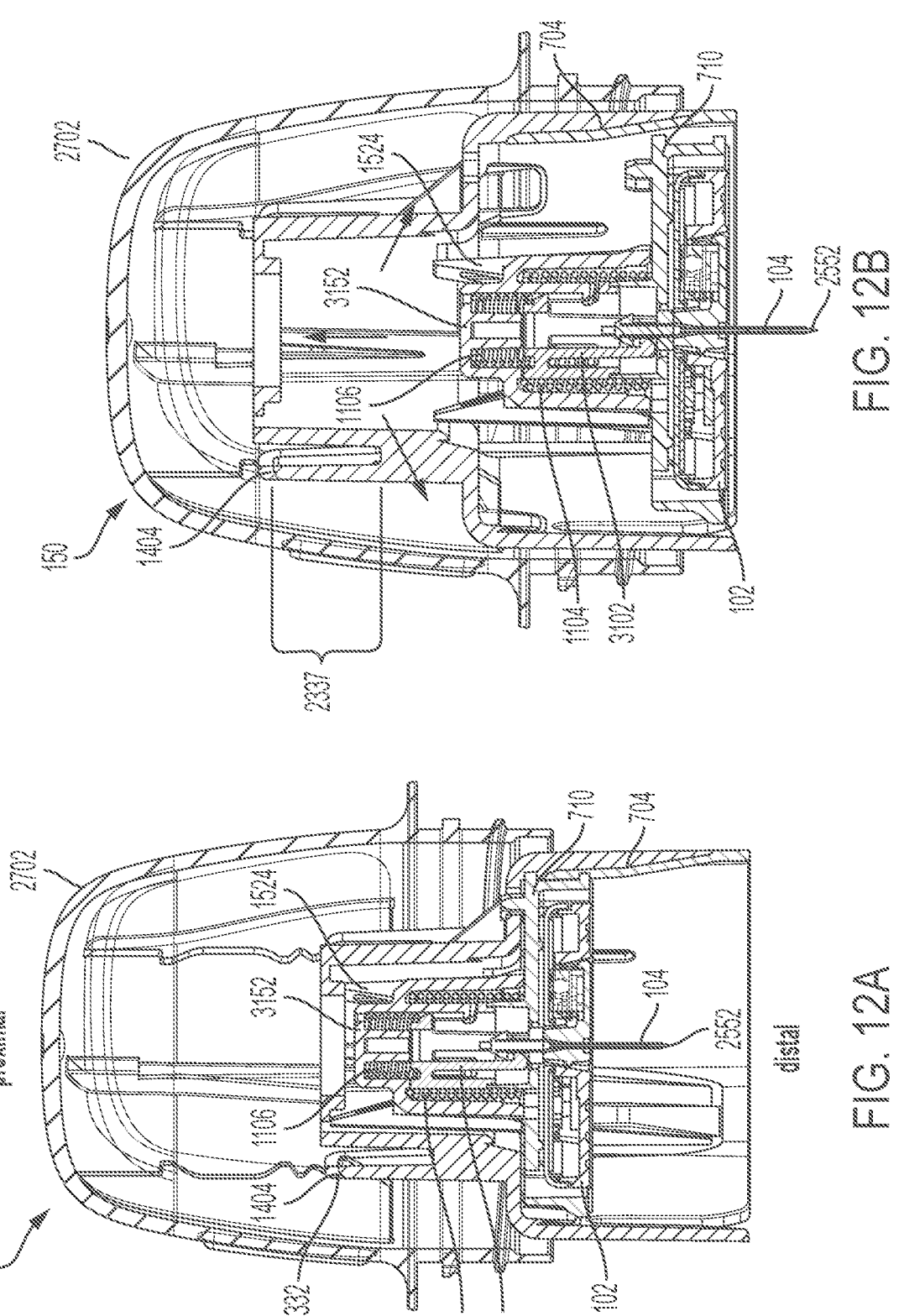
FIGS. 12A to 12D are side cross-sectional views depicting an example embodiment of an applicator device during various stages of deployment.
Figure 13B:
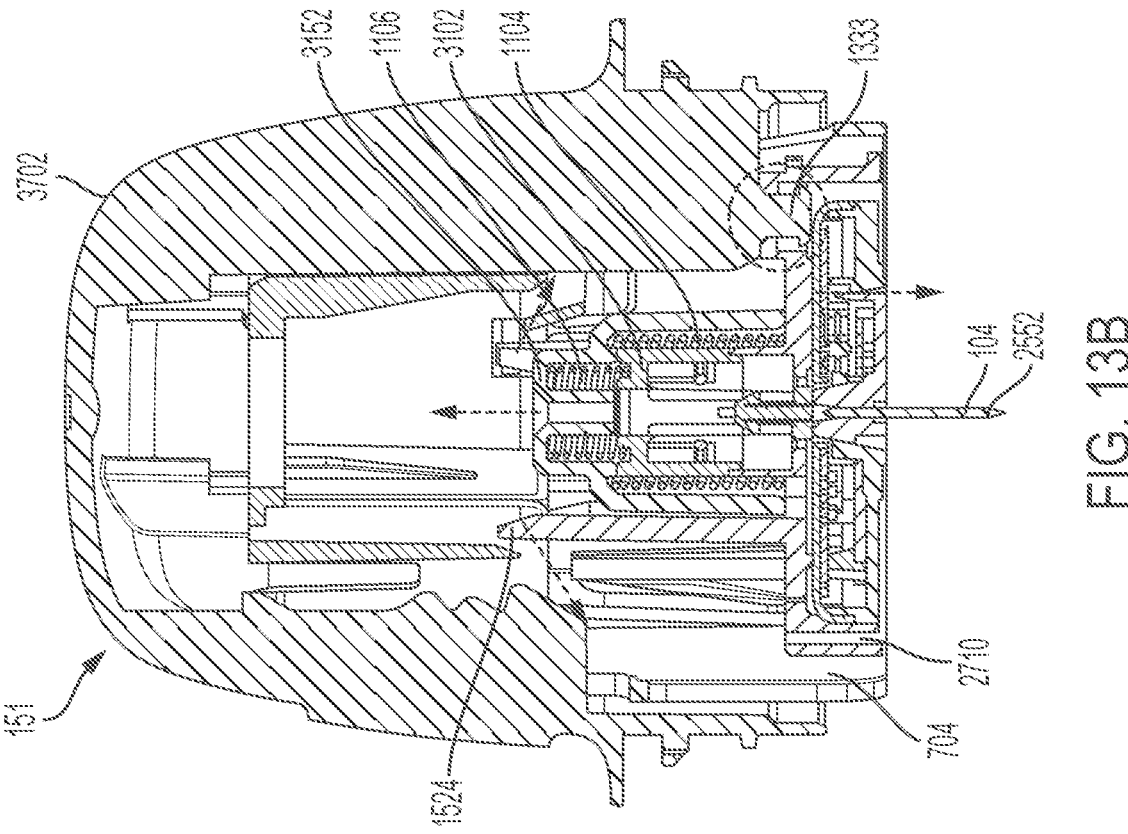
FIGS. 13A to 13D are side cross-sectional views depicting another example embodiment of an applicator device during various stages of deployment.

Referring still to FIG. 10D, the two-piece sharp carrier assembly includes one spring 1104 (in contrast to the two springs depicted in FIG. 10C). In addition, an inner sharp carrier detent 4114 is provided at a distal portion of inner sharp carrier 4102 (as shown in call-out of FIG. 10D) for engaging with a carrier retention detent 1517 located on sensor electronics carrier 710. The engagement of inner sharp carrier detent 4114 with carrier retention detent 1517 causes inner sharp carrier 4102 and sensor electronics carrier 710 to remain locked in place while the sharp penetrates the skin surface during the insertion process. Inner sharp carrier detent 4114 can be disengaged from carrier retention detent 1517 during the "firing" of applicator 150. As sharp carrier lock arms 1524 of sensor electronics carrier 710 are released (as shown in FIGS. 12B and 13B), spring 1104 expands from its preloaded, compressed state. Subsequently, outer sharp carrier 4152 is advanced in a proximal direction while inner sharp carrier 4102 remains relatively in the same position, thereby preventing premature retraction of sharp. As outer sharp carrier 4152 continues to advance in a proximal direction, outer carrier latch 4160 engages inner carrier latch 4110, and a proximal force applied by the outer carrier latch 4160 to inner carrier latch 4110 causes inner sharp carrier detent 4114 to disengage from carrier retention detent 1517. Thereafter, outer carrier latch 4160 pulls inner sharp carrier 4102 in a proximal direction into applicator 150, thereby retracting the sharp (not shown).

With respect to FIG. 10D, those of skill in the art will understand that other retaining devices may be utilized in place of inner carrier detent arm 4112 and carrier retention detent 1517. For example, in alternative embodiments, snaps, hooks, ball locks, latches, pins or other like retaining devices can be utilized to maintain inner sharp carrier 4102 in a "locked" position with sensor electronics carrier 710 until a sufficient force from outer sharp carrier 4152 causes the retaining device to disengage, thereby allowing inner sharp carrier 4102 to advance in a proximal direction. In other alternative embodiments, a screw thread can be utilized between inner sharp carrier 4102 and sensor electronics carrier 710 to retain inner sharp carrier 4102 in position during the "firing" sequence of applicator 150 (as shown in FIGS. 12A-12D and 13A-13D). Subsequently, as outer sharp carrier 4152 continues to advance in a proximal direction, the proximal force of outer sharp carrier 4152 can cause inner sharp carrier 4102 to rotate and disengage itself from sensor electronics carrier 710. It should be understood that these exemplary retention devices and their equivalents are within the scope of the embodiments disclosed herein.

FIG. 10E is a side view of yet another embodiment of a two-piece sharp carrier, consisting of inner sharp carrier 5102 and outer sharp carrier 5152. Similar to the previous embodiment, inner sharp carrier 5102 can include one or more sharp retention arms 5104 with sharp retention clips 5106. Outer sharp carrier 5152 can include a spring retention channel 5162 for retaining spring 1104.

Referring still to FIG. 10E, outer sharp carrier 5152 can include one or more angled snap arms 5164 extending in an inward direction from a proximal top portion of outer sharp carrier 5152, such that each angled snap arm 5164 can slope in a downward direction towards a distal portion of inner sharp carrier 5102. Each angled snap arm 5164 can include at the distal end, a snap arm ledge 5166 which can consist of an end portion that provides a substantially flat surface facing in a proximal direction (i.e., akin to the outer carrier latch 4160 as described with respect to FIG. 10D). In addition, each distal end of the one or more angled snap arms 5164 can be in fitted contact with one or more angled key slots 5116 of inner sharp carrier 5102. Angled key slots 5116 can consist of cut-outs having a generally "tilted rectangular" shape, in an outer cylindrical surface of inner sharp carrier 5102, and extend circumferentially from a proximal end to a distal end of inner sharp carrier 5102.

Referring again to FIG. 10E, inner sharp carrier 5102 can also include one or more locking nubs 5118 on the outer cylindrical surface of a proximal portion of inner sharp carrier 5102. Locking nub 5118 can consist of a fixed spherical, hemispherical or otherwise rounded structure that protrudes in an outward direction, away from a central longitudinal axis of inner sharp carrier 5102, and can be in fitted contact with a carrier nub slot 1521 located on a distal portion of sensor electronics carrier 710. Carrier nub slot 1521 can consist of a cut-out in spring alignment ridge 1516 of sensor electronics carrier 710, in which the cut-out has an open end from which locking nub 5118 can slidably disengage upon rotation of inner sharp carrier 5102.

With reference to the embodiment shown in FIG. 10E, the relative movements of outer sharp carrier 5152, inner sharp carrier 5102 and spring 1104 during "firing" of applicator 150 will now be generally described. As sharp carrier lock arms 1524 of sensor electronics carrier 710 are released (shown in FIGS. 12B and 13B), spring 1104 expands from its preloaded, compressed state. Subsequently, outer sharp carrier 5152 is advanced in a proximal direction. Inner sharp carrier 5102 remains relatively in the same position due to locking nub 5118 being engaged in carrier nub slot 1521, thereby preventing premature retraction of sharp. As outer sharp carrier 5152 continues to advance in a proximal direction, the force exerted by angled snap arm 5164 upon angled key slot 5116 causes inner sharp carrier 5102 to rotate due to the angular orientation of angled key slot 5116. Due to the rotation of inner sharp carrier 5102, locking nub 5118 is slidably advanced toward the open end of carrier nub slot 1521 of sensor electronics carrier 710. When locking nub 5118 reaches the open end of carrier nub slot 1521, inner sharp carrier 5102 disengages from sensor electronics carrier 710. As outer sharp carrier 5152 further advances in a proximal direction, snap arm ledge 5166 engages the proximal end portion of angled key slot 5116, and begins to pull inner sharp carrier 5102 in a proximal direction into applicator 150, thereby retracting the sharp (not shown).

As shown in FIG. 10E, two angled snap arms 5164 and two angled key slots 5116 are depicted. It is to be understood, however, that any number of angled snap arms 5164 and/or angled key slots 5116 can be utilized. In addition, although carrier nub slot 1521 is shown in FIG. 10E as having an "L-shaped" cut-out, any number of cut-out shapes (e.g., "curve" or "linear slope") having one open end from which locking nub 5118 can slidably disengage are suitable.

Figure 10F:
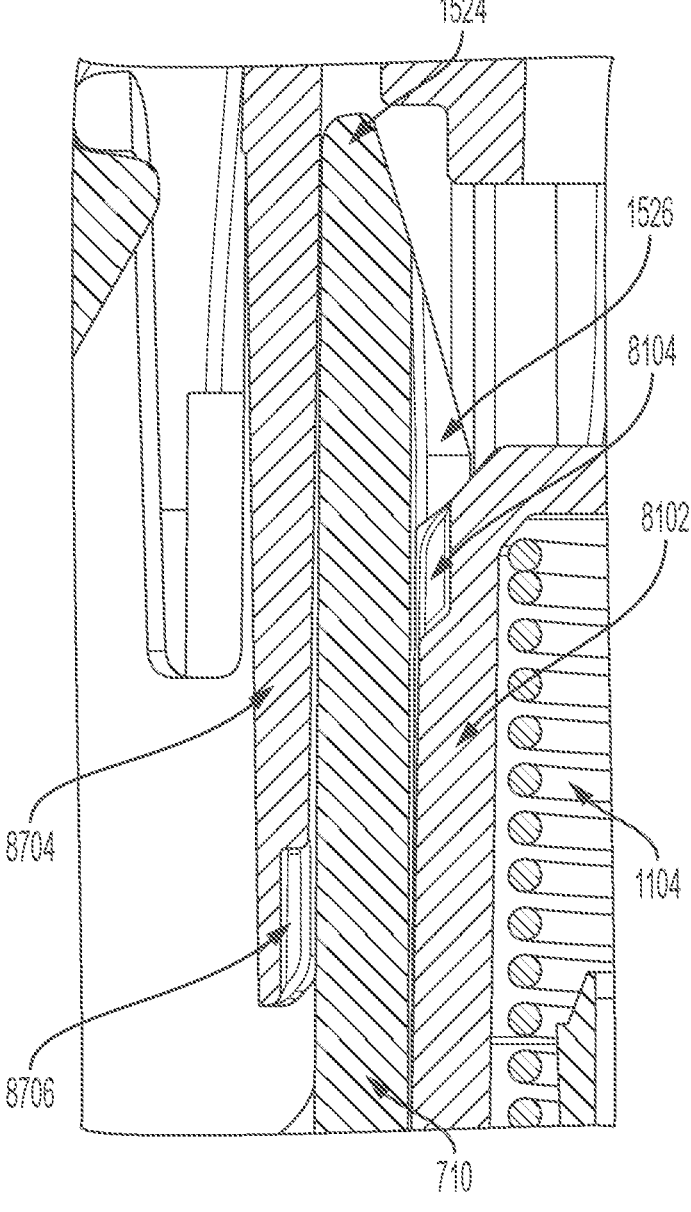
FIG. 10F is a side cross-sectional view depicting another example embodiment of a sharp carrier assembly and sheath within an applicator.

FIG. 10F is a close-up, side cross-sectional view depicting another example embodiment of a sharp carrier assembly 8102 and sheath 8704 within an applicator. According to one aspect of the embodiments, sharp carrier assembly 8102 can include a sharp carrier slot 8104 disposed on a surface of sharp carrier assembly 8102, and along the path upon which sharp carrier retention feature 1526 of the sensor electronics carrier 710 travels during retraction of the needle (not shown). Similarly, according to another aspect of the embodiments, sheath 8704 can include a sheath slot 8706 disposed on a surface of sheath 8704, and along the path upon which sharp carrier lock arm 1524 of sensor electronics carrier 710 travels during retraction of the needle. As further described below, with respect to FIGS. 16A-16C, sharp carrier slot 8104 and sheath slot 8706 can be configured to receive, respectively, sharp carrier lock retention feature 1526 and sharp carrier lock arm 1524 to allow for a dual-stage needle retraction process. In particular, according to some embodiments, as lock arms 1524 of sensor electronics carrier 710 are received into sharp carrier slot 8104 and sheath slot 8706, lock arms 1524 can partially deflect in an outward direction, which can cause the sharp carrier 8102 to move a limited distance in a proximal direction from the force of expansion of preloaded compression spring 1104 disposed in sharp carrier 8102. In this manner, the needle can be partially retracted, or maintained at a stationary position relative to the skin surface, such that further penetration into the subject's dermis or subcutaneous tissue by the needle can be prevented.

Example Embodiments of Sharp Modules

FIG. 11A is a perspective view depicting an example embodiment of sharp module 2500 prior to assembly within sensor module 504 (FIG. 6B). Sharp 2502 can include a distal tip 2506 which can penetrate the skin while carrying sensor tail in a hollow or recess of sharp shaft 2504 to put the active surface of the sensor tail into contact with bodily fluid. A hub push cylinder 2508 can provide a surface for a sharp carrier to push during insertion. A hub small cylinder 2512 can provide a space for the extension of sharp hub contact faces 1622 (FIG. 10B). A hub snap pawl locating cylinder 2514 can provide a distal-facing surface of hub snap pawl 2516 for sharp hub contact faces 1622 to abut. A hub snap pawl 2516 can include a conical surface that opens clip 1620 during installation of sharp module 2500.

FIGS. 11B to 11H show example embodiments of sharp modules, in various stages of assembly, for use in the insertion of dermal analyte sensors. According to one aspect of the embodiments, angling the sensor and/or insertion sharp relative to a reference point can enable co-localization of the tip of the insertion needle and the tip of the sensor, and furthermore, can create a single contact point at the surface of the skin. As such, the sharp can create a leading edge at the surface of the skin to form an insertion path into the dermal layer for the sensor, as the sensor is inserted into a subject. In some embodiments, for example, the sharp and/or dermal sensor may be angled relative to a reference point (e.g., each other, surface of the skin, or the base of the applicator) for insertion, where the angle of the sharp differs from the angle of the sensor. For example, the reference point may be the skin surface to be breached for dermal insertion, or may be a reference or component of the sensor applicator set. In some embodiments, the sharp may be disposed at an angle relative to the sensor. For example, when designed so that that the sharp is angled relative to the sensor, the needle creates a leading edge for the sensor during operation of the applicator set. Furthermore, the needle design itself, and the positioning of the needle with respect to the sensor can be implemented in any desired configuration, including all of those configurations disclosed in U.S. Patent Publication No. 2014/0171771, which is incorporated by reference herein in its entirety for all purposes.

Furthermore, although many of the example embodiments described with respect to FIGS. 11B to 11J make reference to dermal analyte sensors and dermal insertion, it will be understood by those of skill in the art that any of the embodiments can be dimensioned and configured for use with analyte sensors that can be positioned beyond the dermal space, such as into (or even fully through) subcutaneous tissue (e.g., 3 mm to 10 mm beneath the surface of the skin depending on the location of the skin on the body).

Figure 11B:
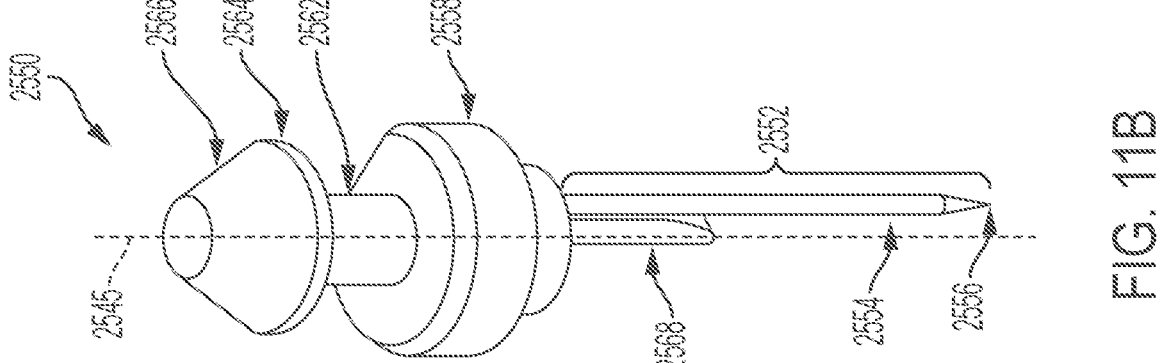
FIG. 11B is a perspective view of another example embodiment of a sharp module.

FIG. 11B is a perspective view depicting an example embodiment of a sharp module 2550 that can be used for the insertion of a dermal sensor. Sharp module 2550 is shown here prior to assembly with sensor module 504 (FIG. 6B), and can include components similar to those of the embodiment described with respect to FIG. 11A, including sharp 2552, sharp shaft 2554, sharp distal tip 2556, hub push cylinder 2558, hub small cylinder 2562, hub snap pawl 2566 and hub snap pawl locating cylinder 2564. Sharp 2552 can be positioned within sharp module 2550 at an off-center location relative to a longitudinal axis 2545 that extends through center of hub snap pawl 2566, hub small cylinder 2562 and hub push cylinder 2558. In addition, sharp module 2550 can include a sharp spacer 2568 that is parallel to and adjacent with a portion of sharp 2552. Sharp spacer 2568 can be positioned in between sensor 104 (not shown) and sharp 2552 along a proximal portion of sharp 2552, and can ensure that sensor 104 and sharp 2552 remain spaced apart at a proximal portion of sharp 2552. Sharp 2552 can be positioned in an off-center location during a molding process with hub components 2558, 2562, 2566, each of which may consist of a rigid plastic material.

Figure 11D:
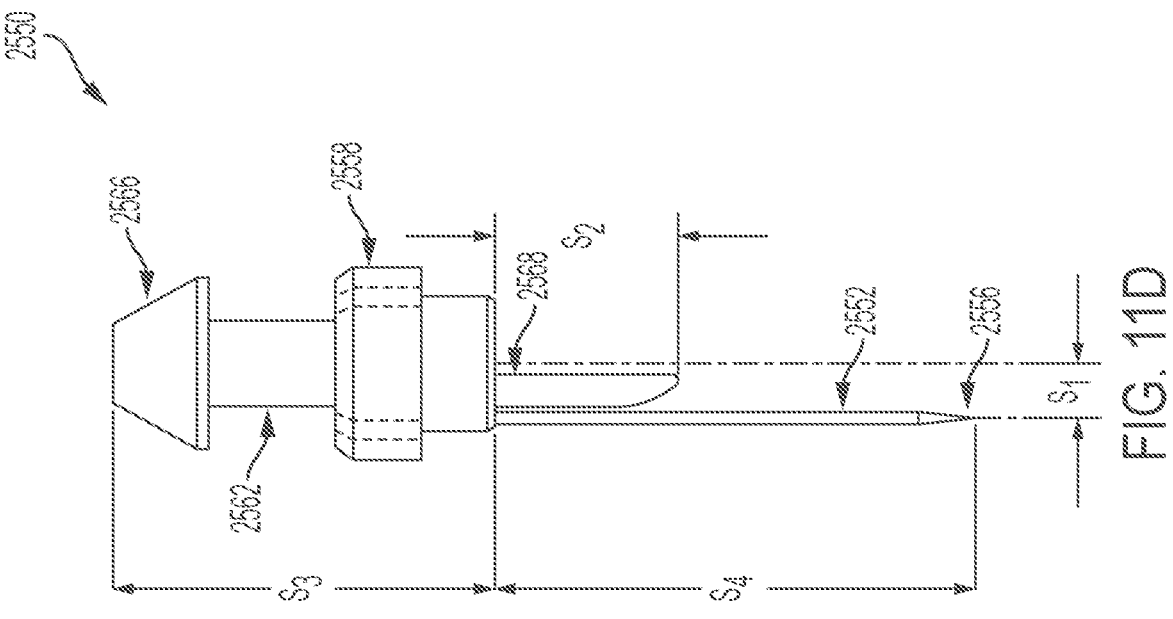
FIGS. 11C and 11D are schematic views depicting the sharp module of FIG. 11B.
Figure 11C:
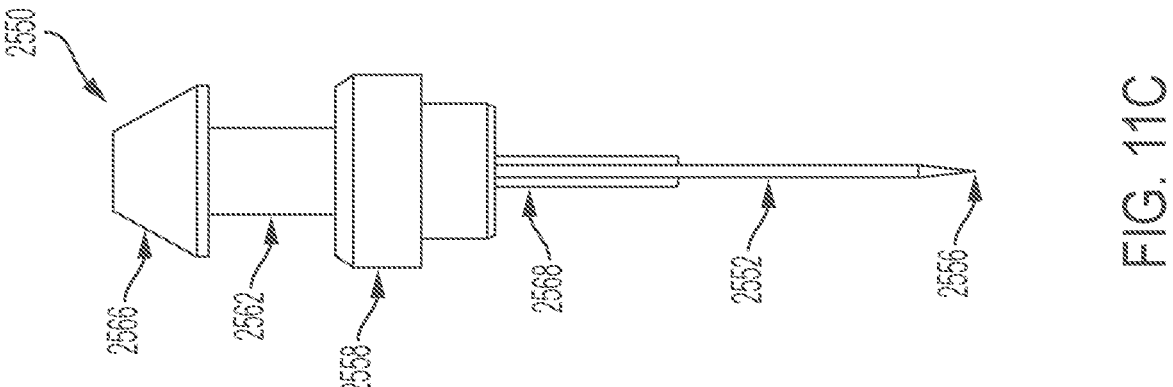

FIGS. 11C and 11D are two side views depicting sharp module 2550 prior to assembly with sensor module 504 (FIG. 6B), and include sharp 2552, spacer 2568, hub push cylinder 2558, hub small cylinder 2562 and hub snap pawl 2566. In some embodiments, the relative distances between the sharp 2552 and hub components can be positioned as follows. For example, distance, $S_1$, between the sharp 2552 and the radial center of hub can range from 0.50 mm to 1 mm (e.g., 0.89 mm). Height, $S_2$, of sharp spacer 2568 can range from 3 to 5 mm (e.g., 3.26 mm). Height, $S_3$, of hub can range from 5 to 10 mm (e.g., 6.77 mm). Length, $S_4$, of sharp 2552 can range from 1.5 mm to 25 mm (e.g., 8.55 mm), and may depend on the location of the insertion site on the subject.

Figure 11F:
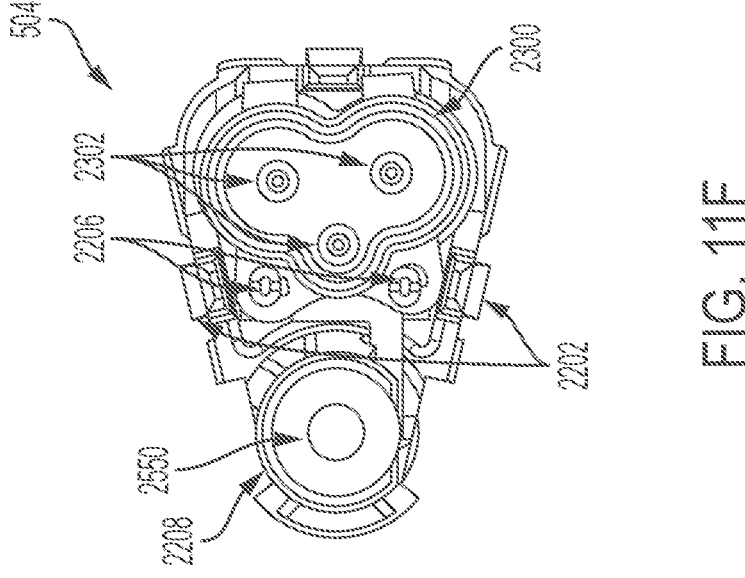
FIGS. 11E and 11F are a side schematic view and a top-down schematic view, respectively, of the sharp module of FIG. 11B, as assembled with a sensor module.
Figure 11E:
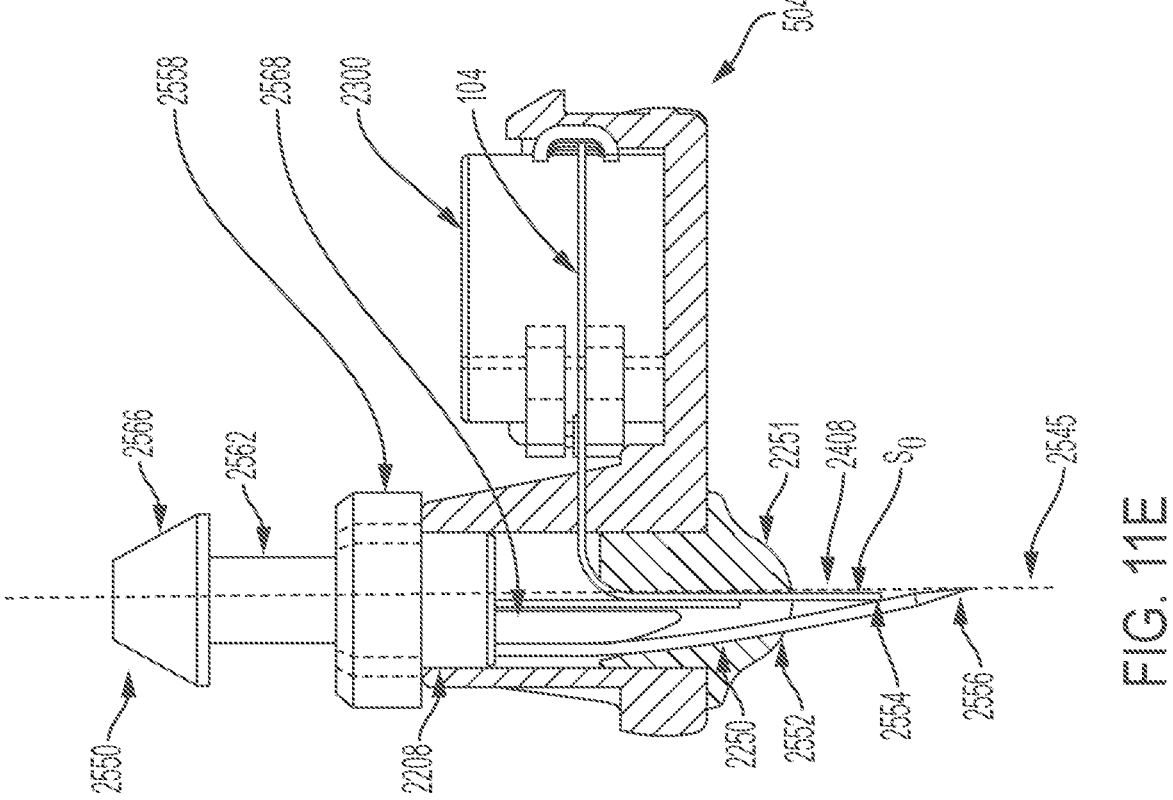
Figure 11H:
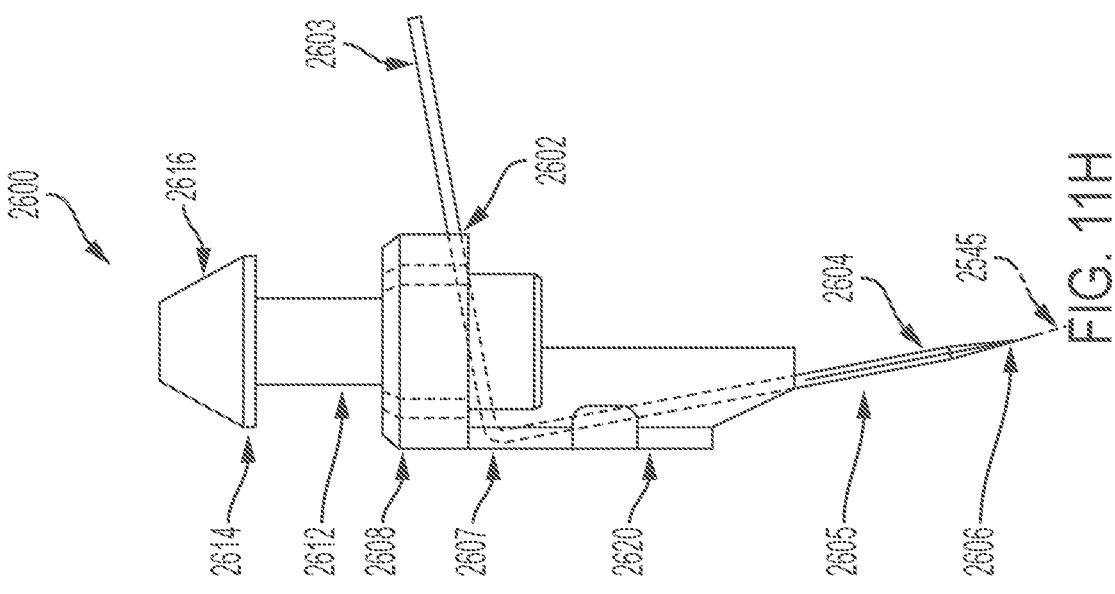
FIG. 11H is a side schematic view depicting the sharp module of FIG. 11G.

FIG. 11E depicts a side cross-sectional side view of sharp module 2550, including sharp 2552, sharp spacer 2568 and hub components (hub snap pawl 2566, hub small cylinder 2562, and hub push cylinder 2558), as assembled with sensor module 504. As can be seen in FIG. 11E, sharp 2552 is positioned within sharp slot 2208 of sensor module 504 that includes a curved interior surface 2250, located at a distal end. Curved interior surface 2250 of sensor module 504 can be in contact with a portion of sharp 2552 and cause a deflection such that sharp distal tip 2556 is oriented toward central longitudinal axis 2545. As best seen in FIG. 11H, sharp 2552 can be positioned such that the distal portion and central longitudinal axis 2545 form an acute angle, $S_\ominus$, that can range between 5° and 20°. In some embodiments, for example, $S_\ominus$, can range from 5° to 17°, or 7° to 15°, or 9° to 13°, e.g., 9°, 10°, 11°, 12°, or 13°.

Referring still to FIG. 11E, near a distal end of sensor module 504 is protrusion 2251, which can enhance the perfusion of bodily fluid, such as dermal fluid. Although shown as a curved surface in FIG. 11E, protrusion 2251 can be shaped in any desired fashion. In addition, in some embodiments, multiple protrusions can be present. U.S. Patent Publication No. 2014/0275907, which is incorporated by reference herein in its entirety for all purposes, describes sensor devices having different protrusion configurations, each of which can be implemented with the embodiments described herein. Many of the embodiments described herein show the needle exiting from the protrusion, and in other embodiments, the needle can exit from the base of the sensor device adjacent the protrusion, and from that position extend over the tip of sensor 104.

Referring still to FIGS. 11E and 11F, sensor 104 can be a dermal sensor and can include sensor tail 2408, located at a distal end of sensor 104, and which can be positioned in a substantially parallel orientation to central longitudinal axis 2545. Distal end of sensor tail 2408 can be proximal to distal sharp tip 2556, either in a spaced relation with, at rest in, or at rest against a portion of sharp shaft 2554. As further depicted in FIG. 11E, sharp spacer 2568 provides a spaced relation between a proximal portion of sharp 2552 and sensor 104, such that the proximal portion of sharp 2552 and sensor 104 are not in contact. Sensor module 504 can further include sensor connector 2300 for housing a proximal portion of sensor 104 that is relatively perpendicular to a distal end of sensor 104.

FIG. 11F is a top-down cross-sectional view of sensor module 504. Sensor module 504 can include one or more sensor module snaps 2202 for coupling with a housing (not shown) of sensor control device 102. Sensor module 504 can also include sensor connector 2300, which can have sensor contacts 2302 for coupling with a proximal portion of sensor 104. Sensor connector 2300 can be made of silicone rubber that encapsulates compliant carbon impregnated polymer modules that serve as electrical conductive contacts 2302 between sensor 104 and electrical circuitry contacts for the electronics within sensor control device 102. The connector can also serve as a moisture barrier for sensor 104 when assembled in a compressed state after transfer from a container to an applicator and after application to a user's skin. Although three contacts 2302 are depicted, it should be understood that connector 2300 can have fewer contacts (e.g., two) or more contacts (e.g., four, five, six, etc.), depending on the particular type or configuration of sensor 104. Sensor connector 2300 can be further coupled with sensor module 504 by two connector posts 2206 positioned through a like number of apertures in connector 2300. Although two connector posts 2206 are depicted, it should be understood that any number of connector posts 2206 can be used to couple connector 2300 to sensor module 504.

Figure 11G:
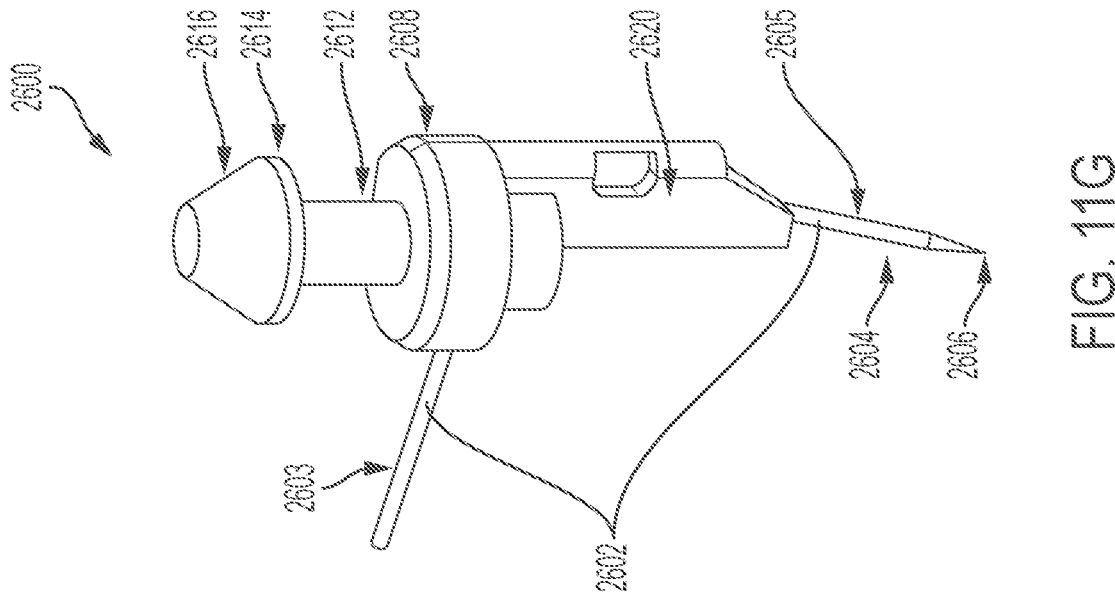
FIG. 11G is a perspective view of another example embodiment of a sharp module.

FIGS. 11G and 11H are, respectively, a perspective view and a side view of another example embodiment of sharp module 2600 that can be used for the insertion of a dermal sensor. Sharp module 2600 is shown here prior to assembly with sensor module 504 (FIG. 6B), and can include components similar to those of the embodiments described with respect to FIGS. 11A and 11B, including sharp 2602, sharp shaft 2604, sharp distal tip 2606, hub push cylinder 2608, hub small cylinder 2612, hub snap pawl 2616 and hub snap pawl locating cylinder 2614. In some embodiments, sharp 2602 can be a "pre-bent" needle that includes a proximal portion 2603 that originates from a point external to sharp module 2600 and intersects, at an angle, a central point of the hub (e.g., through hub push cylinder 2608). Sharp 2602 can also include a distal portion 2605 that extends in a distal direction, at an angle, from a point near a distal portion of hub toward the insertion point of the user's skin. As shown in FIG. 11H, sharp 2602 can include an angled portion 2607 located external to hub push cylinder 2608, which can have a substantially 90° angle between proximal portion 2603 and distal portion 2605 of sharp 2602. Sharp module 2600 can also include a bend fin guide 2620 for maintaining "pre-bent" sharp 2602 in position during assembly and/or use, and can prevent lateral or rotational movement of sharp 2602 relative to hub components. Proximal portion 2603 of sharp 2602 can be "trimmed" from the hub after molding process is completed, and prior to assembly of sharp module 2600 with sensor module 504.

Figure 11J:
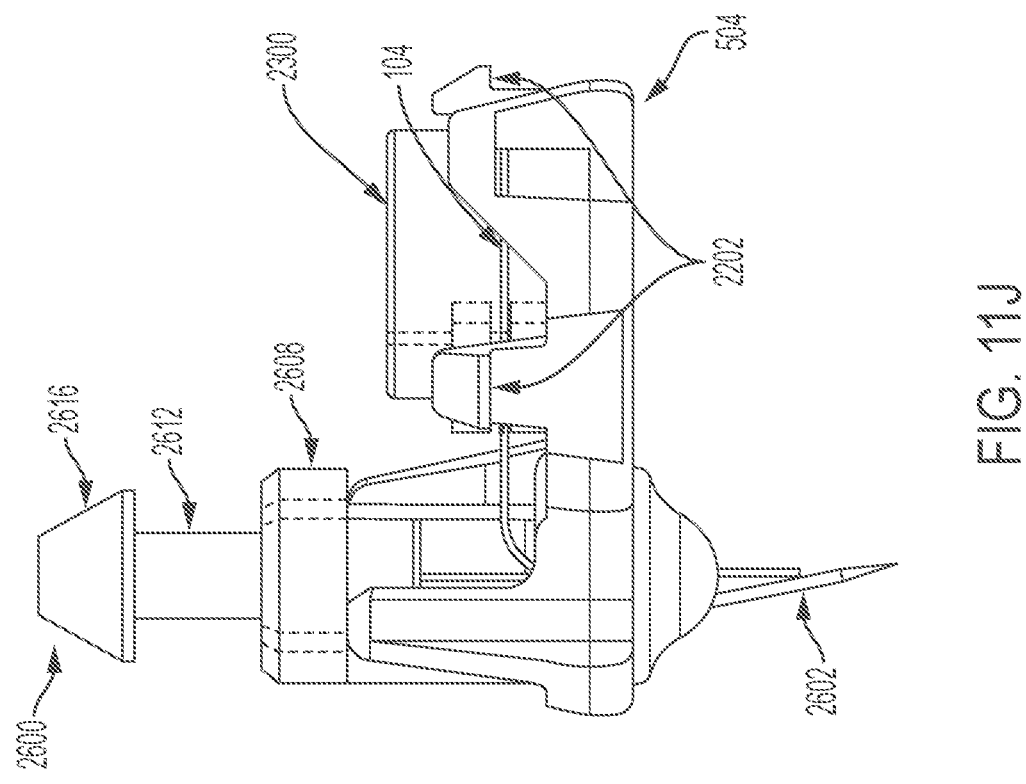
FIGS. 11I and 11J are a side cross-sectional view and a side view, respectively, of the sharp module of FIG. 11G, as assembled with a sensor module.
Figure 11I:
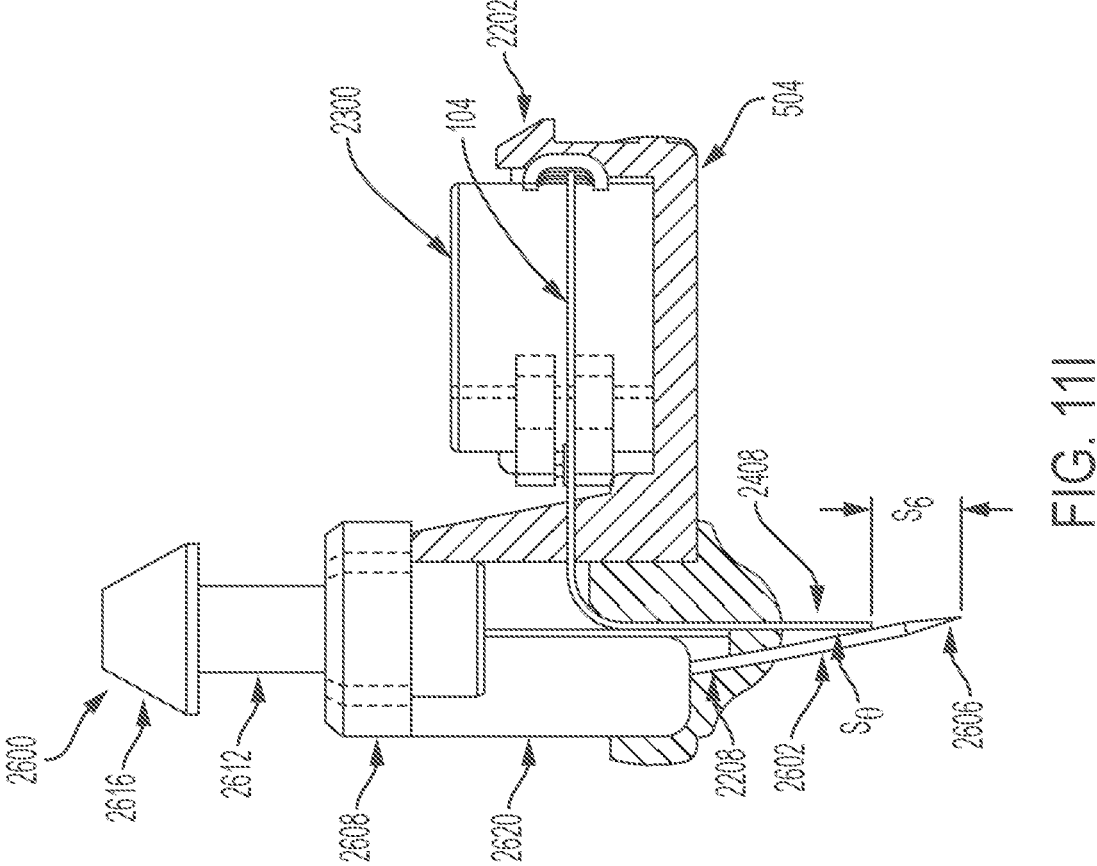

FIGS. 11I and 11J show, respectively, a side cross-sectional view and a side view of sharp module 2600 (including hub snap pawl 2616, hub small cylinder 2612, and hub push cylinder 2608), as assembled with sensor module 504. As can be seen in FIG. 11I, sensor module 504 includes sharp slot 2208, through which sharp 2602 can extend in an angled and distal direction. As described earlier, a proximal portion of sharp 2602 passes through bend fin guide 2620, which is coupled with a distal portion of sensor module 504. Sensor module 504 can also include sensor 104, which can be a dermal sensor. As seen in FIG. 11I, sharp 2602 and sensor tail 2408 can form an acute angle, $S_\Theta$, at a point where their respective longitudinal axes converge. Angle $S_\Theta$ can range between 5° and 20°. In some embodiments, for example, $S_\Theta$, can range from 5° to 17°, or 7° to 15°, or 9° to 13°, e.g., 9°, 10°, 11°, 12°, or 13°. In some embodiments, distal sharp tip 2606 is located at a distance, $S_6$, that is proximal to an end of sensor tail 2408. Distance, $S_6$, can range between 0.02 mm to 0.10 mm, e.g., 0.05 mm, 0.06 mm or 0.07 mm.

Referring still to FIGS. 11I and 11J, sensor module 504 can also include sensor connector 2300 for housing a proximal portion of sensor 104 that is relatively perpendicular to a distal end of sensor 104. Sensor module 504 can further include one or more sensor module snaps 2202 for coupling with a housing (not shown) of sensor control device 102. Sensor connector 2300 can include the same structures described with respect to FIG. 11F.

In the above embodiments, the sharp can be made of stainless steel or a like flexible material (e.g., material used to manufacture acupuncture needles), and dimensioned such that the applicator provides for insertion of at least a portion of the dermal sensor into the dermal layer, but not through the dermal layer of the skin. According to certain embodiments, the sharp has a cross sectional diameter (width) of from 0.1 mm to 0.5 mm. For example, the sharp may have a diameter of from 0.1 mm to 0.3 mm, such as from 0.15 mm to 0.25 mm, e.g., 0.16 mm to 0.22 mm in diameter. A given sharp may have a constant, i.e., uniform, width along its entire length, or may have a varying, i.e., changing, width along at least a portion of its length, such as the tip portion used to pierce the surface of the skin. For example, with respect to the embodiment shown in FIG. 11I, width of sharp 2602 can narrow along a distal portion between bend fin guide 1620 and distal sharp tip 2606.

A sharp can also have a length to insert a dermal sensor just into the dermal layer, and no more. Insertion depth may be controlled by the length of the sharp, the configuration of the base and/or other applicator components that limit insertion depth. A sharp may have a length between 1.5 mm and 25 mm. For example, the sharp may have a length of from 1 mm to 3 mm, from 3 mm to 5 mm, from 5 mm to 7 mm, from 7 mm to 9 mm, from 9 mm to 11 mm, from 11 mm to 13 mm, from 13 mm to 15 mm, from 15 mm to 17 mm, from 17 mm to 19 mm, from 19 mm to 21 mm, from 21 mm to 23 mm, from 23 mm to 25 mm, or a length greater than 25 mm. It will be appreciated that while a sharp may have a length up to 25 mm, in certain embodiments the full length of the sharp is not inserted into the subject because it would extend beyond the dermal space. Non-inserted sharp length may provide for handling and manipulation of the sharp in an applicator set. Therefore, while a sharp may have a length up to 25 mm, the insertion depth of the sharp in the skin on a subject in those certain embodiments will be limited to the dermal layer, e.g., about 1.5 mm to 4 mm, depending on the skin location, as described in greater detail below. However, in all of the embodiments disclosed herein, the sharp can be configured to extend beyond the dermal space, such as into (or even fully through) subcutaneous tissue (e.g., 3 mm to 10 mm beneath the surface of the skin depending on the location of the skin on the body). Additionally, in some example embodiments, the sharps described herein can include hollow or partially hollow insertion needles, having an internal space or lumen. In other embodiments, however, the sharps described herein can include solid insertion needles, which do not have an internal space and/or lumen. Furthermore, a sharp of the subject applicator sets can also be bladed or non-bladed.

Likewise, in the above embodiments, a dermal sensor is sized so that at least a portion of the sensor is positioned in the dermal layer and no more, and a portion extends outside the skin in the transcutaneously positioned embodiments. That is, a dermal sensor is dimensioned such that when the dermal sensor is entirely or substantially entirely inserted into the dermal layer, the distal-most portion of the sensor (the insertion portion or insertion length) is positioned within the dermis of the subject and no portion of the sensor is inserted beyond a dermal layer of the subject when the sensor is operably dermally positioned.

The dimensions (e.g., the length) of the sensor may be selected according to the body site of the subject in which the sensor is to be inserted, as the depth and thickness of the epidermis and dermis exhibit a degree of variability depending on skin location. For example, the epidermis is only about 0.05 mm thick on the eyelids, but about 1.5 mm thick on the palms and the soles of the feet. The dermis is the thickest of the three layers of skin and ranges from about 1.5 mm to 4 mm thick, depending on the skin location. For implantation of the distal end of the sensor into, but not through, the dermal layer of the subject, the length of the inserted portion of the dermal sensor should be greater than the thickness of the epidermis, but should not exceed the combined thickness of the epidermis and dermis. Methods may include determining an insertion site on a body of a user and determining the depth of the dermal layer at the site, and selecting the appropriately-sized applicator set for the site.

In certain aspects, the sensor is an elongate sensor having a longest dimension (or "length") of from 0.25 mm to 4 mm. The length of the sensor that is inserted, in the embodiments in which only a portion of a sensor is dermally inserted, ranges from 0.5 mm to 3 mm, such as from 1 mm to 2 mm, e.g., 1.5 mm. The dimensions of the sensor may also be expressed in terms of its aspect ratio. In certain embodiments, a dermal sensor has an aspect ratio of length to width (diameter) of about 30:1 to about 6:1. For example, the aspect ratio may be from about 25:1 to about 10:1, including 20:1 and 15:1. The inserted portion of a dermal sensor has sensing chemistry.

However, all of the embodiments disclosed herein can be configured such that at least a portion of the sensor is positioned beyond the dermal layer, such as into (or through) the subcutaneous tissue (or fat). For example, the sensor can be dimensioned such that when the sensor is entirely or substantially entirely inserted into the body, the distal-most portion of the sensor (the insertion portion or insertion length) is positioned within the subcutaneous tissue (beyond the dermis of the subject) and no portion of the sensor is inserted beyond the subcutaneous tissue of the subject when the sensor is operably positioned. As mentioned, the subcutaneous tissue is typically present in the region that is 3 mm to 10 mm beneath the outer skin surface, depending on the location of the skin on the body.

Example Embodiments of Applicator Deployment

FIGS. 12A-12D are side cross-sectional views depicting an example embodiment of an applicator 150 during deployment of sensor control device 102, which can include a dermal sensor for sensing an analyte level in a dermal layer of the subject.

FIG. 12A shows applicator 150, prior to firing, in a state ready to be positioned against a subject's skin surface. Detent round 1404 of sheath 704 is positioned in "locked" groove 2332 in a locking rib of applicator housing 2702. Outer sharp carrier 3152 is coupled to inner spring 1106 and outer spring 1104, with both springs in a preloaded, compressed state. Outer sharp carrier 3152 is also retained by one or more sharp carrier lock arms 1524 of sensor electronics carrier 710. Sensor electronics carrier 710 is positioned within a proximal portion of sheath 704, wherein the inner diameter of sheath 704 is configured to deflect sharp carrier lock arms 1524 in an inward direction. A distal portion of outer sharp carrier 3152 is in contact with a proximally facing surface of sensor electronics carrier 710. Similarly, a distal portion of inner sharp carrier 3102 is coupled to a proximally facing surface of sensor electronics carrier 710. Sharp 2552 and sensor 104 are positioned within sheath 704.

In FIG. 12B, applicator 150 is shown in a "firing" state, where force applied to the proximal end of housing 2702 causes housing 2702 to move in a distal direction with respect to sheath 704. At this point, sharp 2552 and sensor 104 have extended from the distal end of sheath 704 and have already penetrated, or are in the process of penetrating, the subject's skin layer. Advancement of housing 2702 causes detent round 1404 to advance in a proximal direction relative to housing 2702 which, in turn, causes detent round 1404 to enter into a "free flight" state, in which detent round 1404 moves over firing surface 2337 with non-continuous contact or no contact. Sharp carrier lock arms 1524 of sensor electronics carrier 710 have also cleared the inner diameter of sheath 704 and are free to deflect outward into their biased position (indicated by outward arrows). Subsequently, sharp carrier lock arms 1524 disengage from outer sharp carrier 3152 which, in turn, begins to move in a proximal direction due to expansion of inner spring 1106 and outer spring 1104 (indicated by upward arrow). The expansion of inner spring 1106 also exerts a force in a distal direction causing inner sharp carrier 3102 to remain coupled to sensor electronics carrier 710. Similarly, the expansion of outer spring 1104 also exerts force in a distal direction securing sensor electronics carrier 710 in a distal position.

Figure 12D:
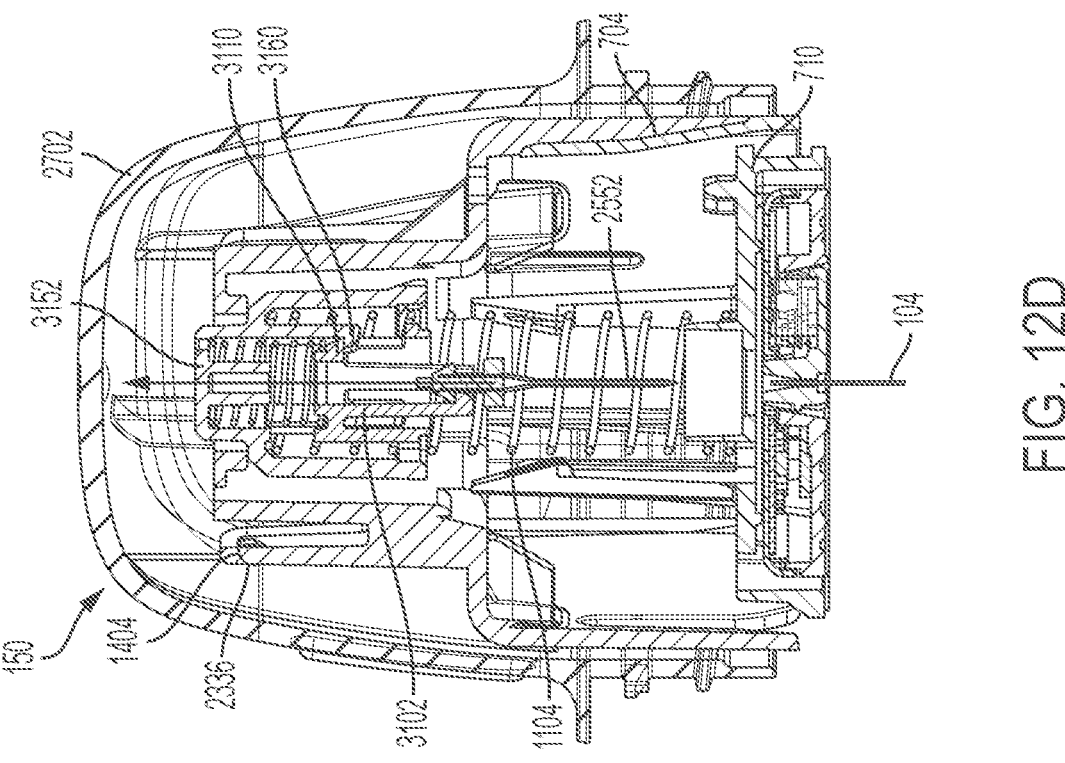
Figure 12C:
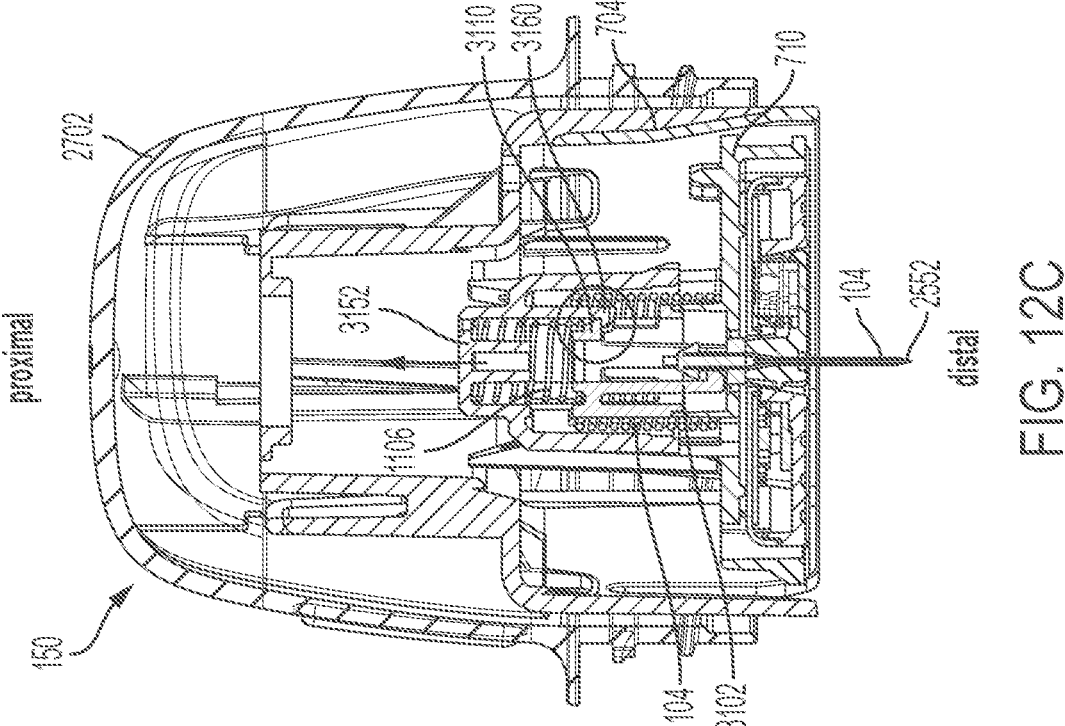

In FIG. 12C, outer sharp carrier 3152 continues to move in a proximal direction (indicated by upward arrow) due to continuing expansion of inner spring 1106 and outer spring 1104. After moving a predetermined distance in the proximal direction, outer carrier latch 3160 of outer sharp carrier 3152 engages inner carrier latch 3110 of inner sharp carrier 3102. As shown in FIG. 12C, sharp 2552 and sensor 104 remain in their respective positions due to the expansion forces in a distal direction created by springs 1104, 1106.

In FIG. 12D, inner sharp carrier 3102 is pulled in a proximal direction (indicated by elongated upward arrow) by force of outer carrier latch 3160. In turn, inner sharp carrier 3102 retracts sharp 2552 through sensor electronics carrier 710, leaving behind sensor 104 implanted in a dermal layer of the subject. Applicator 150 is shown in a "lockout" state, in which detent round 1404 of sheath 704 has advanced past the sheath stopping ramp (not shown) and within final lockout groove 2336 of housing 2702. As further shown in FIG. 12D, both inner sharp carrier 3102 and outer sharp carrier 3152 are fully retracted within applicator 150.

FIGS. 13A-13D are side cross-sectional views depicting an alternative embodiment of an applicator 151 during deployment of sensor control device 102 which can include a dermal sensor for sensing an analyte level in a dermal layer of the subject. Generally, applicator 151 operates in a similar manner as applicator 150, as described with respect to FIGS. 12A-12D, but additionally includes a retention mechanism to couple housing 3702 and sensor electronics carrier 2710. The retention mechanism operates to further increase the velocity of sharp insertion during firing, while delaying the sharp retraction sequence, as further described below.

Figure 13A:
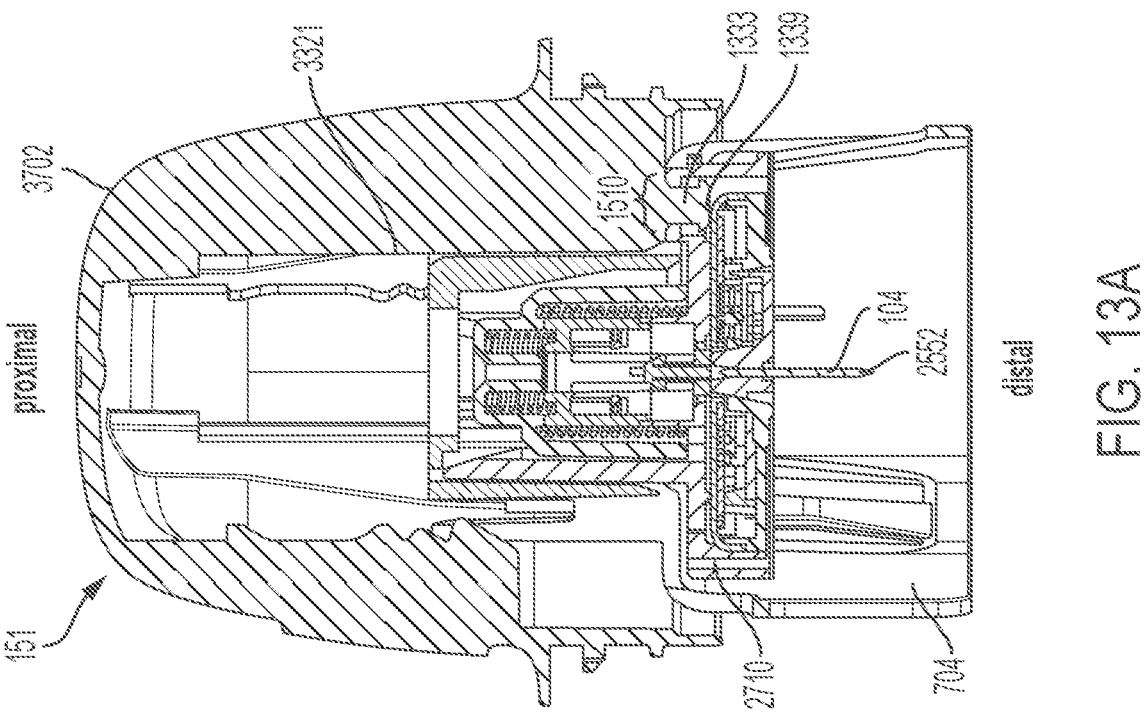

As shown in FIG. 13A, applicator 151 is in a "locked" state, prior to firing. Sharp 2552 and sensor 104 are positioned within sheath 704, and applicator 151 is ready to be positioned against the subject's skin. Applicator housing 3702 includes heat stake post 1333 located on a distal portion of housing guide rib 3321. Heat stake post 1333 includes a flared end 1339, and protrudes from housing guide rib 3321 in a distal direction through aperture 1510 of sensor electronics carrier 2710. During the "locked" state, the proximally facing portion of sensor electronics carrier 2710 abuts against the proximal base of heat stake post 1333.

FIG. 13B shows applicator 151 in a "firing" state, wherein a force applied to the proximal end of housing 3702 causes housing 3702 to move in a distal direction with respect to sheath 704. Sharp 2552 and sensor 104 have extended from the distal end of sheath 704 and have already penetrated, or are in the process of penetrating, the subject's skin layer. Sharp carrier lock arms 1524, having cleared the inner diameter of sheath 704, deflect outward into their biased positions (indicated by outward arrows), and disengage from outer sharp carrier 3152. Outer sharp carrier 3152, in turn, begins to move in a proximal direction due to expansion of inner spring 1106 and outer spring 1104. Expansion of inner spring 1106 and outer spring 1104, as well as the movement of outer sharp carrier 3152 in a proximal direction, creates a corresponding opposing force in a distal direction against inner sharp carrier 3102 and sensor electronics carrier 2710 (indicated by downward arrow). This force causes inner sharp carrier 3102 and sensor electronics carrier 2710 to further advance in a distal direction along heat stake post 1333, thereby increasing the velocity of the sharp in a distal direction during insertion. At this point, inner sharp carrier 3102 and sensor electronics carrier 2710 remain coupled.

Figure 13D:
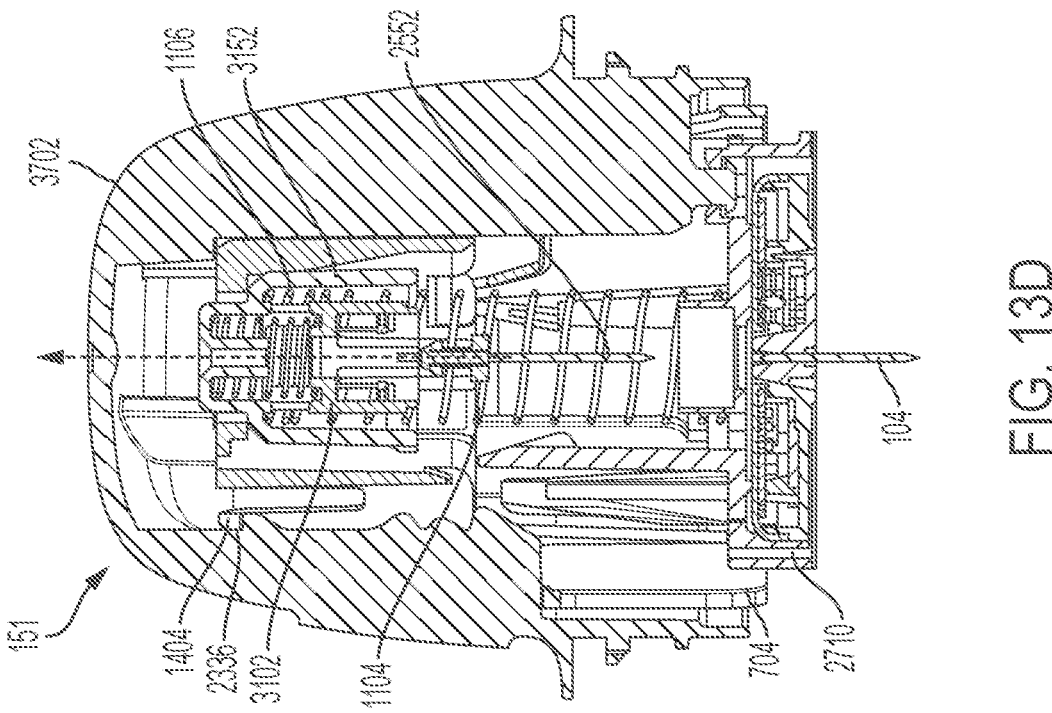
Figure 13C:
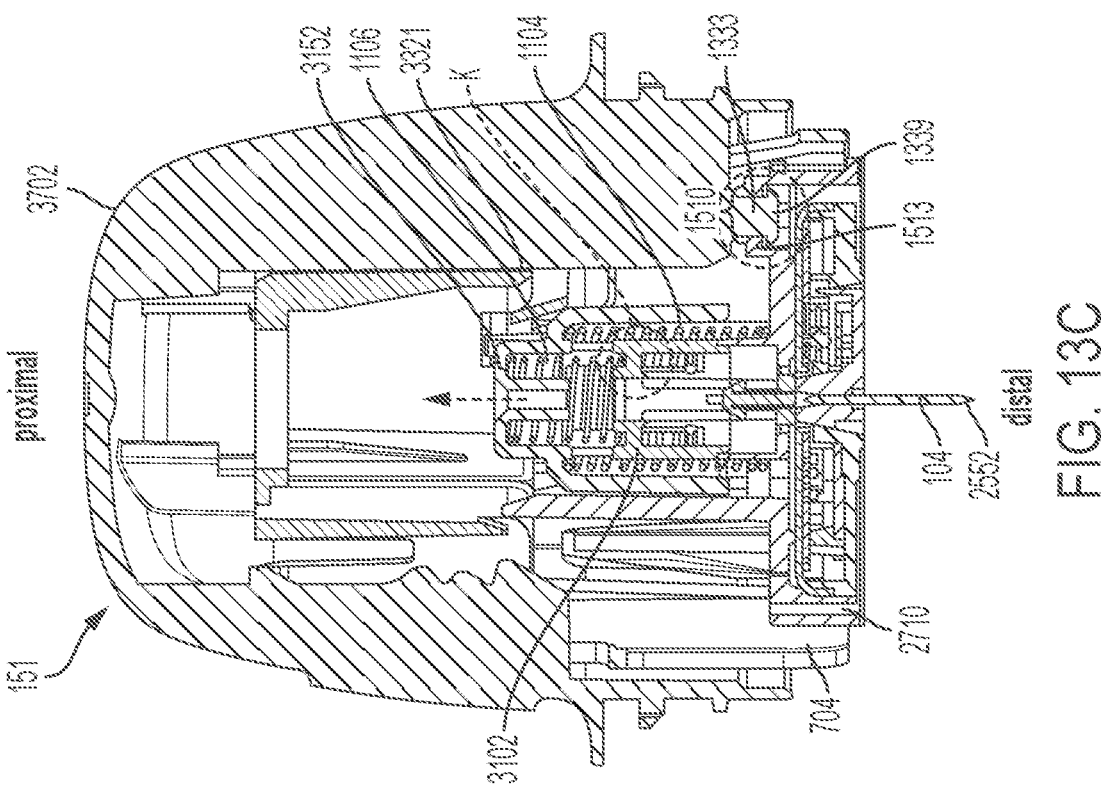

In FIG. 13C, outer sharp carrier 3152 continues to move in a proximal direction (indicated by upward arrow) due to continuing expansion of inner spring 1106 and outer spring 1104. Sensor electronics carrier 2710 has advanced in a distal direction along heat stake post 1333 until it reaches flared end 1339 of the post. Flared end 1339, which is larger than aperture 1510, abuts against ledges 1513 in sensor electronics carrier 2710, thereby preventing sensor electronics carrier 2710 from completely disengaging from housing guide rib 3321 of housing 3702. After moving a predetermined distance in the proximal direction, outer carrier latch 3160 (not shown) of outer sharp carrier 3152 engages inner carrier latch 3110 (not shown) of inner sharp carrier 3102 (in circled area 'K'). Sharp 2552 and sensor 104 remain in an extended state outside of sheath 704.

FIG. 13D shows applicator 151 in the "lockout" state. The continuing expansion of inner spring 1106 and outer spring 1104 cause outer sharp carrier 3152 to further advance in a proximal direction. Subsequently, outer carrier latch 3160 (not shown) engages with inner sharp carrier 3102 and pulls inner sharp carrier 3102 in a proximal direction (indicated by elongated upward arrow). In turn, inner sharp carrier 3102 retracts sharp 2552 through sensor electronics carrier 2710, leaving behind sensor 104 implanted in a dermal layer of the subject. Detent round 1404 of sheath 704 is positioned in the final lockout groove 2336, and both inner sharp carrier 3102 and outer sharp carrier 3152 are fully retracted within applicator 151.

With regard to the embodiments in FIGS. 13A-13D, heat stake post 1333 is described as a retention mechanism to couple housing 3702 and sensor electronics carrier 2710. It should be understood, however, that different retention mechanisms may be utilized, such as snap-in arms 1329, as described with respect to FIG. 9E, snaps, hooks, ball locks, latches, pins and/or other like retaining devices and structures.

With regard to the embodiments in FIGS. 12A-12D and 13A-13D, a sharp carrier assembly including an inner spring for maintaining the position of the inner sharp carrier is described. It will be understood by those of skill in the art that other devices and mechanisms for maintaining the position of the inner sharp carrier are fully within the scope of the disclosed embodiments. For example, an inner sharp carrier detent for engaging with the sensor electronics carrier (as described with respect to FIG. 10D), inner sharp carrier having one or more locking nubs for engaging with the sensor electronics carrier (as described with respect to FIG. 10E), as well as snaps, hooks, ball locks, latches, pins, and screw threads, can be used individually or in combination to retain inner sharp carrier in position during the "firing" sequence of the applicator.

Figures 1, 2, 14A:
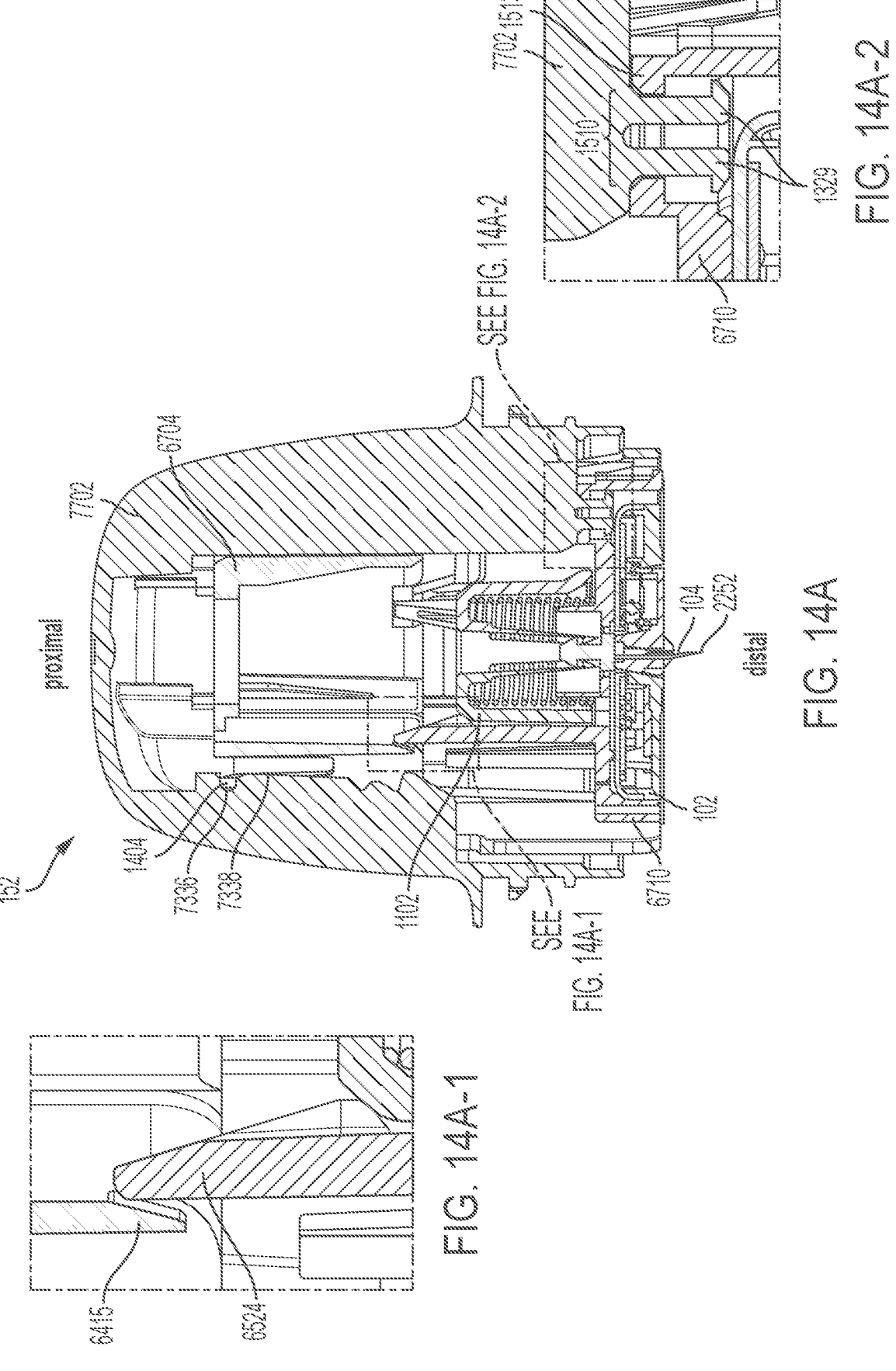
FIGS. 14A to 14C are side cross-sectional views depicting another example embodiment of an applicator device during various stages of deployment.
Figures 1, 2, 14B:
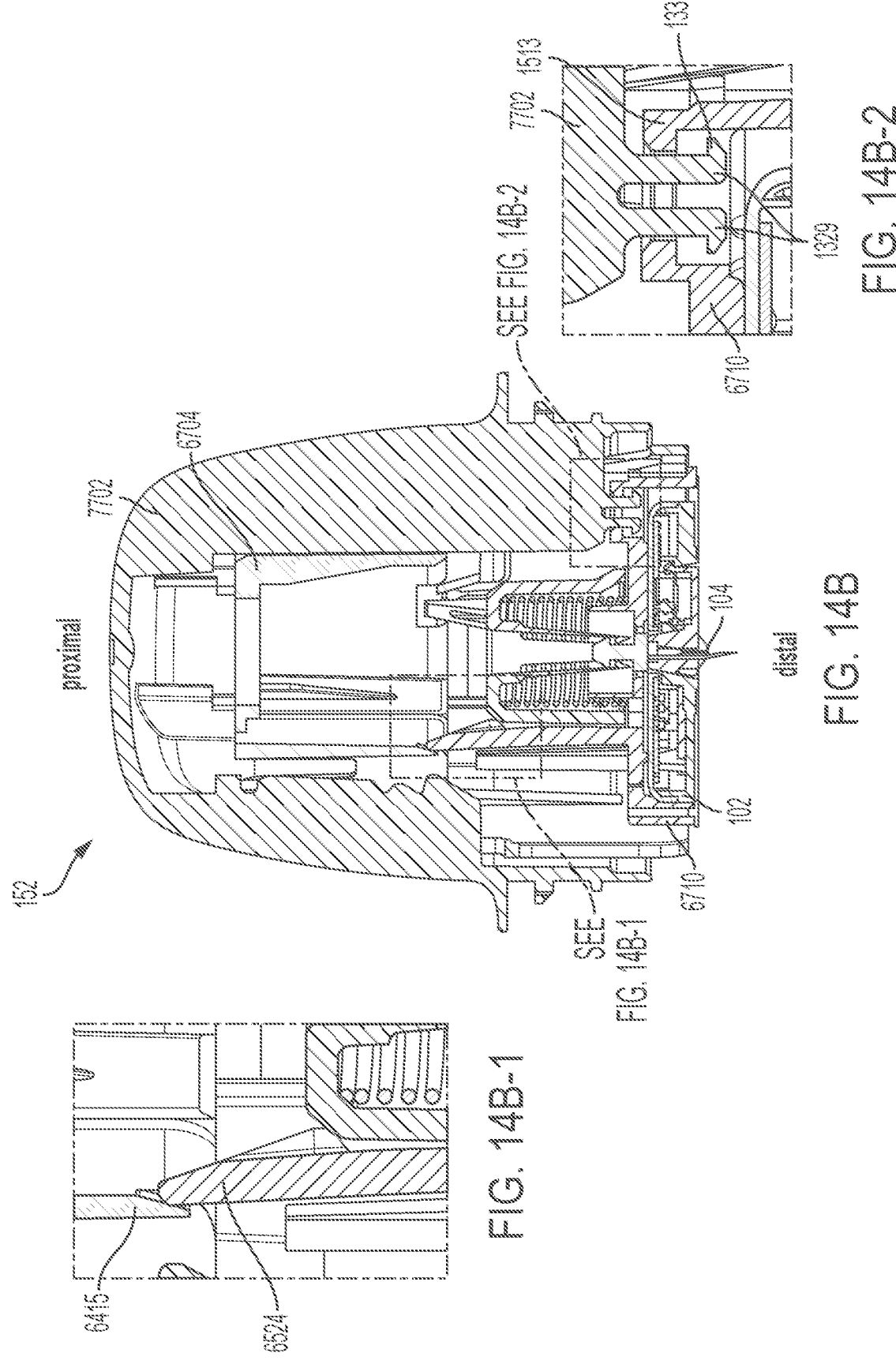
Figures 1, 2, 14C:
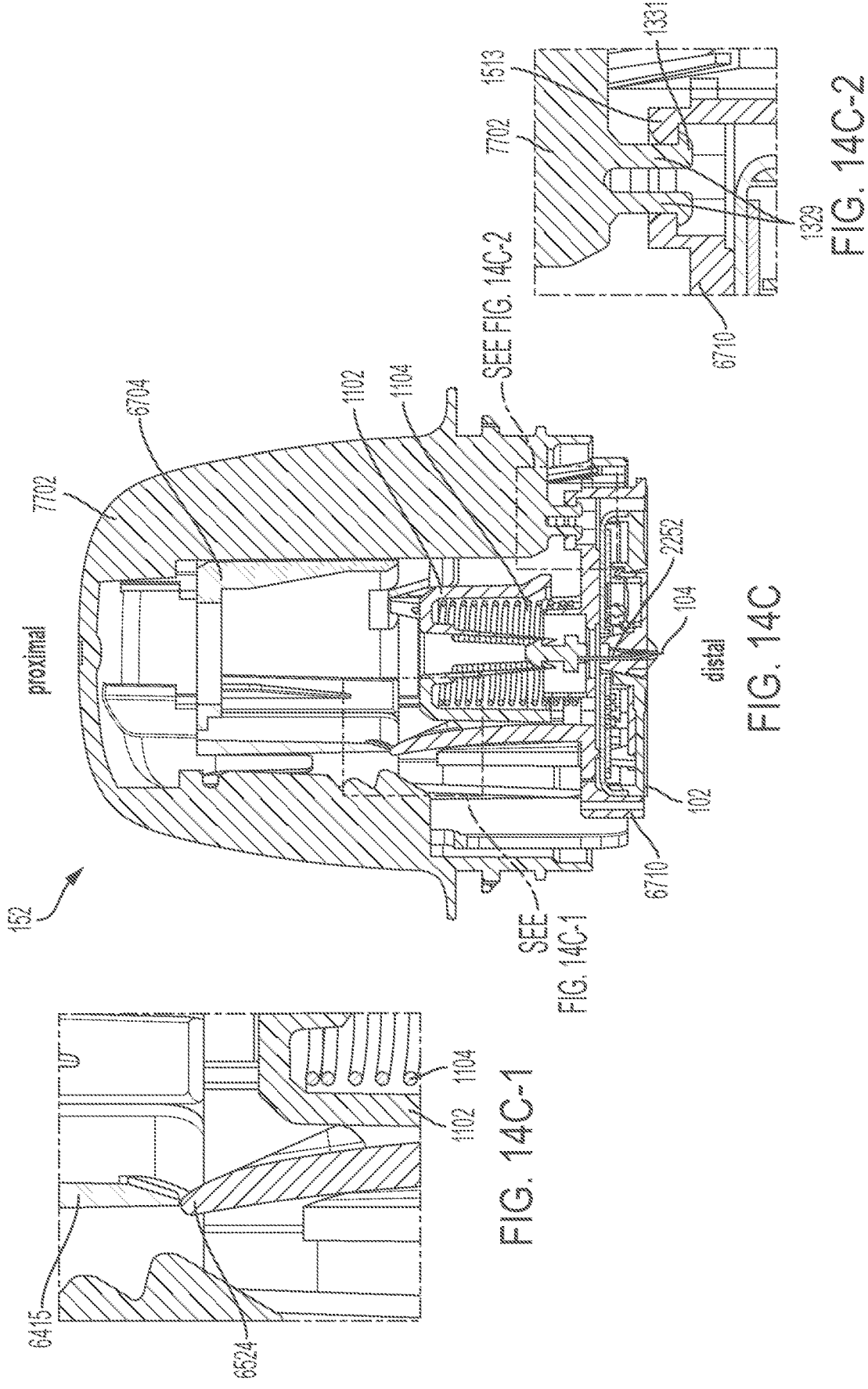

FIGS. 14A-14C are side cross-sectional views depicting another alternative embodiment of applicator 152 during deployment of sensor control device 102. As with the previous embodiments, applicator 152 is initially positioned against the subject's skin and a force is applied to the proximal end of housing 7702, causing housing 7702 to move in a distal direction with respect to sheath 6704. Thereafter, sharp 2552 and sensor 104 extend from the distal end of sheath 6704 and penetrate the subject's skin layer. Unlike the previous embodiments (FIGS. 12A-12D and 13A-13D), however, applicator 152 utilizes a motion-actuated sharp retraction mechanism which, as described in further detail below, retracts the sharp when the user moves applicator 152 away from the skin.

FIG. 14A shows applicator 152 in an early "lockout" state, after detent round 1404 of sheath 6704 has advanced over sloped firing surface 7338, by virtue of the user applying a first force upon the applicator, and reached two-way lockout recess 7336. At this stage, sharp 2252 has penetrated the skin layer and sensor 104 has been inserted into the dermal layer. Furthermore, as best seen in call-out 14A-1, one or more sharp carrier lock arms 6524 of sensor electronics carrier 6710 are biased in an outward direction and pushed against one or more corresponding carrier arm ramps 6415 of sheath 6704. In this position, carrier arm ramps 6415 impart a downward pushing force on lock arms 6524, thereby constraining sharp carrier 1102 against sensor electronics carrier 6710. Additionally, as seen in call-out 14A-2, snap-in arms 1329 of housing 7702 protrude through aperture 1510 of sensor electronics carrier 6710. At this stage, the distal edge of the housing is flush against aperture 1510 and aperture ledge 1513 of sensor electronics carrier 6710.

FIG. 14B shows applicator 152, after the "lockout" state, as the user begins to move applicator 152 away from the skin by applying a second force to applicator 152. The second force, which can be in a proximal or "upward" direction, for example, can be in the opposite direction as the first force, which can be in a distal or "downward" direction. An adhesive layer (not shown) on the bottom surface of sensor control device 102 keeps sensor control device 102 against the subject's skin, and movement of applicator 152 in a proximal direction results in a pull force on the sensor electronics carrier 6710 relative to housing 7702. As best seen in call-out 14B-1, carrier arm ramps 6415 include a beveled end surface which imparts a force in a distal direction onto lock arms 6524, and causes sensor electronics carrier 6710 to separate from housing 7702. Consequently, as shown in call-out 14B-2, sensor electronics carrier 6710 moves in a distal direction (i.e., towards the skin) relative to housing 7702, as aperture ledge 1513 moves closer to snap-in detents 1331 of snap-in arms 1329.

FIG. 14C shows applicator 152 as it is pulled away from the skin. As seen in call-out 14C-1, lock arms 6524 have cleared the carrier arm ramps 6415. Subsequently, sharp carrier 1102 is released and moves in a proximal direction from the force of compression spring 1104, thereby retracting sharp 2252. Also, as shown in call-out 14C-2, as snap-in detents 1331 of snap-in arms 1329 abut against ledge 1513, sensor electronics carrier 6710 can move no further away from housing 7702. Subsequently, as user pulls applicator 152 away from the skin, sensor control device 102 separates from sensor electronics carrier 6710 and is now attached to skin with sensor 104 inserted.

Figures 15A, 15B:
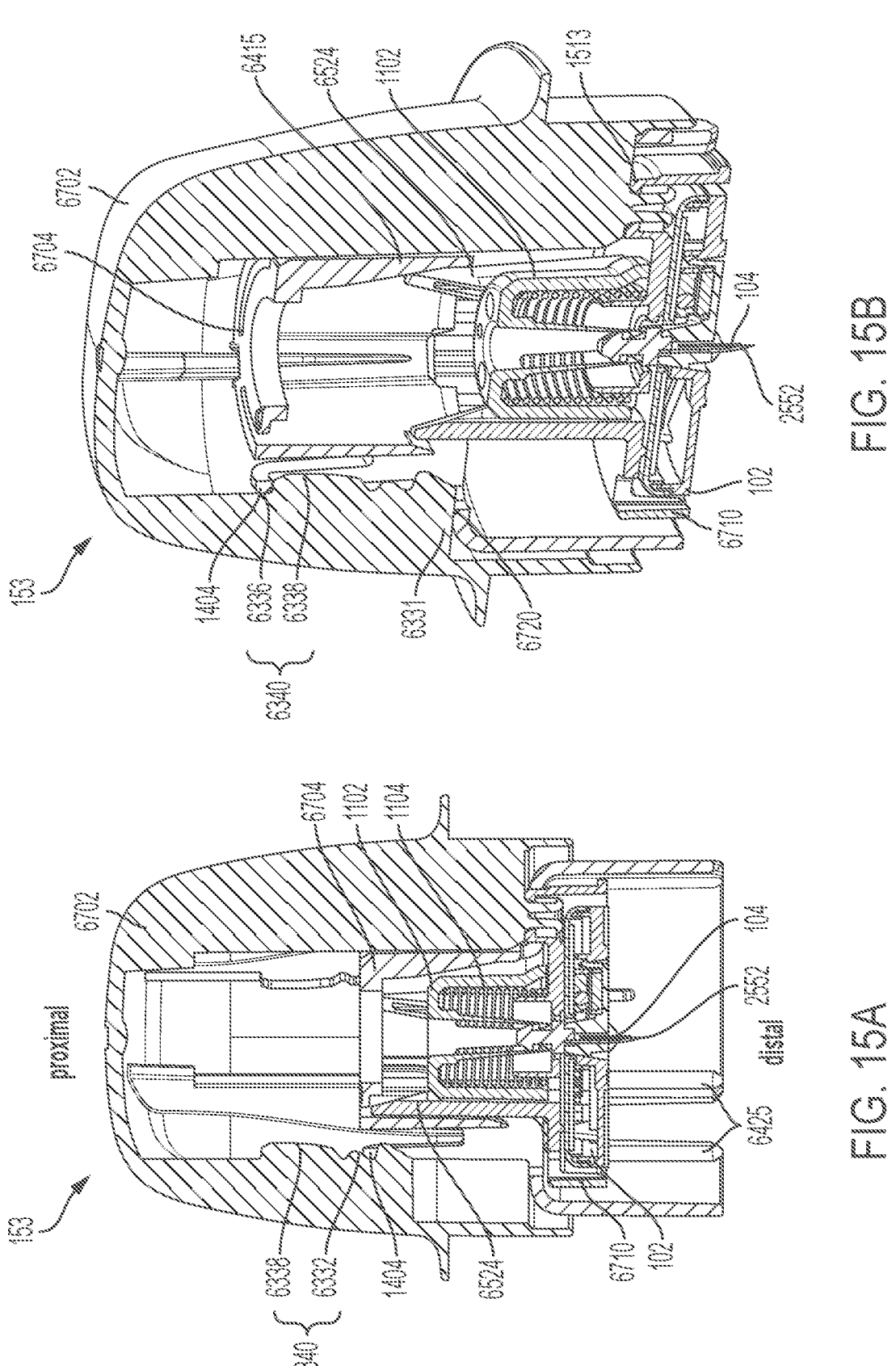
FIGS. 15A and 15B are side cross-sectional views depicting another example embodiment of an applicator device during various stages of deployment.

FIGS. 15A-15B are, respectively, a side cross-sectional view and a perspective cross-sectional view, both depicting another alternative embodiment of an applicator 153 during deployment of sensor control device 102. Applicator 153 also utilizes a motion-actuated sharp retraction mechanism and generally operates in a similar manner to applicator 152, as described with respect to FIGS. 14A-14C.

Turning to FIG. 15A, applicator 153 is shown in a state prior to firing, ready to be positioned against a subject's skin surface. Detent round 1404 of sheath 6704 is positioned in "locked" groove 6332 of locking rib 6340 in housing 6702. In addition, locking rib 6340 includes a sloped firing surface 6338 which creates a downward force on sheath 6704 during firing. Sheath 6704 also includes inner sheath ribs 6425 disposed on the inner surface of sheath 6704. As previously described with respect to FIGS. 8F-8H, the interfaces between inner sheath ribs 6425 and rib notches (not shown) of sensor electronics carrier 6710 maintain the axial alignment of the sheath 6704 and sensor electronics carrier 6710, and further prevent unwanted rotational and/or lateral movement during the sensor insertion process.

Referring still to FIG. 15A, sharp carrier 1102 is coupled with compression spring 1104, which is in a preloaded, compressed state. Sharp carrier 1102 is retained by one or more carrier lock arms 6524 of sensor electronics carrier 6710. Prior to firing, sharp 2552 and sensor 104 are positioned within sheath 6704.

Turning to FIG. 15B, applicator 153 is shown in an early "lockout" state, after sensor 104 has been inserted, but before sharp 2552 has been retracted. Detent round 1404 has advanced over sloped firing surface 6338 and reached the final lockout recess 6336 in locking rib 6340, which prevents further movement of sheath 6704 in a distal direction relative to housing 6702. In addition, sheath 6704 includes a sheath travel limiter ledge 6720 which, in the "lockout" state, abuts against a bottom edge 6331 of housing 6702, thereby preventing further movement of sheath 6704 in a proximal direction relative to housing 6702. Thus, in the "lockout" state, sheath 6704 can be prevented from further traveling in either a proximal or distal direction relative to housing 6702. In addition, at this stage, carrier lock arms 6524 have not cleared ramps 6415 of sheath 6704, and ledge 1513 of sensor electronics carrier 6710 is flush against housing 6702. Thus, the motion-actuated sharp retraction mechanism has not yet been initiated. Subsequently, as the user pulls away applicator 153 from the skin, carrier lock arms 6524 will clear ramps 6415, thereby releasing sharp carrier 1102 and initiating the sharp retraction mechanism (as described with respect to FIG. 14C).

With respect to the embodiments in FIGS. 14A-14C and 15A-15B, it should be understood that embodiments, such as applicators 152 and 153, can generally have a slower effective speed of insertion compared to applicators shown in FIGS. 12A-12D and 13A-13D. In addition, sheath 6704 of FIGS. 14A-14C and 15A-15B can be of shorter length than the sheaths depicted with respect to FIGS. 12A-12D and 13A-13D. Furthermore, in some embodiments, sheath 6704 can also include a base surface coated with an adhesive for adhering to the skin surface of the user.

Figures 16A, 16B, 16C:
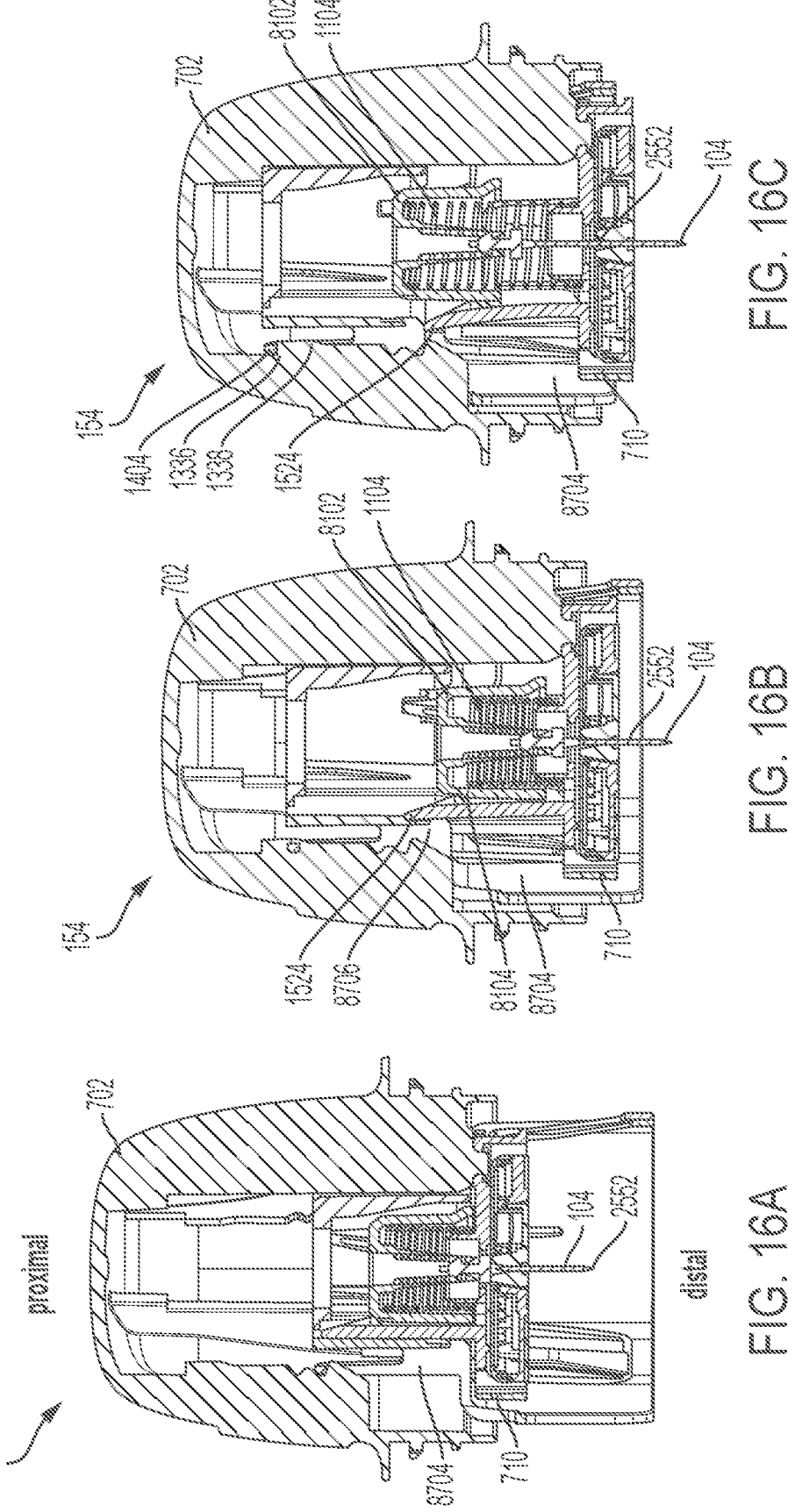
FIGS. 16A to 16C are side cross-sectional views depicting another example embodiment of an applicator device during various stages of deployment.

FIGS. 16A-16C are side cross-sectional views depicting another alternative example embodiment of applicator 154 during deployment of sensor control device 102. As with previous embodiments, applicator 154 is initially positioned against the subject's skin and a force is applied to the proximal end of housing 702, causing housing 702 to move in a distal direction with respect to sheath 8704. Thereafter, sharp 2552 and sensor 104 extend from the distal end of sheath 8704 and penetrate the subject's skin layer. According to one aspect of the disclosed embodiments, applicator 154 can include a dual-stage needle retraction mechanism, in which sharp 2252 is partially retracted at a first stage to minimize further penetration by sharp 2552 into the subject, while sensor 104 can further penetrate the tissue, e.g., the dermis or the subcutaneous tissue, to its final position. As further described below, in many embodiments, the dual-stage needle retraction mechanism can be implemented by a plurality of slots, including a sheath slot 8706 and sharp carrier slot 8104 (as depicted in FIG. 10F), each of which can be configured to receive at least a portion of a sharp carrier lock arm 1524 of sensor electronics carrier 710.

Referring first to FIG. 16A, applicator 154 is shown in a "locked" state, prior to firing, in which applicator 154 is ready to be positioned against a subject's skin surface. Sharp 2552 and sensor 104 are positioned within sheath 8704. Sensor electronics carrier 710 is resting radially against the inner diameter of sheath 8704.

FIG. 16B shows applicator 154 after a force has been applied to the proximal end of housing 702, causing housing 702 to move in a distal direction with respect to sheath 8704. Sharp 2552 and sensor 104 have extended from the distal end of sheath 8704, and have already penetrated, or are in the process of penetrating, the subject's skin layer. As sheath 8704 moves in a proximal direction relative to housing 702 and sensor electronics carrier 710, at least a portion of each sharp carrier lock arm 1524 of sensor electronics carrier 710 can be received into a sharp carrier slot 8104 disposed on sharp carrier 8102 and a sheath slot 8706 disposed on sheath 8704. (See also FIG. 10F.) As a portion of each lock arm 1524 is received into slots 8104 and 8706, lock arm 1524 can partially deflect in an outward direction, allowing sharp carrier 8102 to move a limited distance in a proximal direction due to the force of expansion of preloaded compression spring 1104 in sharp carrier 8102. In this manner, according to one aspect of the embodiments, sharp 2552 can be partially retracted, or maintained in a stationary position relative to the skin surface, during or after the first stage of the dual-stage needle retraction process. In addition, according to another aspect of the embodiments, during the first stage of the dual-stage sharp retraction, a distal portion of sensor 104 can continue to penetrate the tissue, e.g., the dermis or the subcutaneous tissue of the subject, while a proximal portion of sensor 104 can remain within sharp 2552.

FIG. 16C shows applicator 154 at the second stage of the dual-stage needle retraction process. As housing 702 continues to move in a distal direction with respect to sheath 8704, sharp carrier lock arms 1524 of sensor electronics carrier 710 have cleared the inner diameter of sheath 8704, and are free to deflect outward into their biased position.

Subsequently, sharp carrier lock arms 1524 disengage from sharp carrier 8102 which, in turn, moves further in a proximal direction due to further expansion of spring 1104, thereby causing sharp 2552 to further retract into applicator 154. As can also be seen in FIG. 16C, applicator 154 is shown in a "lockout" state, in which detent round 1404 of sheath 8704 has advanced past the sheath stopping ramp 1338 and within final lockout recess 1336 of housing 702.

With respect to the embodiments in FIGS. 16A-16C, those of skill in the art will appreciate that embodiments having a dual-stage needle retraction mechanism, such as applicator 154, can be configured to reduce the depth of penetration by sharp 2252 relative to, for example, the sensor tip. In this manner, these embodiments can reduce early sensor attenuation or sensor inaccuracy during the first few hours after insertion, which can be caused by trauma at the insertion site. Furthermore, although sharp carrier slot 8104 and sheath slot 8706 are depicted at certain positions along sharp carrier 8102 and sheath 8704, respectively, those of skill in the art will appreciate that other positions along the sharp carrier 8102 and/or sheath 8704, configurations (e.g., three, four or five slots) and/or geometries (e.g., angled surfaces, curved surfaces, concave surfaces, etc.) which are adapted to cause a partial release of the sharp carrier lock arms are fully within the scope of the present disclosure. In some embodiments, for example, the height of sheath slot 8706 in sheath 8704 can be varied to change the timing of the retraction relative to how far sheath 8704 has been retracted. Similarly, in other embodiments, the height of sharp carrier slot 8104 can be varied to change the distance of the partial retraction of sharp 2552.

Figures 1, 17:
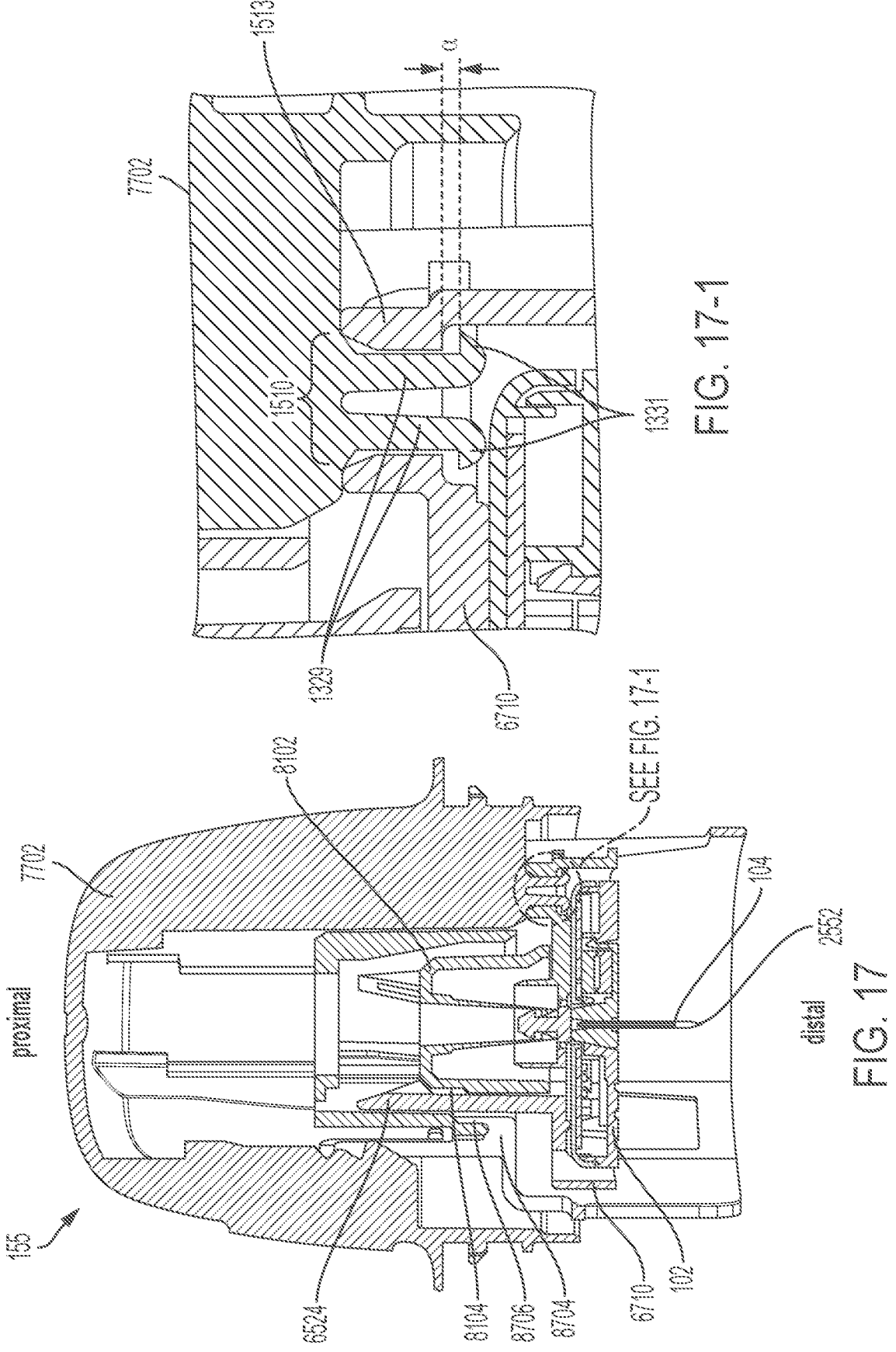
FIG. 17 is a side cross-sectional view depicting another example embodiment of an applicator device.

Turning to FIG. 17, a side cross-sectional view of another example alternative embodiment is provided, with applicator 155 shown ready for use in an "armed" position. According to one aspect of the embodiments, applicator 155 can include a compliant dual-stage needle retraction mechanism which can operate in a similar manner to the embodiments described with respect to FIGS. 16A-C. In many embodiments, for example, applicator 155 can include a sharp carrier slot 8104 of sharp carrier 8102 and a sheath slot 8706 of sheath 8704, each of which can be configured to receive at least a portion of lock arms 6524 of sensor electronics carrier 6710. During operation, as a portion of each lock arm 6524 is received into slots 8104 and 8706, lock arm 6524 can partially deflect in an outward direction, allowing sharp carrier 8102 to move a limited distance in a proximal direction due to the force of expansion of a preloaded compression spring (not shown) disposed in sharp carrier 8102. In this manner, according to one aspect of the embodiments, sharp 2552 can be partially retracted, or maintained in a stationary position relative to the skin surface, during or after the first stage of the dual-stage needle retraction process, while a distal portion of sensor 104 can continue to penetrate the tissue, e.g., the dermis or the subcutaneous tissue. As housing 7702 continues to move in a distal direction, the second stage of the dual-stage needle retraction mechanism is initiated. In particular, lock arms 6524 can clear the inner diameter of sheath 8704 and deflect outward into their biased position, thereby disengaging from sharp carrier 8102, which, in turn, moves further in a proximal direction due to further expansion of the spring, and retracts sharp 2552 into applicator 155.

Referring still to FIG. 17, according to another aspect of the embodiments, applicator 155 can include a compliance mechanism between sensor electronics carrier 6710 and housing 7702. In some embodiments, as best seen in call-out 17-1 of FIG. 17, housing 7702 of applicator 155 can include one or more snap-in arms 1329, which can protrude through aperture 1510 of sensor electronics carrier 6710. At a distal portion of snap-in arms 1329, one or more snap-in detents 1331 can prevent snap-in arms 1329 from disengaging from sensor electronics carrier 6710. Furthermore, as seen in call-out 17-1 of FIG. 17, the bottom edge of aperture ledge 1513 and the one or more snap-in detents 1331 are in a spaced relation by a predetermined amount of clearance, α, which can allow for limited movement by, collectively, sheath 8704, sharp carrier 8102, sensor electronics carrier 6710, and sensor control unit 102 relative to housing 7702.

According to one aspect of the embodiments, the predetermined clearance, α, can allow for gimbaling by sensor electronics carrier 6710 relative to housing 7702 which, in turn, can cause an angular displacement of sharp 2552 and sensor 104 relative to housing 7702 during insertion. For example, when applicator 155 is in the "armed" position, as shown in FIG. 17, a distal portion of analyte sensor 104 and a longitudinal axis 8545 of housing 7702 are substantially parallel to each other. According to one aspect of the embodiments, as force is applied to the housing 7702 and applicator 155 is fired, sensor electronics carrier 6710 can gimbal in relation to housing 7702 and cause the distal portion of analyte sensor 104 and the longitudinal axis 8545 to be in a non-parallel relation. In this regard, sharp 2552 and sensor 104 can follow a path of least resistance through the tissue, rather than being forced in the same axial direction as housing 7702, which, in turn, can reduce trauma to tissue during penetration and reduce early signal attenuation or sensor inaccuracy during the first few hours after insertion.

Figure 18:
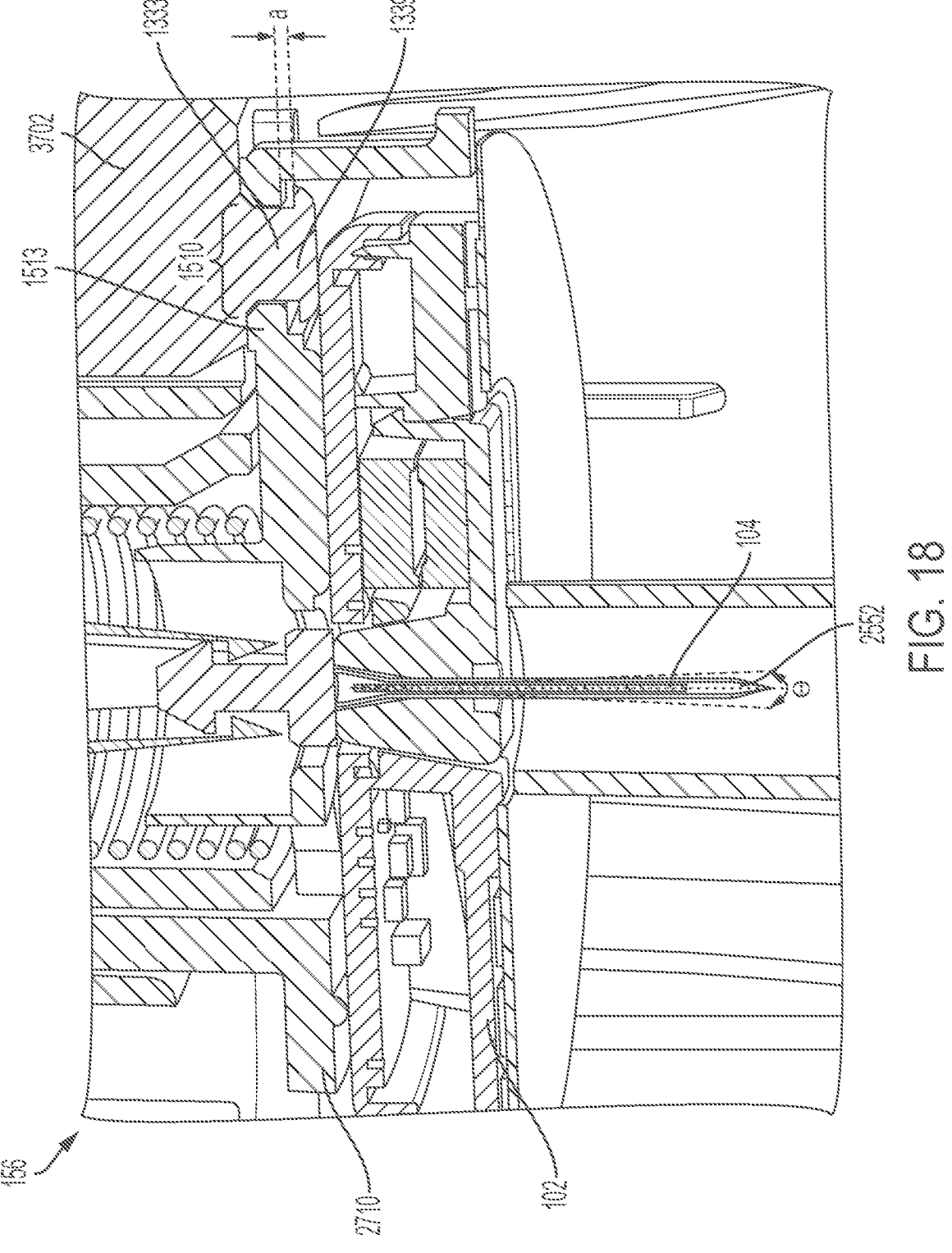
FIG. 18 is a partial cross-sectional view depicting another example embodiment of an applicator device.

FIG. 18 is a partial cross-sectional view of another example embodiment of an applicator 156, also having a compliance mechanism. According to one aspect of some embodiments, housing 3702 of applicator 156 can include a heat stake post 1333, which can protrude through aperture 1510 of sensor electronics carrier 2710. Heat stake post 1333 can have a flared distal end 1339, which can be configured to prevent heat stake post 1333 from disengaging from sensor electronics carrier 2710. Furthermore, like the embodiments described with respect to FIG. 17, the bottom edge of aperture ledge 1513 and flared distal end 1339 of heat stake post 1333 can be in a spaced relation by a predetermined amount of clearance, α, which can allow for limited freedom of movement by sensor electronics carrier 2710.

According to another aspect of the embodiments, predetermined clearance, α, can allow for gimballing movement by the sheath, sensor electronics carrier 2710, and sensor control unit 102 relative to housing 3702, as well as angular displacement of sharp 2552 and sensor 104 during insertion. Referring still to FIG. 18, the degree and range of angular displacement, Θ, by sharp 2552 and sensor 104 can be a function of the amount of the predetermined clearance, α. In some embodiments, for example, a predetermined clearance, α, of 0.5 millimeters can result in an angular displacement of approximately 2 degrees and 0.6 millimeters. Those of skill in the art will recognize that these measurements are provided solely for the purpose of illustration, and are in no way meant to limit the predetermined clearance or angular displacement to any particular value or range of values.

With respect to the embodiments in FIGS. 17 and 18, although some embodiments including the compliance mechanism are described in combination with the dual-stage needle retraction mechanism, it will be understood by those of skill in the art that the compliance mechanism can be combined with applicators having other types of retraction mechanisms, such as those embodiments described with respect to FIGS. 12A-12D, 13A-13D, 14A-14C, and 15A-15B, as well as applicators described in U.S. Patent Publication No. 2013/0150691 and U.S. Patent Publication No. 2016/0331283, which are incorporated by reference herein in its entirety for all purposes.

With respect to the embodiments in FIGS. 12A-12D, 13A-13D, 14A-14C, 15A-15B, 16A-16C, 17 and 18, although sharp 2552 is described, it should be understood that any of the sharps, sharp modules and sensor modules described herein with respect to FIGS. 11A-11J can be used.

With respect to any of the applicator embodiments in FIGS. 12A-12D, 13A-13D, 14A-14C, 15A-15B, 16A-16C, 17, and 18, as well as any of the components thereof, including but not limited to the sharp, sharp module and sensor module embodiments of FIGS. 11A-11J, those of skill in the art will understand that said embodiments can be dimensioned and configured for use with sensors configured to sense an analyte level in a bodily fluid in the epidermis, dermis, or subcutaneous tissue of a subject. In some embodiments, for example, sharps and distal portions of analyte sensors disclosed herein can both be dimensioned and configured to be positioned at a particular end-depth (i.e., the furthest point of penetration in a tissue or layer of the subject's body, e.g., in the epidermis, dermis, or subcutaneous tissue). With respect to some applicator embodiments, e.g., in embodiments having a dual-stage needle retraction mechanism, those of skill in the art will appreciate that certain embodiments of sharps can be dimensioned and configured to be positioned at a different end-depth in the subject's body relative to the final end-depth of the analyte sensor. In some embodiments, for example, a sharp can be positioned at a first end-depth in the subject's epidermis prior to retraction, while a distal portion of an analyte sensor can be positioned at a second end-depth in the subject's dermis. In other embodiments, a sharp can be positioned at a first end-depth in the subject's dermis prior to retraction, while a distal portion of an analyte sensor can be positioned at a second end-depth in the subject's subcutaneous tissue. In still other embodiments, a sharp can be positioned at a first end-depth prior to retraction and the analyte sensor can be positioned at a second end-depth, wherein the first end-depth and second end-depths are both in the same layer or tissue of the subject's body.

A number of deflectable structures are described herein, including but not limited to deflectable detent snaps 1402, deflectable locking arms 1412, sharp carrier lock arms 1524, sharp retention arms 1618, and module snaps 2202. These deflectable structures are composed of a resilient material such as plastic or metal (or others) and operate in a manner well known to those of ordinary skill in the art. The deflectable structures each has a resting state or position that the resilient material is biased towards. If a force is applied that causes the structure to deflect or move from this resting state or position, then the bias of the resilient material will cause the structure to return to the resting state or position once the force is removed (or lessened). In many instances these structures are configured as arms with detents, or snaps, but other structures or configurations can be used that retain the same characteristics of deflectability and ability to return to a resting position, including but not limited to a leg, a clip, a catch, an abutment on a deflectable member, and the like.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An assembly comprising:
an inserter, comprising:
a first carrier assembly disposed in an interior of the inserter, the first carrier assembly comprising a sharp configured to insert a portion of a glucose sensor into a subject's body;
a retraction spring disposed in the interior of the inserter, the retraction spring comprising a proximal end disposed in an interior of the first carrier assembly;
a second carrier assembly comprising one or more proximally-extending carrier arms; and
wherein the first carrier assembly further comprises one or more detents configured to detachably engage with the one or more proximally extending carrier arms;
wherein the first carrier assembly, the retraction spring, and the second carrier assembly are configured to advance in a distal direction toward the subject's skin from a proximal position entirely in the interior of the inserter to a distal position,
wherein engagement of the one or more proximally-extending carrier arms and the one or more detents is configured to prevent relative movement of the first carrier assembly and the second carrier assembly in the proximal position,
wherein, after the first carrier assembly, the retraction spring, and the second carrier assembly advance from the proximal position, each proximally-extending carrier arm of the one or more proximally-extending carrier arms is configured to disengage from a corresponding detent of the one or more detents,
wherein advancement of the first carrier assembly, the retraction spring, and the second carrier assembly causes insertion of the portion of the glucose sensor into the subject's body, wherein the retraction spring is configured to expand after the insertion of the portion of the glucose sensor into the subject's body, wherein the one or more proximally-extending carrier arms extend through an interior of the retraction spring, wherein the each proximally-extending carrier arm of the one or more proximally-extending carrier arms and the corresponding detent of the one or more detents form a latch, wherein the each proximally-extending carrier arm of the one or more proximally-extending carrier arms is configured to disengage from the corresponding detent of the one or more detents in response to a force applied in a proximal direction to the first carrier assembly.

2. The assembly of claim 1, further comprising a sensor control device comprising the glucose sensor coupled with sensor electronics.

3. The assembly of claim 2, wherein the sensor control device is configured to be positioned on the subject's skin when the first carrier assembly, the retraction spring, and the second carrier assembly are in the distal position.

4. The assembly of claim 3, wherein the each proximally-extending carrier arm of the one or more proximally-extending carrier arms comprises a corresponding laterally-extending retention feature.

5. The assembly of claim 4, wherein the corresponding laterally-extending retention feature is disposed on a proximal end of the each proximally-extending carrier arm.

6. The assembly of claim 4, wherein the each proximally-extending carrier arm of the one or more proximally-extending carrier arms is configured to prevent expansion of the retraction spring via the corresponding laterally-extending retention feature.

7. The assembly of claim 3, wherein at least a part of the glucose sensor is disposed in the sharp when the first carrier assembly, the retraction spring, and the second carrier assembly are in the proximal position.

8. The assembly of claim 2, wherein the sensor control device further comprises an adhesive portion configured to secure the sensor control device to the subject's skin.

9. The assembly of claim 2, wherein the sensor electronics comprises a processor, memory, a power source, and communication circuitry configured to wirelessly communicate data indicative of a glucose level.

10. The assembly of claim 2, wherein the sensor control device further comprises a sensor hub, wherein the portion of the glucose sensor is a part of a distal sensor portion, wherein the glucose sensor comprises the distal sensor portion and a proximal sensor portion, wherein the part of the distal sensor portion is configured to sense a glucose level of the subject, wherein the proximal sensor portion is engaged with the sensor hub, and wherein the distal sensor portion is substantially orthogonal to the proximal sensor portion.

11. The assembly of claim 1, wherein the each proximally-extending carrier arm of the one or more proximally-extending carrier arms is biased against the corresponding detent of the one or more detents.

12. The assembly of claim 1, wherein the retraction spring comprises a compression spring.

13. The assembly of claim 12, wherein the compression spring is in a preloaded, compressed state while the first carrier assembly, the retraction spring, and the second carrier assembly are advanced from the proximal position to the distal position.

14. The assembly of claim 12, wherein the compression spring is biased to retract the first carrier assembly in a proximal direction away from the subject's skin.

15. The assembly of claim 1, wherein the first carrier assembly, the retraction spring, and the second carrier assembly are further configured to advance along a linear path.

16. The assembly of claim 1, further comprising a cap removably attached to the inserter by a plurality of threads, and wherein the cap comprises an interior space comprising a sterile environment.

17. The assembly of claim 1, wherein the first carrier assembly is releasably coupled with the second carrier assembly when the first carrier assembly, the retraction spring, and the second carrier assembly are in the proximal position.

18. The assembly of claim 17, wherein the first carrier assembly is configured to decouple from the second carrier assembly after the first carrier assembly, the retraction spring, and the second carrier assembly reach the distal position.

19. The assembly of claim 1, wherein the retraction spring is configured to apply a second force that retracts the first carrier assembly after the first carrier assembly, the retraction spring, and the second carrier assembly reach the distal position.

* * * * *